United States Patent
Mizuno et al.

(10) Patent No.: US 10,124,004 B2
(45) Date of Patent: Nov. 13, 2018

(54) PYRIDO[3,4-D]PYRIMIDINE DERIVATIVE AND PHARMACEUTICALLY ACCEPTABLE SALT THEREOF

(71) Applicant: Teijin Pharma Limited, Tokyo (JP)

(72) Inventors: Tsuyoshi Mizuno, Tokyo (JP); Tomohiro Shimada, Tokyo (JP); Gen Unoki, Tokyo (JP); Masaru Ebisawa, Tokyo (JP); Susumu Takeuchi, Tokyo (JP); Kunio Minamizono, Tokyo (JP); Kosuke Sasaki, Tokyo (JP); Takuya Yokosaka, Tokyo (JP); Junji Igarashi, Tokyo (JP); Akinobu Maruyama, Tokyo (JP); Hiroshi Takahashi, Tokyo (JP); Kyohei Horie, Tokyo (JP); Yuri Sakai, Tokyo (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 15/577,802

(22) PCT Filed: May 27, 2016

(86) PCT No.: PCT/JP2016/065770
§ 371 (c)(1),
(2) Date: Nov. 29, 2017

(87) PCT Pub. No.: WO2016/194831
PCT Pub. Date: Dec. 8, 2016

(65) Prior Publication Data
US 2018/0161329 A1 Jun. 14, 2018

(30) Foreign Application Priority Data
May 29, 2015 (JP) .................................. 2015-110684

(51) Int. Cl.
| | |
|---|---|
| *A61K 31/506* | (2006.01) |
| *A61K 31/519* | (2006.01) |
| *A61K 31/5377* | (2006.01) |
| *A61K 31/5386* | (2006.01) |
| *A61K 31/541* | (2006.01) |
| *A61K 31/55* | (2006.01) |
| *A61K 31/551* | (2006.01) |
| *A61K 31/553* | (2006.01) |
| *C07D 471/04* | (2006.01) |
| *C07D 519/00* | (2006.01) |
| *A61P 9/10* | (2006.01) |
| *A61P 19/02* | (2006.01) |
| *A61P 35/00* | (2006.01) |

(52) U.S. Cl.
CPC ........ *A61K 31/519* (2013.01); *A61K 31/5377* (2013.01); *A61K 31/5386* (2013.01); *A61K 31/541* (2013.01); *A61K 31/55* (2013.01); *A61K 31/551* (2013.01); *A61K 31/553* (2013.01); *A61P 9/10* (2018.01); *A61P 19/02* (2018.01); *A61P 35/00* (2018.01); *C07D 471/04* (2013.01); *C07D 519/00* (2013.01)

(58) Field of Classification Search
CPC .............. A61K 31/519; A61K 31/5377; A61K 31/5386; A61K 31/541; A61K 31/55; A61K 31/551; A61K 31/553; A61P 9/10; A61P 19/02; A61P 35/00; C07D 471/04; C07D 519/00
See application file for complete search history.

(56) References Cited

U.S. PATENT DOCUMENTS

| | | | |
|---|---|---|---|
| 7,709,475 B2 * | 5/2010 | Iwasawa ............... | C07D 417/12 514/230.5 |
| 2003/0149001 A1 | 8/2003 | Barvian et al. | |
| 2005/0059670 A1 | 3/2005 | Beylin et al. | |

FOREIGN PATENT DOCUMENTS

| | | |
|---|---|---|
| JP | 2005-519909 A | 7/2005 |
| JP | 2007-530425 A | 11/2007 |
| WO | 03/062236 A1 | 7/2003 |
| WO | 2010/020675 A1 | 2/2010 |
| WO | 2010/075074 A1 | 7/2010 |
| WO | 2014/037750 A1 | 3/2014 |

(Continued)

OTHER PUBLICATIONS

L. Anders et al., 20 Cancer Cell, 620-634 (2011).*

(Continued)

*Primary Examiner* — Alexander R Pagano
(74) *Attorney, Agent, or Firm* — Sughrue Mion, PLLC

(57) ABSTRACT

The purpose of the present invention is to provide a compound having an excellent CDK4/6 inhibiting activity. The present invention is a compound represented by general formula (I) or a pharmaceutically acceptable salt thereof.

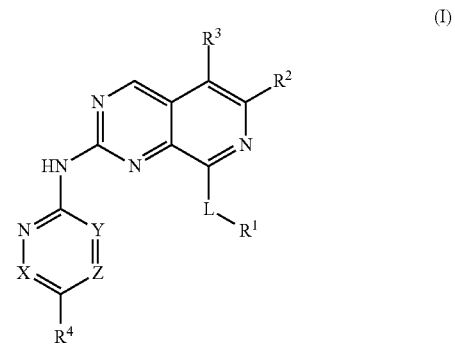

27 Claims, 1 Drawing Sheet

(56) References Cited

FOREIGN PATENT DOCUMENTS

WO    WO-2014037750 A1 *  3/2014  ........... C07D 401/14

OTHER PUBLICATIONS

Y. Li et al., 17 Journal of Cerebral Blood Flow and Metabolism, 846-856 (1997).*
J. Shi et al., 221 Annals of Operations Research, 331-356 (2014).*
A.T. Cohen et al., The Lancet, 387-394 (2008).*
Innocenti et al., "Expanding the scope of fused pyrimidines as kinase inhibitor scaffolds: synthesis and modification of pyrido[3,4-d]pyrimidines", Organic & Biomolecular Chemistry 2015, vol. 13, pp. 893-904, The Royal Society of Chemistry (12 pages total).
Johnson et al., "Cyclins and Cell Cycle Checkpoints", Annu. Rev. Pharmacol. Toxicol., 1999, vol. 39, pp. 295-312 (18 pages total).
Ortega et al., "Cyclin D-dependent kinases, INK4 inhibitors and cancer", Biochimica et Biophysica Acta 1602 (2002), pp. 73-87 (15 pages total).
Shapiro, "Cyclin-Dependent Kinase Pathways as Targets for Cancer Treatment", Journal of Clinical Oncology, vol. 24, No. 11, Apr. 10, 2006, pp. 1770-1783 (14 pages total).
Lundberg et al., "Functional Inactivation of the Retinoblastoma Protein Requires Sequential Modification by at Least Two Distinct Cyclin-cdk Complexes", Molecular and Cellular Biology, vol. 18, No. 2, Feb. 1998, pp. 753-761 (9 pages total).
Olaharski et al., "Identification of a Kinase Profile that Predicts Chromosome Damage Induced by Small Molecule Kinase Inhibitors", PLOS Computational Biology, Jul. 2009, vol. 5, Issue 7, e1000446 (10 pages total).
Kamb et al., "A Cell Cycle Regulator Potentially Involved in Genesis of Many Tumor Types", Science, vol. 264, Apr. 15, 1994, pp. 436-440 (5 pages total).
Taniguchi et al., "Induction of the p16INK4a senescence gene as a new therapeutic strategy for the treatment of rheumatoid arthritis", Nature Medicine, vol. 5, No. 7, Jul. 1999, pp. 760-767 (8 pages total).
Sekine et al., "Successful Treatment of Animal Models of Rheumatoid Arthritis with Small-Molecule Cyclin-Dependent Kinase Inhibitors", The Journal of Immunology, 2008, vol. 180, pp. 1954-1961 (8 pages total).
Hosoya et al., "Cell cycle regulation therapy combined with cytokine blockade enhances antiarthritic effects without increasing immune suppression", Ann Rheum Dis, 2016, vol. 75, pp. 253-259, Published on-line in 2014 (7 pages total).
Nonomura et al., "Direct Modulation of Rheumatoid Inflammatory Mediator Expression in Retinoblastoma Protein-Dependent and -Independent Pathways by Cyclin-Dependent Kinase 4/6", Arthritis & Rheumatism, vol. 54, No. 7, Jul. 2006, pp. 2074-2083 (11 pages total).
Chang et al., "Adenovirus-mediated Over-expression of the Cyclin/Cyclin-dependent Kinase Inhibitor, p21 Inhibits Vascular Smooth Muscle Cell Proliferation and Neointima Formation in the Rat Carotid Artery Model of Balloon Angioplasty", J. Clin. Invest., The American Society for Clinical Investigation, Inc., vol. 96, Nov. 1995, pp. 2260-2268 (9 pages total).
Yang et al., "Role of the p21 cyclin-dependent kinase inhibitor in limiting intimal cell proliferation in response to arterial injury", Proc. Natl. Acad. Sci. USA, Medical Sciences, vol. 93, pp. 7905-7910, Jul. 1996 (6 pages total).
Bukanov et al., "Long-lasting arrest of murine polycystic kidney disease with CDK inhibitor roscovitine", Nature, vol. 444, Dec. 14, 2006, pp. 949-952 (4 pages total).
Inoshima et al., "Induction of CDK inhibitor p21 gene as a new therapeutic strategy against pulmonary fibrosis", Am J Physiol Lung Cell Mol Physiol, vol. 286: L727-L733, 2004 (7 pages total).
Osuga et al., "Cyclin-dependent kinases as a therapeutic target for stroke", PNAS, Aug. 29, 2000, vol. 97, No. 18, pp. 10254-10259 (6 pages total).
Weinberg, "Tumor Suppressor Genes", Science, vol. 254, Nov. 22, 1991, pp. 1138-1146 (9 pages total).
Khatib et al., "Coamplification of the CDK4 Gene with MDM2 and GLI in Human Sarcomas", Cancer Research, vol. 53, pp. 5535-5541. Nov. 15, 1993 (7 pages total).
Bartek et al., "The retinoblastoma protein pathway and the restriction point", Current Opinion in Cell Biology, vol. 8, 1996, pp. 805-814 (10 pages total).
Guha, "Blockbuster dreams for Pfizer's CDK inhibitor", Nature Biotechnology, vol. 31, No. 3, Mar. 2013, p. 187 (1 page total).
Johnson et al., "Mitigation of hematologic radiation toxicity in mice through pharmacological quiescence induced by CDK4/6 inhibition", The Journal of Clinical Investigation, vol. 120, No. 7, Jul. 2010, pp. 2528-2536 (9 pages total).
VanderWel et al., "Pyrido[2,3-d]pyrimidin-7-ones as Specific Inhibitors of Cyclin-Dependent Kinase 4", Journal of Medical Chemistry, 2005, vol. 48. No. 7, pp. 2371-2387 (17 pages total).
Barvian et al., "Pyrido[2,3-d]pyrimidin-7-one Inhibitors of Cyclin-Dependent Kinases", Journal of Medicinal Chemistry, 2000, vol. 43, No. 24, pp. 4606-4616 (11 pages total).
Toogood et al., "Discovery of a Potent and Selective Inhibitor of Cyclin-Dependent Kinase 4/6", Journal of Medicinal Chemistry, 2005, vol. 48, No. 7, pp. 2388-2406 (19 pages total).
Cho et al., "4-(Pyrazol-4-yl)-pyrimidines as Selective Inhibitors of Cyclin-Dependent Kinase 4/6", Journal of Medicinal Chemistry, 2010, vol. 53, No. 22, pp. 7938-7957 (20 pages total).
Li et al., "Discovery of AMG 925, a FLT3 and CDK4 Dual Kinase Inhibitor with Preferential Affinity for the Activated State of FLT3", Journal of Medicinal Chemistry, 2014, vol. 57, pp. 3430-3449 (20 pages total).
Innocenti et al., "Rapid Discovery of Pyrido[3,4-d]pyrimidine Inhibitors of Monopolar Spindle Kinase 1 (MPS1) Using a Structure-Based Hybridization Approach", Journal of Medicinal Chemistry, 2016, vol. 59, pp. 3671-3688 (18 pages total).
International Search Report dated Aug. 30, 2016, issued by the International Searching Authority in International Application No. PCT/JP2016/065770.

* cited by examiner

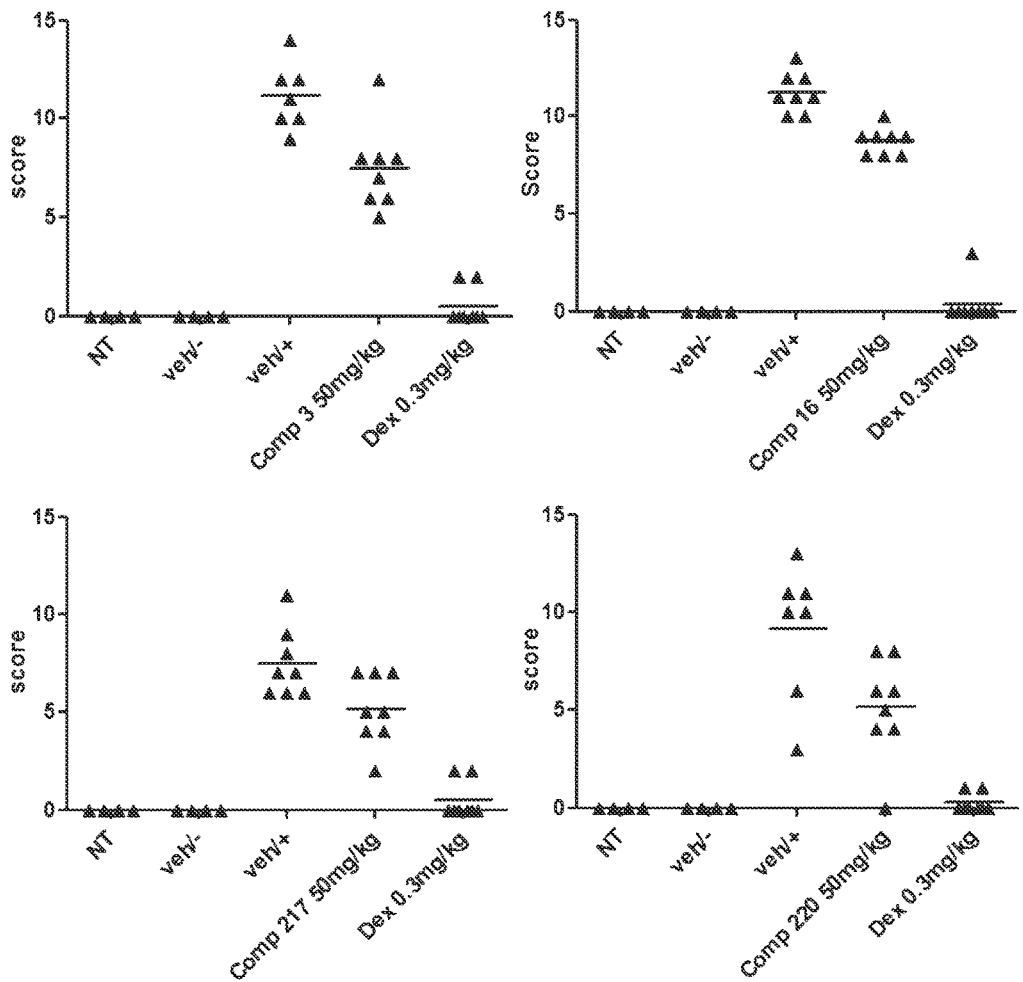
*Abbreviations
NT: no treatment group, Veh/-: group of no disease induction/solvent administration,
Veh/+: group of disease induction/solvent administration,
Comp: group of disease induction/example compound administration,
Dex: group of disease induction/dexamethasone administration

PYRIDO[3,4-D]PYRIMIDINE DERIVATIVE AND PHARMACEUTICALLY ACCEPTABLE SALT THEREOF

CROSS REFERENCE TO RELATED APPLICATIONS

This application is a National Stage of International Application No. PCT/JP2016/065770 filed May 27, 2016, claiming priority based on Japanese Patent Application No. 2015-110684 filed May 29, 2015, the contents of all of which are incorporated herein by reference in their entirety.

TECHNICAL FIELD

The present invention relates to a pyrido[3,4-d]pyrimidine derivative and a pharmaceutically acceptable salt thereof. In particular, the present invention relates to a compound that exhibits an inhibitory activity against cyclin-dependent kinase 4 and/or cyclin-dependent kinase 6 (hereinafter referred to as "CDK4/6") and that is useful for the prevention or treatment of rheumatoid arthritis, arteriosclerosis, pulmonary fibrosis, cerebral infarction, or cancer.

BACKGROUND ART

Cell growth, which is a process involving proliferation and division of cells, occurs in response to various stimuli.

Pathological conditions caused by hyperproliferation of cells, such as cancer, are characterized by uncontrollable cell cycle progression and thus excessive progression of the cell cycle, for example, resulting from abnormality in genes or proteins that directly or indirectly regulate the cell cycle progression. Substances that regulate hyperproliferation of cells through control of the cell cycle can be used for the treatment of various pathological conditions characterized by uncontrollable or unwanted cell growth.

Cell cycle progression is a complicated process involving highly regulated transition of phases and multiple checkpoints.

Cyclin-dependent kinases and associated serine/threonine protein kinases are important intracellular enzymes that play essential roles in the regulation of division and proliferation of cells. Catalytic subunits of cyclin-dependent kinases are activated by regulatory subunits known as cyclins, and multiple cyclins have been identified in mammals (NPL 1).

The retinoblastoma (Rb) protein is a checkpoint protein for transition from the G1 phase to the S phase in the cell cycle. The Rb protein associates with the E2F transcription factor family and inhibits the activity thereof in the absence of appropriate growth stimulation (NPLs 2 and 3). A cell stimulated by a mitogen enters the S phase through synthesis of cyclin D, which is a CDK4/6 activator. The cyclin D-bound CDK 4/6 inactivates the Rb protein through phosphorylation. The phosphorylation of the Rb protein releases E2F in order to indirective the transcription of a gene necessary for the S phase. The complete inactivation of the Rb protein requires phosphorylation of both cyclin D-CDK4/6 and cyclin E-CDK2. The phosphorylation of the Rb protein by CDK4/6 at a specific site is essential in the phosphorylation of cyclin E-CDK2 (NPL 4). Thus, cyclin D-CDK4/6 is an important enzyme complex which controls the transition from the G1 phase to the S phase.

CDK2 forms a complex with cyclin E and also forms a complex with cyclin A. CDK2 also acts on steps subsequent to the S phase and is responsible for DNA replication. The inhibition of CDK2 probably leads to the expression of genotoxicity (NPL 5).

Cyclin D has a molecular mechanism that positively regulates the activity of CDK4/6. In contrast, p16 encoded by the INK4a gene negatively regulates the activity of CDK4/6 (NPL 6).

CDK inhibitors can be used for the treatment of various diseases caused by abnormal cell growth, such as cancer, cardiovascular disorder, renal disease, specific infections, and autoimmune diseases. CDK inhibitors is also expected to be effective for the treatment of diseases including but not limited to rheumatoid arthritis, arteriosclerosis, pulmonary fibrosis, cerebral infarction, and cancer. The inhibition of cell cycle progression and cell growth through CDK inhibition is expected to be effective for such a disease on the basis of the technical findings described below.

Rheumatoid arthritis involves the formation of pannus through hyperproliferation of synovial cells. This hyperproliferation can be reduced by the introduction of p16 into an affected area of a model animal or the administration of a CDK4/6 inhibitor to the animal (NPLs 7 to 9). A CDK4-cyclin D complex regulates the production of MMP3 in synovial cells derived from a patient with rheumatoid arthritis. The negative regulation of the activity of CDK4/6 inhibits not only the proliferation but also production of MMP3 (NPL 10).

Thus, CDK4/6 inhibitors are expected to exhibit both an inhibitory effect on proliferation of synovial cells and a cartilage protective effect in rheumatoid arthritis.

A pathway for the regulation of cell growth including genes responsible for the checkpoints in the G1 and S phases of the cell cycle is associated with plaque progression, stenosis, and restenosis after angiogenesis. The overexpression of the CDK inhibitory protein p21 inhibits angiogenesis and subsequent growth of vascular smooth muscle and intimal hyperplasia (NPLs 11 and 12).

Abnormal regulation of the cell cycle is also associated with polycystic kidney disease, which is characterized by growth of cysts filled with fluid in the renal tubule. A small-molecule CDK inhibitor is effective for the treatment of the disease (NPL 13).

The induction of expression of the cell cycle inhibitory protein p21 with an adenoviral vector is effective in a murine pulmonary fibrosis model (NPL 14).

The level of cyclin D1/CDK4 is known to increase in a rat cerebral infarction model in association with neuronal death caused by local ischemia. The neuronal death is reduced by administering flavopiridol, which is a nonselective CDK inhibitor (NPL 15).

The cyclin D-CDK4/6-INK4a-Rb pathway is frequently detected in human cancer caused by abnormality of any factors contributing to growth of cancer cells, such as loss of functional p16INK4a, overexpression of cyclin D1, overexpression of CDK4, or loss of functional Rb (NPLs 16 to 18). Such abnormality promotes the cell cycle progression from the G1 phase to the S phase, and this pathway certainly plays an important role in oncogenic transformation or abnormal growth of cancer cells.

CDK4/6 inhibitors may be effective, particularly for tumors involving abnormality in genes that activate the CDK4/6 kinase activity, such as cancers involving the translocation of cyclin D, cancers involving the amplification of cyclin D, cancers involving the amplification or overexpression of CDK4 or CDK6, and cancers involving the inactivation of p16. CDK4/6 inhibitors may be effective for the treatment of cancers involving genetic abnormality in the upstream regulator of cyclin D, the amount of which increases due to defects in the upstream regulator.

In fact, many compounds that inhibit the CDK4/6 activity have been synthesized and disclosed in the art, and such compounds have been clinically tested for the treatment of cancers, such as breast cancer (NPL 19).

Most acute and severe radiotherapeutic and chemotherapeutic toxicities are caused by the effects on stem cells and progenitor cells. A CDK4/6 inhibitor causes temporary cell cycle arrest to hematopoietic stem and progenitor cells, and protects them from radiotherapeutic or chemotherapeutic cytotoxicity. After the treatment with the inhibitor, hematopoietic stem and progenitor cells (HSPCs) return from the temporary dormancy and then function normally. Thus, the chemotherapeutic resistance with use of a CDK4/6 inhibitor is expected to provide a significant protection of bone marrow (NPL 20).

Hence, CDK4/6 inhibitors are expected to be effective for the treatment of rheumatoid arthritis, arteriosclerosis, pulmonary fibrosis, cerebral infarction, or cancer, and the protection of bone marrow, in particular, for the treatment of rheumatoid arthritis or cancer and the protection of bone marrow.

PTL 1 and NPL 21 disclose CDK4 inhibitors, PTLs 2 and 3 and NPLs 22 to 24 disclose CDK4/6-containing CDK inhibitors, and NPL 25 discloses CDK4/FLT3 inhibitors.

Pyrido[3,4-d]pyrimidine derivatives exhibit an inhibitory effect on Mps1 (also known as TTK) (PTL 4). This inhibitory effect is completely different from the CDK4/6 inhibitory effect disclosed in the present invention.

NPL 26 and NPL 27 disclose that a plurality of pyrido[3,4-d]pyrimidine derivatives exhibit a CDK2 inhibitory activity, which is completely different from the superior CDK4/6 inhibitory effect exhibited by the present invention.

LIST OF CITATIONS

Patent Literature

[PTL 1] WO2003/062236
[PTL 2] WO2010/020675
[PTL 3] WO2010/075074
[PTL 4] WO2014/037750

Non-Patent Literature

[NPL 1] Johnson D. G. and Walker C. L., Annual Review of Pharmacology and Toxicology 1999; 39: p. 295-312
[NPL 2] Ortega et al., Biochimica et Biophysica Acta-Reviews on Cancer 2002; 1602 (1): p. 73-87
[NPL 3] Shapiro, Journal of Clinical Oncology 2006; 24 (11): p. 1770-1783
[NPL 4] Lundberg et al., Molecular and Cellular Biology 1998; 18 (2): p. 753-761
[NPL 5] Andrew J. Olaharski, PLoS Computational Biology 2009; 5 (7): e1000446
[NPL 6] Kamb et al., Science 1994; 264 (5157): p. 436-440
[NPL 7] Taniguchi, K et al., Nature Medicine, Vol. 5, p. 760-767 (1999)
[NPL 8] Sekine, C et al., Journal of immunology 2008, 180: p. 1954-1961
[NPL 9] Hosoya, T et al., Annnl Rheumatic Diseases 2014 Aug. 27 Epub ahead of print
[NPL 10] Nonomura Y et al., Arthritis & Rheumatology 2006, July; 54 (7): p. 2074-83
[NPL 11] Chang M. W. et al., Journal of Clinical Investigation, 1995, 96: p. 2260
[NPL 12] Yang Z-Y. et al., Proceedings of the National Academy of Sciences (USA) 1996, 93: p. 9905
[NPL 13] Bukanov N. O. et al., Nature, 2006, 4444: p. 949-952
[NPL 14] American Journal Physiology: Lung Cellular and Molecular Physiology, 2004, Vol. 286, p. L727-L733
[NPL 15] Proceedings of the National Academy of Sciences of the United States of America, 2000, Vol. 97, p. 10254-10259
[NPL 16] Science, Vol. 254, p. 1138-1146 (1991)
[NPL 17] Cancer Research, 1993, Vol. 53, p. 5535-5541
[NPL 18] Current Opinion in Cell Biology, 1996, Vol. 8, p. 805-814
[NPL 19] Guha M, Nature Biotechnology 2013, March; 31 (3): p. 187
[NPL 20] Journal of Clinical Investigation 2010; 120 (7): p. 2528-2536 Soren M. Johnson
[NPL 21] Journal of Medicinal Chemistry, 2005, 48, p. 2371-2387
[NPL 22] Journal of Medicinal Chemistry, 2000, 43, p. 4606-4616
[NPL 23] Journal of Medicinal Chemistry, 2005, 48, p. 2388-2406
[NPL 24] Journal of Medicinal Chemistry, 2010, 53, p. 7938-7957
[NPL 25] Journal of Medicinal Chemistry, 2014, 57, p. 3430-3449
[NPL 26] Organic & Biomolecular Chemistry, 2015, 13, p. 893-904
[NPL 27] Rapid Discovery of Pyrido[3,4-d]pyrimidine Inhibitors of Monopolar Spindle Kinase 1 (MPS1) Using a Structure-Based Hybridization Approach, Paolo Innocenti et al, J. Med. Chem., Article ASAP, Publication Date (Web): Apr. 7, 2016, DOI: 10.1021/acs.jmedchem.5b01811.

SUMMARY OF INVENTION

Problem to be Solved by the Invention

An object of the present invention is to provide a compound exhibiting a superior CDK4/6 inhibitory activity.

Means to Solve the Problem

The present inventors have conducted extensive studies for solving the problems described above and have found that a novel pyrido[3,4-d]pyrimidine derivative represented by Formula (I) exhibits a CDK4/6 inhibitory activity. The present invention has been accomplished on the basis of this finding.

The present invention includes the following aspects:

Aspect (1): A compound represented by Formula (I), or a pharmaceutically acceptable salt thereof:

[Formula 1]

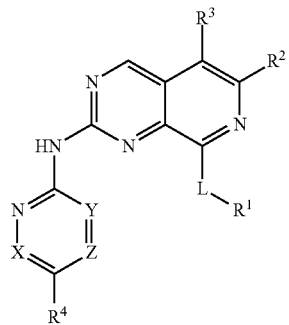

(I)

[wherein

L represents —NR$^5$—, —O—, or —S—;

R$^5$ represents a hydrogen atom or a C$_{1-6}$ alkyl group substituted with zero to two —OH groups, zero to two C$_{1-8}$ alkoxy groups, and zero to six fluorine atoms;

R$^1$ represents a C$_{1-8}$ alkyl, C$_{3-12}$ cycloalkyl, (C$_{3-12}$ cycloalkyl)-C$_{1-6}$ alkyl, 4- to 12-membered heterocyclyl, (4- to 12-membered heterocyclyl)-C$_{1-6}$ alkyl, C$_{6-10}$ aryl, (C$_{6-10}$ aryl)-C$_{1-6}$ alkyl, 5- to 10-membered heteroaryl, (5- to 10-membered heteroaryl)-C$_{1-6}$ alkyl, C$_{1-8}$ alkylsulfonyl, or C$_{1-8}$ acyl group;

each of the heteroatom-containing groups represented by R$^1$ contains one to four heteroatoms selected from oxygen, sulfur, and nitrogen atoms;

R$^1$ is optionally substituted with one to six substituents selected from the group consisting of a halogen atom, =O, —OH, —CN, —COOH, —COOR$^6$, —R$^7$, a C$_{3-6}$ cycloalkyl group substituted with zero to two —OH groups, zero to two C$_{1-8}$ alkoxy groups, and zero to six fluorine atoms, a 3- to 10-membered heterocyclyl group substituted with zero to two —OH groups, zero to two C$_{1-8}$ alkoxy groups, and zero to six fluorine atoms, a C$_{1-8}$ acyl group substituted with zero to two —OH groups, zero to two C$_{1-8}$ alkoxy groups, and zero to six fluorine atoms, and a C$_{1-8}$ alkoxy group substituted with zero to two —OH groups, zero to two C$_{1-8}$ alkoxy groups, and zero to six fluorine atoms;

R$^6$ and R$^7$ each independently represent a C$_{1-6}$ alkyl group substituted with zero to two —OH groups, zero to two C$_{1-8}$ alkoxy groups, and zero to six fluorine atoms;

R$^2$ represents a C$_{1-8}$ alkyl, C$_{3-8}$ cycloalkyl, 4- to 6-membered heterocyclyl, or C$_{1-8}$ acyl group, —COOR$^8$, or —CONR$^9$R$^{10}$;

each of the C$_{1-8}$ alkyl and C$_{3-8}$ cycloalkyl groups represented by R$^2$ is substituted with zero or one —OH group, zero to two C$_{1-8}$ alkoxy groups substituted with zero or one —OH group, zero or one C$_{1-4}$ alkoxy group, and zero to three fluorine atoms, and zero to five fluorine atoms;

R$^2$ is neither an unsubstituted C$_{1-8}$ alkyl, nor unsubstituted C$_{3-8}$ cycloalkyl, nor trifluoromethyl group;

R$^8$, R$^9$, and R$^{10}$ each independently represent a hydrogen atom or a C$_{1-8}$ alkyl group;

the 4- to 6-membered heterocyclyl group represented by R$^2$ is optionally substituted with one to four substituents selected from the group consisting of a fluorine atom, —OH, and C$_{1-4}$ alkyl and C$_{1-4}$ alkoxy groups;

each of the C$_{1-8}$ acyl group, —COOR$^8$, and —CONR$^9$R$^{10}$ represented by R$^2$ is optionally substituted with one to four substituents selected from the group consisting of a fluorine atom, —OH, and a C$_{1-4}$ alkoxy group;

R$^9$ and R$^{10}$ of —CONR$^9$R$^{10}$ represented by R$^2$ are optionally bonded via a single bond or —O— to form a ring including the nitrogen atom bonded to R$^9$ and R$^{10}$;

the heterocyclyl group represented by R$^2$ having a 4- or 5-membered ring contains one oxygen heteroatom, and the heterocyclyl group having a 6-membered ring contains one or two oxygen heteroatoms;

R$^3$ represents a hydrogen atom, a C$_{1-8}$ alkyl group, or a halogen atom;

X represents CR$^{11}$ or a nitrogen atom;

Y represents CR$^{12}$ or a nitrogen atom;

Z represents CR$^{13}$ or a nitrogen atom;

R$^{11}$ to R$^{13}$ each independently represent a hydrogen, fluorine, chlorine atom, a C$_{1-6}$ alkyl, or C$_{1-6}$ alkoxy group;

R$^4$ represents -A$^1$-A$^2$-A$^3$;

A$^1$ represents a single bond, a C$_{1-8}$ alkylene, C$_{2-8}$ alkenylene, or C$_{2-8}$ alkynylene group;

one or two sp$^3$ carbon atoms at any positions of A$^1$ are optionally replaced with one or two structures selected from the group consisting of —O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$—, and a structure of —O—O—, —O—NR$^{14}$—, —NR$^{14}$—O—, —O—CH$_2$—O—, —O—CH$_2$—NR$^{14}$—, or —NR$^{14}$—CH$_2$—O— is not formed in the case of replacement of two sp$^3$ carbon atoms;

A$^2$ represents a single bond, a C$_{1-7}$ alkylene, C$_{3-12}$ cycloalkylene, C$_{3-12}$ cycloalkylidene, 4- to 12-membered heterocyclylene, 4- to 12-membered heterocyclylidene, C$_{6-10}$ arylene, or 5- to 10-membered heteroarylene group;

A$^3$ represents a halogen atom, —CN, —NO$_2$, —R$^{25}$, —OR$^{26}$, —NR$^{27}$R$^{28}$, —C(=O)R$^{29}$, —C(=O)—OR$^{30}$, —O—C(=O)R$^{31}$, —O—C(=O)—NR$^{32}$R$^{33}$, —C(=O)—NR$^{34}$R$^{35}$, —NR$^{36}$—C(=O)R$^{37}$, —NR$^{38}$—C(=O)—OR$^{39}$, —S(=O)$_2$—R$^4$, —S(=O)$_2$—NR$^{41}$R$^{42}$, or —NR$^{43}$—S(=O)$_2$R$^{44}$;

A$^3$ represents —R$^{25}$, if the A$^1$ end on the A$^2$ side has a structure selected from the group consisting of —O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)—, —S(=O)$_2$—NR$^{21}$—, —NR$^{22}$—S(=O)$_2$—, and —NR$^{23}$—S(=O)$_2$—NR$^{24}$— and A$^2$ is a single bond;

R$^{14}$, R$^{32}$, R$^{34}$, R$^{36}$, R$^{38}$, R$^{41}$, and R$^{43}$ each independently represent a hydrogen atom, a C$_{1-8}$ alkyl, C$_{1-8}$ acyl, C$_{1-8}$ alkylsulfonyl, 4- to 12-membered heterocyclyl, C$_{3-12}$ cycloalkyl, C$_{6-10}$ aryl, 5- to 10-membered heteroaryl, (4- to 12-membered heterocyclyl)-C$_{1-3}$ alkyl, (C$_{3-12}$ cycloalkyl)-C$_{1-3}$ alkyl, (C$_{6-10}$ aryl)-C$_{1-3}$ alkyl, or (5- to 10-membered heteroaryl)-C$_{1-3}$ alkyl group;

R$^{15}$ to R$^{31}$, R$^{33}$, R$^{35}$, R$^{37}$, R$^{39}$, R$^{40}$, R$^{42}$, and R$^{44}$ each independently represent a hydrogen atom or a C$_{1-8}$ alkyl, 4- to 12-membered heterocyclyl, C$_{3-12}$ cycloalkyl, C$_{6-10}$ aryl, 5- to 10-membered heteroaryl, (4- to 12-membered heterocyclyl)-C$_{1-3}$ alkyl, (C$_{3-12}$ cycloalkyl)-C$_{1-3}$ alkyl, (C$_{6-10}$ aryl)-C$_{1-3}$ alkyl, or (5- to 10-membered heteroaryl)-C$_{1-3}$ alkyl group;

A$^1$, A$^2$, A$^3$, and R$^{14}$ to R$^{44}$ in A$^1$, A$^2$, and A$^3$ are each optionally substituted with one to four substituents selected from the group consisting of —OH, =O, —COOH, —SO$_3$H, —PO$_3$H, —CN, —NO$_2$, a halogen atom, a C$_{1-8}$ alkyl group substituted with zero to two —OH groups, zero to two —OR$^{45}$ groups, and zero to six fluorine atoms, a C$_{3-12}$ cycloalkyl group substituted with zero to two —OH groups, zero to two —OR$^{46}$ groups, and zero to six fluorine atoms, a $C_{1-8}$ alkoxy group substituted with zero to two —OH groups, zero to two —OR$^{47}$ groups, and zero to six fluorine atoms, and a 4- to 12-membered heterocyclyl group substituted with zero to two —OH groups, zero to two —OR$^{49}$ groups, and zero to six fluorine atoms;

$R^{14}$ to $R^{44}$ are optionally bonded in $A^1$, $A^2$, or $A^3$ or between $A^1$ and $A^2$, between $A^1$ and $A^3$, or between $A^2$ and $A^3$ via a single bond, —O—, —NR$^{50}$—, or —S(=O)$_p$— to form a ring;

$R^{11}$ or $R^{13}$ is optionally bonded to $A^1$, $A^2$, or $A^3$ via a single bond, —O—, —NR$^{51}$—, or —S(=O)$_p$— to form a ring;

$R^{45}$ to $R^{51}$ each represent a hydrogen atom or a $C_{1-4}$ alkyl group substituted with zero or one —OH group and zero to six fluorine atoms;

p represents an integer of 0 to 2; and each of the heteroatom-containing groups represented by $A^1$, $A^2$, and $A^3$ contains one to four heteroatoms selected from oxygen, sulfur, and nitrogen atoms].

Aspect (2): The compound or pharmaceutically acceptable salt thereof according to Aspect (1), wherein L represents —NH—.

Aspect (3): The compound or pharmaceutically acceptable salt thereof according to Aspect (1) or (2), wherein R1 represents a C1-8 alkyl, C3-12 cycloalkyl, (C3-12 cycloalkyl)-C1-6 alkyl, 4- to 12-membered heterocyclyl, or (4- to 12-membered heterocyclyl)-C1-6 alkyl group.

Aspect (4): The compound or pharmaceutically acceptable salt thereof according to any one of Aspects (1) to (3), wherein R2 is a C1-8 alkyl group substituted with one to four fluorine atoms.

Aspect (5): The compound or pharmaceutically acceptable salt thereof according to any one of Aspects (1) to (3), wherein R2 is a C1-8 alkyl group substituted with zero or one —OH group and zero to two C1-8 alkoxy groups substituted with zero or one —OH group, zero or one C1-4 alkoxy group, and zero to three fluorine atoms.

Aspect (6): The compound or pharmaceutically acceptable salt thereof according to any one of Aspects (1) to (3), wherein R2 is a 4- to 6-membered heterocyclyl group optionally substituted with one to four substituents selected from the group consisting of a fluorine atom, —OH, and C1-4 alkyl and C1-4 alkoxy groups.

Aspect (7): The compound or pharmaceutically acceptable salt thereof according to any one of Aspects (1) to (3), wherein R2 is —COOR8, —CONR9R10, or a C1-8 acyl group, optionally each group being substituted with one to four substituents selected from the group consisting of a fluorine atom, —OH, and a C1-8 alkoxy group.

Aspect (8): The compound or pharmaceutically acceptable salt thereof according to any one of Aspects (1) to (7), wherein X represents CR11, Y represents CR12, and Z represents CR13.

Aspect (9): The compound or pharmaceutically acceptable salt thereof according to any one of Aspects (1) to (7), wherein X represents a nitrogen atom, Y represents CR12, and Z represents CR13.

Aspect (10): The compound or pharmaceutically acceptable salt thereof according to any one of Aspects (1) to (7), wherein X represents CR11, Y represents a nitrogen atom, and Z represents CR13.

Aspect (11): The compound or pharmaceutically acceptable salt thereof according to any one of Aspects (1) to (7), wherein X represents CR11, Y represents CR12, and Z represents a nitrogen atom.

Aspect (12): The compound or pharmaceutically acceptable salt thereof according to any one of Aspects (1) to (11), wherein A1 is a single bond.

Aspect (13): The compound or pharmaceutically acceptable salt thereof according to any one of Aspects (1) to (11), wherein A1 represents a C1-8 alkylene group, and no sp3 carbon atom in A1 is replaced with another structure.

Aspect (14): The compound or pharmaceutically acceptable salt thereof according to any one of Aspects (1) to (11), wherein A1 represents a C1-8 alkylene group, and one sp3 carbon atom at any position of A1 is replaced with —O—.

Aspect (15): The compound or pharmaceutically acceptable salt thereof according to any one of Aspects (1) to (11), wherein A1 represents a C1-8 alkylene group, and one sp3 carbon atom at any position of A1 is replaced with —NR14-.

Aspect (16): The compound or pharmaceutically acceptable salt thereof according to any one of Aspects (1) to (11), wherein A1 represents a C1-8 alkylene group, one sp3 carbon atom at any position of A1 is replaced with —NR14-, and one sp3 carbon atom at any other position of A1 is optionally replaced with —O—.

Aspect (17): The compound or pharmaceutically acceptable salt thereof according to any one of Aspects (1) to (16), wherein A2 represents a 4- to 12-membered heterocyclylene group; and A2 is optionally substituted with one to four substituents selected from the group consisting of —OH, —COOH, —SO3H, —PO3H, —CN, —NO2, a halogen atom, a C1-8 alkyl group optionally substituted with zero to two —OH groups, zero to two —OR45 groups, and zero to six fluorine atoms, a C3-12 cycloalkyl group optionally substituted with zero to two —OH groups, zero to two —OR46 groups, and zero to six fluorine atoms, a C1-8 alkoxy group optionally substituted with zero to two —OH groups, zero to two —OR47 groups, and zero to six fluorine atoms, and a 4- to 12-membered heterocyclyl group substituted with zero to two —OH groups, zero to two —OR49 groups, and zero to six fluorine atoms.

Aspect (18): The compound or pharmaceutically acceptable salt thereof according to any one of Aspects (1) to (16), wherein A2 represents a 4- to 12-membered heterocyclylene group substituted with =O; and A2 is optionally substituted with one to four substituents selected from the group consisting of —OH, =O, —COOH, —SO3H, —PO3H, —CN, —NO2, a halogen atom, a C1-8 alkyl group substituted with zero to two —OH groups, zero to two —OR45 groups, and zero to six fluorine atoms, a C3-12 cycloalkyl group substituted with zero to two —OH groups, zero to two —OR46 groups, and zero to six fluorine atoms, a C1-8 alkoxy group substituted with zero to two —OH groups, zero to two —OR47 groups, and zero to six fluorine atoms, and a 4- to 12-membered heterocyclyl group substituted with zero to two —OH groups, zero to two —OR49 groups, and zero to six fluorine atoms.

Aspect (19): The compound or pharmaceutically acceptable salt thereof according to any one of Aspects (1) to (18), wherein X represents CR11, Y represents CR12, Z represents CR13, and R11 or R13 is bonded to A1, A2, or A3 via a single bond, —O—, —NR51—, or —S(=O)p- to form a ring.

Aspect (20): The compound or pharmaceutically acceptable salt thereof according to any one of Aspects (1) to (19), wherein A3 is a hydrogen atom.

Aspect (21): The compound or pharmaceutically acceptable salt thereof according to any one of Aspects (1) to (19), wherein A3 is a halogen atom, —CN, —R25, —OR26, —NR27R28, —C(=O)R29, or —C(=O)—OR30, and R25 to R30 each independently represent a hydrogen atom, an optionally substituted C1-8 alkyl group, an optionally substituted 4- to 12-membered heterocyclyl group, an optionally substituted C3-12 cycloalkyl group, an optionally substituted (4- to 12-membered heterocyclyl)-C1-3 alkyl group, or an optionally substituted (C3-12 cycloalkyl)-C1-3 alkyl group.

Aspect (22): The compound or pharmaceutically acceptable salt thereof according to any one of Aspects (1) to (21), wherein R3 is a hydrogen atom.

Aspect (23): The compound or pharmaceutically acceptable salt thereof according to any one of Aspects (1) to (21), wherein R3 represents a C1-4 alkyl group, a fluorine atom, or a chlorine atom.

Aspect (24):

The compound, or pharmaceutically acceptable salt thereof, selected from;

6-(difluoromethyl)-N8-isopropyl-N2-(5-piperazin-1-yl-2-pyridyl)pyrido[3,4-d]pyrimidine-2,8-diamine (1R)-1-[8-(isopropylamino)-2-[(5-piperazin-1-yl-2-pyridyl)amino]pyrido[3,4-d]pyrimidin-6-yl]ethanol 1-[2-[(5-piperazin-1-yl-2-pyridyl)amino]-8-(tetrahydrofuran-3-ylamino)pyrido[3,4-d]pyrimidin-6-yl]ethanol 1-[2-[(5-piperazin-1-yl-2-pyridyl)amino]-8-(tetrahydropyran-3-ylamino)pyrido[3,4-d]pyrimidin-6-yl]ethanol N8-isopropyl-6-[(1R)-1-methoxyethyl]-N2-(6-piperazin-1-ylpyridazin-3-yl)pyrido[3,4-d]pyrimidine-2,8-diamine N8-isopropyl-6-[(1R)-1-methoxyethyl]-N2-[5-(piperazin-1-ylmethyl)-2-pyridyl]pyrido[3,4-d]pyrimidine-2,8-diamine 1-[6-[[6-[(1R)-1-hydroxyethyl]-8-(isopropylamino)pyrido[3,4-d]pyrimidin-2-yl]amino]-3-pyridyl]piperazin-2-one 1-[6-[[5-chloro-6-[(1R)-1-hydroxyethyl]-8-(isopropylamino)pyrido[3,4-d]pyrimidin-2-yl]amino]-3-pyridyl]piperazin-2-one (1R)-1-[2-[(6-piperazin-1-ylpyridazin-3-yl)amino]-8-(tetrahydropyran-4-ylamino)pyrido[3,4-d]pyrimidin-6-yl]ethanol (1R)-1-[2-[(6-piperazin-1-ylpyridazin-3-yl)amino]-8-[[(3S)-tetrahydropyran-3-yl]amino]pyrido[3,4-d]pyrimidin-6-yl]ethanol (1R)-1-[2-[(6-piperazin-1-ylpyridazin-3-yl)amino]-8-[[(3R)-tetrahydropyran-3-yl]amino]pyrido[3,4-d]pyrimidin-6-yl]ethanol (1R)-1-[2-[[5-(piperazin-1-ylmethyl)-2-pyridyl]amino]-8-(tetrahydropyran-4-ylamino)pyrido[3,4-d]pyrimidin-6-yl]ethanol (1R)-1-[2-[[5-(piperazin-1-ylmethyl)-2-pyridyl]amino]-8-[[(3S)-tetrahydropyran-3-yl]amino]pyrido[3,4-d]pyrimidin-6-yl]ethanol (1R)-1-[2-[[5-(piperazin-1-ylmethyl)-2-pyridyl]amino]-8-[[(3R)-tetrahydropyran-3-yl]amino]pyrido[3,4-d]pyrimidin-6-yl]ethanol 1-[6-[[6-[(1R)-1-hydroxyethyl]-8-(isopropylamino)pyrido[3,4-d]pyrimidin-2-yl]amino]pyridazin-3-yl]piperidin-4-ol (1R)-1-[8-(isopropylamino)-2-[(6-piperazin-1-ylpyridazin-3-yl)amino]pyrido[3,4-d]pyrimidin-6-yl]ethanol 1-[[6-[[6-[(1R)-1-hydroxyethyl]-8-(isopropylamino)pyrido[3,4-d]pyrimidin-2-yl]amino]-3-pyridyl]methyl]piperazin-2-one 6-[(1R)-1-methoxyethyl]-N2-[5-(piperazin-1-ylmethyl)-2-pyridyl]-N8-[(3S)-tetrahydropyran-3-yl]pyrido[3,4-d]pyrimidine-2,8-diamine 6-[(1R)-1-methoxyethyl]-N2-(6-piperazin-1-ylpyridazin-3-yl)-N8-[(3S)-tetrahydropyran-3-yl]pyrido[3,4-d]pyrimidine-2,8-diamine 6-[(1R)-1-methoxyethyl]-N2-[5-(piperazin-1-ylmethyl)-2-pyridyl]-N8-(tetrahydropyran-4-ylmethyl)pyrido[3,4-d]pyrimidine-2,8-diamine N8-isopropyl-6-[(1R)-1-methoxyethyl]-N2-(5-piperazin-1-ylpyrazin-2-yl)pyrido[3,4-d]pyrimidine-2,8-diamine N8-isopropyl-6-[(1R)-1-methoxyethyl]-N2-[6-[(2S)-2-methylpiperazin-1-yl]pyridazin-3-yl]pyrido[3,4-d]pyrimidine-2,8-diamine N8-isopropyl-6-[(1R)-1-methoxyethyl]-N2-[6-[(2R)-2-methylpiperazin-1-yl]pyridazin-3-yl]pyrido[3,4-d]pyrimidine-2,8-diamine (1R)-1-[2-[[6-(4,7-diazaspiro[2.5]octan-7-yl)pyridazin-3-yl]amino]-8-(isopropylamino)pyrido[3,4-d]pyrimidin-6-yl]ethanol (1R)-1-[2-[[5-(4,7-diazaspiro[2.5]octan-7-ylmethyl)-2-pyridyl]amino]-8-(isopropylamino)pyrido[3,4-d]pyrimidin-6-yl]ethanol 2-[1-[[6-[[6-[(1R)-1-hydroxyethyl]-8-(isopropylamino)pyrido[3,4-d]pyrimidin-2-yl]amino]-3-pyridyl]methyl]-4-piperidyl]propan-2-ol (1R)-1-[2-[[5-[[4-(2-hydroxyethyl)piperazin-1-yl]methyl]-2-pyridyl]amino]-8-(isopropylamino)pyrido[3,4-d]pyrimidin-6-yl]ethanol (1R)-1-[2-[[5-[2-(dimethylamino)ethoxy]-2-pyridyl]amino]-8-[[(3S)-tetrahydropyran-3-yl]amino]pyrido[3,4-d]pyrimidin-6-yl]ethanol (1R)-1-[2-[[6-(4-methylpiperazin-1-yl)pyridazin-3-yl]amino]-8-[[(3S)-tetrahydropyran-3-yl]amino]pyrido[3,4-d]pyrimidin-6-yl]ethanol 2-hydroxy-1-[4-[6-[[6-[(1R)-1-hydroxyethyl]-8-(isopropylamino)pyrido[3,4-d]pyrimidin-2-yl]amino]pyridazin-3-yl]piperazin-1-yl]ethanone 1-[6-[[8-(isopropylamino)-6-[(2S)-tetrahydrofuran-2-yl]pyrido[3,4-d]pyrimidin-2-yl]amino]-3-pyridyl]piperazin-2-one (1R)-1-[8-(isopropylamino)-2-(5,6,7,8-tetrahydro-1,6-naphthyridin-2-ylamino)pyrido[3,4-d]pyrimidin-6-yl]ethanol 2-[4-[[6-[[6-[(1R)-1-hydroxyethyl]-8-(isopropylamino)pyrido[3,4-d]pyrimidin-2-yl]amino]-3-pyridyl]methyl]piperazin-1-yl]-2-methyl-propan-1-ol 4-[6-[[6-[(1R)-1-hydroxyethyl]-8-(isopropylamino)pyrido[3,4-d]pyrimidin-2-yl]amino]-3-pyridyl]-1-[(2S)-2-hydroxypropyl]-1,4-diazepan-5-one 4-[6-[[6-[(1R)-1-hydroxyethyl]-8-(isopropylamino)pyrido[3,4-d]pyrimidin-2-yl]amino]-3-pyridyl]-1-[(2R)-2-hydroxypropyl]-1,4-diazepan-5-one N8-isopropyl-N2-[5-(piperazin-1-ylmethyl)-2-pyridyl]-6-[(2S)-tetrahydrofuran-2-yl]pyrido[3,4-d]pyrimidine-2,8-diamine 1-[6-[[6-[(1R)-1-hydroxyethyl]-8-(isopropylamino)pyrido[3,4-d]pyrimidin-2-yl]amino]-2-methyl-3-pyridyl]piperazin-2-one 1-[6-[[8-(isopropylamino)-6-[(3S)-tetrahydrofuran-3-yl]pyrido[3,4-d]pyrimidin-2-yl]amino]-3-pyridyl]piperazin-2-one (1R)-1-[2-(5,6,7,8-tetrahydro-1,6-naphthyridin-2-ylamino)-8-[[(3S)-tetrahydropyran-3-yl]amino]pyrido[3,4-d]pyrimidin-6-yl]ethanol 1-[6-[[8-(isopropylamino)-6-(3-methyloxetan-3-yl)pyrido[3,4-d]pyrimidin-2-yl]amino]-3-pyridyl]piperazin-2-one (1R)-1-[2-[[5-[4-(dimethylamino)cyclohexoxy]-2-pyridyl]amino]-8-[[(3S)-tetrahydropyran-3-yl]amino]pyrido[3,4-d]pyrimidin-6-yl]ethanol 6-[(1R)-1-methoxyethyl]-N2-[5-(piperazin-1-ylmethyl)-2-pyridyl]-N8-propyl-pyrido[3,4-d]pyrimidine-2,8-diamine 6-[(1R)-1-methoxyethyl]-N2-(6-piperazin-1-ylpyridazin-3-yl)-N8-propyl-pyrido[3,4-d]pyrimidine-2,8-diamine 1-[[6-[[6-(difluoromethyl)-8-[(4-methylcyclohexyl)amino]
pyrido[6-[[6-hexy)amino]pyrido[3,4-d]pyrimidin-2-yl]
amino]-3-pyridyl]methyl]piperidine-4-carboxylic acid (1R)-1-[8-(ethylamino)-2-[[5-[[4-(2-hydroxyethyl)piper-
azin-1-yl]methyl]-2-pyridyl]amino]pyrido[3,4-d]pyrimi-
din-6-yl]ethanol (1R)-1-[2-[[5-[[4-(2-hydroxyethyl)piperazin-1-yl]methyl]-
2-pyridyl]amino]-8-(propylamino)pyrido[3,4-d]pyrimi-
din-6-yl]ethanol N8-isopropyl-6-(3-methyloxetan-3-yl)-N2-(6-piperazin-1-
ylpyridazin-3-yl)pyrido[3,4-d]pyrimidine-2,8-diamine N8-isopropyl-6-(3-methyloxetan-3-yl)-N2-[5-(piperazin-1-
ylmethyl)-2-pyridyl]pyrido[3,4-d]pyrimidine-2,8-di-
amine 6-(3-methyloxetan-3-yl)-N2-[5-(piperazin-1-ylmethyl)-2-
pyridyl]-N8-[(3S)-tetrahydropyran-3-yl]pyrido[3,4-d]py-
rimidine-2,8-diamine 4-[6-[[6-[(1R)-1-hydroxyethyl]-8-[isopropyl(methyl)
amino]pyrido[3,4-d]pyrimidin-2-yl]amino]-3-pyridyl]-1,
4-diazepan-5-one (1R)-1-[8-(isopropylamino)-2-[(6-methyl-5-piperazin-1-yl-
2-pyridyl)amino]pyrido[3,4-d]pyrimidin-6-yl]ethanol (1R)-1-[2-[[6-(2-hydroxyethyl)-7,8-dihydro-5H-1,6-naph-
thyridin-2-yl]amino]-8-(isopropylamino)pyrido[3,4-d]
pyrimidin-6-yl]ethanol (1R)-1-[8-(isopropylamino)-2-[[6-[2-(methylamino)ethyl]-
7,8-dihydro-5H-1,6-naphthyridin-2-yl]amino]pyrido[3,4-
d]pyrimidin-6-yl]ethanol N2-(6-piperazin-1-ylpyridazin-3-yl)-6-[(3S)-tetrahydro-
furan-3-yl]-N8-[(3S)-tetrahydropyran-3-yl]pyrido[3,4-d]
pyrimidine-2,8-diamine N2-[5-(piperazin-1-ylmethyl)-2-pyridyl]-6-[(3R)-tetrahy-
drofuran-3-yl]-N8-[(3S)-tetrahydropyran-3-yl]pyrido[3,
4-d]pyrimidine-2,8-diamine (1R)-1-[2-[[6-[2-(dimethylamino)ethyl]-7,8-dihydro-5H-1,
6-naphthyridin-2-yl]amino]-8-(isopropylamino)pyrido[3,
4-d]pyrimidin-6-yl]ethanol (2S)-1-[4-[[6-[[8-(ethylamino)-6-[(1R)-1-hydroxyethyl]
pyrido[3,4-d]pyrimidin-2-yl]amino]-3-pyridyl]methyl]
piperazin-1-yl]propan-2-ol (2R)-1-[4-[[6-[[8-(ethylamino)-6-[(1R)-1-hydroxyethyl]
pyrido[3,4-d]pyrimidin-2-yl]amino]-3-pyridyl]methyl]
piperazin-1-yl]propan-2-ol (1R)-1-[8-(isopropylamino)-2-[[5-[(2R)-2-methylpiperazin-
1-yl]-2-pyridyl]amino]pyrido[3,4-d]pyrimidin-6-yl]etha-
nol (1R)-1-[8-(isopropylamino)-2-[[5-[(2S)-2-methylpiperazin-
1-yl]-2-pyridyl]amino]pyrido[3,4-d]pyrimidin-6-yl]etha-
nol N8-isopropyl-N2-(5-piperazin-1-yl-2-pyridyl)-6-[(2S)-tet-
rahydrofuran-2-yl]pyrido[3,4-d]pyrimidine-2,8-diamine (1R)-1-[8-(cyclobutylamino)-2-[[5-[[4-(2-hydroxyethyl)
piperazin-1-yl]methyl]-2-pyridyl]amino]pyrido[3,4-d]
pyrimidin-6-yl]ethanol (1R)-1-[8-(cyclopropylmethylamino)-2-[[5-[[4-(2-hydroxy-
ethyl)piperazin-1-yl]methyl]-2-pyridyl]amino]pyrido[3,
4-d]pyrimidin-6-yl]ethanol 6-(3-methyloxetan-3-yl)-N2-(5-piperazin-1-yl-2-pyridyl)-
N8-propyl-pyrido[3,4-d]pyrimidine-2,8-diamine 6-(3-methyloxetan-3-yl)-N2-[5-(piperazin-1-ylmethyl)-2-
pyridyl]-N8-propyl-pyrido[3,4-d]pyrimidine-2,8-diamine N2-(5-piperazin-1-yl-2-pyridyl)-N8-propyl-6-tetrahydro-
furan-3-yl-pyrido[3,4-d]pyrimidine-2,8-diamine N2-[5-(piperazin-1-ylmethyl)-2-pyridyl]-N8-propyl-6-tetra-
hydrofuran-3-yl-pyrido[3,4-d]pyrimidine-2,8-diamine N8-isopropyl-6-(3-methyloxetan-3-yl)-N2-(5-piperazin-1-
yl-2-pyridyl)pyrido[3,4-d]pyrimidine-2,8-diamine N8-isopropyl-N2-(5-piperazin-1-yl-2-pyridyl)-6-tetrahy-
drofuran-3-yl-pyrido[3,4-d]pyrimidine-2,8-diamine 2-[4-[[6-[[8-(isopropylamino)-6-tetrahydrofuran-3-yl-
pyrido[3,4-d]pyrimidin-2-yl]amino]-3-pyridyl]methyl]
piperazin-1-yl]ethanol 2-[4-[[6-[[6-tetrahydrofuran-3-yl-8-[[(3S)-tetrahydropyran-
3-yl]amino]pyrido[3,4-d]pyrimidin-2-yl]amino]-3-
pyridyl]methyl]piperazin-1-yl]ethanol (1R)-1-[2-[[5-[[4-(hydroxymethyl)-1-piperidyl]methyl]-2-
pyridyl]amino]-8-(isopropylamino)pyrido[3,4-d]pyrimi-
din-6-yl]ethanol 1-[[6-[[6-[(1R)-1-hydroxyethyl]-8-(isopropylamino)pyrido
[3,4-d]pyrimidin-2-yl]amino]-3-pyridyl]methyl]piperi-
din-4-ol 1-[[6-[[8-(tert-butylamino)-6-[(1R)-1-hydroxyethyl]pyrido
[3,4-d]pyrimidin-2-yl]amino]-3-pyridyl]methyl]piperi-
din-4-ol (1R)-1-[8-(tert-butylamino)-2-[[5-[[4-(hydroxymethyl)-1-
piperidyl]methyl]-2-pyridyl]amino]pyrido[3,4-d]pyrimi-
din-6-yl]ethanol 1-[[6-[[6-[(1R)-1-hydroxyethyl]-8-(isobutylamino)pyrido
[3,4-d]pyrimidin-2-yl]amino]-3-pyridyl]methyl]piperi-
din-4-ol (1R)-1-[2-[[5-[[4-(hydroxymethyl)-1-piperidyl]methyl]-2-
pyridyl]amino]-8-(isobutylamino)pyrido[3,4-d]pyrimi-
din-6-yl]ethanol 1-[6-[[6-[(1R)-1-hydroxypropyl]-8-(isopropylamino)pyrido
[3,4-d]pyrimidin-2-yl]amino]-3-pyridyl]piperazin-2-one (1R)-1-[2-[[5-[[4-(2-hydroxyethyl)piperazin-1-yl]methyl]-
6-methyl-2-pyridyl]amino]-8-(propylamino)pyrido[3,4-
d]pyrimidin-6-yl]ethanol Aspect (25): A pharmaceutical composition comprising the compound or pharmaceutically acceptable salt thereof according to any one of Aspects (1) to (24) and a pharmaceutically acceptable carrier.

Aspect (26): A pharmaceutical composition exhibiting a CDK4/6 inhibitory activity, comprising the compound or pharmaceutically acceptable salt thereof according to any one of Aspects (1) to (24) as an active ingredient.

Aspect (27): A drug for prevention or treatment of rheumatoid arthritis, arteriosclerosis, pulmonary fibrosis, cerebral infarction, or cancer, the drug comprising the compound or pharmaceutically acceptable salt thereof according to any one of Aspects (1) to (24) as an active ingredient.

Advantageous Effects of Invention

The compound of the present invention exhibits a superior CDK4/6 inhibitory activity and is useful as a drug for prevention or treatment of rheumatoid arthritis, arteriosclerosis, pulmonary fibrosis, cerebral infarction, or cancer.

BRIEF DESCRIPTION OF DRAWINGS

FIG. 1 is graphs showing the results (scores) obtained through administration of the compound of the present invention to mice.

DESCRIPTION OF EMBODIMENTS

Now will be described the structures (groups) of the compound of the present invention represented by Formula (I). The description of "groups" with parentheses is as follows: For example, the term "(cycloalkyl)-alkyl" refers to a cycloalkyl group bonded to an alkyl group such that the alkyl group is bonded to a structure other than the cycloalkyl group. Similarly, the term "(heterocyclyl)-alkyl" refers to a heterocyclyl group bonded to an alkyl group such that the alkyl group is bonded to a structure other than the heterocyclyl group.

It must be noted that, as used herein and the annexed claims, the singular form "a", "an" or "the" may include plural referents unless the context clearly dictates otherwise.

As used herein, "$C_{3-6}$ cycloalkyl group substituted with zero to two —OH groups, zero to two $C_{1-8}$ alkoxy groups, and zero to six fluorine atoms" refers to the case where the $C_{3-6}$ cycloalkyl group is substituted with the following substituents: zero to two —OH groups, zero to two $C_{1-8}$ alkoxy groups, and zero to six fluorine atoms. Examples of the substituted $C_{3-6}$ cycloalkyl group include a $C_{3-6}$ cycloalkyl group substituted with two —OH groups, one $C_{1-8}$ alkoxy group, and three fluorine atoms; a $C_{3-6}$ cycloalkyl group substituted with two $C_{1-8}$ alkoxy groups and four fluorine atoms; and a $C_{3-6}$ cycloalkyl group substituted with one —OH group, and the like. The $C_{3-6}$ cycloalkyl group is not substituted in the case where the number of all the substituents is zero.

As used herein, "$C_{1-8}$" refers to a group having one to eight carbon atoms, and "$C_{1-6}$" refers to a group having one to six carbon atoms. Similarly, "5- to 10-membered" refers to a structure having 5 to 10 carbon atoms, and "5- or 6-membered" refers to a structure having five or six carbon atoms.

Non-limiting examples of the groups described in this specification are as follows:

The term "alkyl" as used herein refers to a monovalent group obtained by removal of one hydrogen atom from an alkane at any carbon atom.

The term "alkylene" as used herein refers to a divalent group obtained by removal of two hydrogen atoms from an alkane at any two different carbon atoms.

The term "alkane" as used herein refers to a saturated aliphatic hydrocarbon.

The term "$C_{1-8}$ alkyl" as used herein refers to a linear or branched hydrocarbon group having one to eight carbon atoms. Examples of the $C_{1-8}$ alkyl include methyl, ethyl, n-propyl, isopropyl, n-butyl, isobutyl, sec-butyl, tert-butyl, n-pentyl, neopentyl, isopentyl, 1,2-dimethylpropyl, n-hexyl, isohexyl, 1,1-dimethylbutyl, 2,2-dimethylbutyl, 1-ethylbutyl, 2-ethylbutyl, isoheptyl, n-octyl, isooctyl, and the like.

The alkane of "$C_{1-8}$ alkylene" as used herein refers to a linear or branched hydrocarbon having one to eight carbon atoms. Examples of the alkane include methane, ethane, propane, n-butane, 2-methylpropane, n-pentane, 2,2-dimethylpropane, n-hexane, 2-methylpentane, 3-methylpentane, 2,2-dimethylbutane, 2,3-dimethylbutane, n-heptane, 2,2-dimethylhexane, 2,3-dimethylhexane, n-octane, 2-methylheptane, and the like.

The term "cycloalkyl" as used herein refers to a monovalent group obtained by removal of one hydrogen atom from a cycloalkane at any carbon atom.

The term "cycloalkylene" as used herein refers to a divalent group obtained by removal of two hydrogen atoms from a cycloalkane at any two different carbon atoms.

The term "cycloalkylidene" refers to a divalent group obtained by removal of two hydrogen atoms from a cycloalkane at any one carbon atom.

The term "cycloalkane" as used herein refers to an alicyclic hydrocarbon.

The cycloalkane of "$C_{3-12}$ cycloalkyl," "$C_{3-12}$ cycloalkylene," or "$C_{3-12}$ cycloalkylidene" as used herein refers to a monocyclic or polycyclic 3- to 12-membered aliphatic hydrocarbon ring. Specific examples of the cycloalkane include cyclopropane, cyclobutane, cyclopentane, cyclohexane, cycloheptane, cyclooctane, spiro[3.3]heptane, bicyclo[1.1.1]pentane, bicyclo[2.2.2]octane, adamantane, and the like.

The term "heterocyclyl" as used herein refers to a monovalent group obtained by removal of one hydrogen atom from a heterocycle at any carbon or nitrogen atom.

The term "heterocyclylene" as used herein refers to a divalent group obtained by removal of two hydrogen atoms from a heterocycle at any two different carbon or nitrogen atoms.

The term "heterocyclylidene" as used herein refers to a divalent group obtained by removal of two hydrogen atoms from a heterocycle at any one carbon atom.

The term "heterocycle" as used herein refers to a ring containing a heteroatom selected from sulfur, nitrogen, and oxygen atoms.

The heterocycle of "4- to 12-membered heterocyclyl," "4- to 12-membered heterocyclylene," or "4- to 12-membered heterocyclylidene" as used herein refers to "4- to 12-membered heterocycloalkane," "4- to 12-membered heterocycloalkane" having an unsaturated bond, a 4- to 12-membered ring composed of a heterocycloalkane and a heteroarene or arene bonded to a portion of the heterocycloalkane, a 4- to 12-membered ring composed of a cycloalkane and a heteroarene bonded to a portion of the cycloalkane, a 4- to 12-membered ring containing a heteroatom and having a spiro structure, or a 4- to 12-membered ring containing a heteroatom and having a cross-linked structure. The term "4- to 12-membered heterocycloalkane" refers to a 4- to 12-membered cyclic heteroalkane; i.e., a monocyclic or polycyclic aliphatic hydrocarbon ring containing one to four heteroatoms selected from sulfur, nitrogen, and oxygen atoms. Specific examples of the "4- to 12-membered heterocycloalkane" include aziridine, thiirane, azetidine, oxetane, thietane, tetrahydrofuran, tetrahydropyran, 1,4-dioxane, piperidine, piperazine, pyrrolidine, imidazolidine, pyrazolidine, morpholine, thiomorpholine, tetrahydrothiopyran, tetrahydrothiophene, 1,4-diazepane, oxepane, and the like. A compound having a "spiro structure" is composed of two cyclic structures (cycloalkanes or heterocycloalkanes) that are bonded to one common carbon atom. Examples of the compound include 2-azaspiro[3.3]heptane, 1,6-diazaspiro[3.3]heptane, 2,6-diazaspiro[3.3]heptane, 2,6-diazaspiro[3.4]octane, 2,7-diazaspiro[3.5]nonane, 1,7-diazaspiro[4.5]decane, 2,8-diazaspiro[4.5]decane, 4,7-diazaspiro[2.5]octane, and the like. A compound having a "cross-linked structure" is composed of two cyclic structures (cycloalkanes and heterocycloalkanes) that are bonded to two or more common carbon, nitrogen, or oxygen atoms. Examples of the compound include 2,5-diazabicyclo[2.2.2]octane, 3,8-diazabicyclo[3.2.1]octane, 1,4-diazabicyclo[3.2.2]nonane, octahydropyrrolo[3,4-b]pyrrole, and the like.

The term "aryl" as used herein refers to a monovalent group obtained by removal of one hydrogen atom from an arene at any carbon atom.

The term "arylene" as used herein refers to a divalent group obtained by removal of two hydrogen atoms from an arene at any two different carbon atoms.

The term "arene" as used herein refers to an aromatic hydrocarbon.

The arene of "$C_{6-10}$ aryl" or "$C_{6-10}$ arylene" as used herein refers to an aromatic hydrocarbon ring having six to ten carbon atoms. Specific examples of the arene include benzene, naphthalene, and the like.

The term "heteroaryl" as used herein refers to a monovalent group obtained by removal of one hydrogen atom from a heteroarene at any carbon or nitrogen atom.

The term "heteroarylene" as used herein refers to a divalent group obtained by removal of two hydrogen atoms from a heteroarene at any two different carbon or nitrogen atoms.

The term "heteroarene" as used herein refers to an aromatic heterocyclic ring containing a heteroatom selected from sulfur, nitrogen, and oxygen atoms.

The heteroarene of "5- to 10-membered heteroaryl" or "5- to 10-membered heteroarylene" as used herein refers to a 5- to 10-membered aromatic heterocyclic ring containing one to four heteroatoms selected from sulfur, nitrogen, and oxygen atoms. Specific examples of the heteroarene include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinolone, isoquinolone, benzofuran, benzothiophene, indole, indazole, benzimidazole, and the like.

The term "(4- to 12-membered heterocyclyl)-$C_{1-6}$ alkyl" as used herein refers to a 4- to 12-membered heterocyclyl group bonded to a $C_{1-6}$ alkyl group such that the $C_{1-6}$ alkyl group is bonded to a structure other than the 4- to 12-membered heterocyclyl group. Specific examples of the (4- to 12-membered heterocyclyl)-$C_{1-6}$ alkyl include groups prepared by bonding of any of the above-exemplified 4- to 12-membered heterocyclyl groups to any of the above-exemplified $C_{1-6}$ alkyl groups.

The term "($C_{6-10}$ aryl)-$C_{1-6}$ alkyl" as used herein refers to a $C_{6-10}$ aryl group bonded to a $C_{1-6}$ alkyl group such that the $C_{1-6}$ alkyl group is bonded to a structure other than the $C_{6-10}$ aryl group. Specific examples of the ($C_{6-10}$ aryl)-$C_{1-6}$ alkyl include groups prepared by bonding of any of the above-exemplified $C_{6-10}$ aryl groups to any of the above-exemplified $C_{1-6}$ alkyl groups.

The term "(5- to 10-membered heteroaryl)-$C_{1-6}$ alkyl" as used herein refers to a 5- to 10-membered heteroaryl group bonded to a $C_{1-6}$ alkyl group such that the $C_{1-6}$ alkyl group is bonded to a structure other than the 5- to 10-membered heteroaryl group. Specific examples of the (5- to 10-membered heteroaryl)-$C_{1-6}$ alkyl include groups prepared by bonding of any of the above-exemplified 5- to 10-membered heteroaryl groups to any of the above-exemplified $C_{1-6}$ alkyl groups.

The term "$C_{1-8}$ alkylsulfonyl" as used herein refers to a $C_{1-8}$ alkyl group bonded to a sulfonyl (—S(=O)$_2$—) group such that the sulfonyl group is bonded to a structure other than the $C_{1-8}$ alkyl group.

The term "$C_{1-8}$ acyl" as used herein refers to a $C_{1-7}$ alkyl group bonded to a carbonyl (—CO—) group such that the carbonyl group is bonded to a structure other than the $C_{1-7}$ alkyl group.

The term "halogen" as used herein refers to a fluorine, chlorine, bromine, or iodine atom.

The term "$C_{1-8}$ alkoxy" as used herein refers to a linear, branched, or cyclic alkoxy group having one to eight carbon atoms. Specific examples of the $C_{1-8}$ alkoxy include methoxy, ethoxy, n-propoxy, isopropoxy, n-butoxy, isobutoxy, sec-butoxy, tert-butoxy, n-pentyloxy, neopentyloxy, tert-pentyloxy, 2-methylbutoxy, n-hexyloxy, isohexyloxy, cyclopropyloxy, cyclobutyloxy, cyclopentyloxy, cyclohexyloxy, cycloheptyloxy, cyclooctyloxy, spiro[3.3]heptyloxy, bicyclo[2.2.2]octyloxy, and the like.

The term "alkenyl" as used herein refers to a monovalent group obtained by removal of one hydrogen atom from an alkene at any carbon atom.

The term "alkenylene" as used herein refers to a divalent group obtained by removal of two hydrogen atoms from an alkene at any two different carbon atoms.

The term "alkene" as used herein refers to an unsaturated aliphatic hydrocarbon having one double bond.

The term "$C_{2-8}$ alkenyl" as used herein refers to a chain aliphatic hydrocarbon having one double bond. Examples of the $C_{2-8}$ alkenyl include ethenyl (or vinyl), propenyl (or allyl), butenyl, and the like.

The term "alkynyl" as used herein refers to a monovalent group obtained by one hydrogen atom from an alkyne at any carbon atom.

The term "alkynylene" as used herein refers to a divalent group obtained by removal of two hydrogen atoms from an alkyne at any two different carbon atoms.

The term "alkyne" as used herein refers to an unsaturated aliphatic hydrocarbon having one triple bond.

The term "$C_{2-4}$ alkynyl" as used herein refers to a chain hydrocarbon group having one triple bond. Examples of the $C_{2-4}$ alkynyl include ethynyl, propynyl, butynyl, and the like.

L is preferably —$NR^5$—.

The "$C_{1-6}$ alkyl" of $R^5$ is preferably methyl or ethyl.

$R^5$ is preferably a hydrogen atom or a methyl group.

The "$C_{1-8}$ alkyl" of $R^1$ is preferably methyl, ethyl, n-propyl, isopropyl, n-butyl, isobutyl, sec-butyl, tert-butyl, n-pentyl, neopentyl, isopentyl, 1,2-dimethylpropyl, n-hexyl, isohexyl, 1,1-dimethylbutyl, 2,2-dimethylbutyl, 1-ethylbutyl, 2-ethylbutyl, isoheptyl, n-octyl, or isooctyl.

The "$C_{3-12}$ cycloalkyl" of $R^1$ is preferably cyclopropyl, cyclobutyl, cyclopentyl, cyclohexyl, spiro[3.3]heptyl, bicyclo[1.1.1]pentane, bicyclo[2.2.2]octyl, or adamantyl.

The "($C_{3-12}$ cycloalkyl)-$C_{1-6}$ alkyl" of $R^1$ is preferably cyclopropylmethyl, cyclobutylmethyl, cyclopentylmethyl, cyclohexylmethyl, or cyclopentylethyl.

The heterocycle of "4- to 12-membered heterocyclyl" in $R^1$ is preferably azetidine, oxetane, thietane, tetrahydrofuran, 1,4-dioxane, morpholine, thiomorpholine, tetrahydropyran, tetrahydrothiophene, or oxepane.

The "(4- to 12-membered heterocyclyl)-$C_{1-6}$ alkyl" of $R^1$ is preferably (tetrahydrofuranyl)methyl, (tetrahydropyranyl)methyl, (tetrahydrofuranyl)ethyl, or (tetrahydropyranyl)ethyl.

The "$C_{6-10}$ aryl" of $R^1$ is preferably phenyl.

The "($C_{6-10}$ aryl)-$C_{1-6}$ alkyl" of $R^1$ is preferably phenylmethyl or phenylethyl.

The "5- to 10-membered heteroaryl" of $R^1$ is preferably furanyl, pyrazolyl, or thienyl.

The "halogen" in the substituent of $R^1$ is preferably a fluorine or chlorine atom.

The "—$COOR^6$" in the substituent of $R^1$ is preferably —COOH or —COOCH$_3$.

The "$R^7$" in the substituent of $R^1$ is preferably ethyl, n-propyl, isopropyl, n-butyl, isobutyl, sec-butyl, tert-butyl, n-pentyl, neopentyl, isopentyl, 1,1-dimethyl-2-methoxyethyl, 1-methyl-2-methoxyethyl, 1-methyl-2-hydroxyethyl, 2,2,2-trifluoroethyl, hydroxymethyl, or 1-methyl-2,2,2-trifluoroethyl.

The "$C_{3-6}$ cycloalkyl optionally substituted with a substituent selected from the group consisting of one or two —OH groups, one or two $C_{1-8}$ alkoxy groups, and one to six fluorine atoms" in the substituent of $R^1$ is preferably cyclopentyl, cyclohexyl, 4-methoxycyclohexyl, or 4-isopropoxycyclohexyl.

The 3- to 10-membered heterocyclyl optionally substituted with a substituent selected from the group consisting of one or two —OH groups, one or two $C_{1-8}$ alkoxy groups, and one to six fluorine atoms in the substituent of $R^1$ is preferably tetrahydrofuranyl, tetrahydropyranyl, or 2,2-dimethyltetrahydropyranyl.

R[1] preferably has any of the following structures:
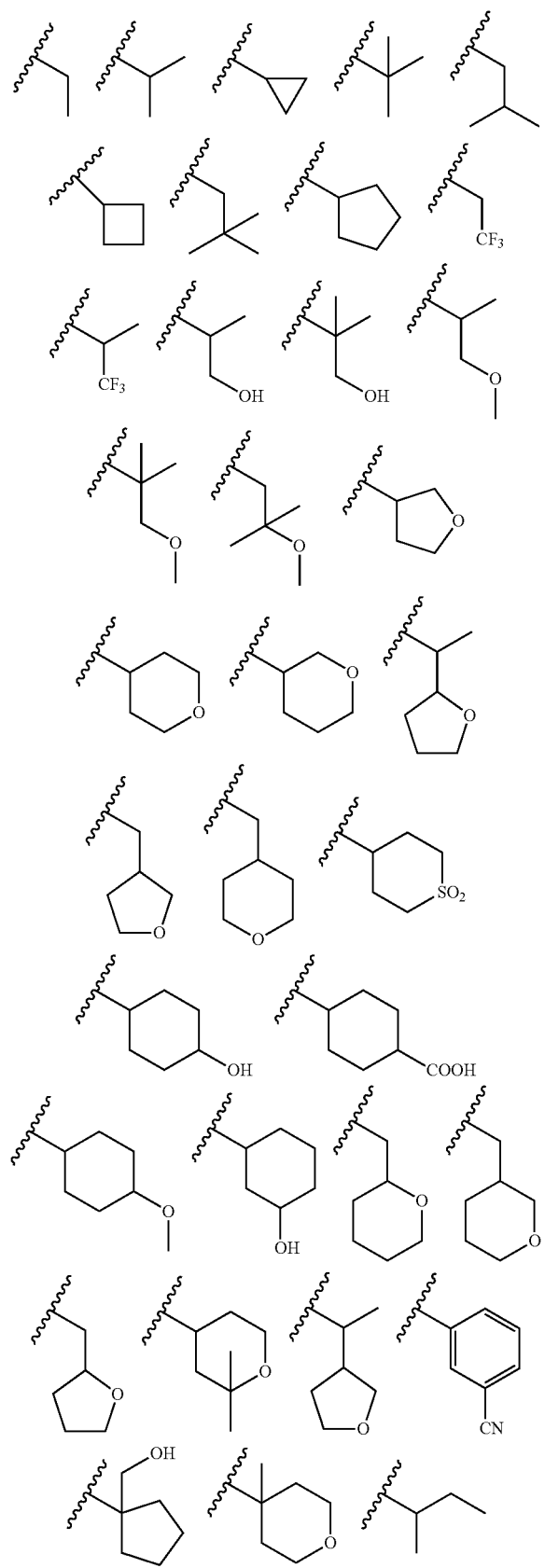
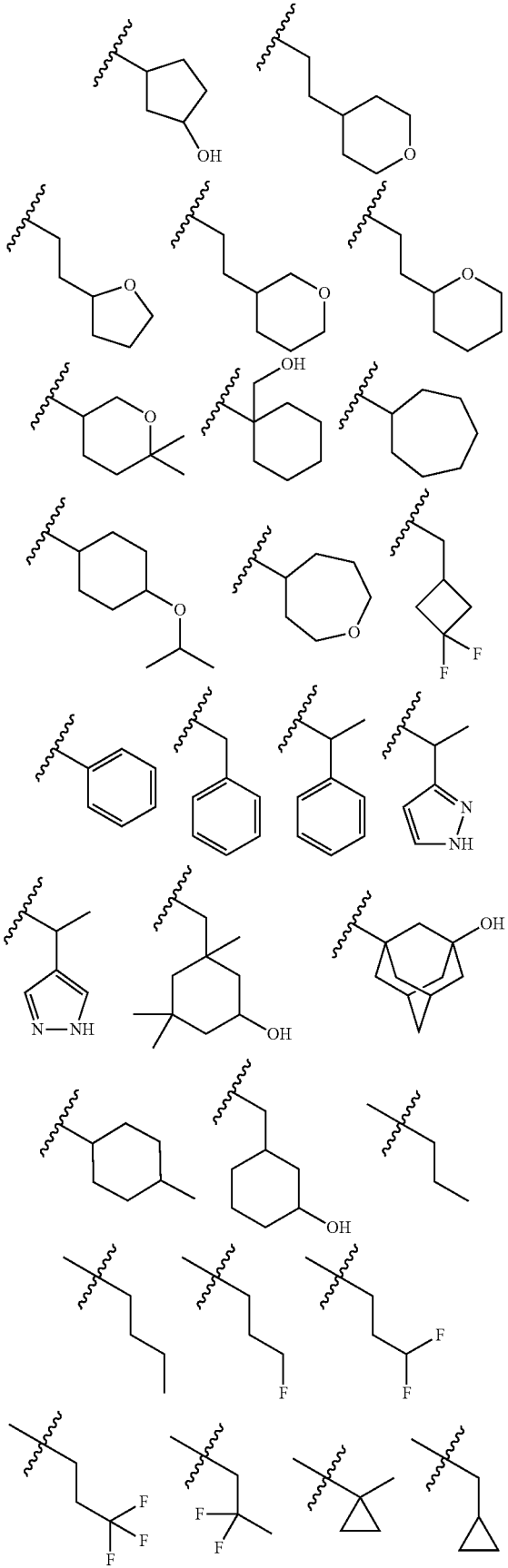

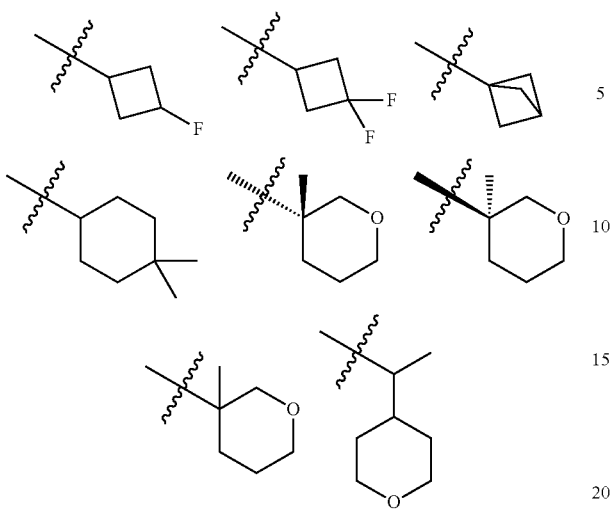
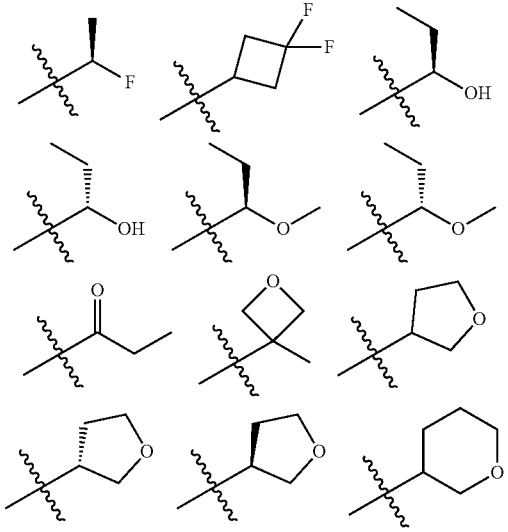

The "C$_{1-8}$ alkyl" of R$^2$ is preferably methyl, ethyl, or n-propyl, and the substituent is preferably a hydroxy, methoxy, or ethoxy group or a fluorine atom. The "4- to 6-membered heterocyclyl" of R$^2$ is preferably oxetane or tetrahydrofuranyl.

The "C$_{1-8}$ acyl" of R$^2$ is preferably acetyl.

The "—COOR$^8$" of R$^2$ is preferably —COOH or —COOCH$_3$.

The "—CONR$^9$R$^{10}$" of R$^2$ is preferably —CON(CH$_3$)$_2$.

R$^9$ and R$^{10}$ of —CONR$^9$R$^{10}$ of R$^2$ may be bonded via a single bond or —O— to form a ring including the nitrogen atom bonded to R$^9$ and R$^{10}$. Examples of such a ring include the following structures:

[Formula 3]

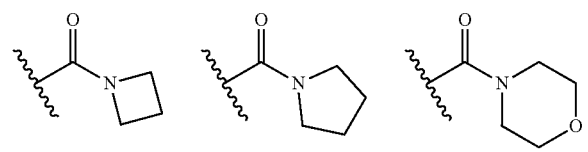

R$^2$ preferably has any of the following structures:

[Formula 4]

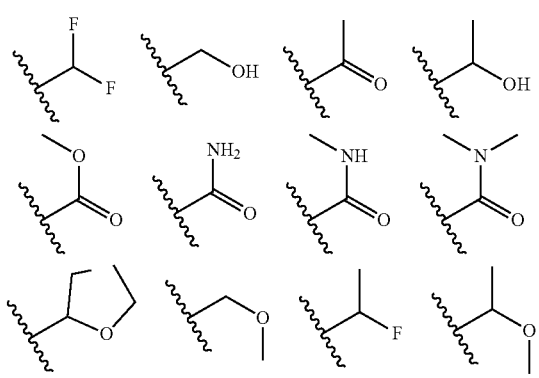

The "C$_{1-8}$ alkyl" of R$^3$ is preferably methyl.

The "halogen" of R$^3$ is preferably a fluorine or chlorine atom.

R$^3$ is preferably a hydrogen, fluorine, or chlorine atom or a methyl group.

X, Y, and Z preferably correspond to any of the following combinations: X, Y, and Z are each CH; X is a nitrogen atom and Y and Z are each CH; Y is a nitrogen atom and X and Z are each CH; and Z is a nitrogen atom and X and Y are each CH.

The "C$_{1-8}$ alkylene" of A$^1$ is preferably methylene, ethylene, or n-propylene.

The structure obtained by replacement of one or two sp$^3$ carbon atoms at any positions of A$^1$ is preferably —O—, —OCH$_2$—, —OCH$_2$CH$_2$—, —OCH$_2$CH$_2$CH$_2$—, —CH$_2$O—, —CH$_2$OCH$_2$—, —CH$_2$OCH$_2$CH$_2$—, —CH$_2$CO—, —COCH$_2$—, —CH$_2$CH$_2$CO—, —COCH$_2$CH$_2$—, —CH$_2$COCH$_2$—, —CH$_2$COCH$_2$CH$_2$—, —NR$^{14}$—, —NR$^4$CH$_2$—, —CH$_2$NR$^{14}$—, —NR$^{14}$CH$_2$CH$_2$—, —CH$_2$NR$^{14}$CH$_2$—, or —CH$_2$CH$_2$NR$^{14}$—.

The "C$_{1-7}$ alkylene" of A$^2$ is preferably methylene, ethylene, or n-propylene.

The "C$_{3-12}$ cycloalkylene" of A$^2$ is preferably cyclopropylene, cyclobutylene, cyclopentylene, or cyclohexylene.

The heterocycle of "4- to 12-membered heterocyclylene" of A$^2$ is preferably piperidine, piperazine, pyrrolidine, morpholine, tetrahydrofuran, tetrahydropyran, 1,4-diazepane, oxepane, 2-azaspiro[3.3]heptane, 1,6-diazaspiro[3.3]heptane, 2,6-diazaspiro[3.3]heptane, 2,6-diazaspiro[3.4]octane, 2,5-diazabicyclo[2.2.2]octane, 3,8-diazabicyclo[3.2.1]octane, 2,7-diazaspiro[3.5]nonane, 1,7-diazaspiro[4.5]decane, 2,8-diazaspiro[4.5]decane, 4,7-diazaspiro[2.5]octane, 1,4-diazabicyclo[3.2.2]nonane, or octahydropyrrolo[3,4-b]pyrrole.

The heterocycle of "4- to 12-membered heterocyclylidene" of A$^2$ is preferably oxetane, tetrahydrofuran, tetrahydropyran, pyrrolidine, piperidine, piperazine, morpholine, or oxepane.

The "C$_{6-10}$ arylene" of A$^2$ is preferably phenylene.

The heteroarene of "5- to 10-membered heteroarylene" of A$^2$ is preferably furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinolone, isoquinoline, benzofuran, benzothiophene, indole, indazole, or benzimidazole.

The "halogen" of $A^3$ is preferably a fluorine or chlorine atom.

The "—$R^{25}$" of $A^3$ is a hydrogen atom or a methyl, ethyl, n-propyl, isopropyl, n-butyl, isobutyl, or tert-butyl group. The —$R^{25}$ substituted with a substituent is preferably a hydroxymethyl, 1-hydroxyethyl, 2-hydroxyethyl, 2-hydroxy-2-propyl, 2-hydroxy-1-propyl, 1-hydroxy-2-propyl, 1-hydroxy-2-methyl-2-propyl, 2-hydroxy-2-methyl-1-propyl, trifluoromethyl, 2,2,2-trifluoroethyl, carboxymethyl, 1-carboxyethyl, 2-carboxyethyl, 2-carboxy-2-propyl, or cyanomethyl group.

The "—$OR^{26}$" of $A^3$ is preferably —OH, methoxy, ethoxy, or isopropoxy.

The "—$NR^{27}R^{28}$" of $A^3$ is preferably amino, dimethylamino, methylamino, pyrrolidin-1-yl, piperidin-1-yl, piperazin-1-yl, or morpholin-1-yl.

The "—C(=O)$R^{29}$" of $A^3$ is preferably acetyl. The —C(=O)$R^{29}$ substituted with a substituent is preferably hydroxyacetyl.

The "—C(=O)—$OR^{30}$" of $A^3$ is preferably —COOH, methoxycarbonyl, ethoxycarbonyl, or isopropoxycarbonyl.

The "—C(=O)—$NR^{34}R^{35}$" of $A^3$ is preferably aminocarbonyl (or carbamoyl), (methylamino)carbonyl, (dimethylamino)carbonyl, (pyrrolidin-1-yl)carbonyl, (piperidin-1-yl)carbonyl, (morpholin-1-yl)carbonyl, or (piperazin-1-yl)carbonyl.

The "—S(=O)$_2$—$R^{40}$" of $A^3$ is preferably methanesulfonyl or ethylsulfonyl.

$R^{14}$ to $R^{44}$ in $A^1$, $A^2$, and $A^3$ may be bonded in $A^1$, $A^2$, or $A^3$ or between $A^1$ and $A^2$, between $A^1$ and $A^3$, or between $A^2$ and $A^3$ via a single bond, —O—, —$NR^{50}$—, or —S(=O)$_p$— to form a ring. Examples of such a ring include the following structures:

[Formula 5]

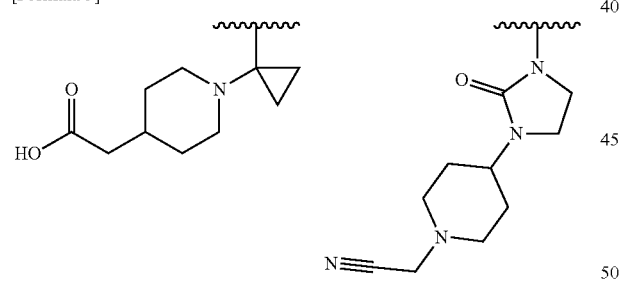

$R^{11}$ or $R^{13}$ may be bonded to $A^1$, $A^2$, or $A^3$ via a single bond, —O—, —$NR^{51}$—, or —S(=O)$_p$— to form a ring. Examples of such a ring include the following structures:

[Formula 6]

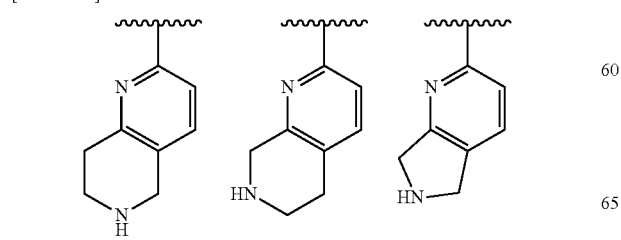

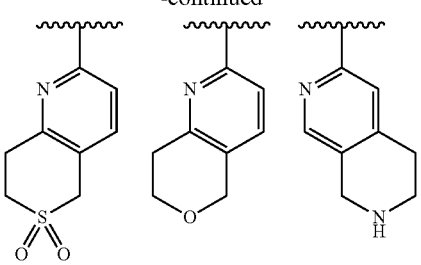

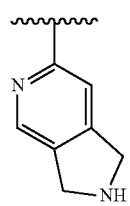

[Formula 7]

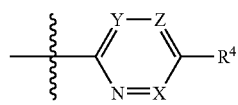

Preferred examples of the aforementioned entire structure are as follows:

[Formula 8]

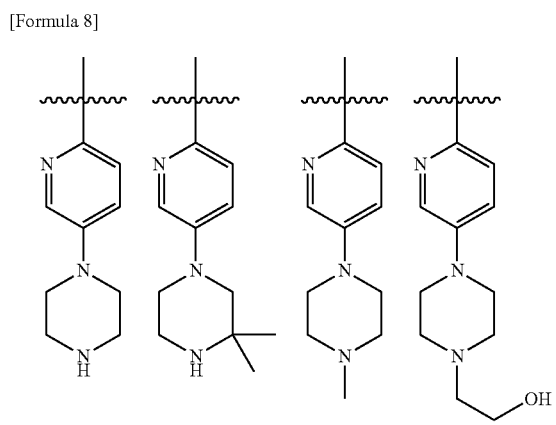

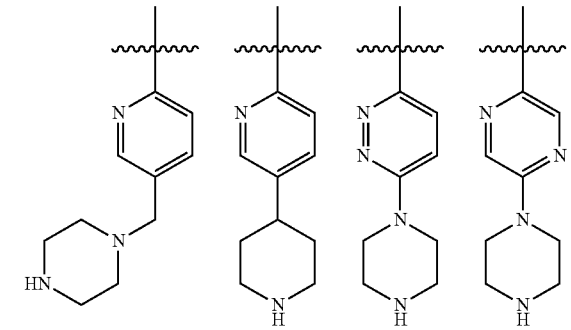

-continued
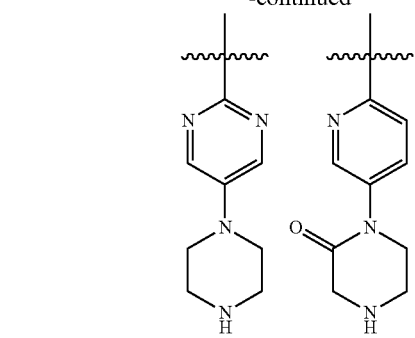
[Formula 9]
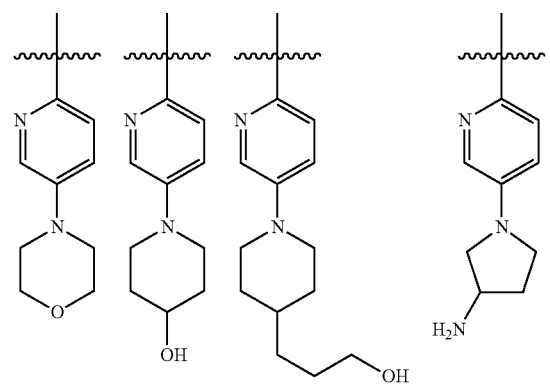
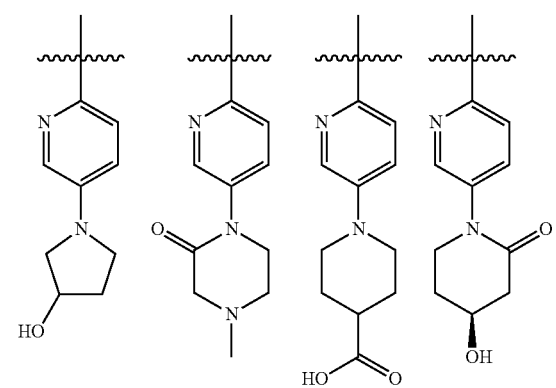
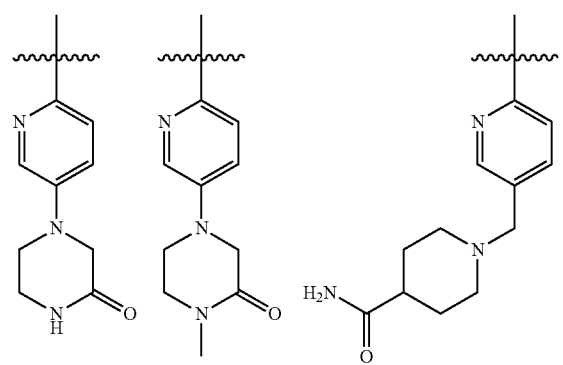
-continued
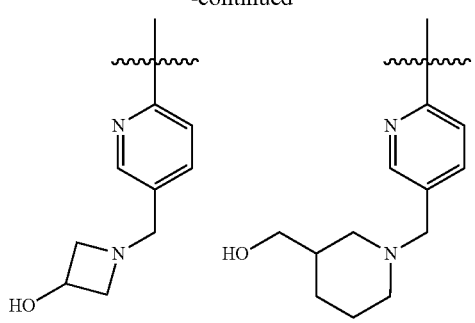
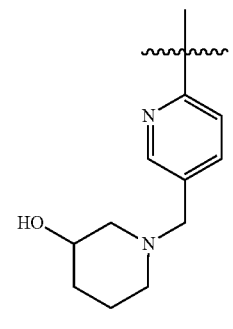
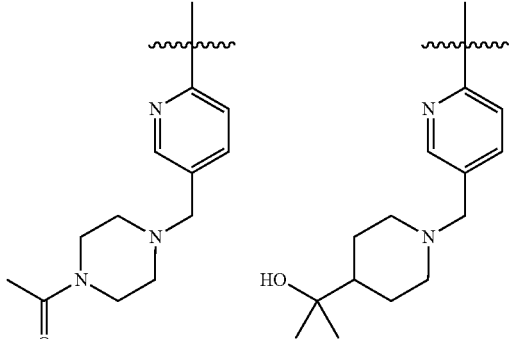
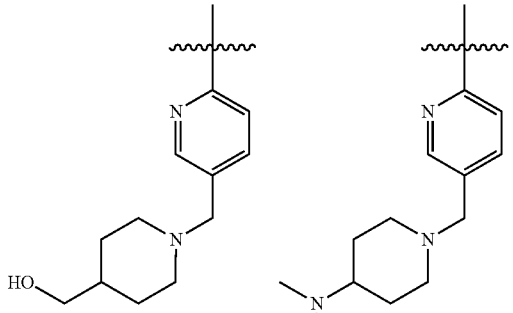

-continued
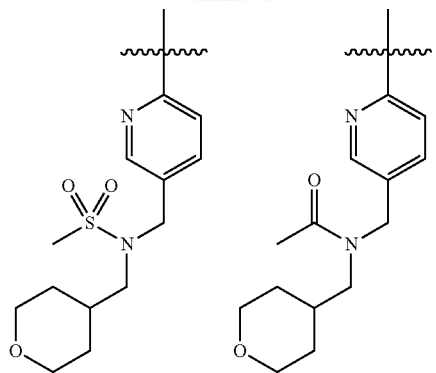 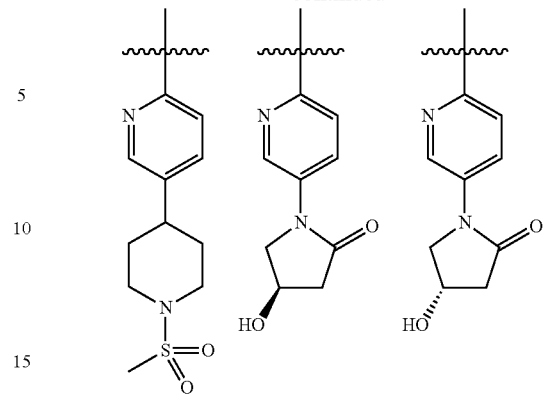
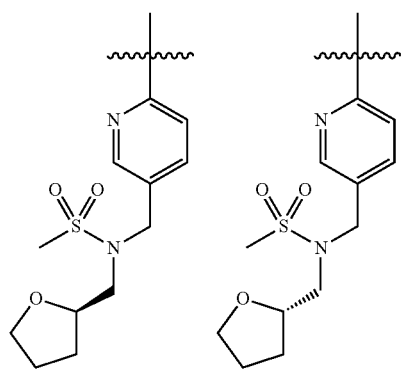 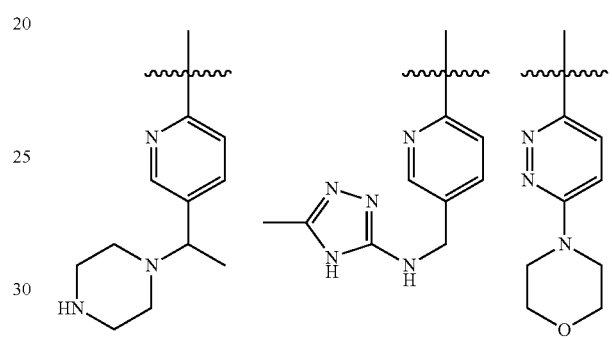
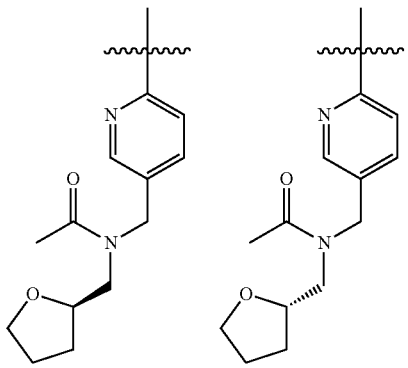 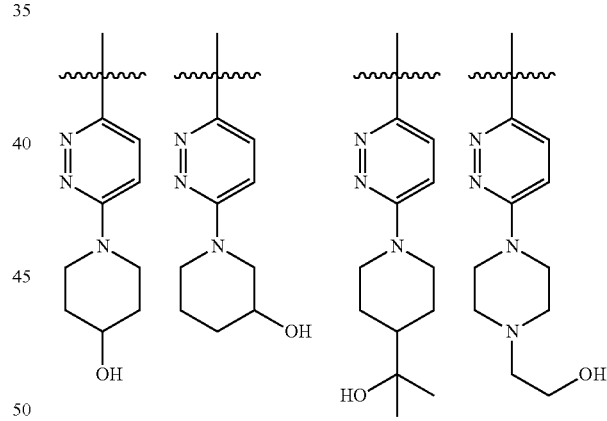
[Formula 10]
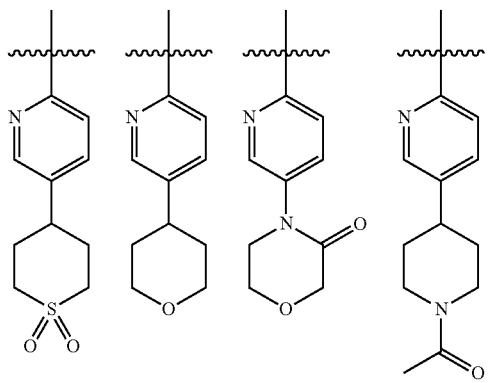 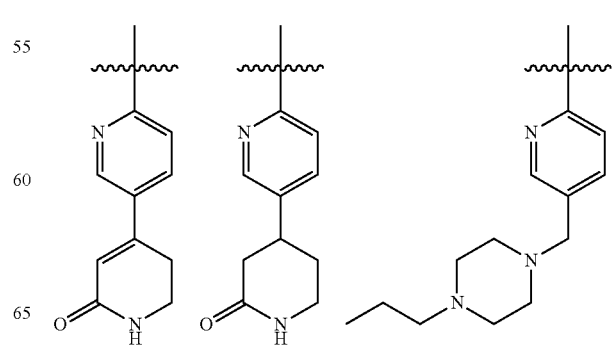

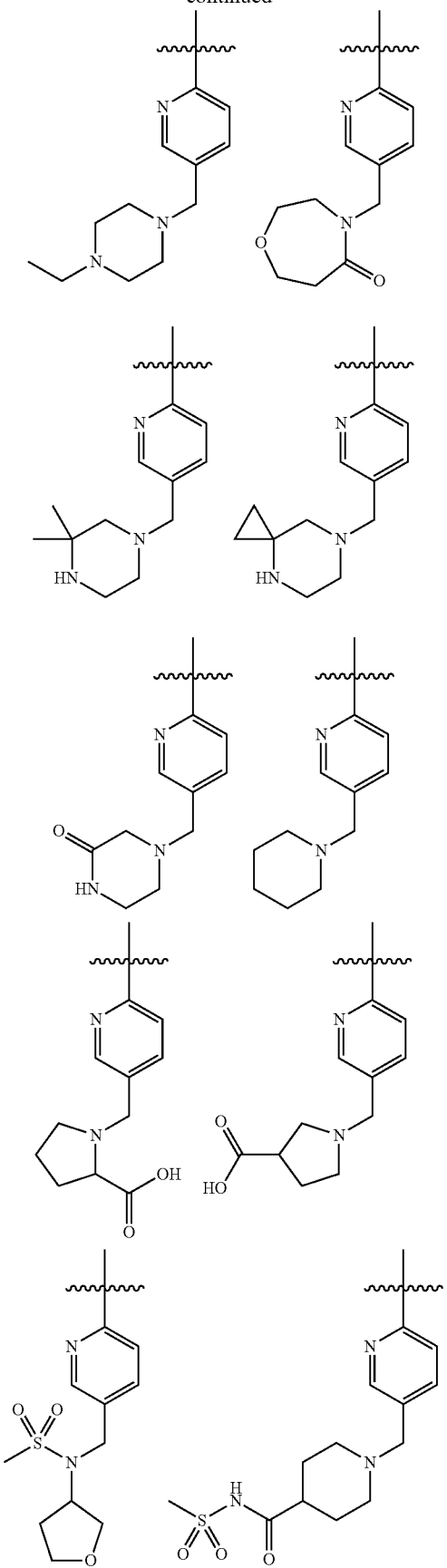
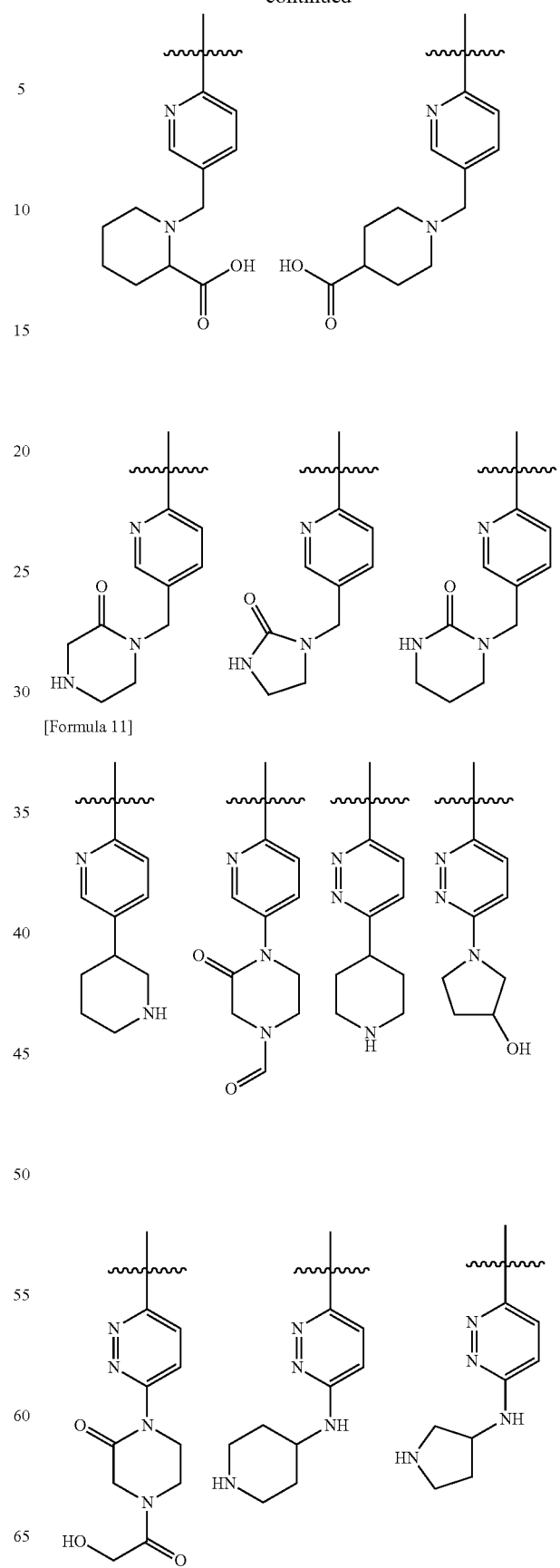
[Formula 11]

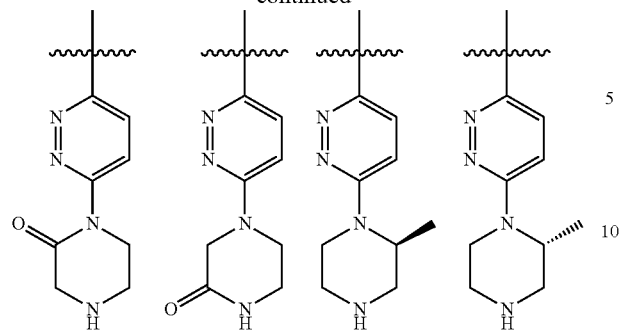
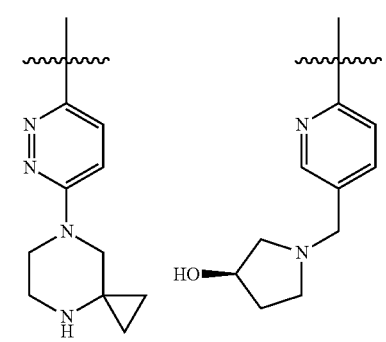
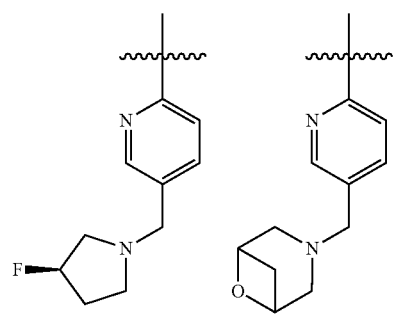
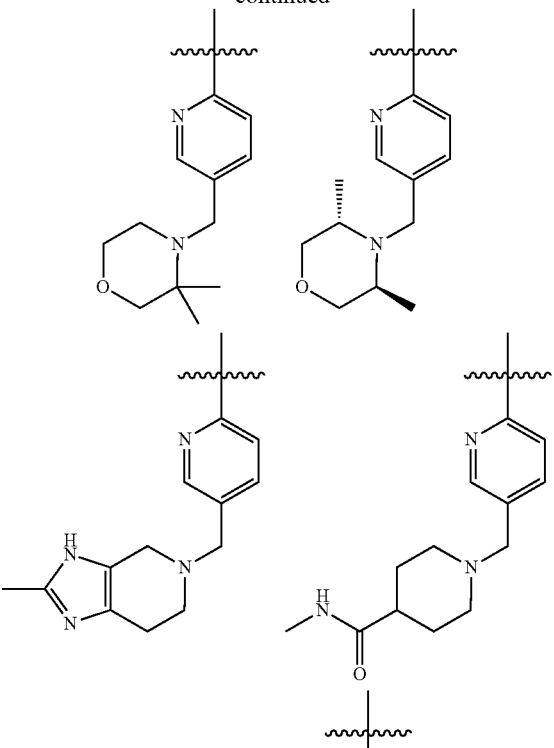
[Formula 12]
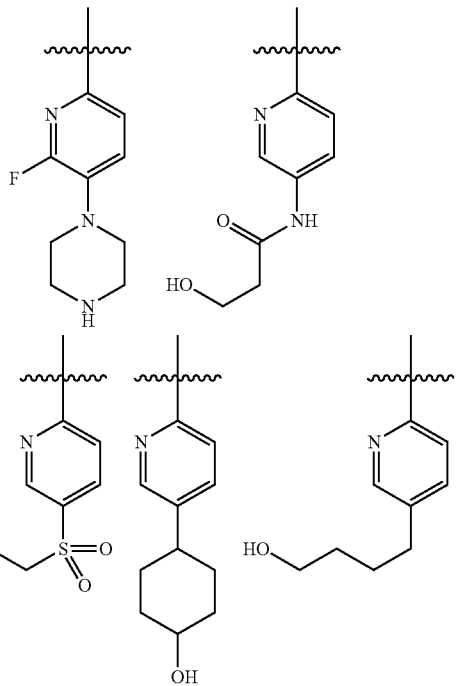

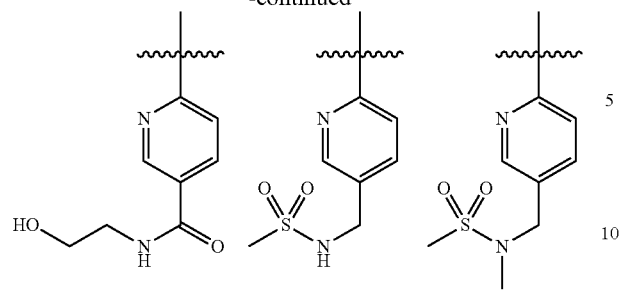
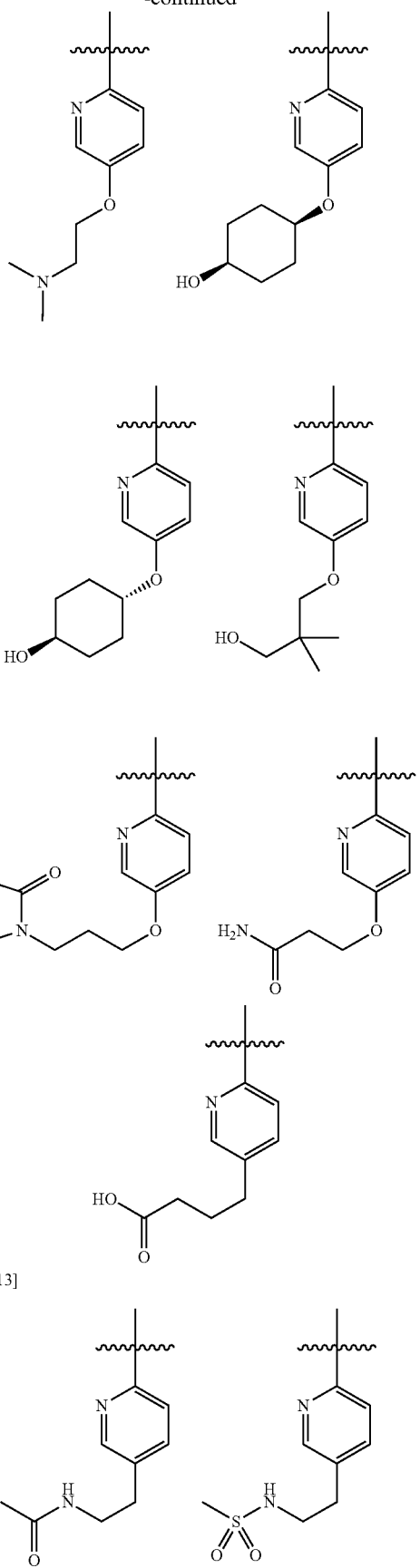
[Formula 13]

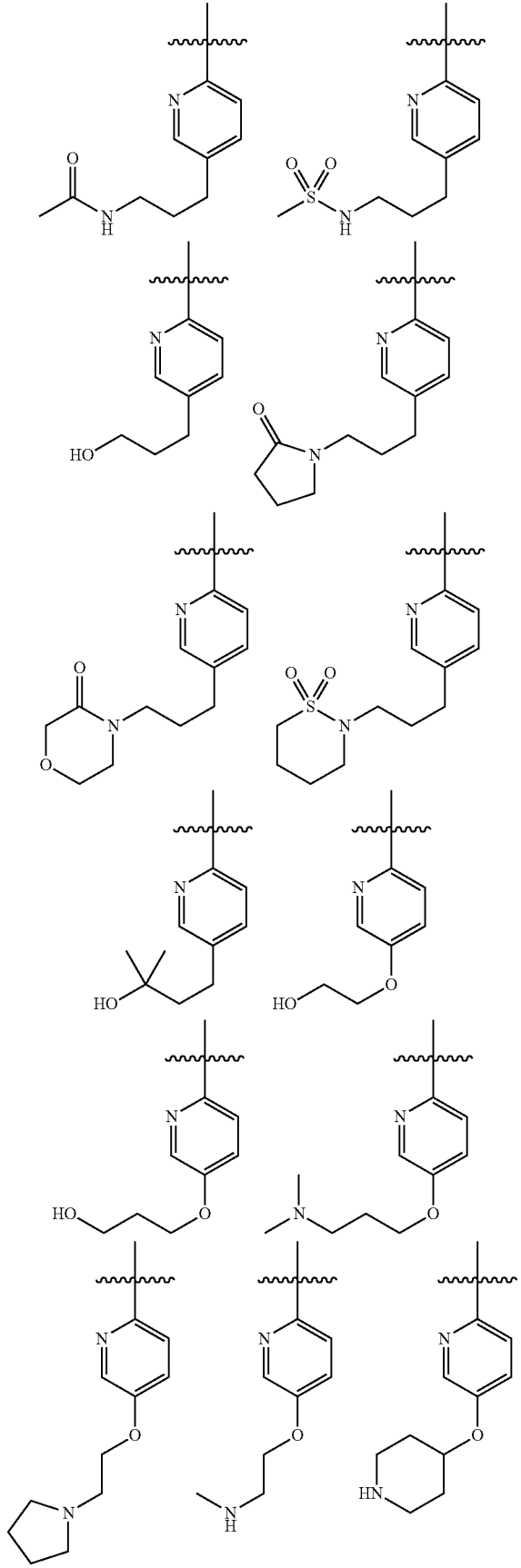
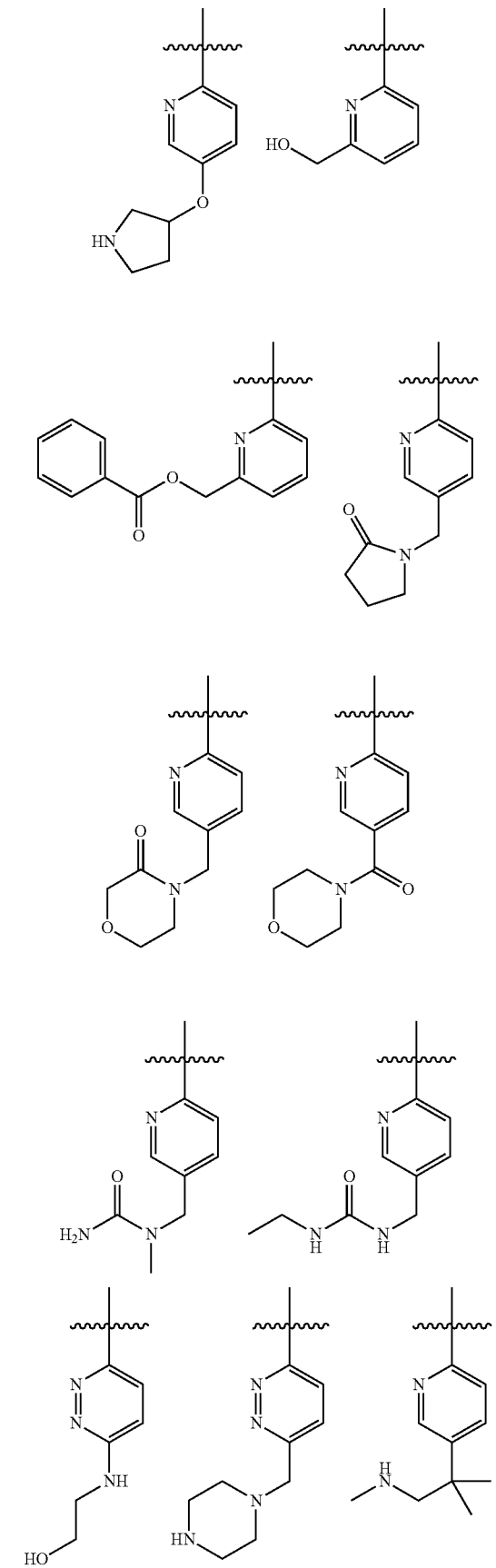

35
-continued
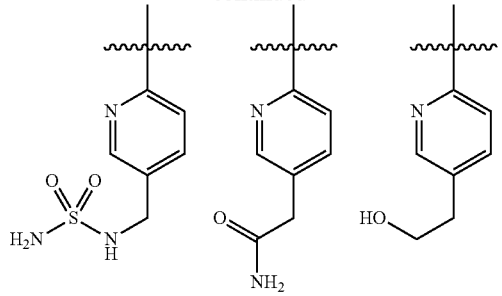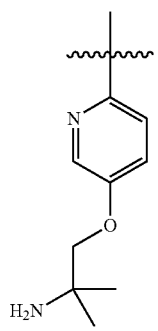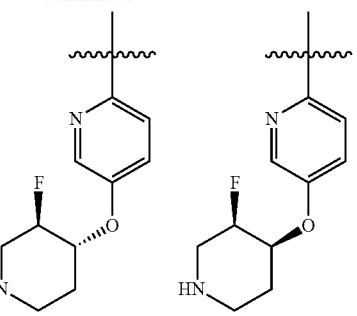
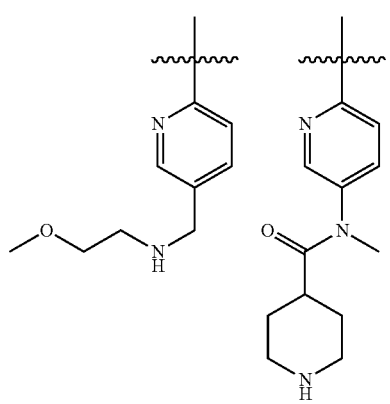
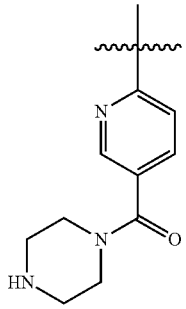
[Formula 14]
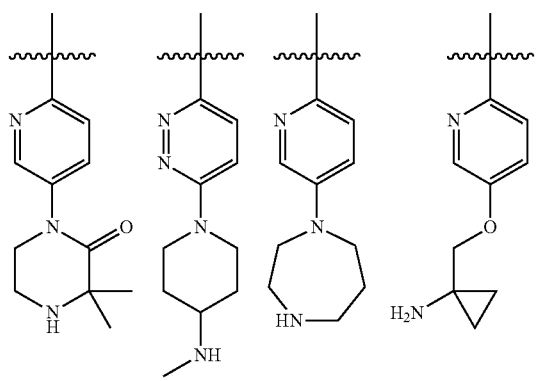
36
-continued
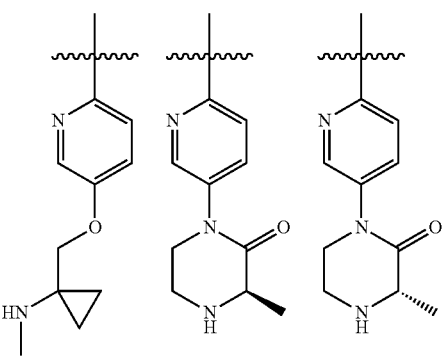
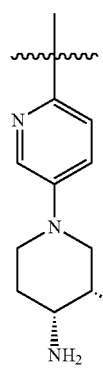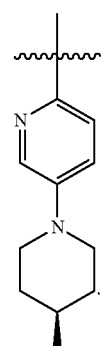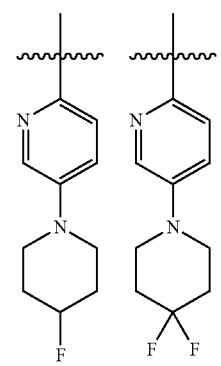
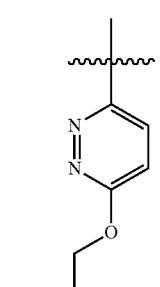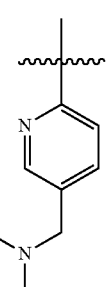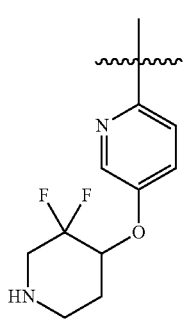

37
-continued
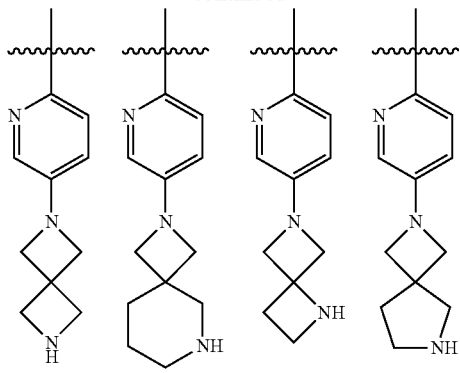
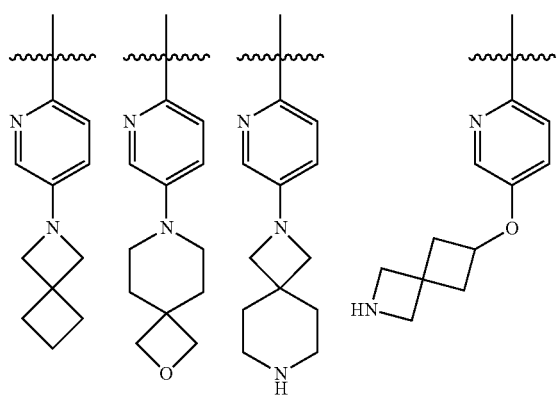
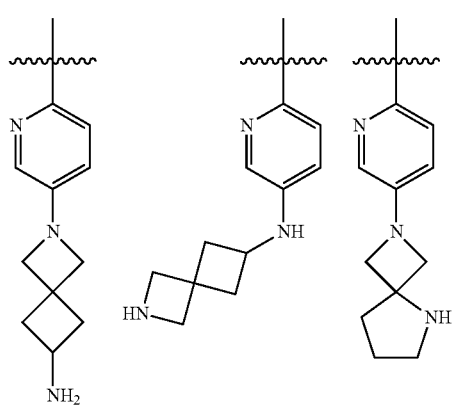
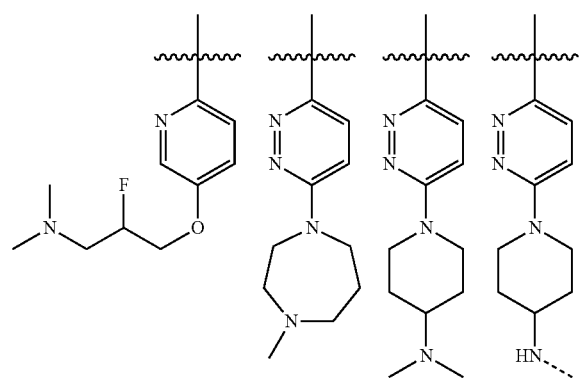
38
-continued
[Formula 15]
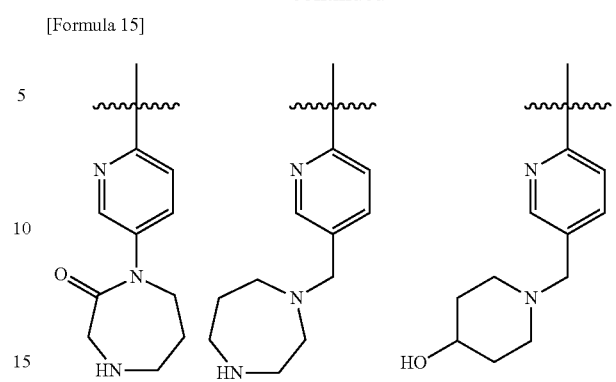
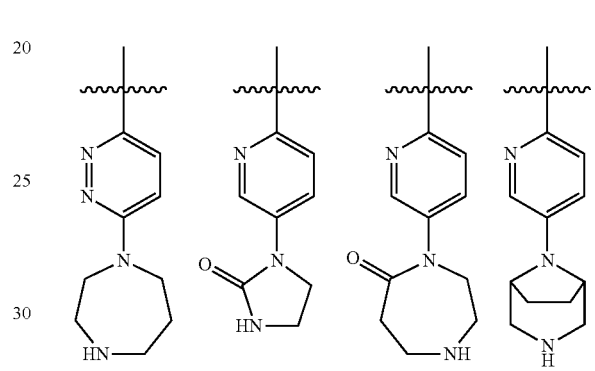
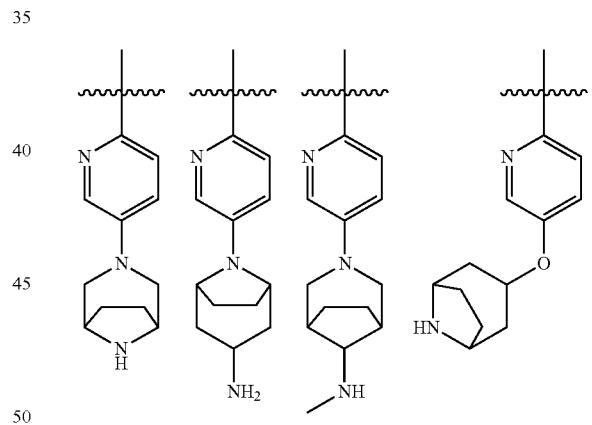
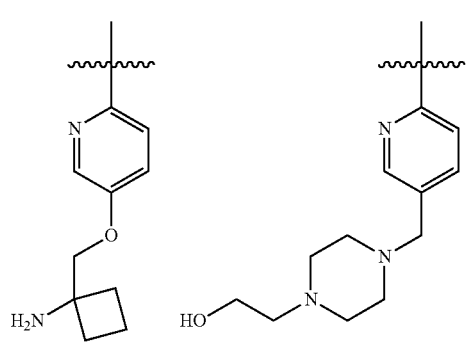

39
-continued
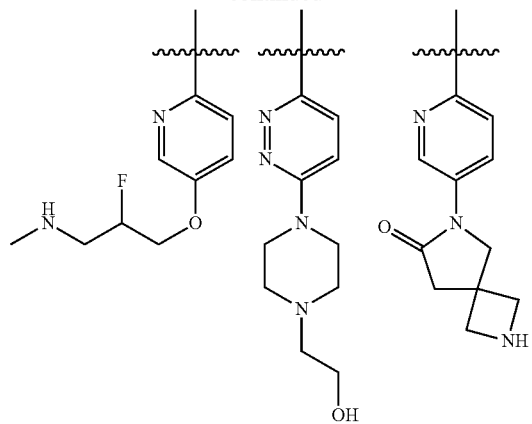
40
-continued
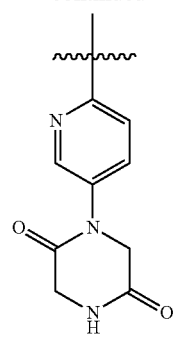
[Formula 16]
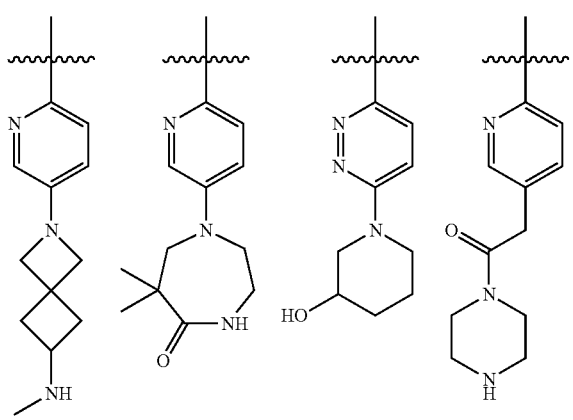
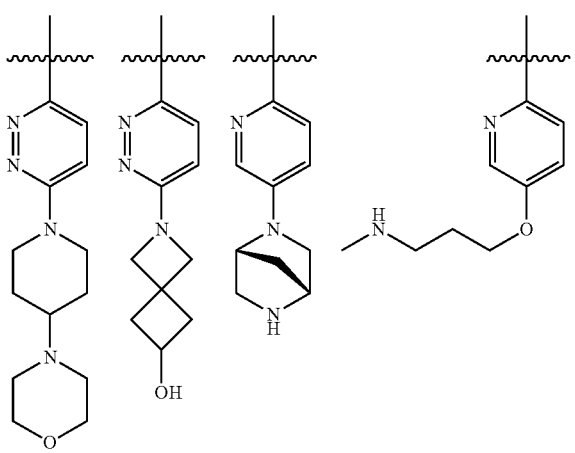
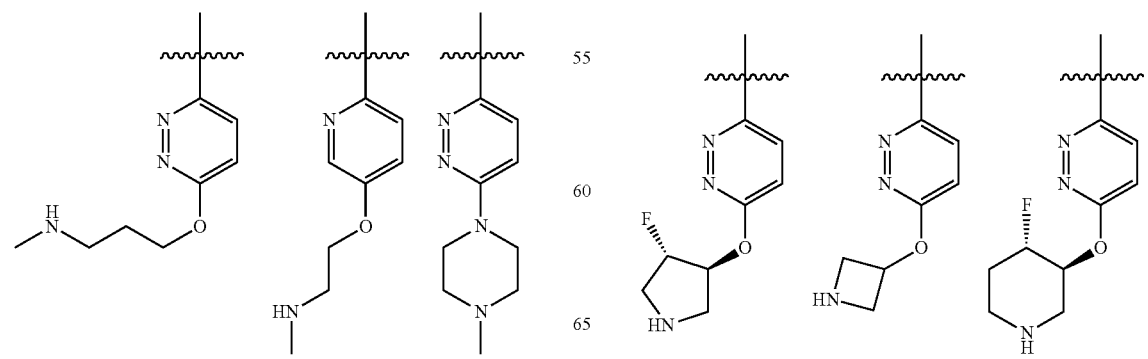

-continued
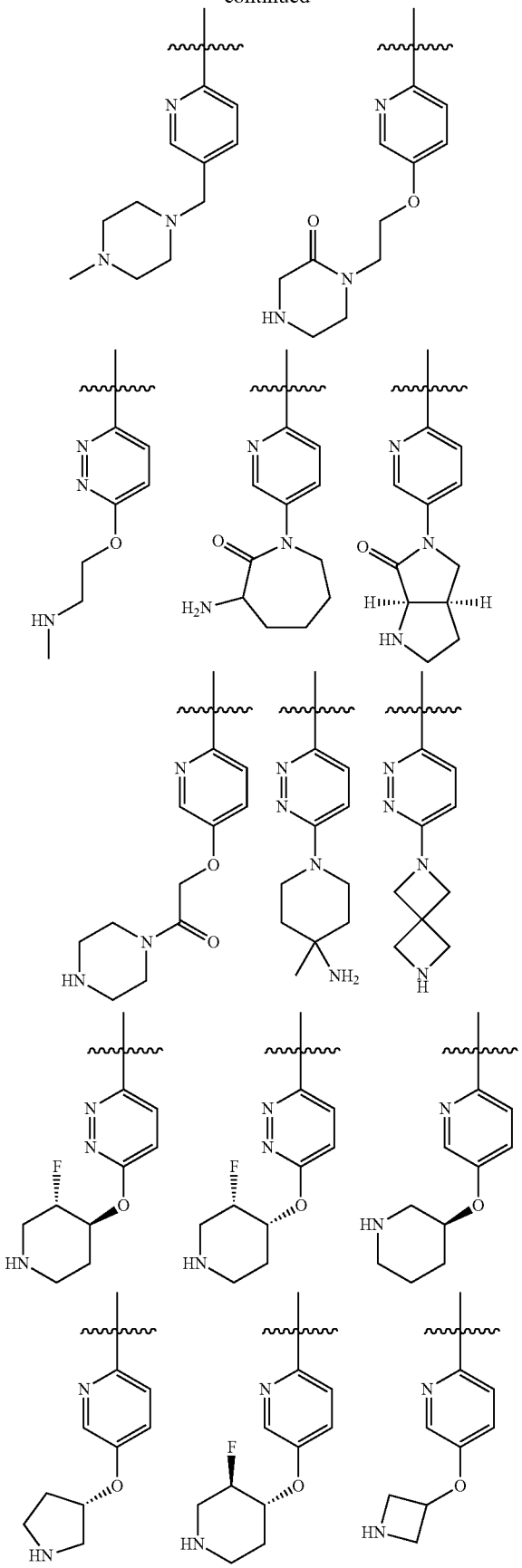
[Formula 17]
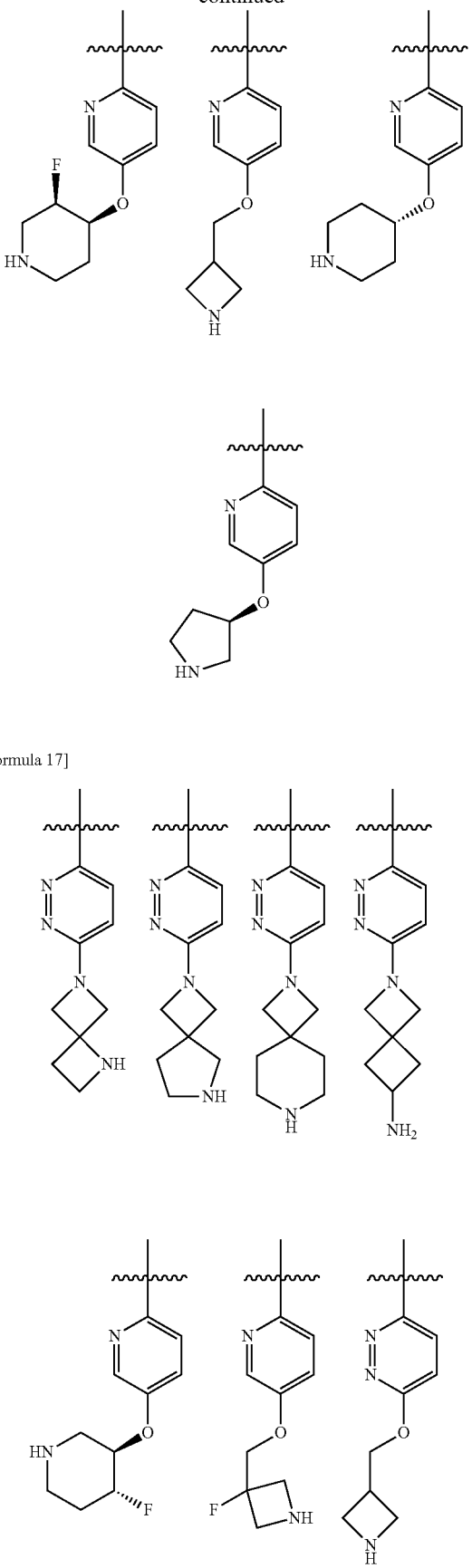

-continued
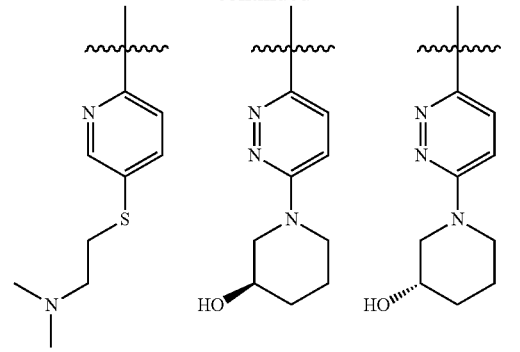
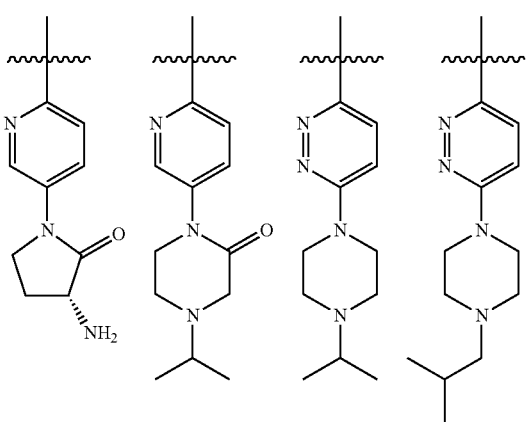
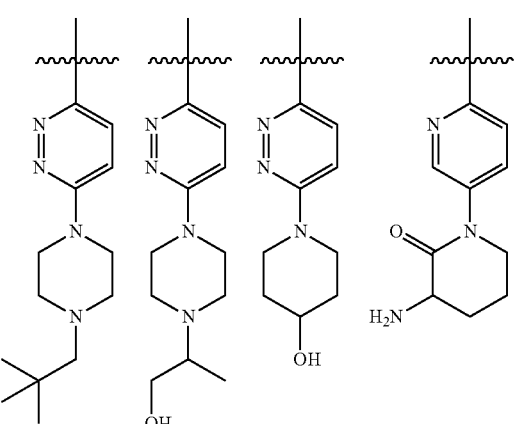
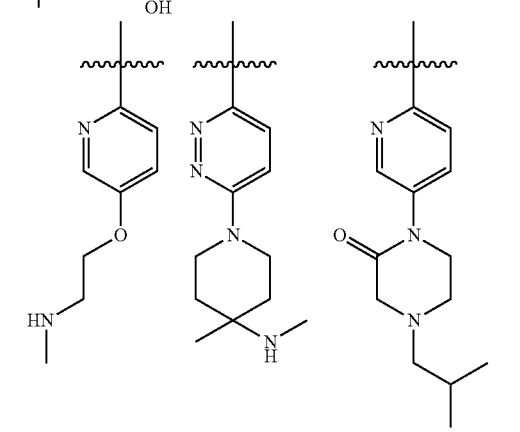
-continued
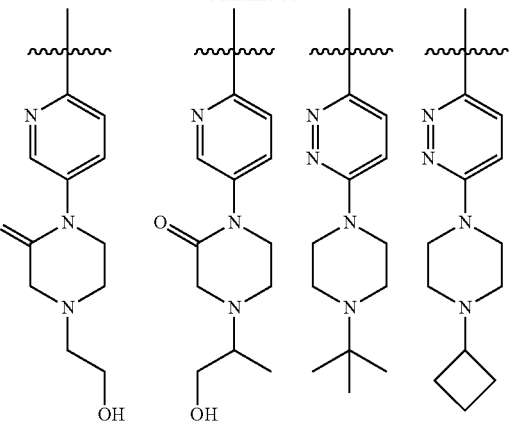
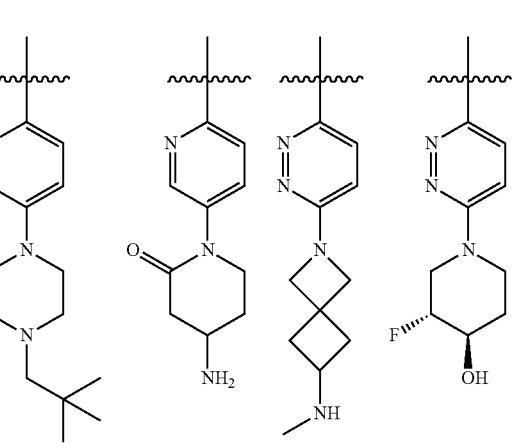
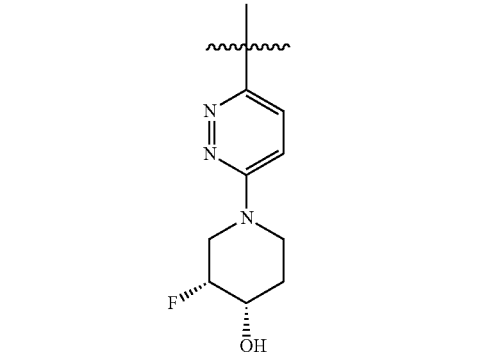
[Formula 18]
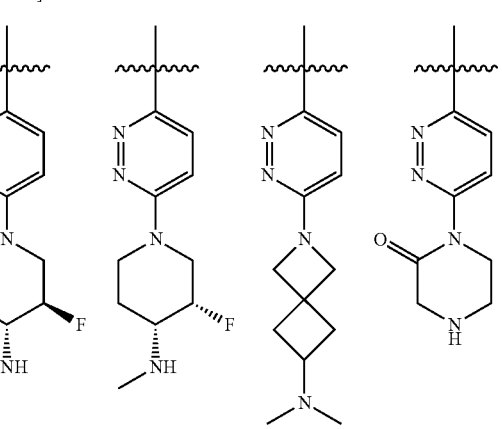

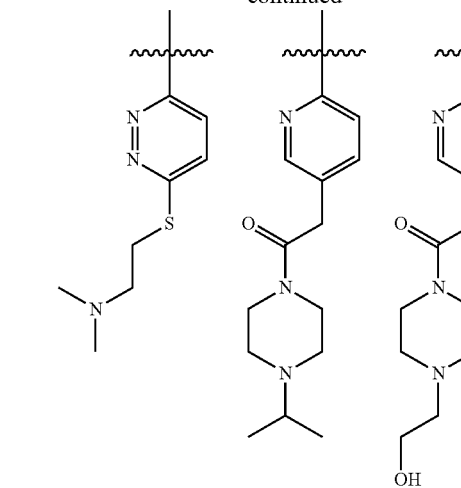
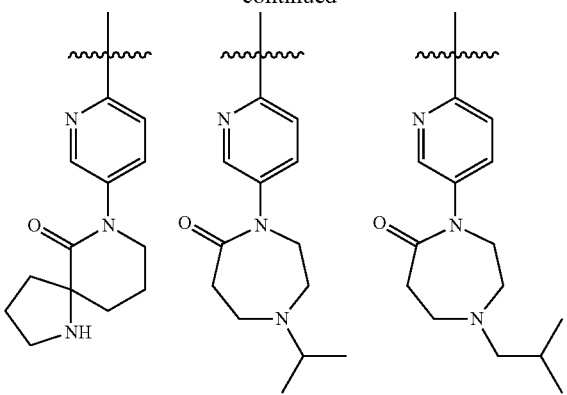
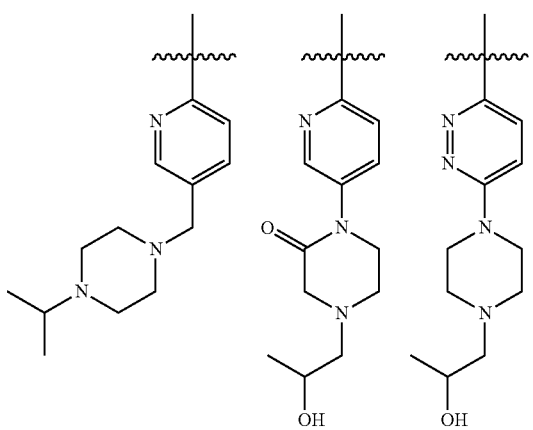
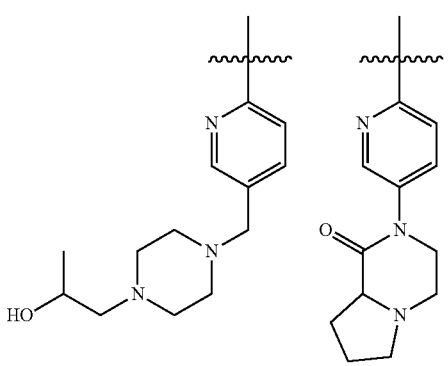
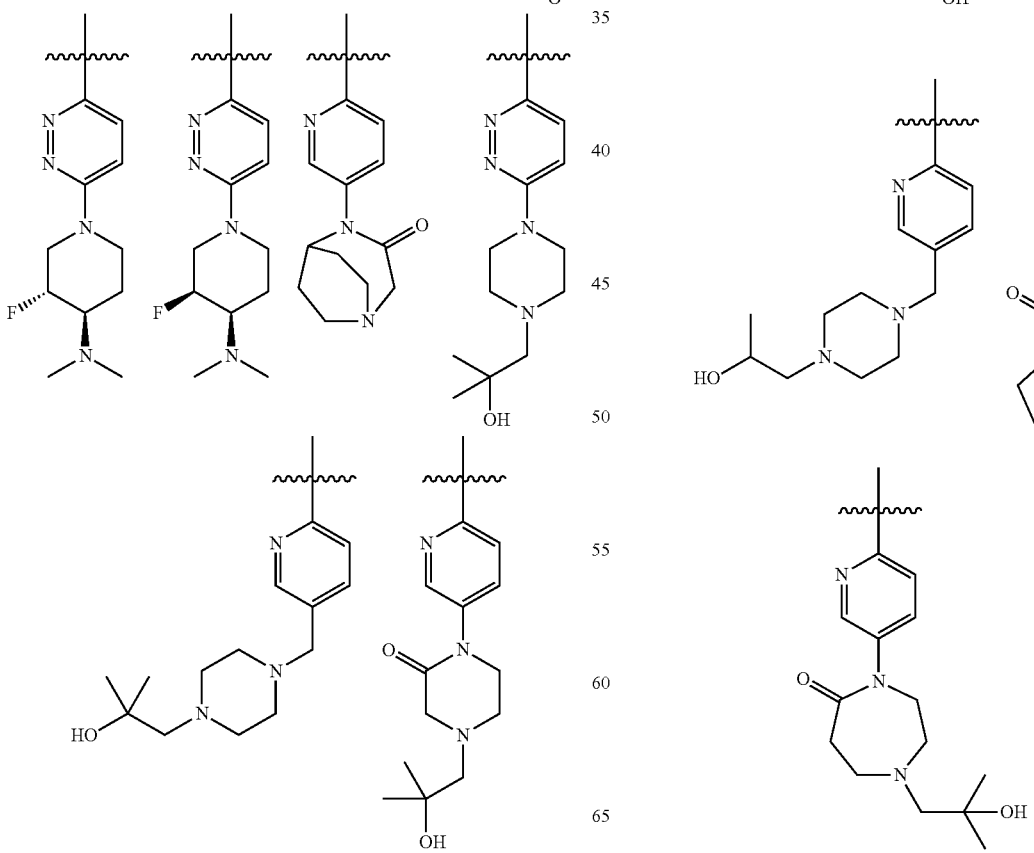

[Formula 19-1]
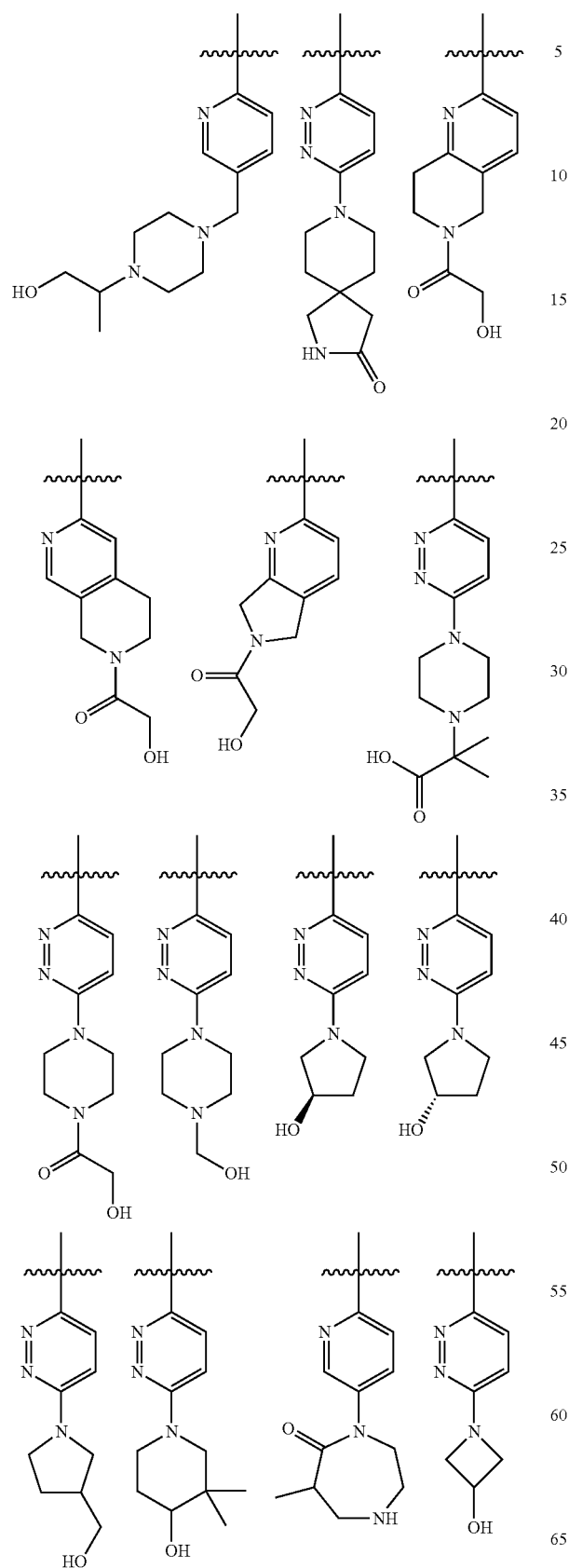
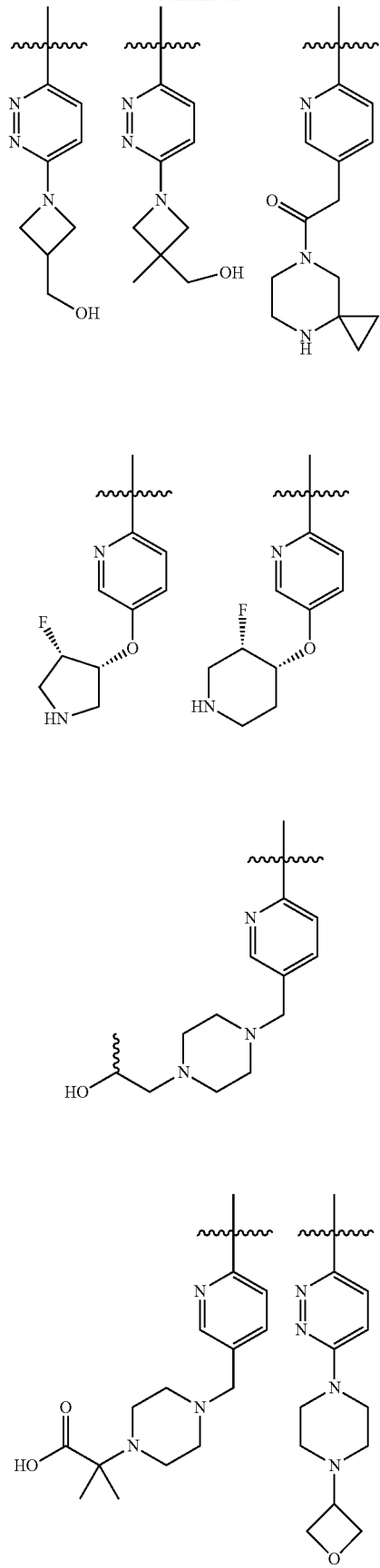

-continued
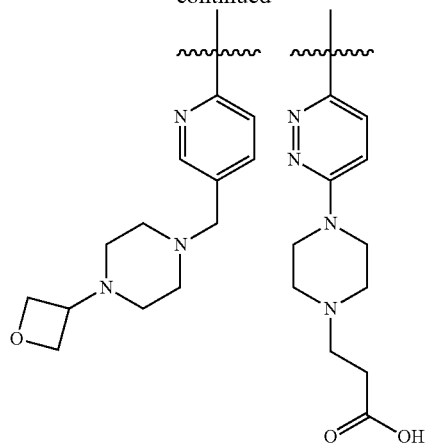
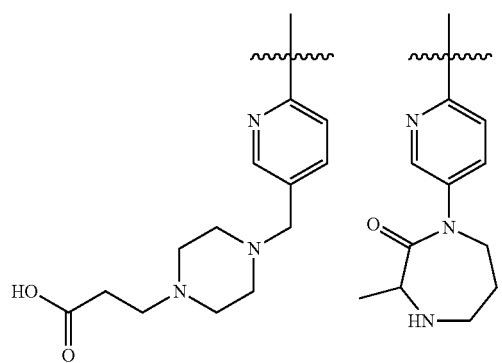
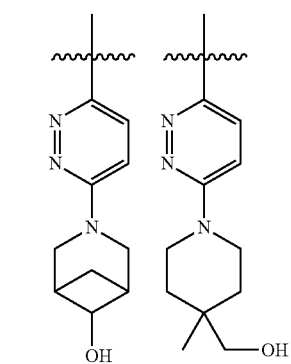
[Formula 19-2]
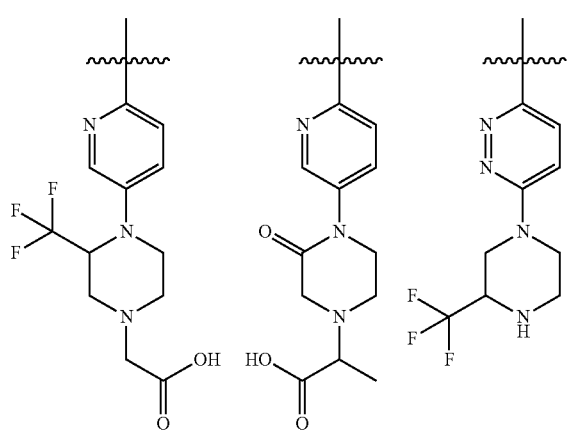
-continued
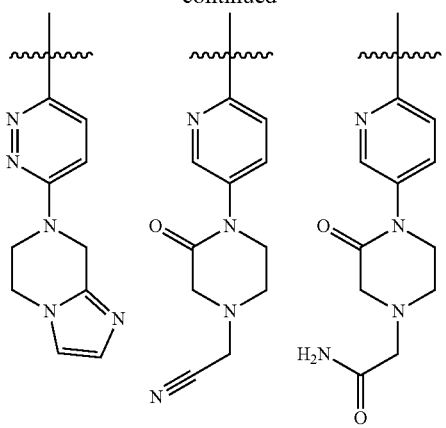
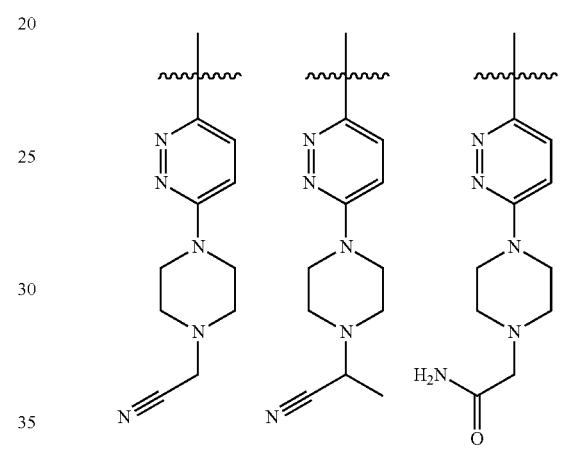
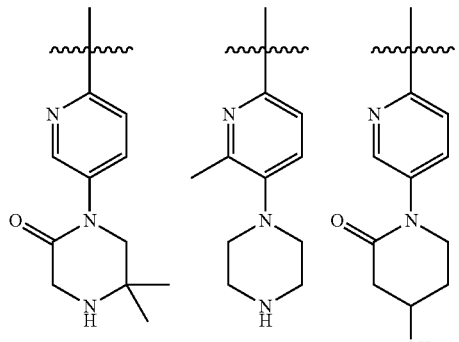
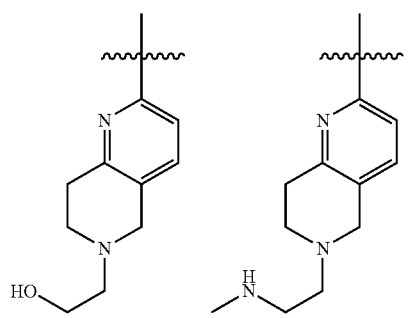

51
-continued
52
-continued
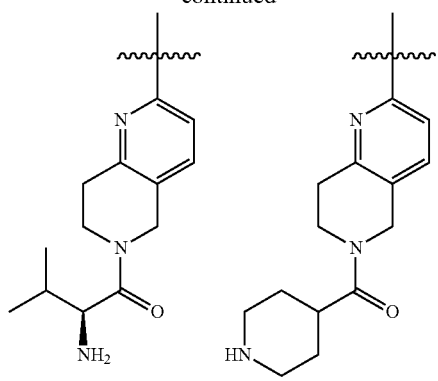
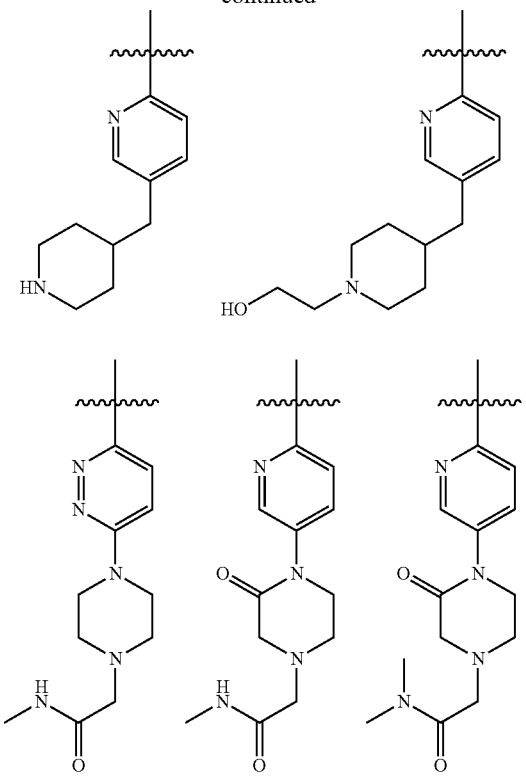
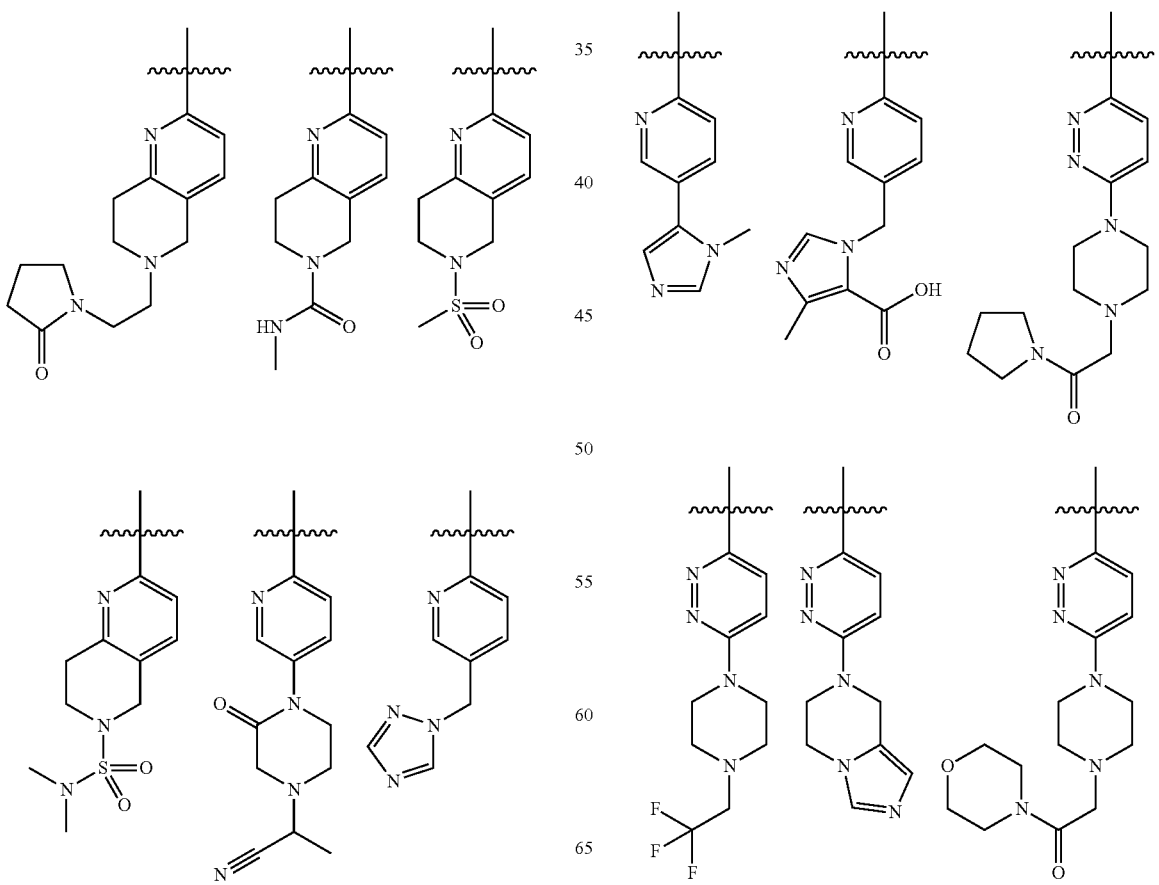
[Formula 19-3]

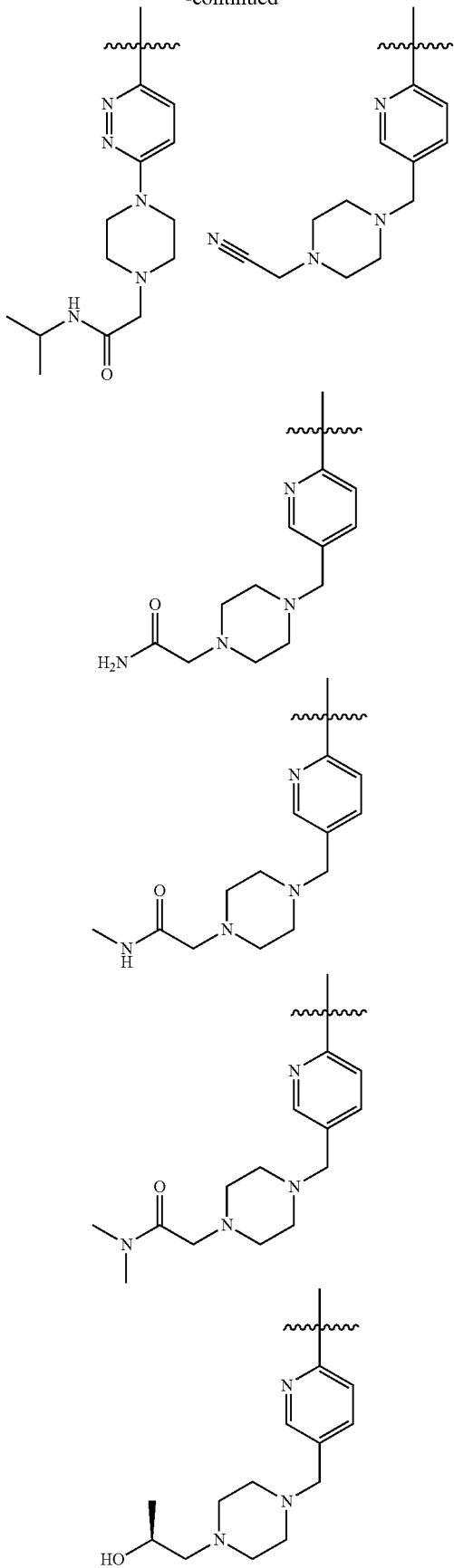
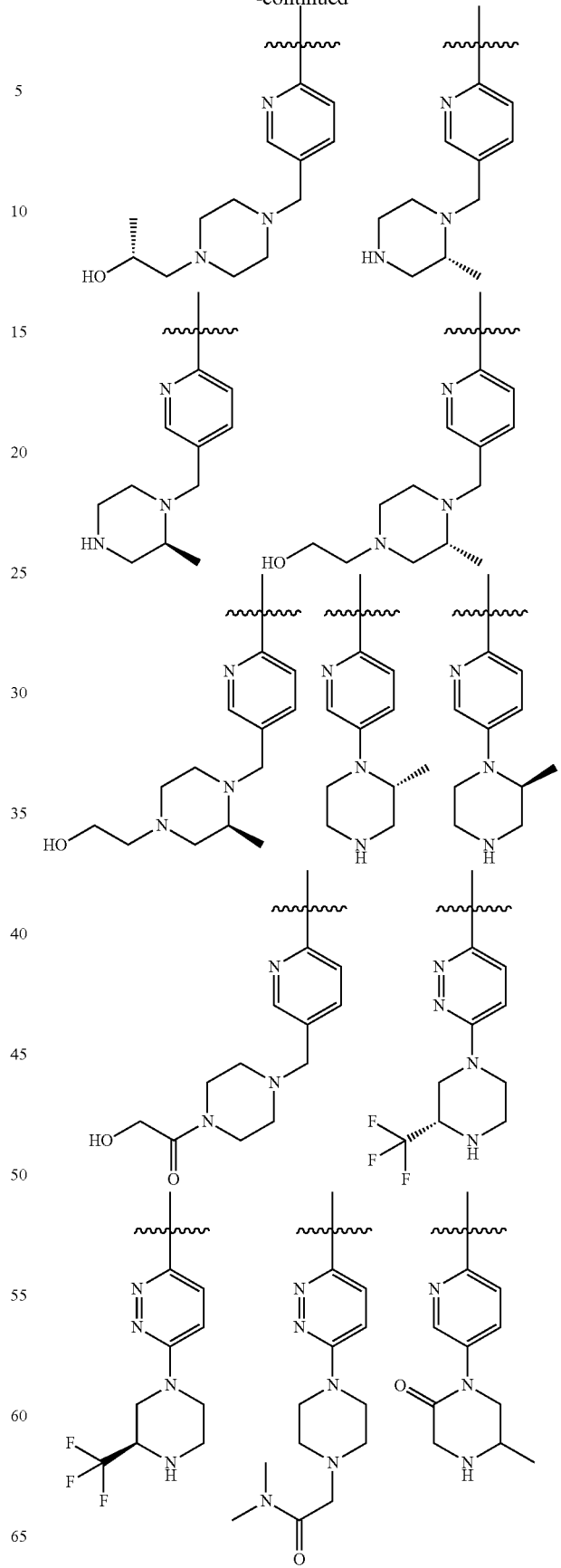

55
-continued
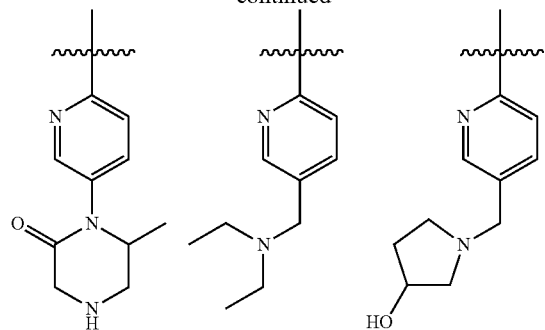
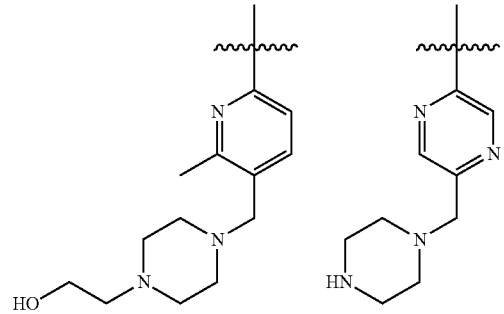
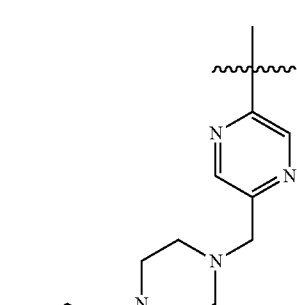
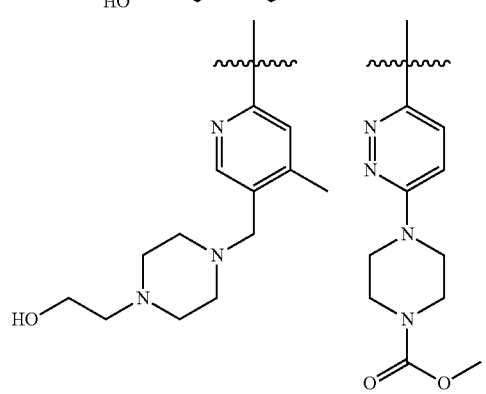
56
-continued
[Formula 19-4]
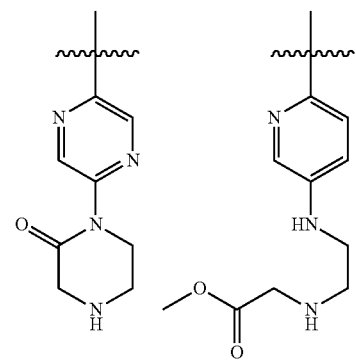
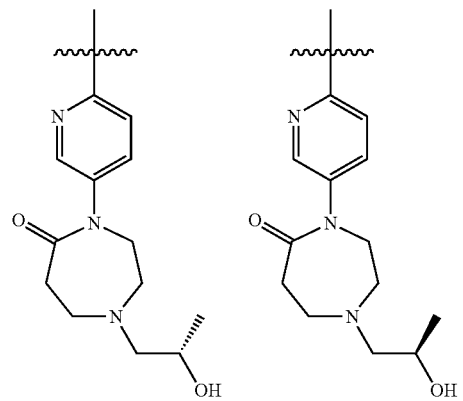
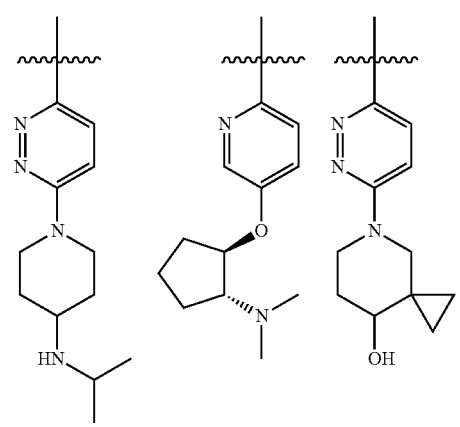
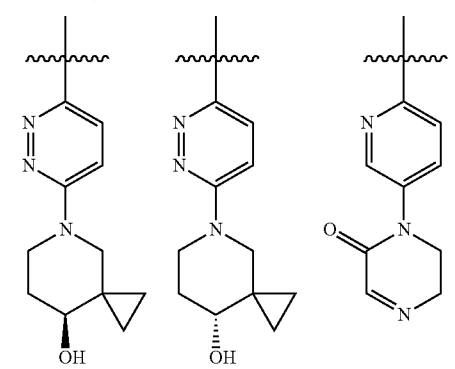

57
-continued
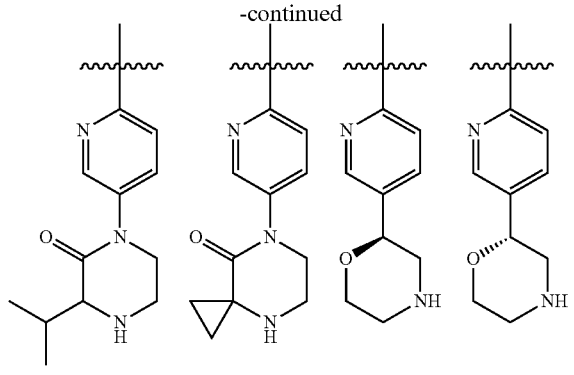
58
-continued
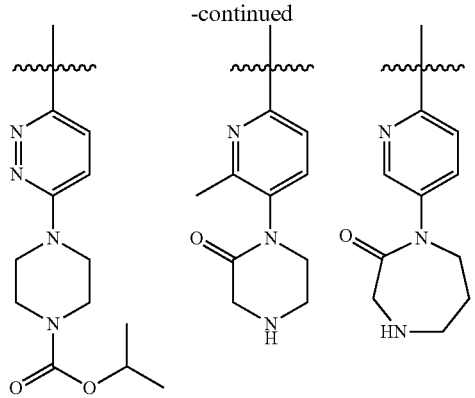
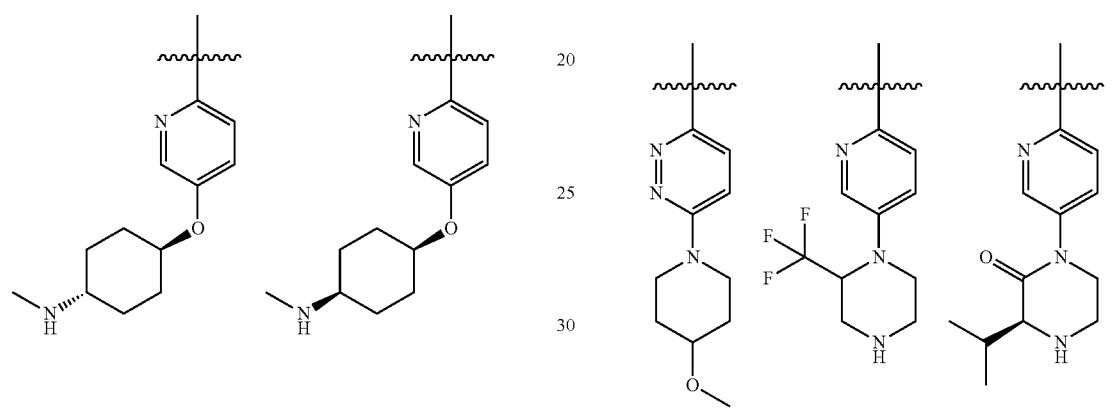
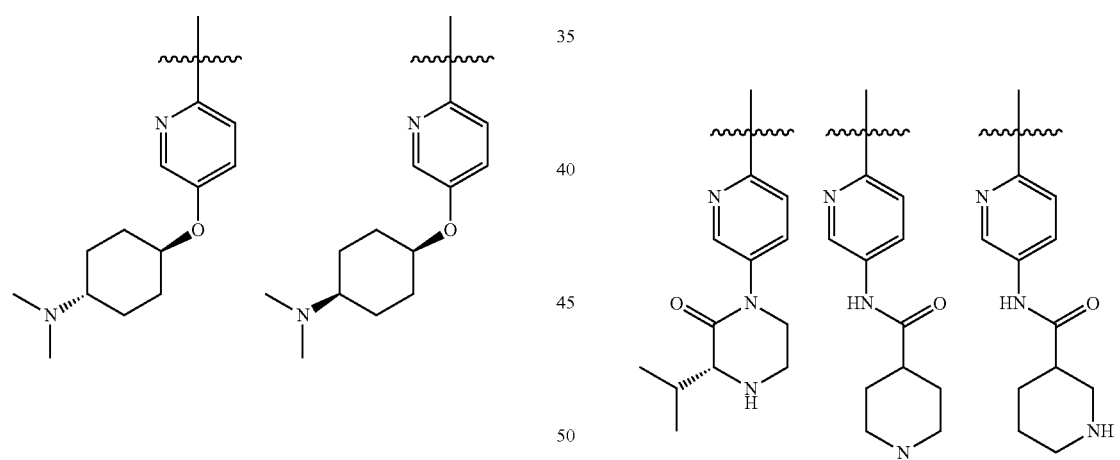
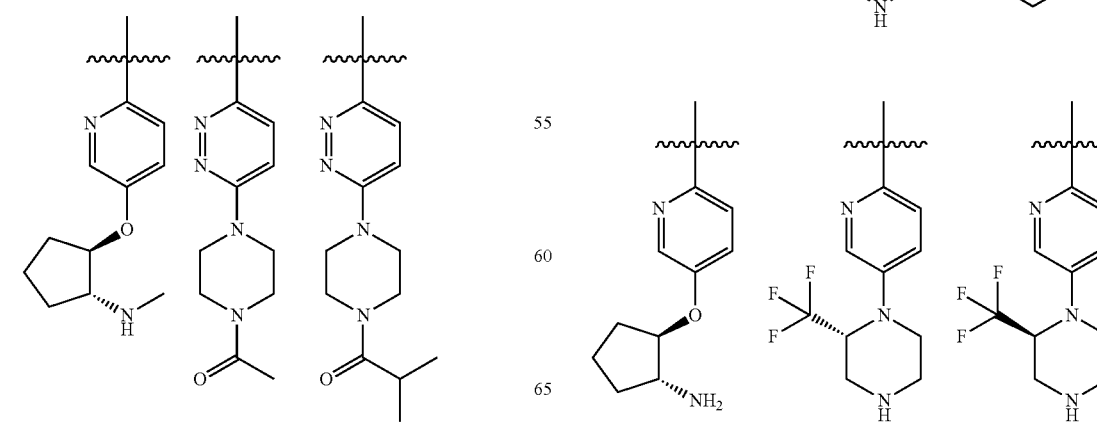

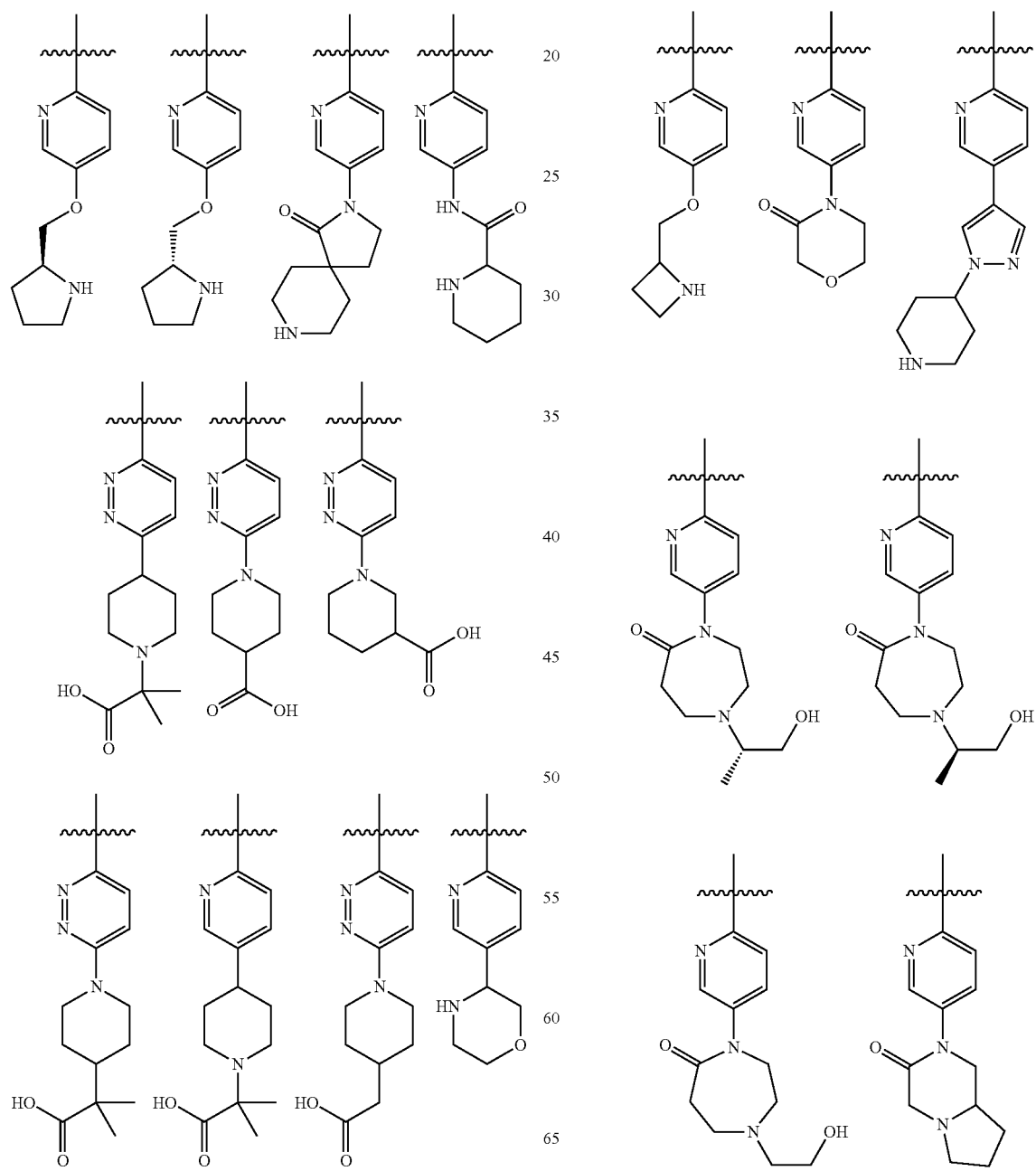

61
-continued
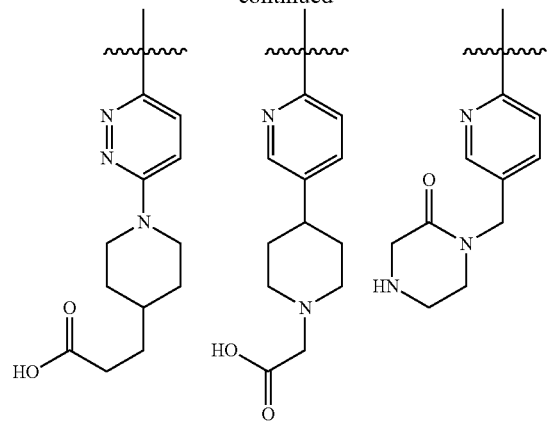
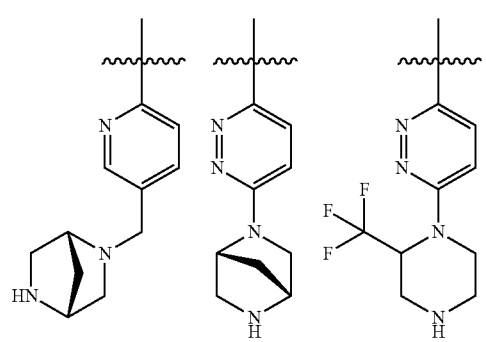
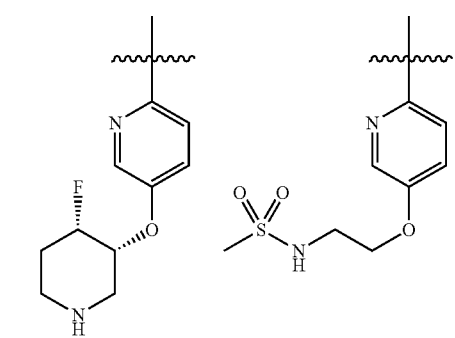
[Formula 19-6]
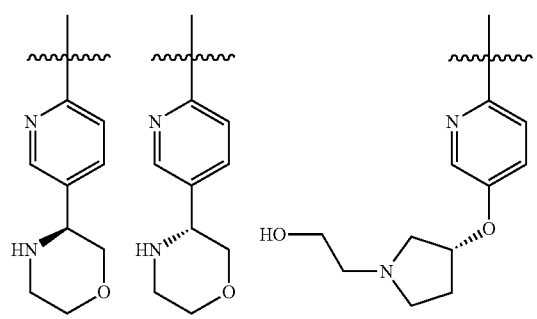
62
-continued
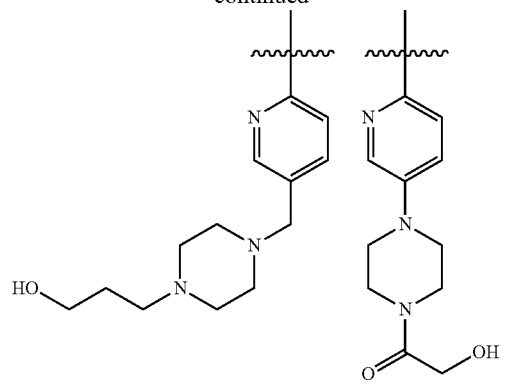
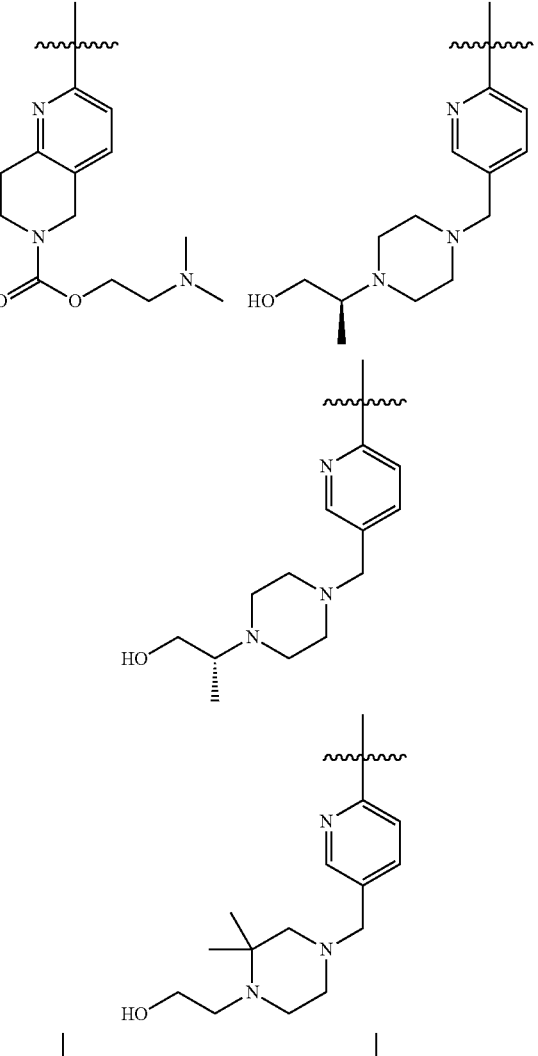
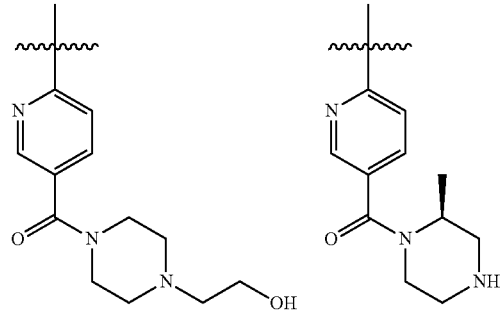

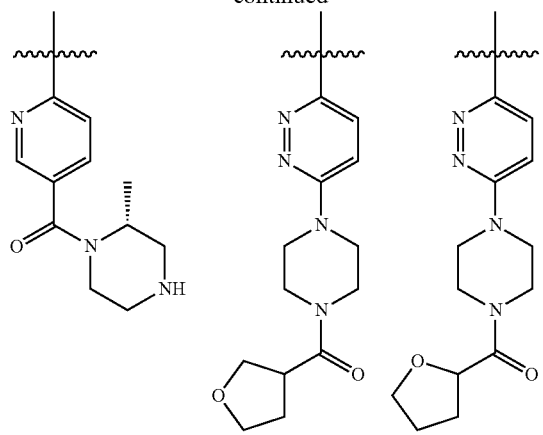
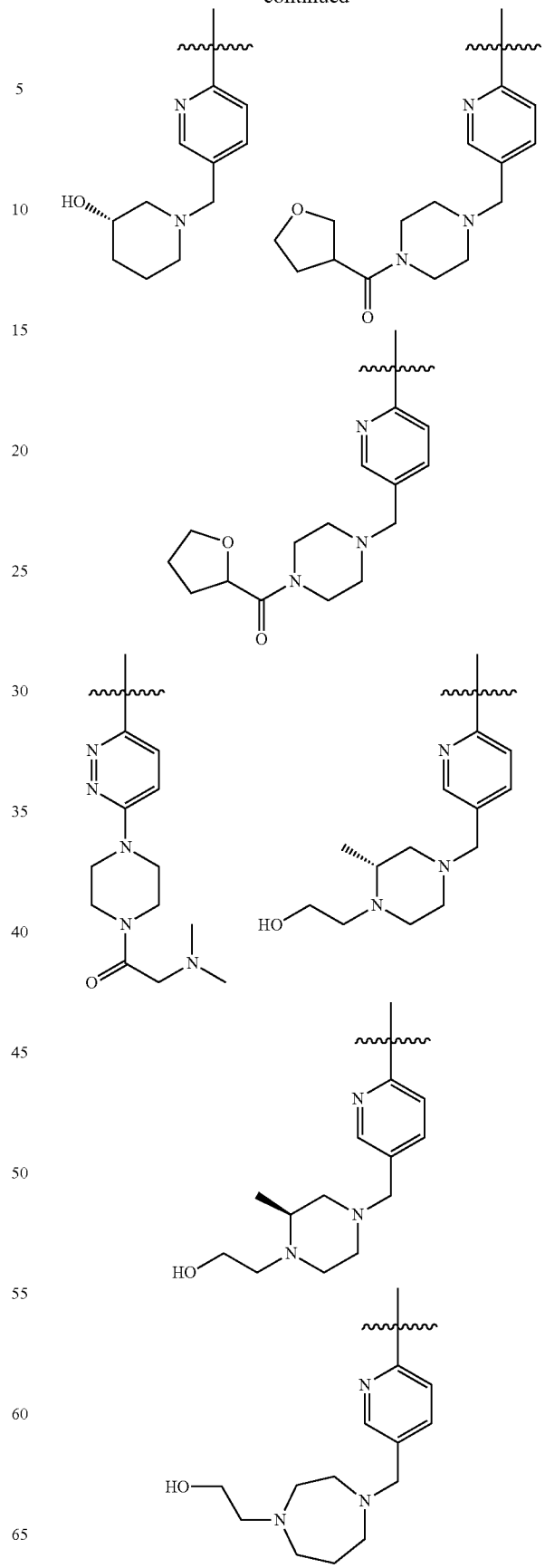

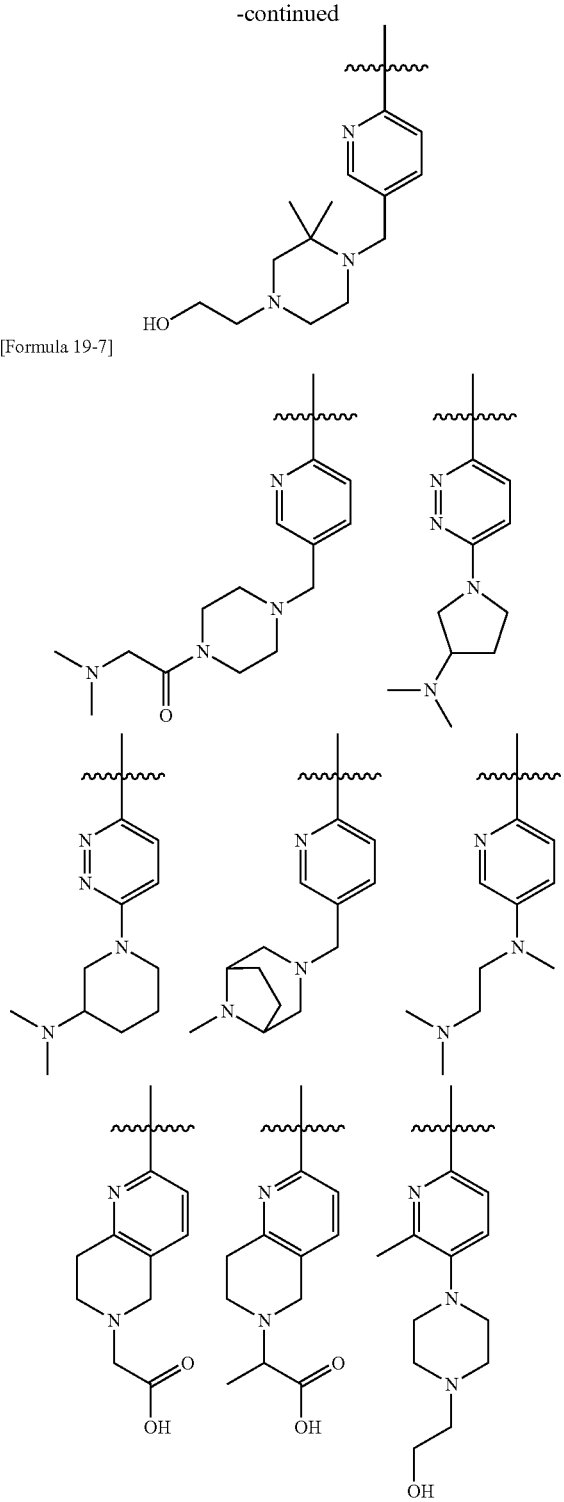

[Formula 19-7]

A preferred compound represented by Formula (I) is composed of a combination of a group selected from the above-defined ones and a preferred group, or a combination of preferred groups.

The compound of the present invention represented by Formula (I) may optionally be formed into a pharmaceutically acceptable salt. Examples of the salt include salts with inorganic acids, such as hydrochloric acid, hydrobromic acid, hydroiodic acid, sulfuric acid, nitric acid, phosphoric acid, carbonic acid, and the like; salts with organic acids, such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid, p-toluenesulfonic acid, and the like; salts with amino acids, such as lysine, arginine, ornithine, glutamic acid, aspartic acid, and the like; salts with alkali metals, such as sodium, potassium, lithium, and the like; salts with alkaline earth metals, such as calcium magnesium, and the like; salts with metals, such as aluminum, zinc, iron, and the like; salts with organic bases, such as methylamine, ethylamine, t-octylamine, diethylamine, trimethylamine, triethylamine, ethylenediamine, piperidine, piperazine, pyridine, picoline, ethanolamine, diethanolamine, triethanolamine, cyclohexylamine, dicyclohexylamine, N-methylglucamine, tris(hydroxymethyl)aminomethane, N,N'-dibenzylethylenediamine, and the like; and ammonium salts and the like.

The present invention also encompasses compounds prepared through replacement of one or more atoms of the compound represented by Formula (I) with stable isotopes or radioisotopes.

The present invention also encompasses stereoisomers, racemates, and all acceptable optical isomers of the compound represented by Formula (I).

Tautomers of the compound of the present invention may be generated depending on the combination of substituents. The present invention also encompasses such tautomers.

Now will be described a typical process for synthesizing the compound of the present invention represented by Formula (I).

The compound of the present invention can be synthesized by the process described below. $R^1$, $R^3$, $R^4$, and $R^7$ shown in the following reaction schemes are as defined in Formula (I). The reagents or solvents and the like shown in the reaction schemes are for illustrative purposes only as described below. Each substituent may optionally be protected with an appropriate protective group or deprotected in an appropriate step (reference: PROTECTIVE GROUPS in ORGANIC SYNTHESIS, 4TH EDITION, John Wiley & Sons, Inc.). The abbreviations of substituents, reagents, and solvents described below and in tables are as follows:

Me: methyl
Et: ethyl
Ph: phenyl
Boc: tert-butoxycarbonyl
Cbz: benzyloxycarbonyl
THF: tetrahydrofuran
DMF: N,N-dimethylformamide
NMP: N-methylpyrrolidone
TFA: trifluoroacetic acid
TBS: tert-butyldimethylsilyl
BINAP: 2,2'-bis(diphenylphosphino)-1,1'-binaphthyl
TBDPS: tert-butyldiphenylsilyl
DIPEA: N,N-Diisopropylethylamine
LAH: Lithium aluminium hydride
DMAP: 4-Dimethylaminopyridine
Ac: acetyl
Ms: mesyl
WSC: water-soluble carbodiimide (1-Ethyl-3-(3-dimethylaminopropyl)carbodiimide)
m-CPBA: m-chloroperoxybenzoic acid
DAST: diethylaminosulfur trifluoride
dba: dibenzylideneacetone DIBAL-H: diisobutylaluminium hydride 1) Synthesis of Compound I-e

[Formula 20]

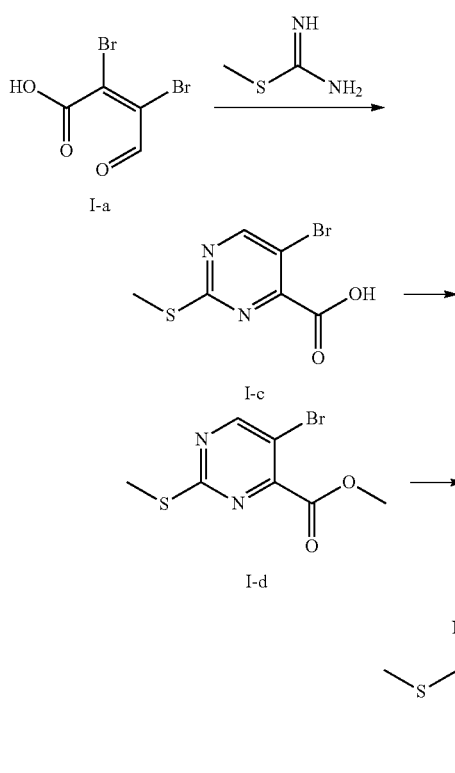

Compound I-e, which is a known compound, can be synthesized by any process known to those skilled in the art; for example, the aforementioned process.

2) Synthesis of Compound I-f from Compound I-e

[Formula 21]

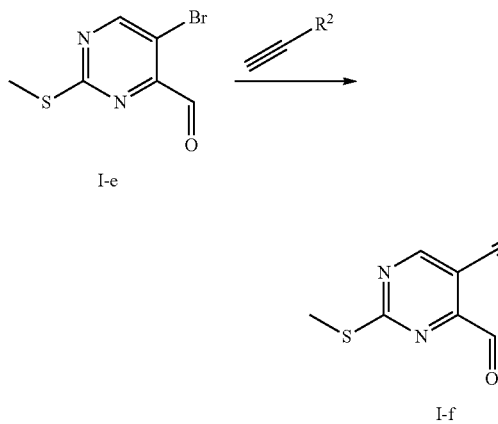

Compound I-e is reacted with a terminal alkyne derivative represented by the formula $R^2$—C≡CH in an appropriate organic solvent (e.g., THF or DMF) in the presence of an appropriate palladium catalyst (e.g., tetrakis(triphenylphosphin)palladium), appropriate copper catalyst (e.g., copper iodide (I)) and appropriate base (e.g., triethylamine) at a temperature of 0° C. to the reflux temperature of the solvent, to yield compound I-f.

3) Synthesis of Compound I-h from Compound I-f

[Formula 22]

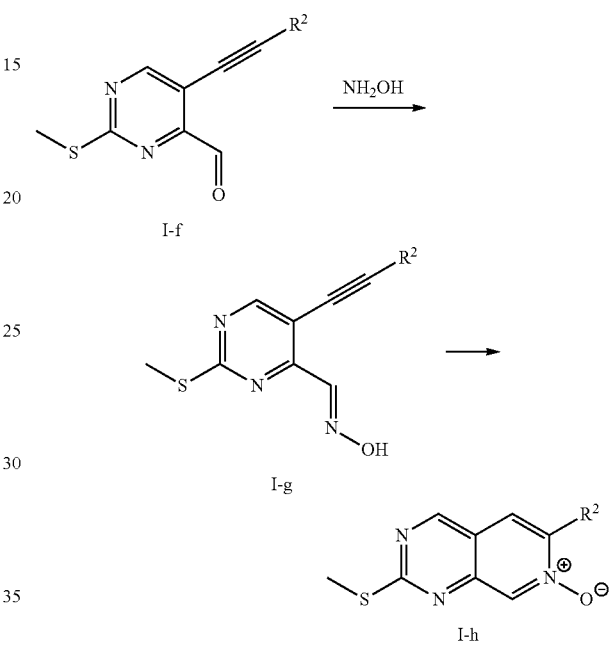

Compound I-f is reacted with hydroxylamine or a salt thereof in an appropriate organic solvent (e.g., ethanol) in the presence or absence of an appropriate base (e.g., sodium acetate) at a temperature of 0° C. to the reflux temperature of the solvent. The resultant hydroxyimine compound is reacted with an appropriate acid or base (e.g., silver triflate or potassium carbonate) to yield compound I-h.

4) Synthesis of Compound I-i from Compound I-h

[Formula 23]

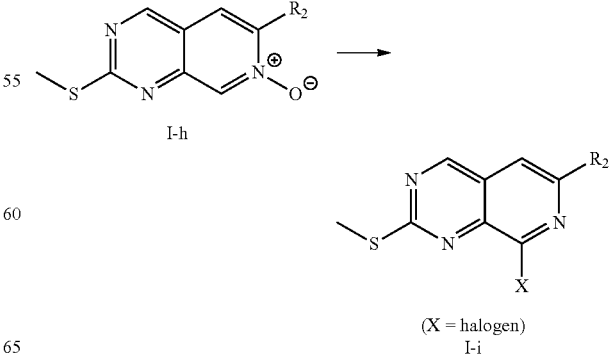

(X = halogen)

Compound I-h is reacted with an appropriate halogenating agent (e.g., thionyl chloride) in an appropriate organic solvent (e.g., dichloromethane) or under solvent-free conditions at a temperature of 0° C. to 140° C., to yield compound I-i.

5) Synthesis of Compound I-j from Compound I-i

[Formula 24]

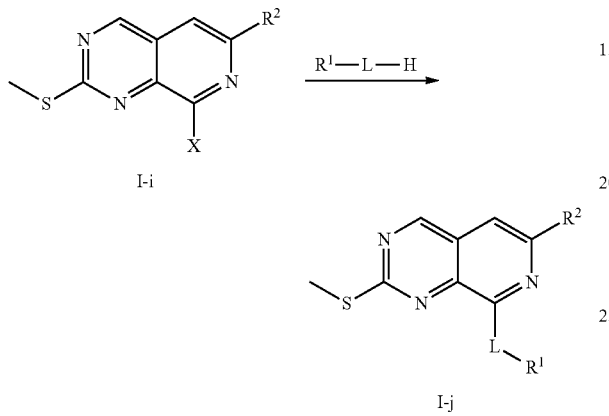

Compound I-i is reacted with an amine, alcohol, or thiol derivative represented by the formula R$^1$-L-H in an appropriate organic solvent (e.g., THF or 1,4-dioxane) or under solvent-free conditions in the presence or absence of an appropriate base (e.g., triethylamine, potassium carbonate, or sodium hydride) at a temperature of 0° C. to the reflux temperature of the solvent, to yield compound I-j.

In this step, R$^2$ may be modified by any process known to those skilled in the art in view of the intended structure of the compound.

6) Synthesis of Compound I-k from Compound I-j

[Formula 25]

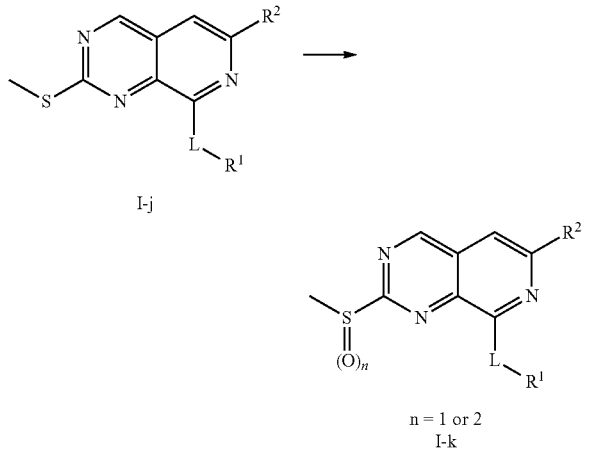

Compound I-j is reacted with an appropriate oxidant (e.g., Oxone® or m-chloroperbenzoic acid) in an appropriate organic solvent (e.g., dichloromethane or water) at a temperature of 0° C. to the reflux temperature of the solvent, to yield compound I-k.

7) Synthesis of Compound I-l from Compound I-k

[Formula 26]

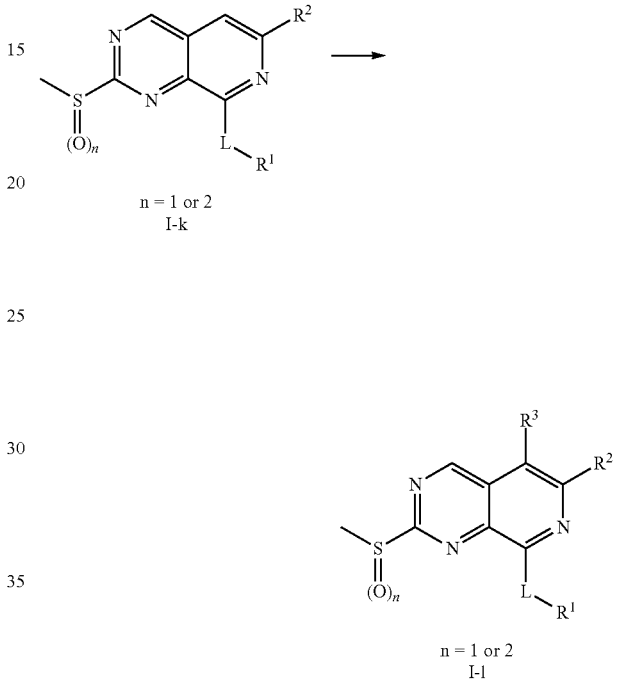

Compound I-k is reacted with an appropriate halogenating agent (e.g., N-chlorosuccinimide) in an appropriate organic solvent (e.g., dichloromethane or 1,2-dichloroethane) at a temperature of 0° C. to the reflux temperature of the solvent, to yield compound I-l.

In this step, R$^3$ may be modified by any process known to those skilled in the art in view of the intended structure of the compound.

8) Synthesis of Compound I-m from Compound I-l

[Formula 27]

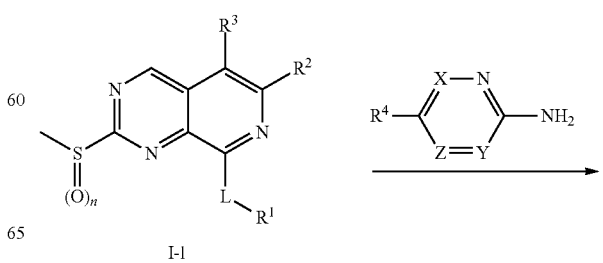

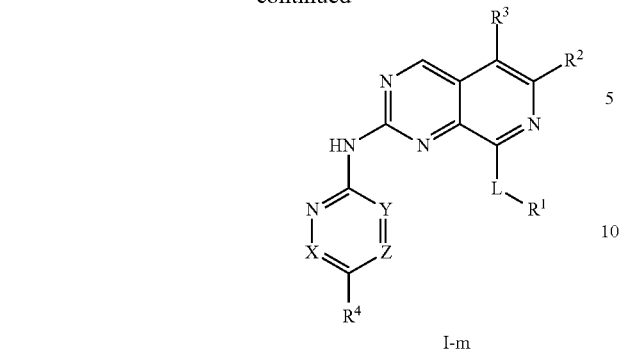

I-m n = 1 or 2

Compound I-1 is reacted with an amine derivative represented by the formula $R^4$-(nitrogen-containing heteroaryl with X, Y, and Z) —$NH_2$ of the above scheme in an appropriate organic solvent (e.g., NMP, THF, or toluene) or under solvent-free conditions in the presence or absence of an appropriate base (e.g., sodium hydride, triethylamine, or N,N-diisopropyl-N-ethylamine) at a temperature of 0° C. to the reflux temperature of the solvent, to yield compound I-m.

If L, $R^1$, $R^2$, or $R^4$ of compound I-m is protected with an appropriate protective group, deprotection can be performed by any process known to those skilled in the art. For example, deprotection can be performed through reaction of the compound with an appropriate deprotecting reagent (e.g., TFA or hydrogen chloride for a Boc protective group, lithium hydroxide for a benzoyl protective group, or hydrogen in the presence of Pd/C for a Cbz protective group) in an appropriate organic solvent (e.g., dichloromethane, methanol, or THF) or under solvent-free conditions at a temperature of 0° C. to the reflux temperature of the solvent (reference: Green's Protective Groups in Organic Synthesis, 4th edition, John Wiley & Sons Inc.).

If compound I-m is protected with two or more protective groups, deprotection may be performed in an appropriate order depending on the structure of compound I-m.

In each of the reactions 9) to 13) described below, L, $R^1$, $R^2$, or $R^4$ of compound I-m is appropriately protected depending on the corresponding reaction conditions. After completion of the reaction, deprotection can be performed by an appropriate process.

9) Synthesis of Compound I-n from Compound I-m

[Formula 28]

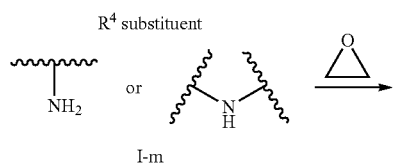

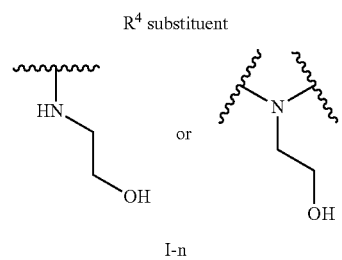

I-n

Compound I-m in which $R^4$ has a primary or secondary amine structure is reacted with an optionally substituted epoxide in an appropriate organic solvent (e.g., dichloromethane, NMP, or THF) in the presence or absence of an appropriate acid (e.g., boron trifluoride-diethyl ether complex) or an appropriate base (e.g., potassium carbonate or triethylamine) at a temperature of 0° C. to the reflux temperature of the solvent, to yield compound I-n.

10) Synthesis of Compound I-o from Compound I-m

[Formula 29]

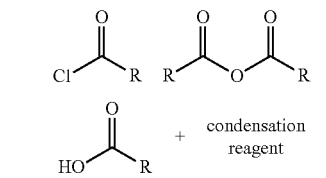

I-m

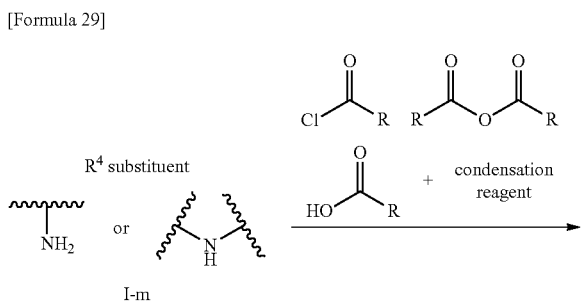

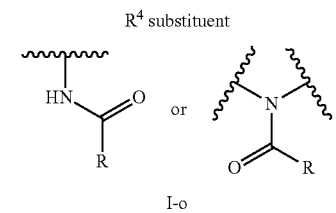

I-o

Compound I-m in which $R^4$ has a primary or secondary amine structure is reacted with a carboxylic acid chloride, a carboxylic anhydride, or a carboxylic acid and a condensation reagent in an appropriate organic solvent (e.g., NMP, THF, or pyridine) in the presence or absence of an appropriate base (e.g., triethylamine or N,N-diisopropyl-N-ethylamine) at a temperature of 0° C. to the reflux temperature of the solvent, to yield compound I-o.

11) Synthesis of Compound I-p from Compound I-m

[Formula 30]

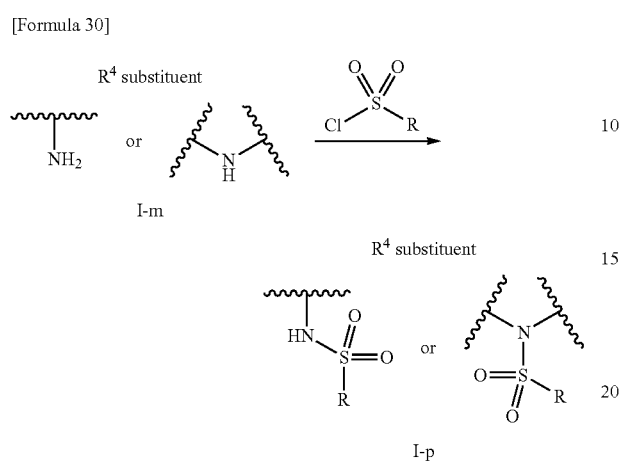

Compound I-m in which $R^4$ has a primary or secondary amine structure is reacted with sulfonic acid chloride in an appropriate organic solvent (e.g., NMP, THF, or pyridine) in the presence or absence of an appropriate base (e.g., triethylamine or N,N-diisopropyl-N-ethylamine) at a temperature of 0° C. to the reflux temperature of the solvent, to yield compound I-p.

12) Synthesis of Compound I-q from Compound I-m

[Formula 31]

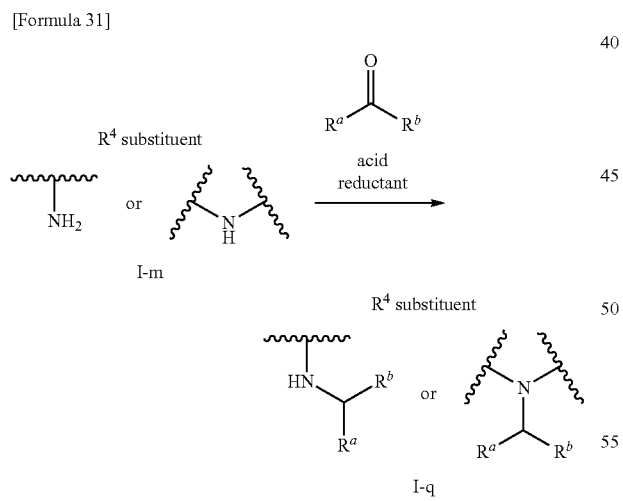

Compound I-m in which $R^4$ has a primary or secondary amine structure is reacted with an optionally substituted ketone or aldehyde and an appropriate reductant (e.g., sodium triacetoxyborohydride or sodium cyanoborohydride) in an appropriate organic solvent (e.g., NMP or methanol) in the presence of an appropriate acid (e.g., acetic acid) at a temperature of room temperature to the reflux temperature of the solvent, to yield compound I-q.

13) Synthesis of Compound I-r from Compound I-m

[Formula 32]

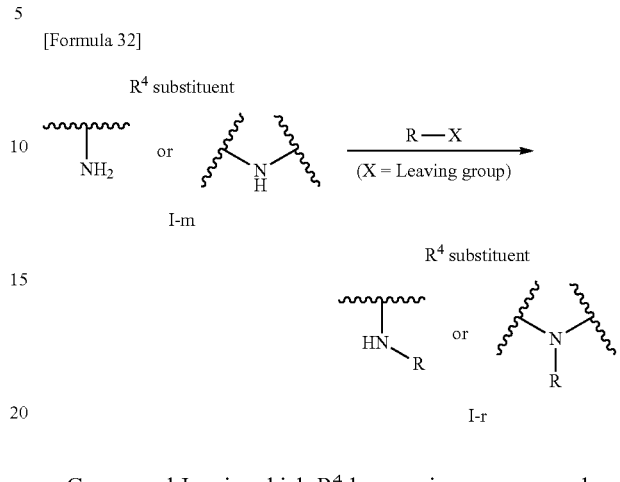

Compound I-m in which $R^4$ has a primary or secondary amine structure is reacted with a compound having a leaving group (e.g., a halogen atom or a sulfonyloxy group) in an appropriate organic solvent (e.g., NMP, THF, or pyridine) in the presence or absence of an appropriate base (e.g., triethylamine or N,N-diisopropyl-N-ethylamine) at a temperature of 0° C. to the reflux temperature of the solvent, to yield compound I-r.

14) Synthesis of Compound I-s from Compound I-m

[Formula 33]

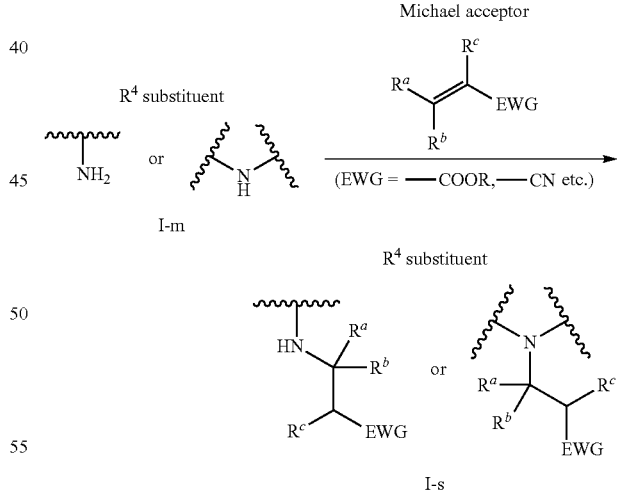

Compound I-m in which $R^4$ has a primary or secondary amine structure is reacted with a compound having a structure of Michael acceptor in an appropriate organic solvent (e.g., methanol, THF) at a temperature of 0° C. to the reflux temperature of the solvent to yield compound I-s.

The compound of the present invention exhibits a CDK4/6 inhibitory activity and thus is useful for the prevention or treatment of a disease associated with CDK4/6. Specifically, the compound is useful for the treatment of rheumatoid arthritis, arteriosclerosis, pulmonary fibrosis, cerebral infarction, or cancer and the protection of bone marrow. In particular, the compound is effective for the treatment of rheumatoid arthritis or cancer and the protection of bone marrow.

The compound of the present invention preferably exhibits selectivity for the CDK4/6 inhibitory activity compared to the inhibitory activity against another cyclin-dependent kinase, such as CDK2 inhibitory activity. Such selectivity of the compound is expected to reduce the expression of genotoxicity because the inhibition of CDK2 is also involved in DNA replication. Preferably, the compound of the present invention selectively inhibits CDK4 rather than CDK2.

The active ingredient of the present invention may be provided in any preparation form, such as a solid, semisolid, or liquid form, and the like. The active ingredient may be provided in any dosage form, such as an oral form or a parenteral form (e.g., an injection, a transdermal agent, an eye drop, a suppository, a nasal agent, or an inhalant, and the like).

A drug containing the active ingredient of the present invention is prepared with a common additive used for drug preparation. Examples of the additive for solid drugs include excipients, such as lactose, sucrose, glucose, cornstarch, potato starch, crystalline cellulose, light silicic anhydride, synthetic aluminum silicate, magnesium aluminometasilicate, calcium hydrogen phosphate, and the like; binders, such as crystalline cellulose, carboxymethyl cellulose, hydroxypropyl cellulose, sodium carboxymethyl cellulose, poly(vinylpyrrolidone), and the like; disintegrants, such as starch, sodium carboxymethyl cellulose, calcium carboxymethyl cellulose, croscarmellose sodium, sodium carboxymethyl starch, and the like; lubricants, such as talc stearic acid, and the like; coating agents, such as hydroxymethyl propyl cellulose, hydroxypropyl methyl cellulose phthalate, ethyl cellulose, and the like; and colorants. Examples of the additive for semisolid drugs include bases, such as white vaseline, and the like. Examples of the additive for liquid drugs include solvents, such as ethanol, and the like; solubilizers, such as ethanol, and the like; preservatives, such as paraoxybenzoic acid esters, and the like; isotonic agents, such as glucose, and the like; buffers, such as citric acid, and the like; antioxidants, such as L-ascorbic acid, and the like; chelators, such as EDTA, and the like; suspending agents and emulsifiers, such as polysorbate 80, and the like; and the like.

The dose of the active ingredient of the present invention is typically about 1 to 1,000 mg/day. The active ingredient is typically administered once to three times a day.

EXAMPLES

The present invention will now be described in detail by way of Examples, which should not be construed as limiting the invention.

The structure of an isolated novel compound was determined by $^1$H-NMR and/or mass spectrometry with a single quadrupole instrumentation equipped with an electron spray source, and other appropriate analytical methods. Chemical shifts (δ: ppm) and coupling constants (J: Hz) are shown for the $^1$H-NMR spectra (400 MHz, DMSO-$d_6$, $CD_3OD$ or $CDCl_3$). Abbreviations are as follows: s (singlet), d (doublet), t (triplet), q (quartet), brs (broad singlet), and m (multiplet). For the results of mass spectrometry, measurements are represented by $(M+H)^+$; i.e., a value corresponding to a proton $(H^+)$ attached to the molecular mass (M) of a compound.

Reference Example 1

Synthesis of 5-bromo-2-(methylthio)pyrimidine-4-carboxylic acid

[Formula 34]

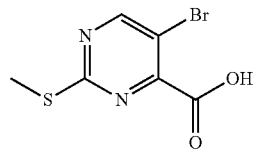

Mucobromic acid (300 g, 1.16 mol) was added to an aqueous solution (2.5 L) of 2-methyl-2-pseudothiourea sulfate (324 g, 1.16 mol) at room temperature. The resultant suspension was cooled to 0° C. with stir, and triethylamine (486 mL, 3.49 mol) was added dropwise thereto over four hours. The resultant reaction mixture was stirred overnight, and the completion of the reaction was confirmed by silica gel TLC. The reaction mixture was then acidified with concentrated hydrochloric acid (about 250 mL). The resultant yellow solid was collected by filtration and washed twice with water (500 mL) and then twice with diethyl ether (500 mL). The solid was dried under reduced pressure to yield the title compound (160 g, 55%).

Reference Example 2

Synthesis of methyl 5-bromo-2-methylthiopyrimidine-4-carboxylate

[Formula 35]

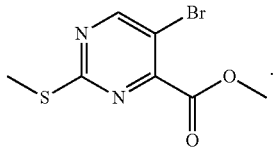

A solution of 5-bromo-2-(methylthio)pyrimidine-4-carboxylic acid (110 g, 0.44 mol) in methanol (1.1 L) was cooled to 0° C. with stir, and thionyl chloride (50 mL, 0.66 mol) was added dropwise thereto. The resultant reaction mixture was slowly heated, and the reaction was allowed to proceed under reflux for four hours. The completion of the reaction was confirmed by LC/MS and TLC, and the reaction mixture was cooled to room temperature. The volatiles were removed through evaporation under reduced pressure, and the residue was dissolved in ethyl acetate (1 L). The resultant solution was washed three times with 10% aqueous sodium carbonate solution (200 mL) and then twice with saturated brine (200 mL). The resultant organic phase was dried over anhydrous magnesium sulfate, and solid was separated by filtration. The filtrate was then concentrated under reduced pressure, and the resultant crude product was purified by silica gel column chromatography to yield the title compound (88 g, 75%).

Reference Example 3

Synthesis of Mixture of 5-bromo-2-methylthiopyrimidine-4-carbaldehyde and (5-bromo-2-methylthiopyrimidin-4-yl)methoxymethanol

[Formula 36]

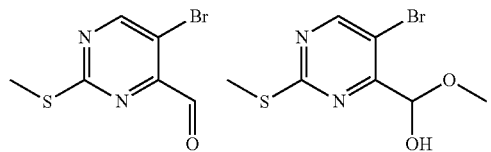

A solution (375 mL) of methyl 5-bromo-2-methylsulfanylpyrimidine-4-carboxylate (25 g, 95 mmol) in THF was cooled to −78° C. and stirred under a nitrogen atmosphere. DIBAL-H (84 mL, 143 mmol, 1.7M toluene solution) was added dropwise to the THF solution, and the mixture was stirred at −78° C. for four hours. The completion of the reaction was confirmed by TLC, and the reaction was quenched through dropwise addition of methanol at −78° C. The resultant reaction mixture was allowed to warm slowly to 0° C. and diluted with ethyl acetate, and the mixture was filtrated through celite. The filtrate was washed twice with saturated brine (200 mL), and the resultant organic phase was dried over anhydrous magnesium sulfate. The resultant solid was separated by filtration, and the filtrate was concentrated to yield the title compound mixture (25 g, crude product). The crude product was used for the subsequent reaction without further purification.

Reference Example 4

Synthesis of tert-butyl 4-(6-nitropyridin-3-yl)piperazine-1-carboxylate

[Formula 37]

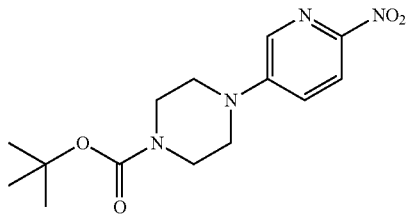

A mixture of 5-Bromo-2-nitropyridine (203 g, 1.37 mol), piperazine (153 g, 1.77 mol), tetrabutylammonium iodide (25.2 g, 0.068 mol), and potassium carbonate (207 g, 1.50 mol) in dimethyl sulfoxide (2.6 L) was stirred at 80° C. overnight. The resultant reaction mixture was cooled to room temperature, and the mixture was poured into water (7 L). The resultant solid was collected by filtration, and the solid was washed with dichloromethane (1 L×2) and dried. The filtrate was extracted with chloroform (2 L×7). The resultant organic phase was washed with water (2 L) and then with saturated brine (2 L), and the organic phase was concentrated under reduced pressure to yield solid. The resultant solid products were combined together and used for the subsequent reaction without further purification.

The solid product (490 g) was dissolved in THF (2 L) and water (500 mL), and sodium hydrogen carbonate (119 g, 1.42 mol) was added to the solution. To the resultant suspension was added di-tert-butyl dicarboxylate (262 g, 1.2 mol), and the mixture was stirred at room temperature for three hours. The reaction mixture was concentrated under reduced pressure, and the residue was diluted with water (1 L) and extracted with dichloromethane (1 L×3). The resultant organic phases were combined together and then washed with water (1 L). The aqueous phase was extracted with dichloromethane (300 mL). The resultant organic phases were combined together and dried over anhydrous magnesium sulfate. The solid was separated by filtration, and the filtrate was concentrated under reduced pressure. The resultant solid was suspended in ethyl acetate (2 L) and heated to 60° C., and the solid was separated by filtration at 60° C. The solid was dried under reduced pressure to yield the title compound (191 g, 62%)

APCI-MS (M+H)$^+$309.1, $C_{14}H_{20}N_4O_4$=308.15

$^1$H-NMR δ(400 MHz, CDCl$_3$): 8.16 (d, J=9 Hz, 1H), 8.11 (d, J=3 Hz, 1H), 7.19 (dd, J=9.3 Hz, 1H), 3.64-3.61 (m, 4H), 3.45-3.42 (m, 4H), 1.47 (s, 9H).

Reference Example 5

Synthesis of tert-butyl 4-(6-aminopyridin-3-yl)piperazine-1-carboxylate

[Formula 38]

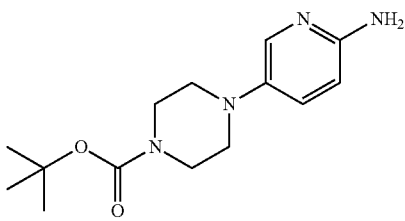

The tert-butyl 4-(6-nitropyridin-3-yl)piperazine-1-carboxylate synthesized in Reference Example 4 (83 g, 269 mmol) was dissolved in methanol (1.3 L) in Parr Shaker and Raney nickel (15 g, 50% aqueous suspension) was added thereto. The resultant reaction mixture was stirred under a hydrogen atmosphere (50 psi) for five hours. The reaction mixture was filtered through a Celite pad to separate solid, and the filtrate was concentrated under reduced pressure. The resultant solid was suspended in diethyl ether (120 mL) and stirred for four hours. Heptane was added to the suspension and cooled at 0° C. for 45 minutes. The resultant solid was separated by filtration and dried under reduced pressure to yield the title compound (62.5 g, 83%).

ESI-MS (M+H)$^+$ 279, $C_{14}H_{22}N_4O_2$=278.17

Intermediates A-1 to A-44 were each synthesized by the process of Reference Example 4 and/or 5 with the corresponding halopyridine derivatives and amine derivatives. Appropriate protection or deprotection was performed as needed.

[Formula 39]
A-1 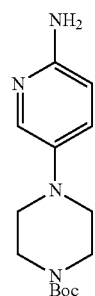
A-2 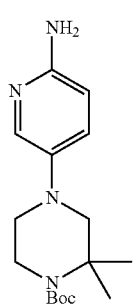
A-3 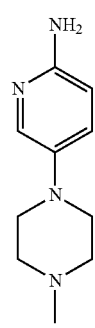
A-4 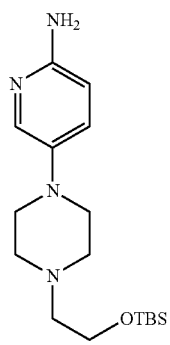
A-5 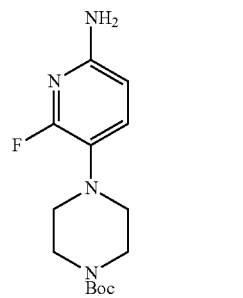
-continued
A-6 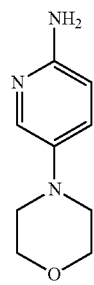
A-7 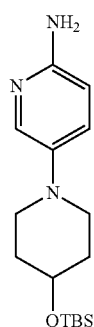
A-8 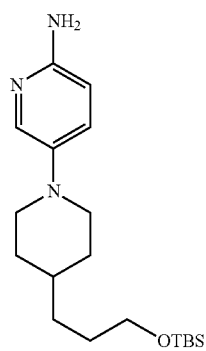
A-9 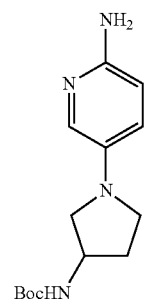
A-10 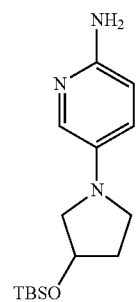

-continued
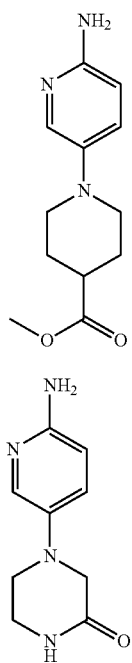
A-11
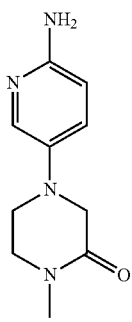
A-12
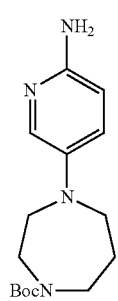
A-13
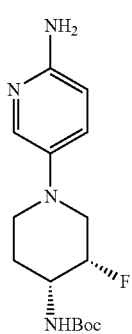
A-14
[Formula 40]
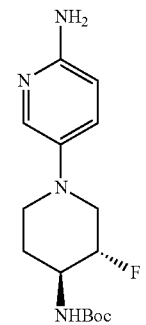
A-15
-continued
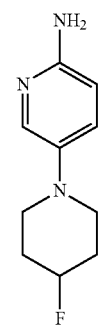
A-16
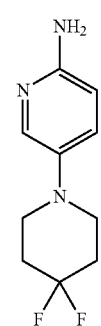
A-17
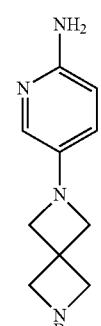
A-18
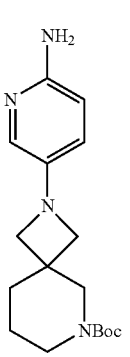
A-19
A-20

-continued
A-21
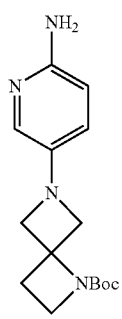
A-22
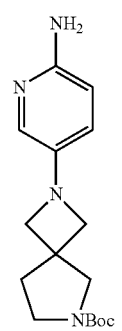
A-23
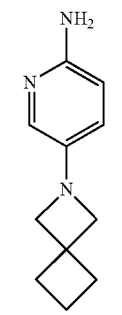
A-24
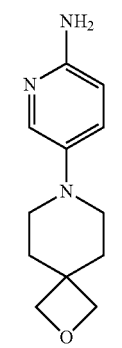
A-25
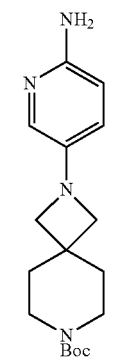
-continued
A-26
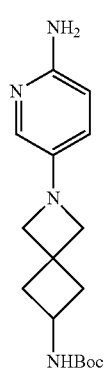
A-27
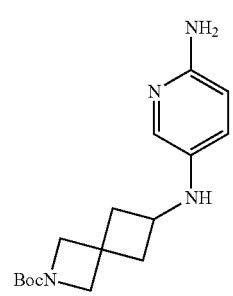
A-28
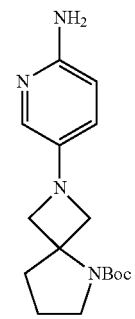
A-29
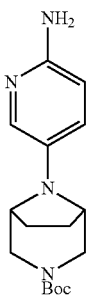
A-30
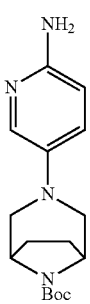

A-31
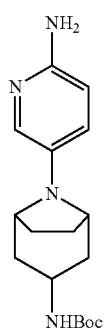
A-32
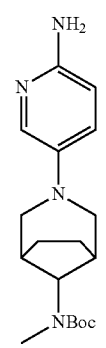
A-33
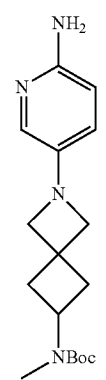
A-34
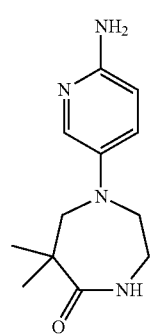
A-35
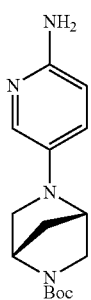
A-36
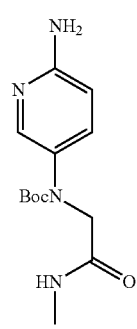
A-37
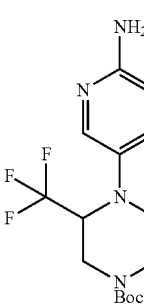
A-38
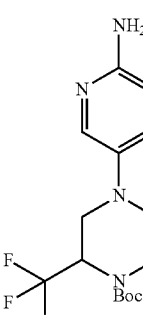
A-39
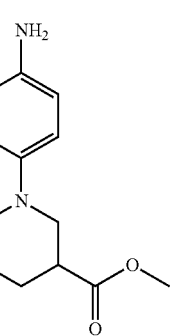

A-40
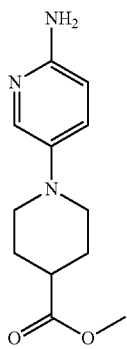

A-41
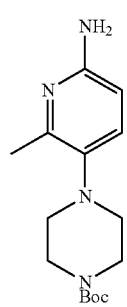

A-42
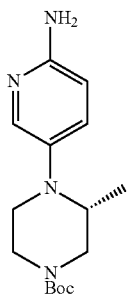

A-43
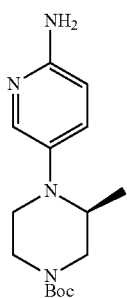

A-44
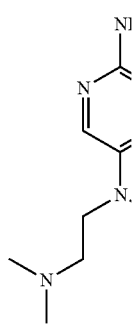

Reference Example 6

Synthesis of 6-aminopyridine-3-carbaldehyde

[Formula 41]

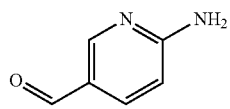

6-Aminopyridine-3-carbonitrile (1.9 g, 16 mmol) was dissolved in THF (160 mL) and cooled to −78° C. with stir. Diisobutylaluminium hydride (106.5 mL, 1.5M toluene solution) was slowly added dropwise to the solution at −78° C. and the mixture was allowed to warm to 20° C. with stir, followed by further stirring for two hours. The reaction was quenched by addition of ice water (100 mL) to the resultant reaction mixture, and the mixture was extracted three times with dichloromethane (50 mL). The resultant organic phases were combined together and then washed once with brine (100 mL) and dried over anhydrous sodium sulfate. The solid was separated by filtration, and the filtrate was concentrated under reduced pressure. The residue was roughly purified by silica gel column chromatography to yield a crude product of the title compound (1.7 g). The crude product was used for the subsequent reaction without further purification.

Reference Example 7

Synthesis of tert-butyl 4-[(6-aminopyridin-3-yl)methyl]piperazine-1-carboxylate

[Formula 42]

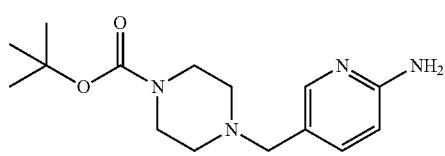

The crude 6-aminopyridine-3-carbaldehyde synthesized in Reference Example 6 (1.7 g, 13.9 mmol) and tert-butyl piperazine-1-carboxylate (3.2 g, 17.2 mmol) were dissolved in dichloromethane (50 mL) and stirred at room temperature for eight hours. To the resultant mixture was added sodium triacetoxyborohydride (8.84 g, 40.9 mmol) and stirred at room temperature for two hours. The reaction was monitored by LC/MS. After completion of the reaction, the reaction was quenched through addition of saturated aqueous sodium carbonate solution (50 mL), and the reaction mixture was extracted three times with ethyl acetate (50 mL). The resultant organic phases were combined together, and the mixture was washed once with brine (100 mL) and dried over anhydrous sodium sulfate. The resultant solid was separated by filtration, and then the filtrate was concentrated under reduced pressure. The residue was roughly purified by silica gel column chromatography to yield the title compound (3.3 g, 81%).

Reference Example 8

Synthesis of di-tert-butyl (5-methylpyridin-2-yl)imidodicarbonate

[Formula 43]

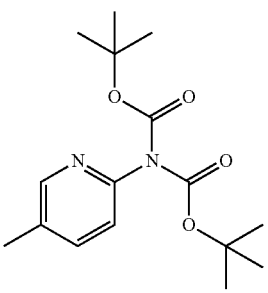

In reference to the process disclosed in WO2010/141406, 5-methylpyridine-2-amine (20 g, 185 mmol) and di-tert-butyl dicarbonate (101 g, 462 mmol) were dissolved in THF (160 mL) and 4-N,N-dimethylaminopyridine (3.6 g, 29.7 mmol) was added to the solution. The resultant reaction mixture was stirred at room temperature for three days. The reaction mixture was concentrated under reduced pressure, and the residue was dissolved in ethyl acetate and washed with water. The resultant organic phase was washed with saturated brine and dried over anhydrous sodium sulfate. The solid was separated by filtration, and the filtrate was concentrated. The resultant solid was dissolved in ethyl acetate (50 mL) and heptane (50 mL) was added thereto. The solid was collected by filtration and dried under reduced pressure, to yield the title compound (25.1 g, 44%). The filtrate was concentrated, and the residue was purified by silica gel column chromatography to yield the title compound (17.9 g, 31%).

Reference Example 9

Synthesis of di-tert-butyl [5-(bromomethyl)pyridin-2-yl]imidodicarbonate

[Formula 44]

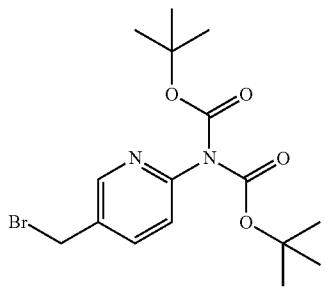

The di-tert-butyl (5-methylpyridin-2-yl)imidodicarbonate synthesized in Reference Example 8 (17.2 g, 55.8 mmol), N-bromosuccinimide (12.17 g, 68.4 mmol), and benzoyl peroxide (1.5 g, 8.1 mmol) were dissolved in carbon tetrachloride (100 mL) and the reaction was stirred at 80° C. for six hours. The reaction mixture was cooled to room temperature, and the resultant solid was separated by filtration. The filtrate was then concentrated under reduced pressure, and the residue was purified by silica gel column chromatography to yield a mixture of the title compound, di-tert-butyl [5-(dibromomethyl)pyridin-2-yl]imidodicarbonate, and di-tert-butyl (5-methylpyridin-2-yl)imidodicarbonate (14.5 g, 60.3:4.4:35.3, determined by the 1H-NMR spectrum). The mixture was used for the subsequent reaction without further purification.

Reference Example 10

[Formula 45]

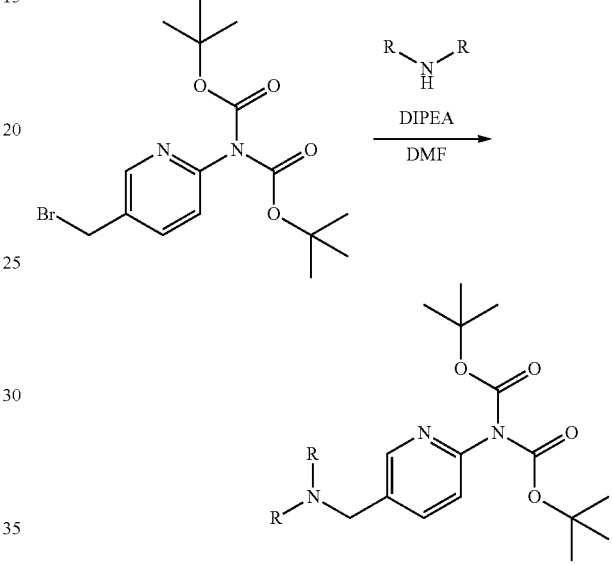

Di-tert-butyl [5-(bromomethyl)pyridin-2-yl]imidodicarbonate (1 equivalent) was dissolved in DMF and an appropriate amine derivative (1.5 equivalents) and N,N-diisopropyl-N-ethylamine (3 equivalents) was added to the solution at room temperature. The reaction mixture was stirred at room temperature for several hours, and the mixture was then diluted with ethyl acetate and washed with saturated brine. The resultant organic phase was dried over anhydrous sodium sulfate, and the solid was separated by filtration. The filtrate was then concentrated under reduced pressure, and the residue was purified by silica gel column chromatography to yield a target amine derivative.

Reference Example 11

[Formula 46]

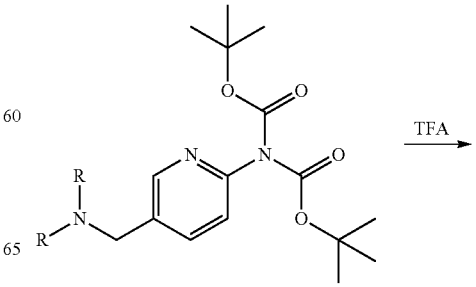

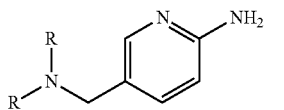

To the compound synthesized in Reference Example 10 was added an excess amount of trifluoroacetic acid and stirred at room temperature for several hours. The reaction mixture was concentrated under reduced pressure, and the resultant TFA salt of the target product was dissolved in methanol and applied onto a strong cation exchange resin (SCX). The SCX column was washed with methanol and the target product was eluted with ammonia (2 mol/L, methanol solution). The eluate was concentrated under reduced pressure to yield a target 2-aminopyridine derivative. The resultant product was used for the subsequent reaction without further purification.

In the case of the presence of a primary or secondary amino group in the compound besides the aminopyridine structure, the crude product was dissolved in THF and reacted with di-tert-butyl dicarbonate at room temperature. After completion of the reaction, the solvent was removed through evaporation, and the residue was roughly purified by silica gel column chromatography to yield a 2-aminopyridine derivative having a primary or secondary amino group protected with a Boc group.

Intermediates B-1 to B-68 were each synthesized by any of the processes of Reference Example 6 and/or 7 or Reference Examples 8 to 11 or a combination of the processes with the corresponding aldehyde or alkyl halide derivatives and amine derivatives. Appropriate protection or deprotection was performed as needed.

[Formula 47]

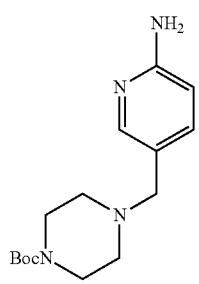

B-1

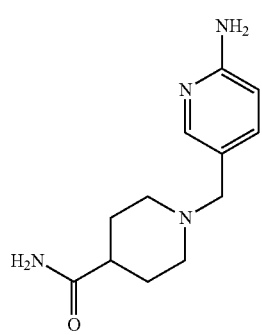

B-2

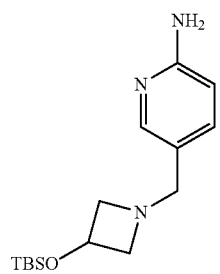

B-3

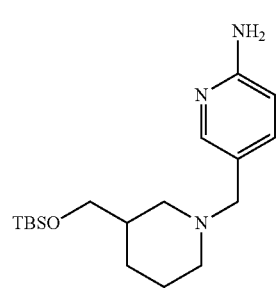

B-4

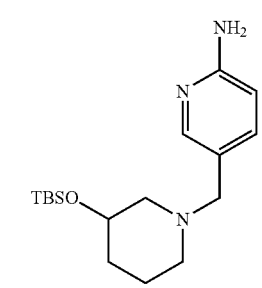

B-5

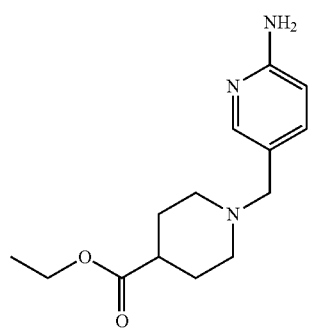

B-6

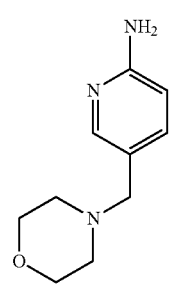

B-7

B-8 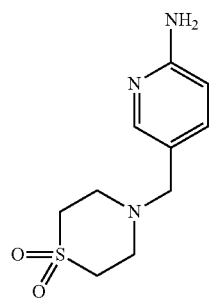
B-9 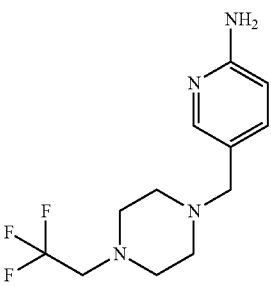
B-10 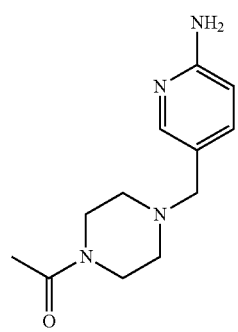
B-11 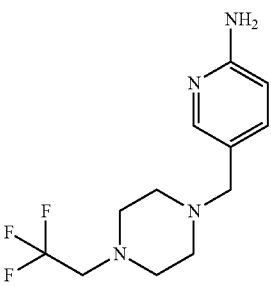
B-12 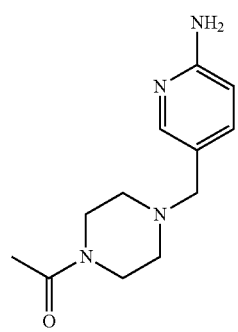
B-13 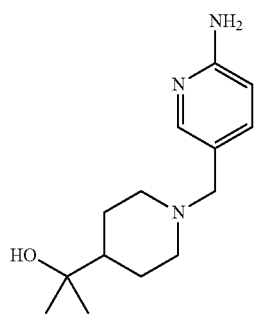
B-14 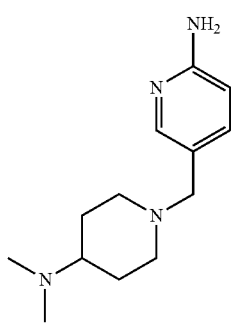
B-15 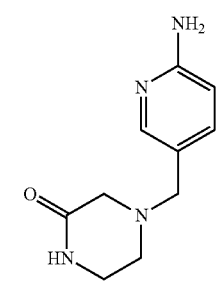
B-16 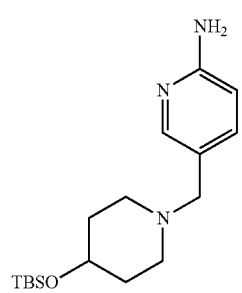
B-17 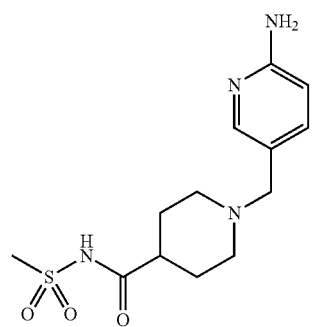

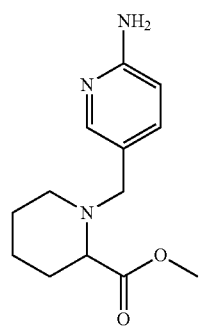
B-18
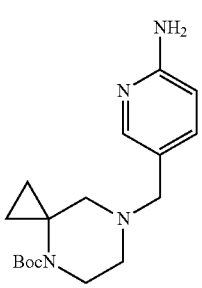
B-23
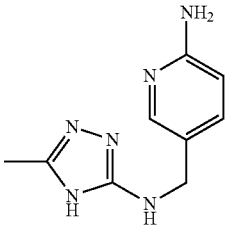
B-19
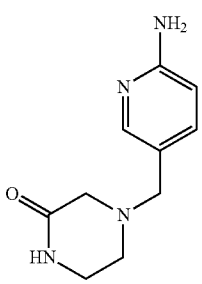
B-24
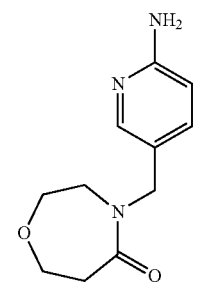
B-20
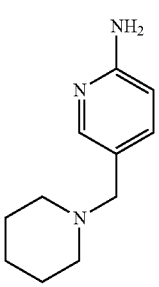
B-25
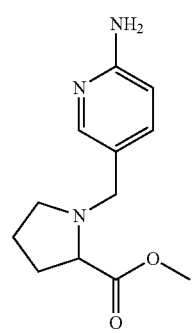
B-21
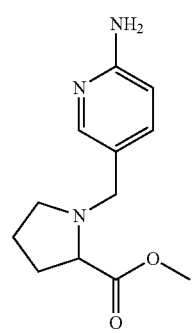
B-26
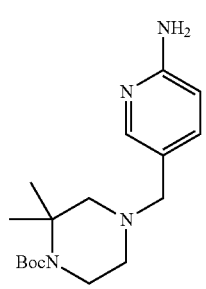
B-22
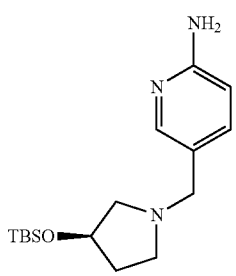
B-27

| | |
|---|---|
| B-28 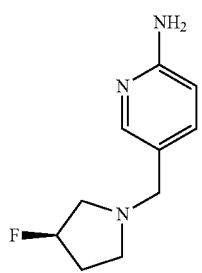 | B-33 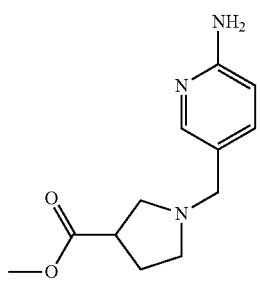 |
| B-29 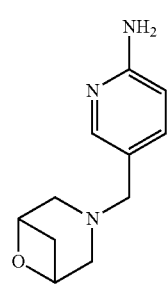 | B-34 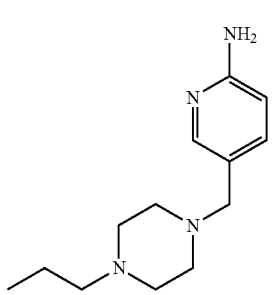 |
| B-30 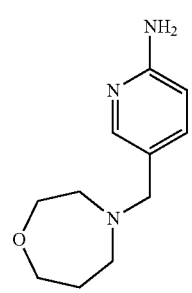 | B-35 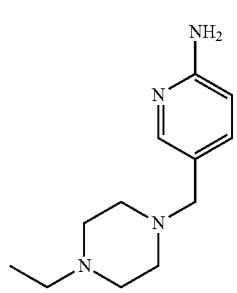 |
| B-31 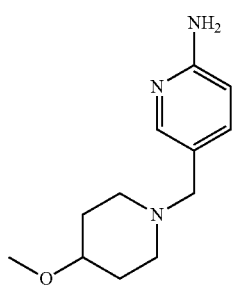 | B-36 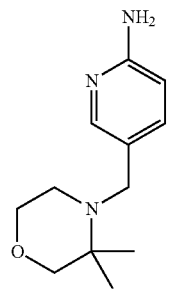 |
| B-32 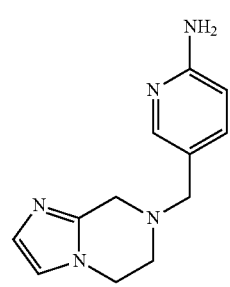 | B-37 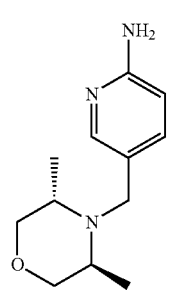 |

B-38 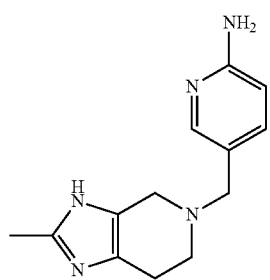
B-39 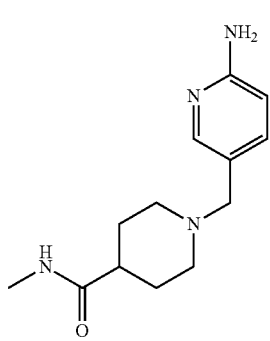
[Formula 48-1]
B-40 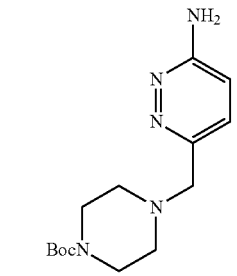
B-41 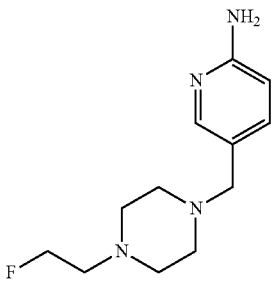
B-42 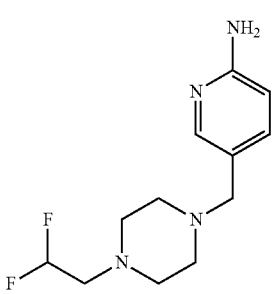
B-43 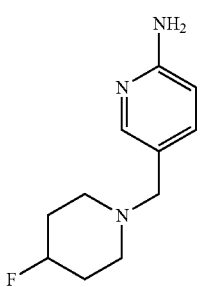
B-44 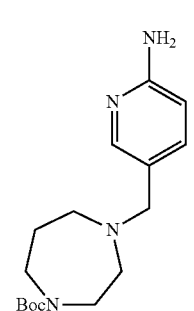
B-45 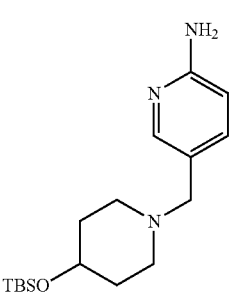
B-46 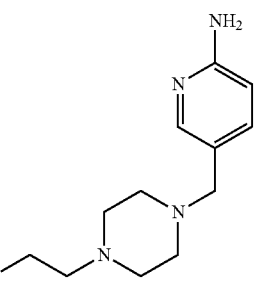
B-47 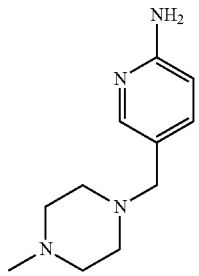

| 101 -continued | | 102 -continued | |
|---|---|---|---|
| B-48 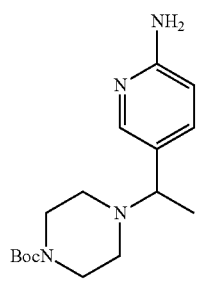 | | B-53 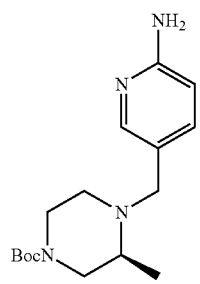 | |
| B-49 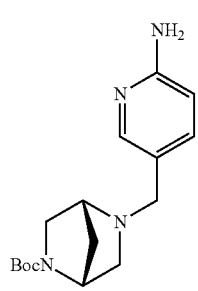 | | B-54 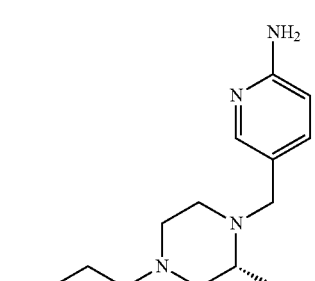 | |
| B-50 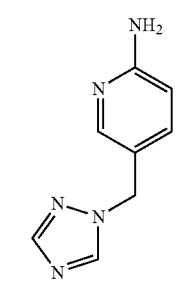 | | B-55 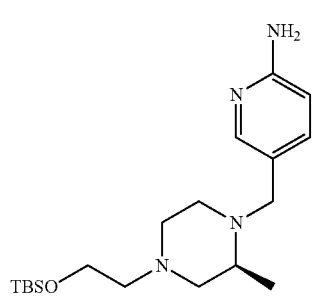 | |
| B-51 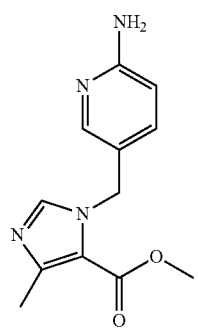 | | B-56 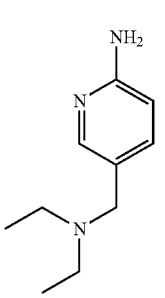 | |
| B-52 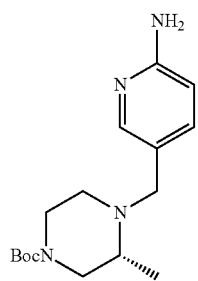 | | B-57 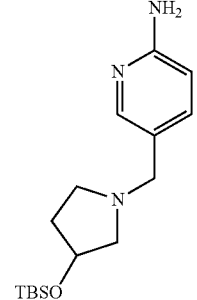 | |

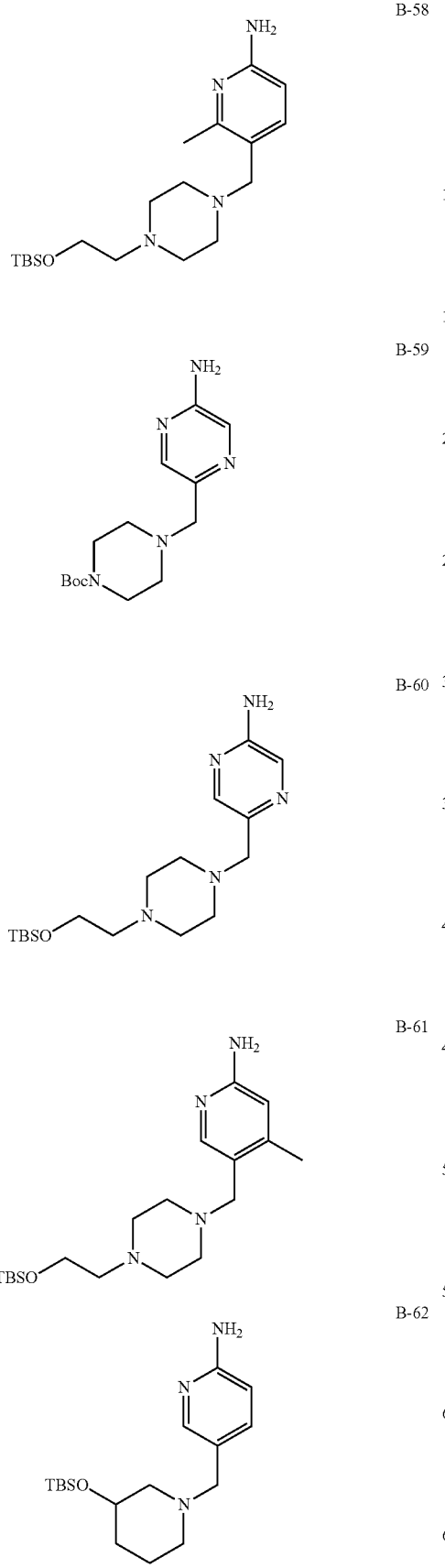
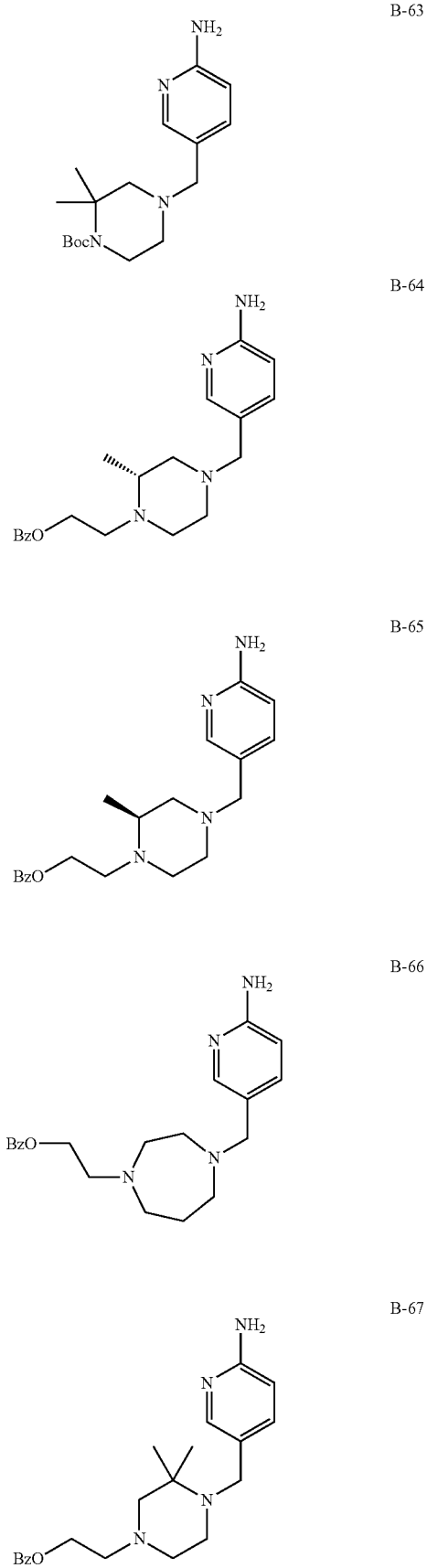

-continued

[Formula 48-2]

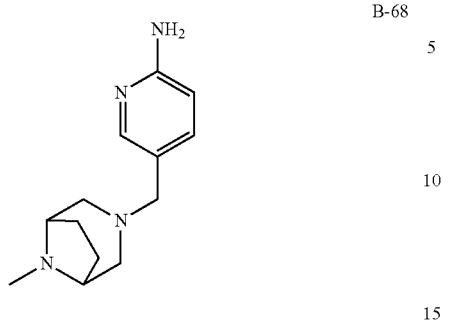

B-68

Reference Example 12

[Formula 49]

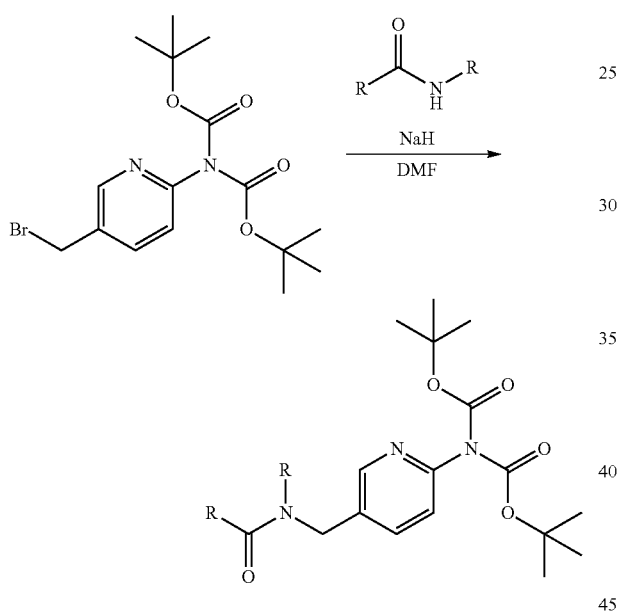

An appropriate amide derivative (1 equivalent) was dissolved in DMF, and sodium hydride (1 equivalent) was gradually added thereto at 0° C. and the mixture was stirred at room temperature for several minutes. The resultant reaction mixture was cooled to 0° C. and di-tert-butyl [5-(bromomethyl)pyridin-2-yl]imidodicarbonate (1.5 equivalents) was gradually added to the mixture. The reaction mixture was stirred at room temperature for several hours and then water was added to the mixture to stop the reaction. The mixture was extracted with ethyl acetate and washed with saturated brine. The resultant organic phase was dried over anhydrous sodium sulfate, and the solid was separated by filtration. The filtrate was concentrated under reduced pressure, and the residue was purified by silica gel column chromatography to yield a target amide derivative.

The following intermediates C-1 to C-5 were synthesized by the process of Reference Example 12 and 11 with the corresponding alkyl halide derivatives, amide derivatives, or urea derivatives. Appropriate protection or deprotection was performed as needed.

[Formula 50]

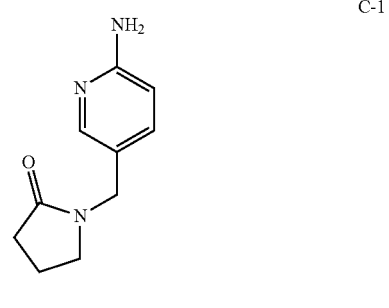
C-1

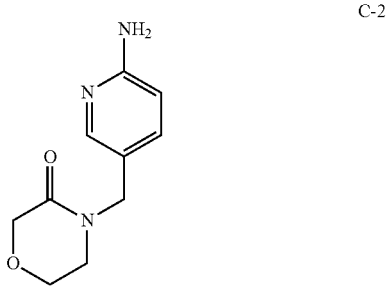
C-2

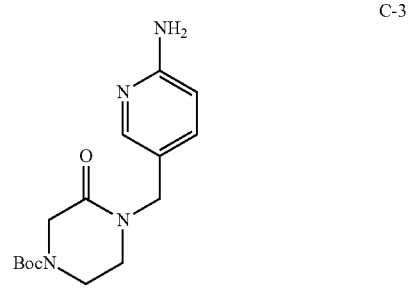
C-3

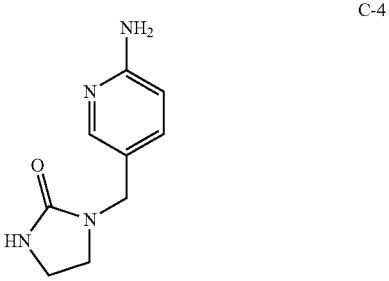
C-4

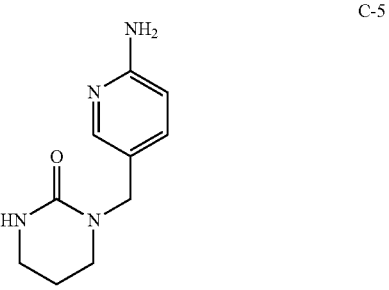
C-5

Reference Example 13

Synthesis of tert-butyl 4-(6-nitropyridin-3-yl)-3-oxopiperazine-1-carboxylate

[Formula 51]

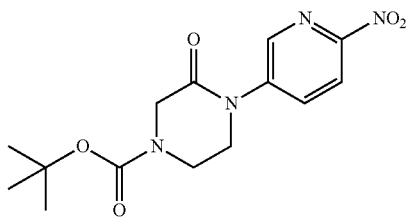

In reference to the process disclosed in WO2012/031004, 2-nitro-5-bromopyridine (1.01 g, 5.0 mmol), tert-butyl 2-oxo-4-piperazinecarboxylate (1.00 g, 5.0 mmol, and cesium carbonate (3.26 g, 10.0 mmol) were suspended in 1,4-dioxane, and the suspension was bubbled with nitrogen gas for 30 minutes. To the suspension was added Xantphos (246 mg, 0.43 mmol) and tris(dibenzylideneacetone)dipalladium (229 mg, 0.25 mmol), and the mixture was stirred under reflux for two hours. The resultant reaction mixture was cooled to room temperature, and water and ethyl acetate were then added to the mixture, followed by filtration with Celite. The organic phase was separated from the filtrate, and the aqueous phase was extracted with ethyl acetate. The resultant organic phases were combined together and dried over anhydrous sodium sulfate, and the resultant solid was separated by filtration. The filtrate was concentrated under reduced pressure, and the residue was purified by silica gel column chromatography to yield the title compound (1.08 g, 67%).

$^1$H-NMR (CDCl$_3$) δ: 8.67 (1H, d, J=2.4 Hz), 8.32 (1H, d, J=8.8 Hz), 8.15 (1H, dd, J=8.8, 2.4 Hz), 4.33 (2H, s), 3.93-3.83 (4H, m), 1.51 (9H, s).

Reference Example 14

Synthesis of tert-butyl 4-(6-aminopyridin-3-yl)-3-oxopiperazine-1-carboxylate

[Formula 52]

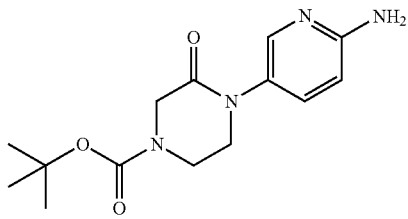

The compound synthesized in Reference Example 13 (1.08 g, 3.34 mmol) was dissolved in ethanol (45 mL) and THF (22 mL). Palladium-carbon (108 mg) was added to the solution, and the mixture was stirred under a hydrogen atmosphere for 24 hours. The resultant reaction mixture was filtered through Celite, and the filtrate was concentrated under reduced pressure. The residue was purified by silica gel column chromatography to yield the title compound (0.928 g, 95%).

$^1$H-NMR (CDCl$_3$) δ: 7.99 (1H, d, J=2.4 Hz), 7.38 (1H, dd, J=8.8, 2.4 Hz), 6.53 (1H, d, J=8.8 Hz), 4.50 (2H, brs), 4.24 (2H, s), 3.78 (2H, t, J=5.1 Hz), 3.67 (2H, t, J=5.4 Hz), 1.50 (9H, s).

Intermediates D-1 to D-41 were each synthesized by the process of Reference Example 13 and/or 14 with the corresponding halopyridine derivatives and amide derivatives. Appropriate protection or deprotection was performed as needed.

[Formula 53-1]

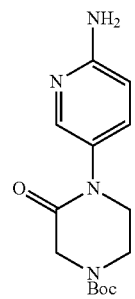

D-1

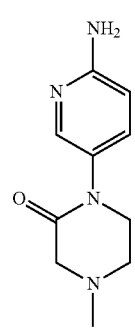

D-2

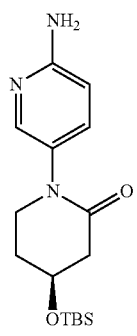

D-3

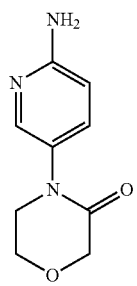

D-4

109
-continued
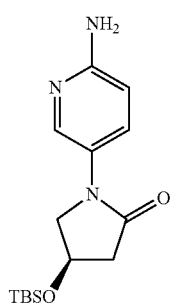
D-5
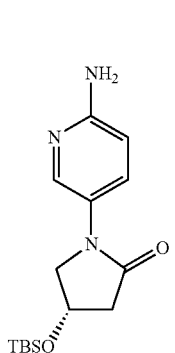
D-6
D-7
D-8
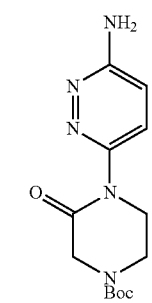
D-9
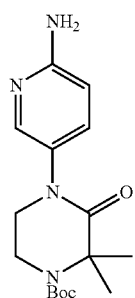
110
-continued
D-10
D-11
D-12
D-13
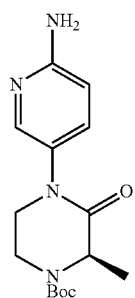
D-14

| | |
|---|---|
| D-15 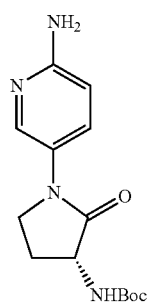 | D-21 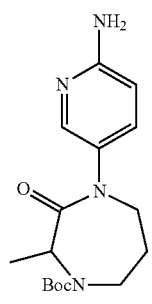 |
| D-16 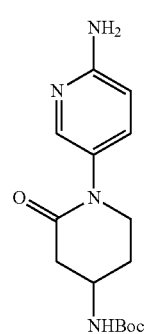 | D-22 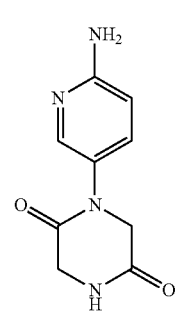 |
| D-18 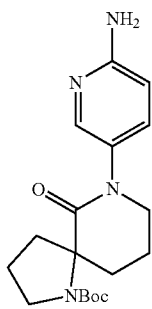 | D-23 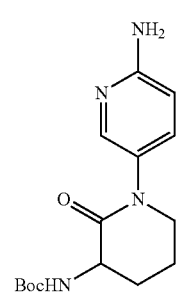 |
| D-19  | D-24 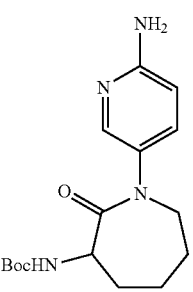 |
| D-20 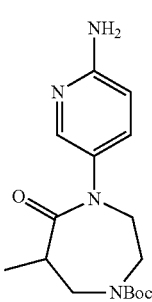 | D-25 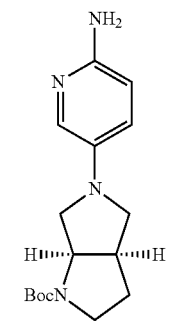 |

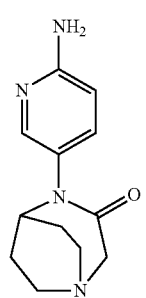
D-26
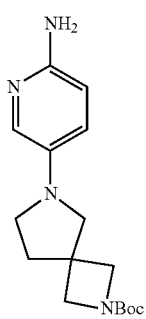
D-27
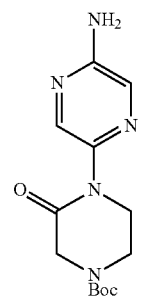
D-28
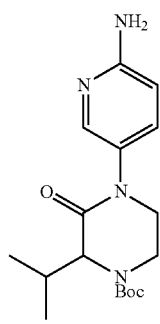
D-29
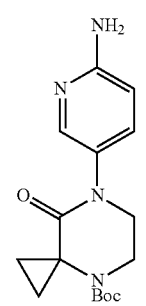
D-30
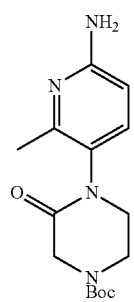
D-31
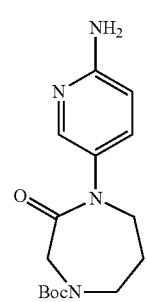
D-32
[Formula 53-2]
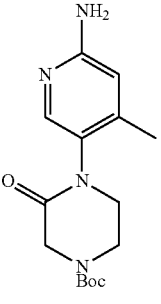
D-33
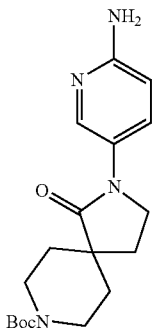
D-34
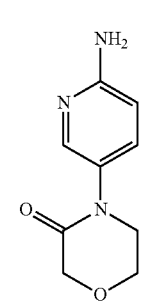
D-35

D-36 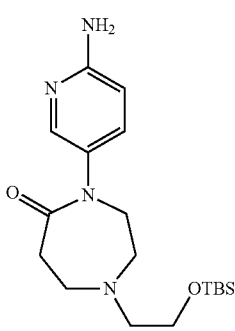

D-37 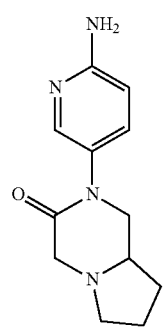

D-38 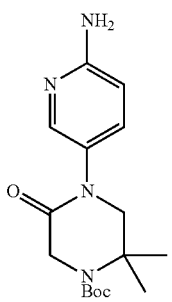

D-39 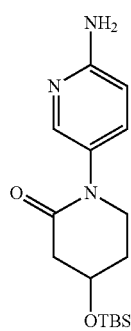

D-40 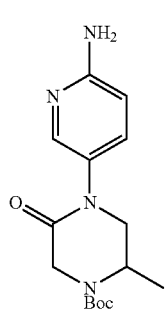

D-41 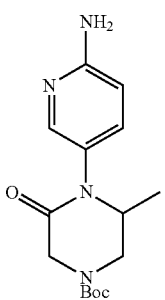

Reference Example 15

Synthesis of dimethyl-[2-(6-nitropyridin-3-yloxy)ethyl]amine

[Formula 54]

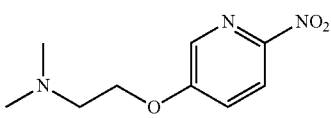

2-Dimethylaminoethanol (0.32 mL, 3.17 mmol) was dissolved in DMF (4 mL) and cesium carbonate (1.03 g, 3.17 mmol) was added thereto, and the resultant suspension was stirred at room temperature for 10 minutes. 5-Fluoro-2-nitropyridine (0.30 g, 2.11 mmol) was added to the suspension at room temperature, and the mixture then was stirred at 80° C. for 16 hours. The reaction was monitored by LC/MS. After completion of the reaction, the reaction was quenched through addition of ice water, and the reaction mixture was extracted with ethyl acetate. The resultant organic phase was dried over anhydrous sodium sulfate, and the solid was separated by filtration. The filtrate was then concentrated under reduced pressure, and the residue was purified by silica gel column chromatography to yield the title compound (0.40 g, 90%).

Reference Example 16

Synthesis of 5-(2-dimethylaminoethoxy)pyridin-2-ylamine

[Formula 55]

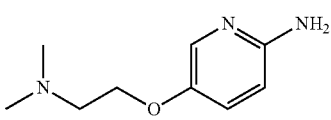

Dimethyl-[2-(6-nitropyridin-3-yloxy)ethyl]amine synthesized in Reference Example 15 (0.40 g, 1.90 mmol) was dissolved in THF (5 mL) and ethanol (5 mL), and palladium-carbon (80 mg) was added to the solution. The mixture was stirred under a hydrogen atmosphere overnight. The resultant reaction mixture was filtered through Celite, and the filtrate was concentrated under reduced pressure. The resultant crude product was washed with a solvent mixture of ethyl acetate and hexane (1:9) to yield the title compound (0.28 g, 82%).

Intermediates E-1 to E-61 were each synthesized by the process of Reference Examples 15 and/or 16 with the corresponding halopyridine derivatives, alcohol derivatives, or thiol derivatives. Appropriate protection or deprotection was performed as needed.

[Formula 56]

E-1
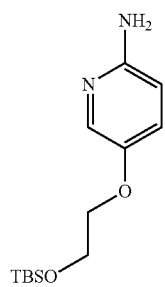

E-2

E-3

E-4

E-5
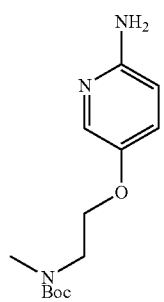

E-6
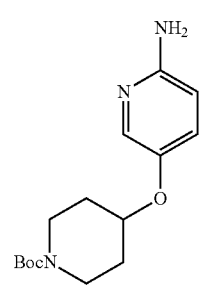

E-7
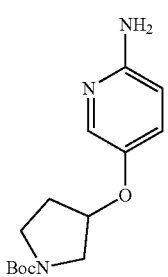

E-8
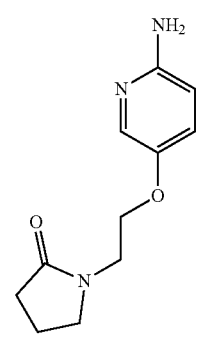

E-9
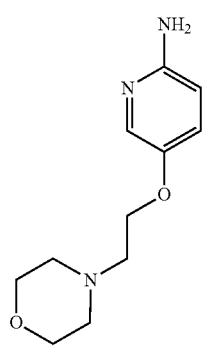

-continued
E-10
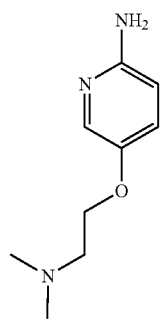
E-11
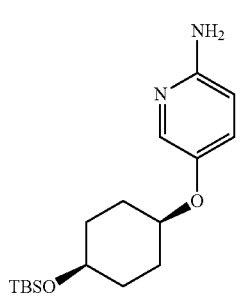
E-12
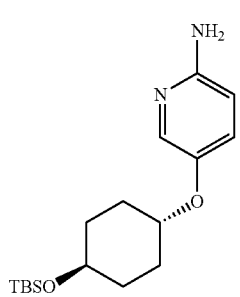
E-43
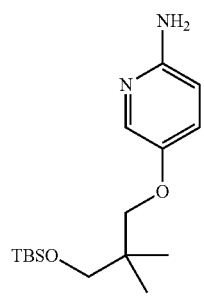
E-13
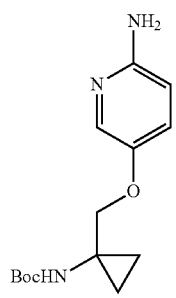
-continued
E-14
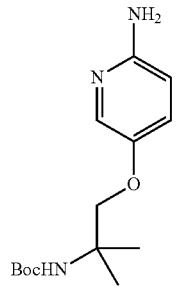
E-15
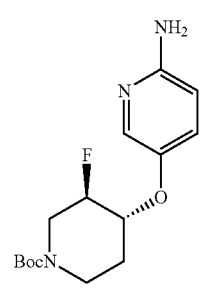
E-16
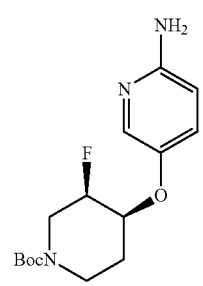
E-17
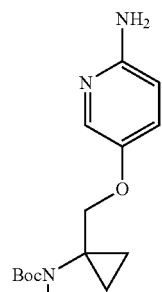
E-18
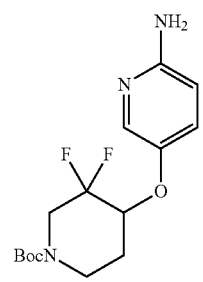

[Formula 57-1]
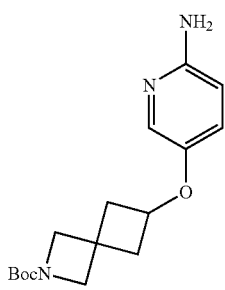
E-19
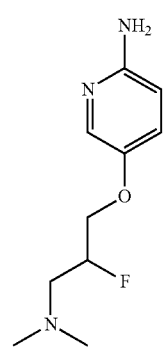
E-20
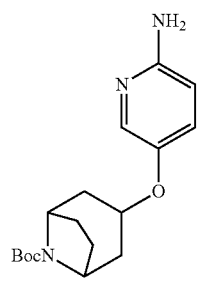
E-21
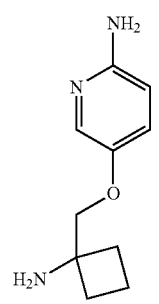
E-22
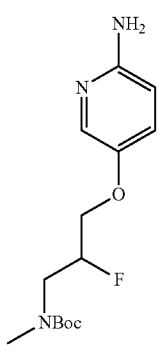
E-23
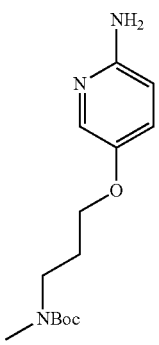
E-24
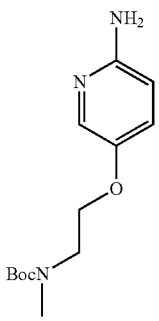
E-25
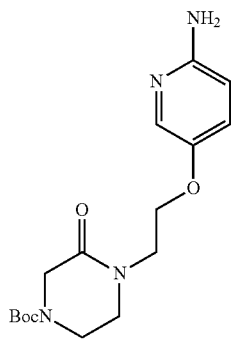
E-26
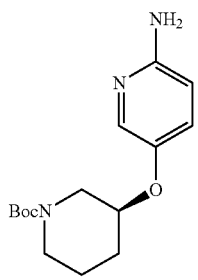
E-27
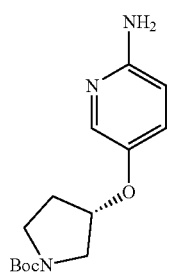
E-28

-continued
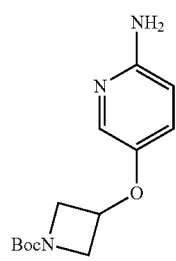
E-30
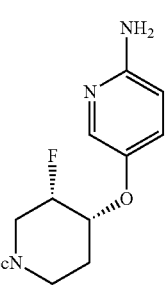
E-32
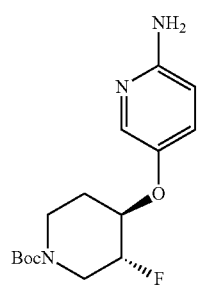
E-33
E-34
E-35
-continued
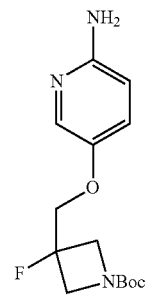
E-36
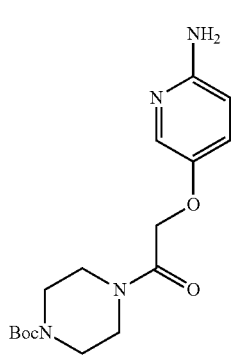
E-38
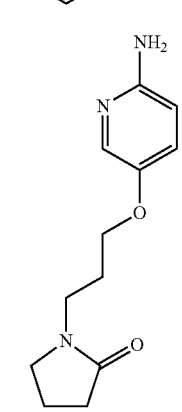
E-39
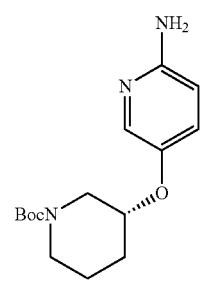
E-40
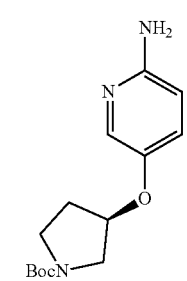
E-41

E-42
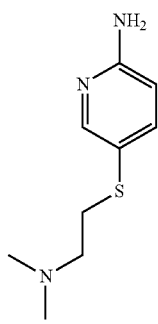
E-44
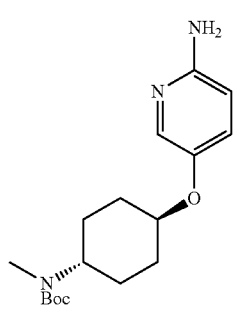
E-45
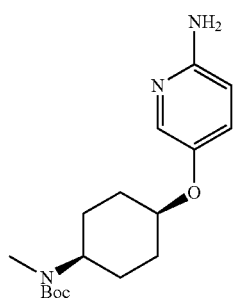
E-46
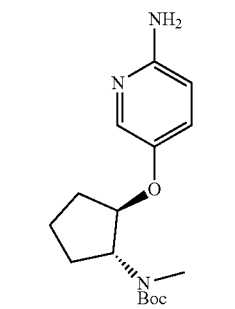
E-47
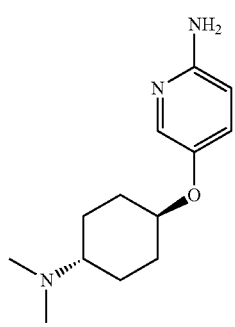
[Formula 57-2]
E-48
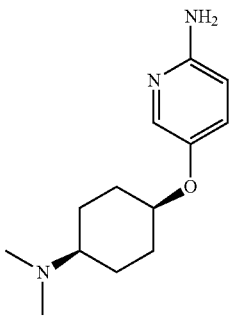
E-49
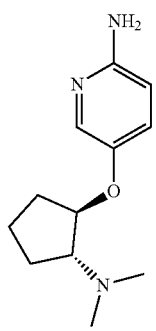
E-50
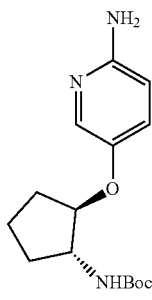
E-51
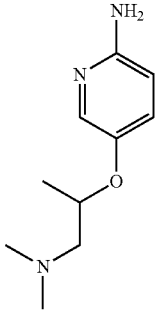
E-52
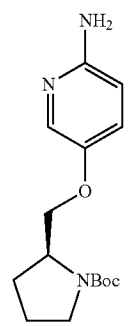

E-53 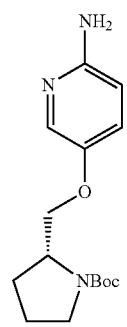
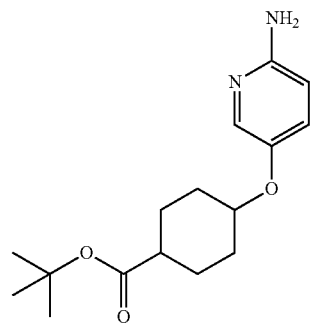 E-58
E-54 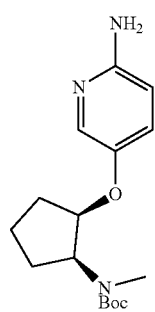
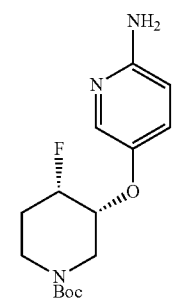 E-59
E-55 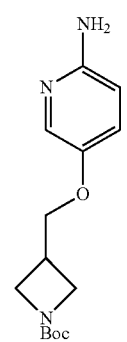
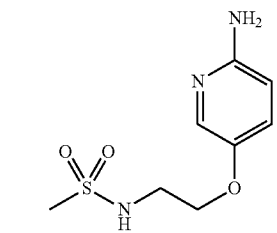 E-60
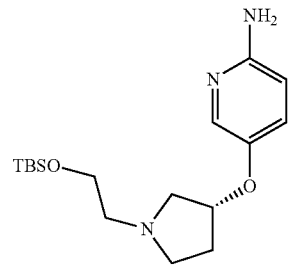 E-61
E-56 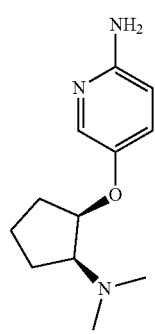
Reference Example 17
Synthesis of tert-butyl 4-(6-chloropyridazin-3-yl)piperazine-1-carboxylate
E-57 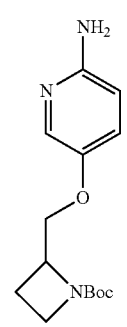
[Formula 58]
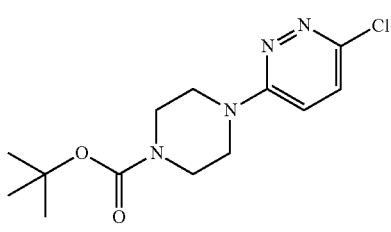

A solution of 3,6-dichloropyridazine (5.01 g, 33.6 mmol) and tert-butyl piperazine-1-carboxylate (6.88 g, 37.0 mmol) in DMF (50 mL) was added triethylamine (11.7 mL, 50.4 mmol) and stirred at 80° C. overnight. The resultant reaction mixture was cooled to room temperature, and water was added to the mixture. The mixture was extracted three times with a solvent mixture of dichloromethane and methanol (95:5) (50 mL). The resultant organic phases were combined together and dried over anhydrous magnesium sulfate. The resultant solid was separated by filtration, and the filtrate was then concentrated under reduced pressure. The resultant crude product was washed with diethyl ether to yield the title compound (7.0 g, 70%).

Reference Example 18

Synthesis of tert-butyl 4-(6-((diphenylmethylene)amino)pyridazin-3-yl)piperazine-1-carboxylate

[Formula 59]

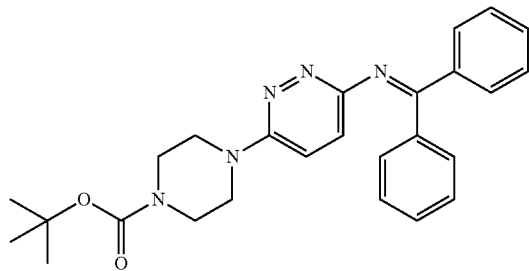

Tert-butyl 4-(6-chloropyridazin-3-yl)piperazine-1-carboxylate synthesized in Reference Example 17 (59.8 mg, 0.20 mmol, benzophenone imine (43.5 mg, 0.24 mmol), tris(dibenzylideneacetone)dipalladium (9.2 mg, 0.010 mmol), BINAP (12.5 mg, 0.020 mmol), and cesium carbonate (130.3 mg, 0.40 mmol) were suspended in toluene (1.0 mL), and the suspension was stirred at 100° C. overnight. The resultant reaction mixture was cooled to room temperature and then filtered through Celite, and the Celite was washed with ethyl acetate. The filtrate was washed with saturated brine and dried over anhydrous magnesium sulfate, and the solid was separated by filtration. The filtrate was concentrated under reduced pressure, and the residue was purified by silica gel column chromatography to yield the title compound (67 mg, 76%).

Reference Example 19

Synthesis of tert-butyl 4-(6-aminopyridazin-3-yl)piperazine-1-carboxylate

[Formula 60]

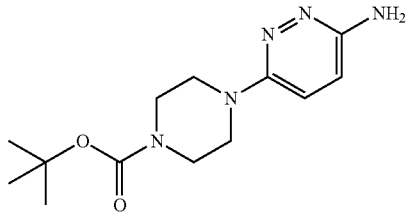

Tert-butyl 4-(6-((diphenylmethylene)amino)pyridazin-3-yl)piperazine-1-carboxylate synthesized in Reference Example 18 (67 mg, 0.151 mmol) was dissolved in THF (0.76 mL). To the solution was added an aqueous citric acid solution (0.378 mL, 0.755 mmol, 2 mol/L) and the mixture was stirred at room temperature overnight. The resultant reaction mixture was neutralized with saturated aqueous sodium hydrogen carbonate solution (5 mL), and the mixture was extracted twice with ethyl acetate (5 mL). The resultant organic phases were combined together and dried over anhydrous magnesium sulfate, and the resultant solid was separated by filtration. The filtrate was concentrated under reduced pressure, and the resultant crude product was washed with tert-butyl methyl ether (5 mL) to yield the title compound (30 mg, 71%).

Intermediates F-1 to F-77 were each synthesized by any of the processes of Reference Examples 17 to 19 or a combination of the processes with the corresponding haloheteroaryl derivatives and amine derivatives. Appropriate protection or deprotection was performed as needed.

[Formula 61]

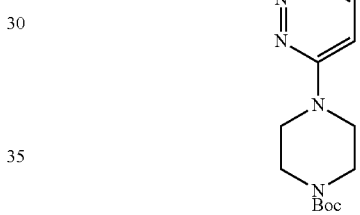

-continued
F-4
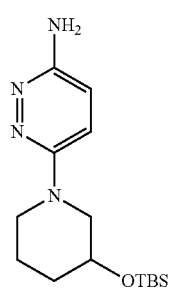
F-5
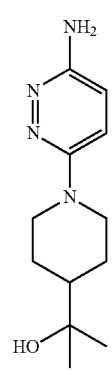
F-6
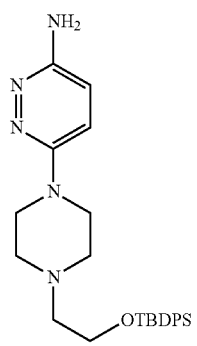
F-7
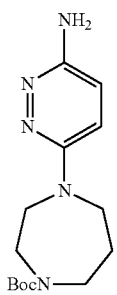
F-8
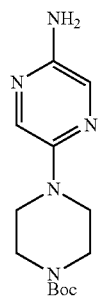
-continued
F-9
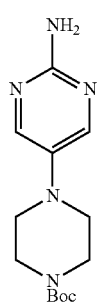
F-10
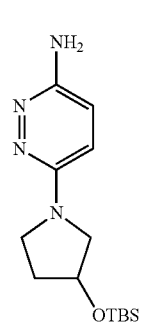
F-11
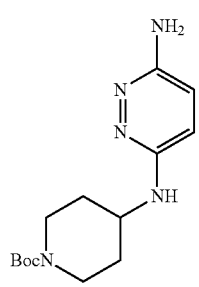
F-12
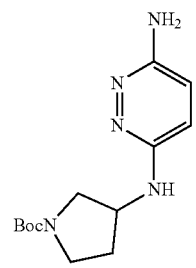
F-13
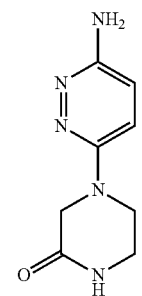

-continued
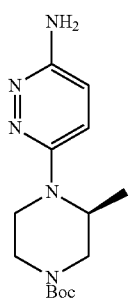
F-14
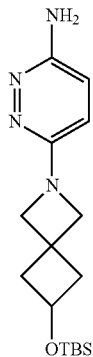
F-15
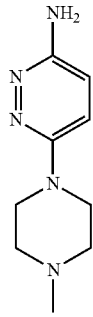
F-16
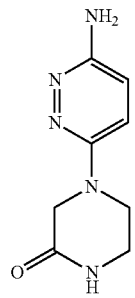
F-17
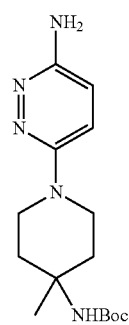
-continued
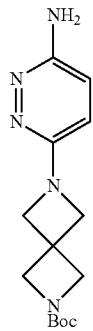
F-18
F-19
F-20
F-21
F-22

-continued
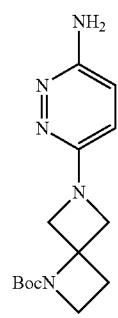
F-23
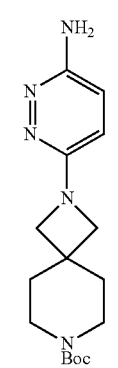
F-24
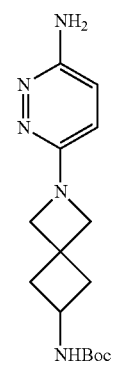
F-25
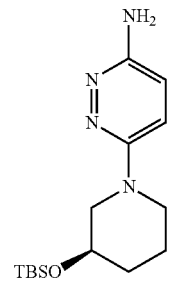
F-26
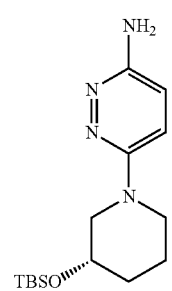
F-27
-continued
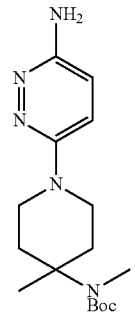
F-28
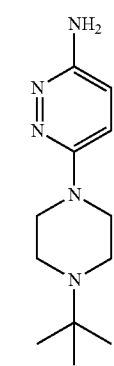
F-29
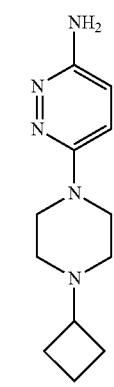
F-30
[Formula 62-1]
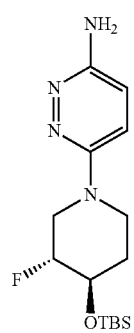
F-31

137
-continued
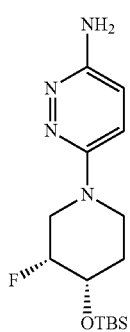
F-32
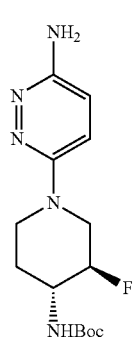
F-36
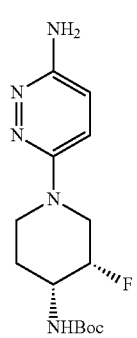
F-33
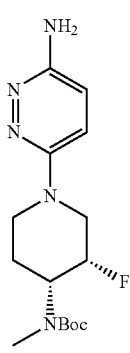
F-37
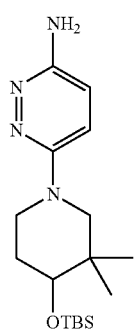
F-34
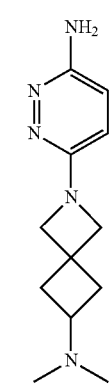
F-38
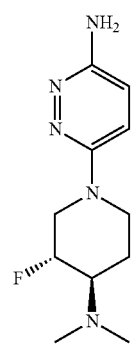
F-35
F-39

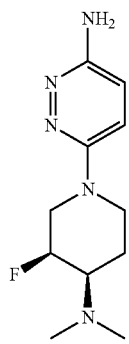
F-40
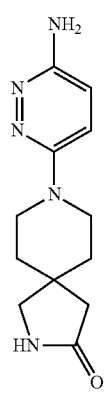
F-41
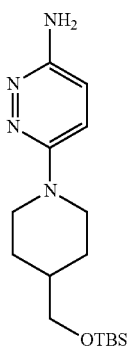
F-42
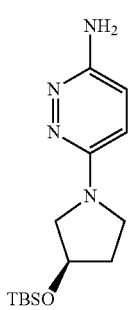
F-44
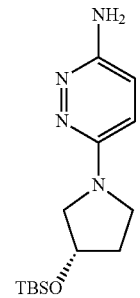
F-45
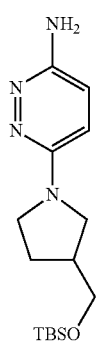
F-46
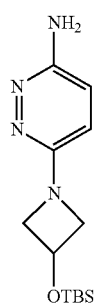
F-47
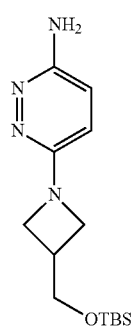
F-48
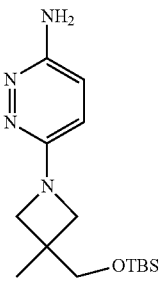
F-49

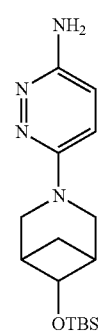 F-50
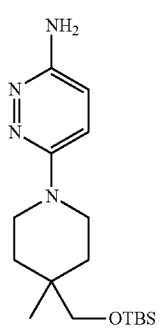 F-51
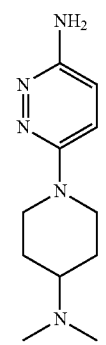 F-52
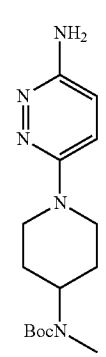 F-53
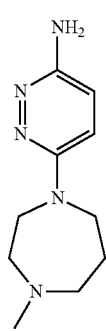 F-54
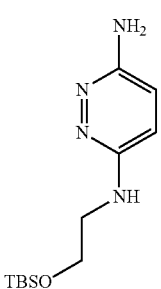 F-55
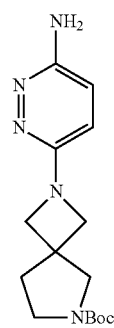 F-56
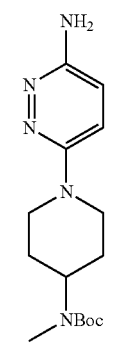 F-57
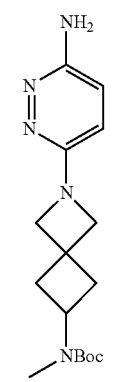 F-58
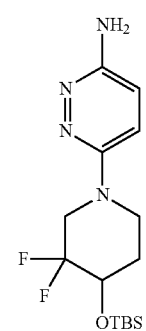 F-59

-continued
F-60
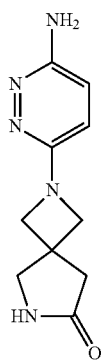
F-62
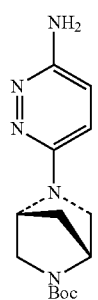
F-63
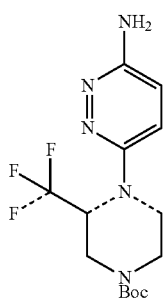
F-64
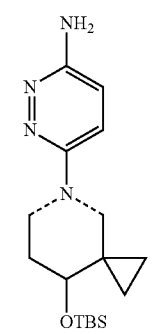
F-65
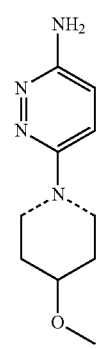
-continued
F-66
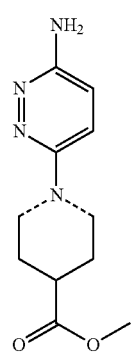
F-67
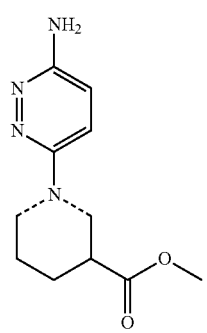
[Formula 62-2]
F-68
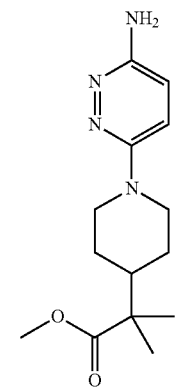
F-69
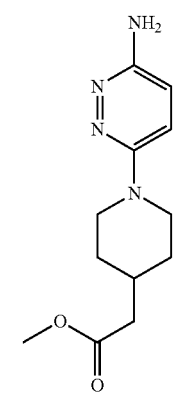

F-70 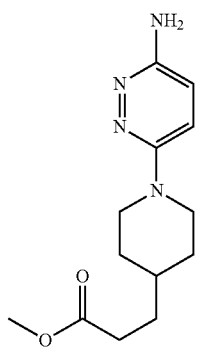
F-71 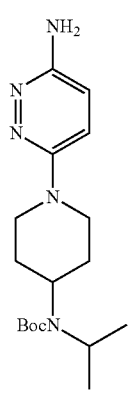
F-72 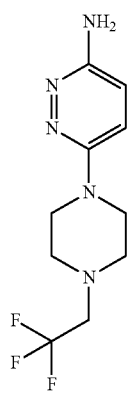
F-73 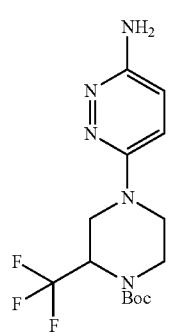
F-74 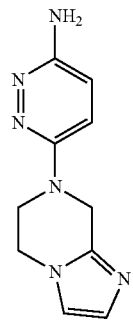
F-75 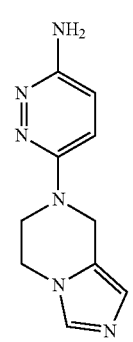
F-76 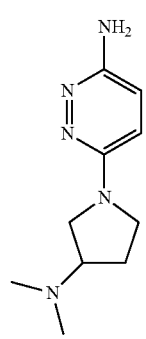
F-77 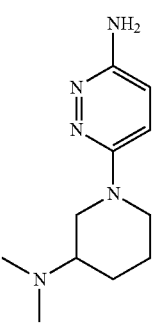
Intermediates G-1 to G-12 were each synthesized by any of the processes of Reference Examples 15, 18, and 19 or a combination of the processes with the corresponding halopyridazine, alcohol, or thiol derivative. Appropriate protection or deprotection was performed as needed.

[Formula 63]
G-1
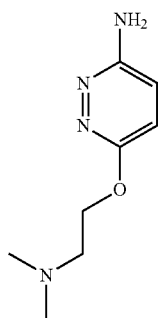
G-2
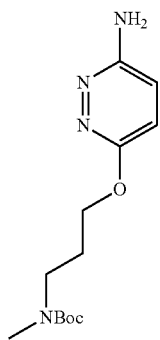
G-3
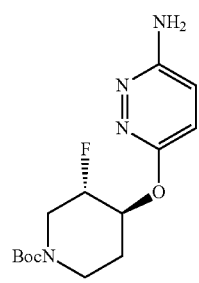
G-4
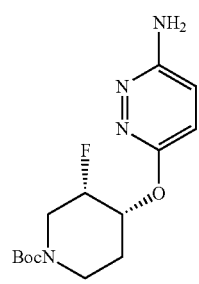
G-5
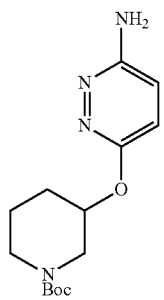
G-6
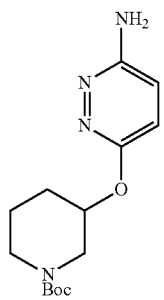
G-7
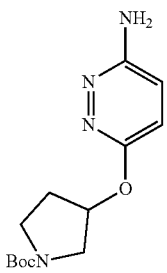
G-8
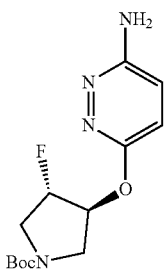
G-9
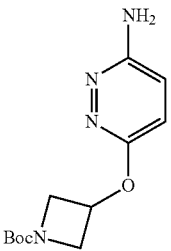
G-10
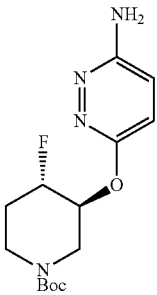

G-11

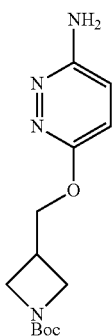

Reference Example 21

Synthesis of tert-butyl 4-(6-aminopyridin-3-yl)piperidine-1-carboxylate

[Formula 65]

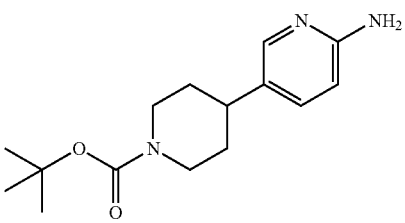

Tert-butyl 4-(6-nitropyridin-3-yl)piperidin-3-ene-1-carboxylate synthesized in Reference Example 20 was reduced under a hydrogen atmosphere in the presence of palladium-carbon by using the process described in J. Med. Chem. 2010, 53, p. 7938-7957 to yield the title compound.

Intermediates H-1 to H-12 were each synthesized by the process of Reference Example 20 and/or 21 with the corresponding haloheteroaryl or boric acid derivative. Appropriate protection or deprotection was performed as needed.

[Formula 66]

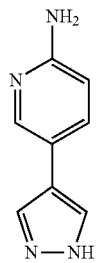

H-1

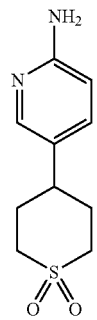

H-2

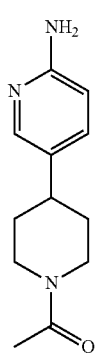

H-3

G-12

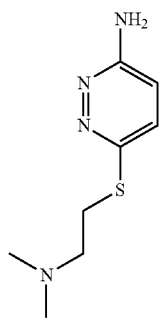

Reference Example 20

Synthesis of tert-butyl 4-(6-nitropyridin-3-yl)piperidin-3-ene-1-carboxylate

[Formula 64]

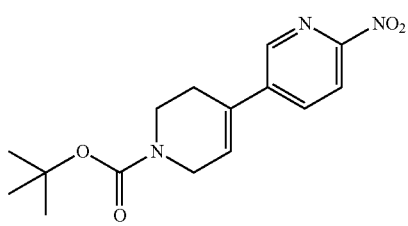

3-Bromo-6-nitropyridine was reacted with tert-butyl 4-(4,4,5,5-tetramethyl-1,3,2-dioxaborolan-2-yl)-5,6-dihydropyridine-1(2H)-carboxylate under heating in the presence of a palladium catalyst by using the process described in J. Med. Chem. 2010, 53, p. 7938-7957, to yield the title compound.

H-4 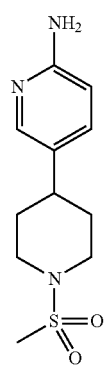
H-5 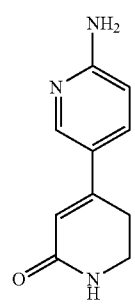
H-6 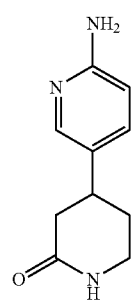
H-7 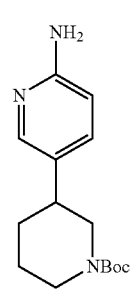
H-8 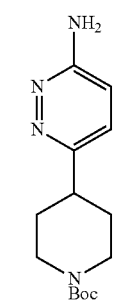
H-9 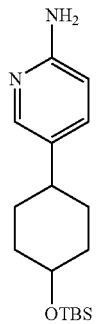
H-10 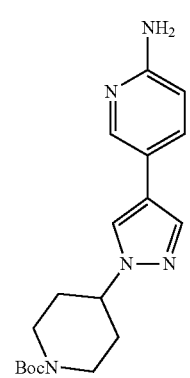
H-11 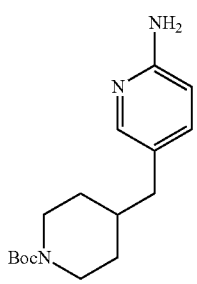
H-12 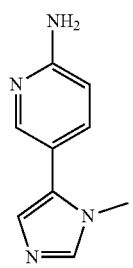
Reference Example 22
Intermediate I-l was synthesized through the reaction of tert-butyl chlorosulfonylcarbamate with tert-butyl N-[5-(aminoethyl)-2-pyridyl]-N-tert-butoxycarbonylcarbamate synthesized by any of the processes of Reference Examples 8 to 10 or a combination of the processes, and then the removal of the Boc groups under acidic conditions.

[Formula 67]

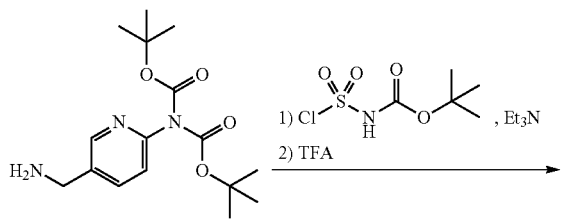

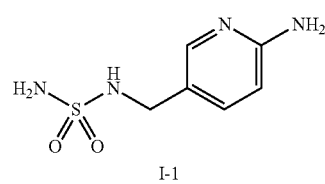

Reference Example 23

Intermediate J-1 was synthesized through the reaction of potassium isocyanate with tert-butyl N-tert-butoxycarbonyl-N-[5-(N-methylaminoethyl)-2-pyridyl]carbamate synthesized as in Reference Example 8 to 10, and the removal of the Boc groups under acidic conditions.

[Formula 68]

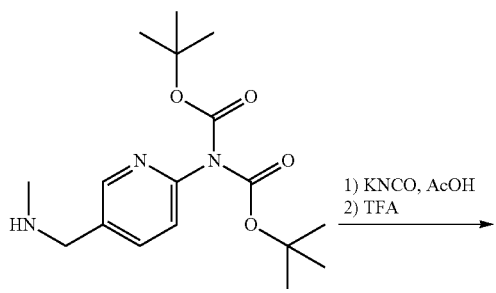

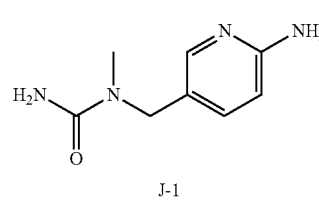

Intermediate J-2 was synthesized through hydrogen reduction of the nitro group of 5-amino-2-nitropyridine in the presence of palladium hydroxide/activated carbon by the process of Reference Example 23.

[Formula 69]

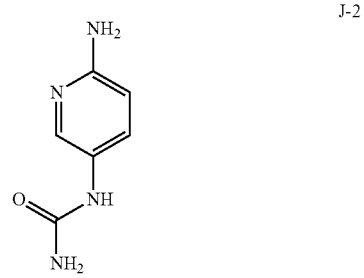

Reference Example 24

Intermediate K-1 was synthesized through the reaction of isocyanatoethane with tert-butyl N-[5-(aminoethyl)-2-pyridyl]-N-tert-butoxycarbonylcarbamate synthesized by any of the processes of Reference Examples 8 to 10 or a combination of the processes, and the removal of the Boc groups under acidic conditions.

[Formula 70]

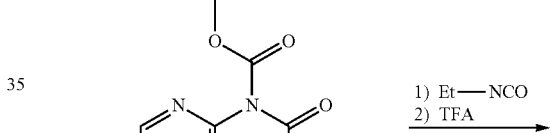

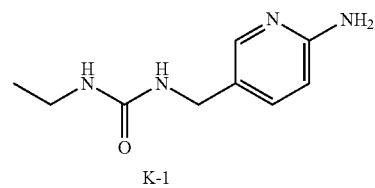

Reference Example 25

Intermediate L-1 was synthesized through the reaction of 2-methoxyethyl bromide with tert-butyl N-[5-(aminoethyl)-2-pyridyl]-N-tert-butoxycarbonylcarbamate synthesized by any of the processes of Reference Examples 8 to 10 or a combination of the processes, the removal of the Boc groups under acidic conditions, and the selective protection of the secondary amino moiety with a Boc group as in Reference Example 11.

[Formula 71]

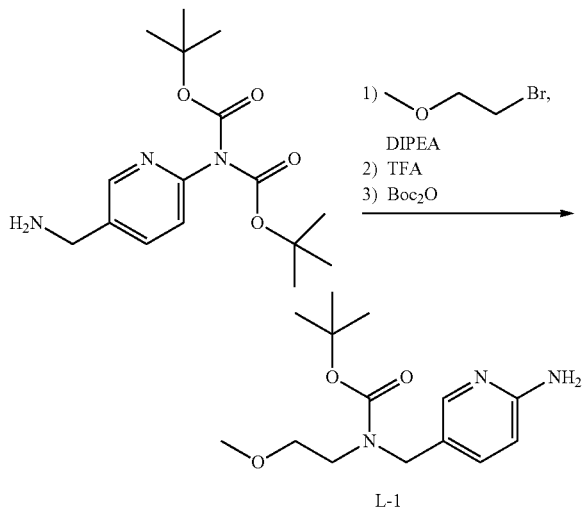

L-1

Reference Example 26

Intermediate M-1 was synthesized through the esterification of the carboxylic acid moiety of 2-(6-chloropyridin-3-yl)acetic acid, dimethylation of the carbonyl group at the α-position, reduction of the ester moiety with LAH, oxidation of the resultant alcohol moiety, reductive amination with methylamine, protection with a Boc group, amination of the 2-chloropyridine moiety in the presence of a Pd catalyst, and deprotection.

[Formula 72]

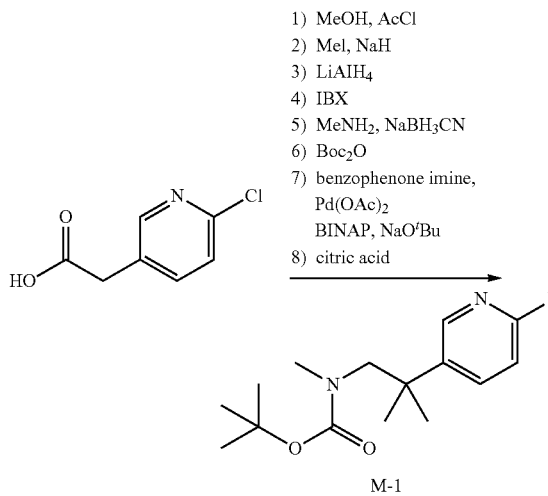

M-1

Reference Example 27

Intermediate N-1 was synthesized through the reaction of 5-bromo-2-nitropyridine with tert-butyl cyanoacetate under basic conditions, removal of the tert-butyl group and decarboxylation under acidic conditions, and reduction of the cyano group.

[Formula 73]

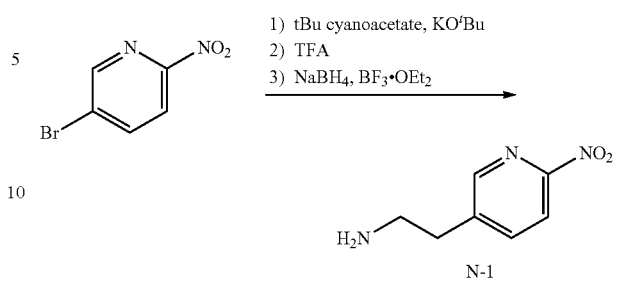

N-1

Reference Example 28

Intermediate O-1 was synthesized through the reaction of an alkyne derivative with imide derivative, subsequent reaction with 5-bromo-2-nitropyridine under Sonogashira coupling reaction conditions, and reduction with hydrogen in the presence of palladium hydroxide/activated carbon, involving protection and deprotection.

[Formula 74]

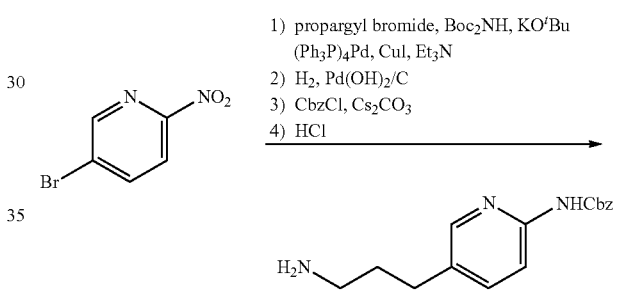

O-1

Reference Example 29

Intermediate P-1 was synthesized through acylation of 2-(6-nitropyridin-3-yl)ethylamine and reduction with hydrogen in the presence of palladium hydroxide/activated carbon.

[Formula 75]

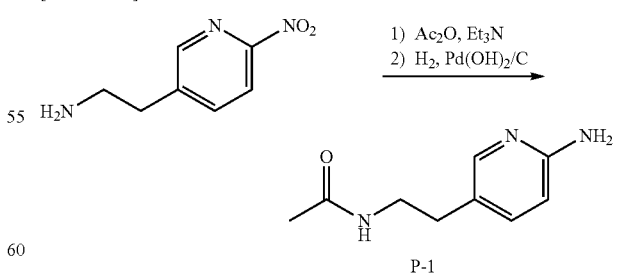

P-1

Intermediates P-2 to P-17 were each synthesized by the process of Reference Example 29 with the corresponding amine derivative synthesized by, for example, any of the processes of Reference Examples 8 to 10 and the corresponding acylating agent, involving appropriate deprotection as needed. Appropriate acylation conditions were selected depending on the structure to be introduced. For example, an acid chloride or combination of a carboxylic acid and a condensing agent was used as the acylating agent in place of an acid anhydride.
[Formula 76]
P-2
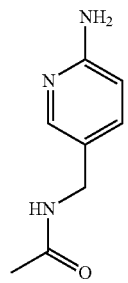
P-3
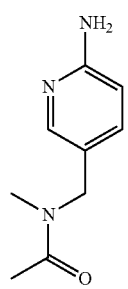
P-4
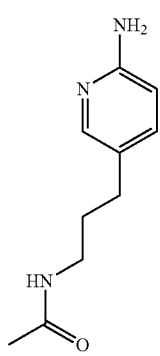
P-5
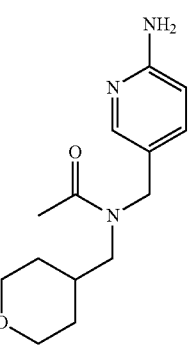
P-6
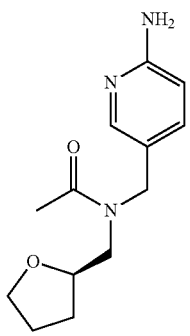
P-7
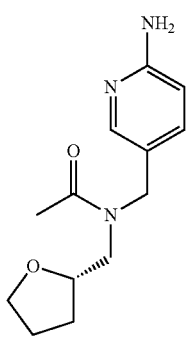
P-8
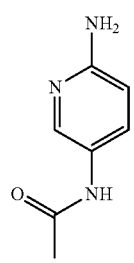
P-9
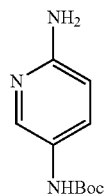
P-10
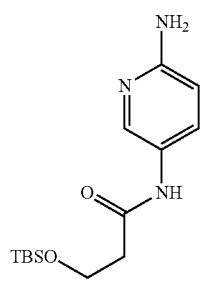

P-11 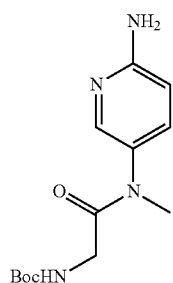

P-12 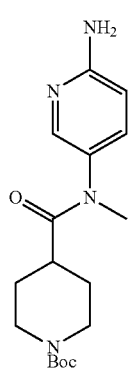

P-13 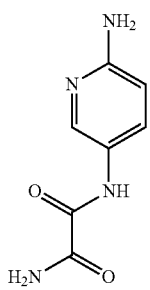

P-14 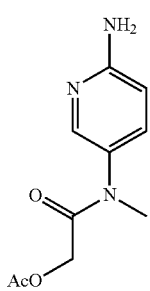

P-15 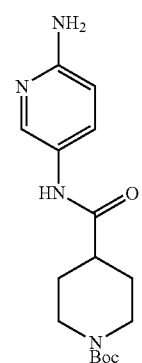

P-16 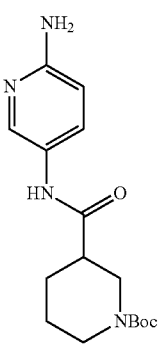

P-17 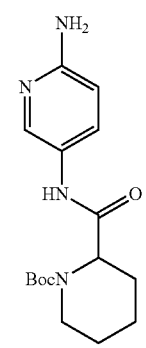

Reference Example 30

Intermediate Q-1 was synthesized by mesylation of 2-(6-nitropyridin-3-yl)ethylamine and reduction with hydrogen in the presence of palladium hydroxide/activated carbon.

[Formula 77]

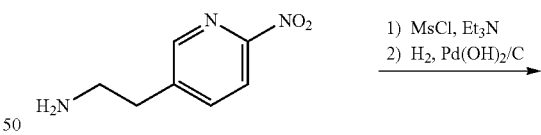

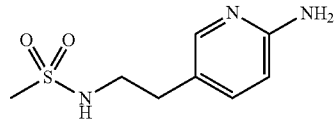

Q-1

Intermediates Q-2 to Q-9 were each synthesized by the process of Reference Example 29 with the corresponding amine derivative synthesized by, for example, any of the processes of Reference Examples 8 to 10, involving appropriate deprotection as needed.

[Formula 78]

Q-2 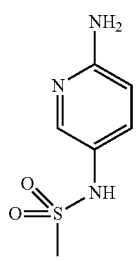

Q-3 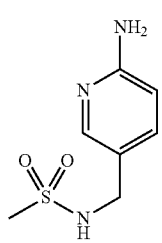

Q-4 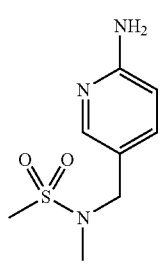

Q-5 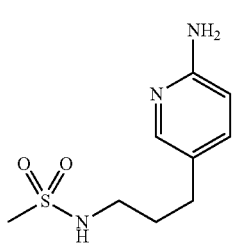

Q-6 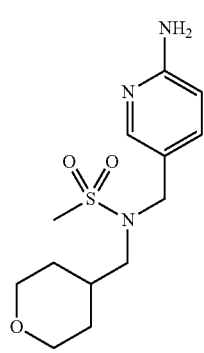

Q-7 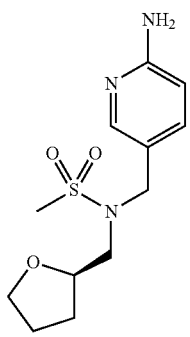

Q-8 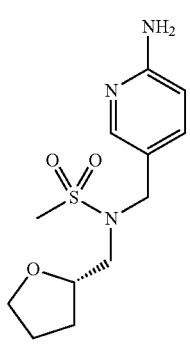

Q-9 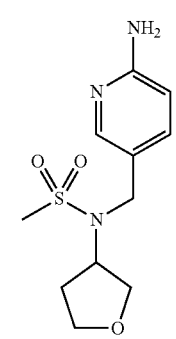

Reference Example 31

Intermediate R-1 was synthesized through the reaction of 5-bromo-2-nitropyridine with an alkyne derivative under Sonogashira coupling reaction conditions, protection and reduction with hydrogen in the presence of palladium hydroxide/activated carbon, involving protection and deprotection.

[Formula 79]

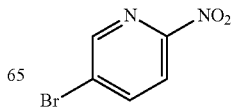

1) propargyl alcohol, (Ph₃P)₄Pd, CuI, Et₃N
2) TBSCl, imidazole
3) H₂, Pd/C
4) Boc₂O, DMAP
5) H₂O—THF—AcOH -continued

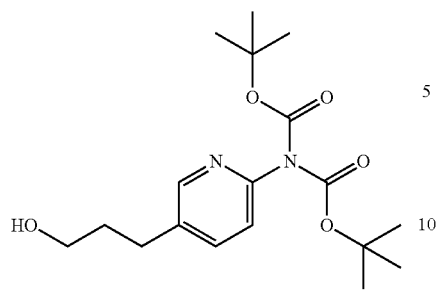

R-1

Intermediates R-2 to R-6 were each synthesized by the process of Reference Example 31; i.e., by the reactions 1) to 3) in Reference Example 31 with a halopyridine derivative and the corresponding terminal alkyne derivative.

[Formula 80]

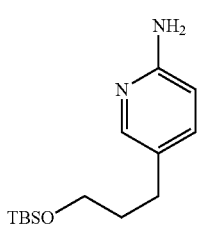

R-2

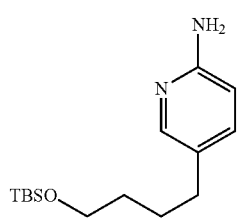

R-3

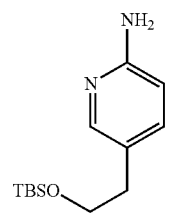

R-4

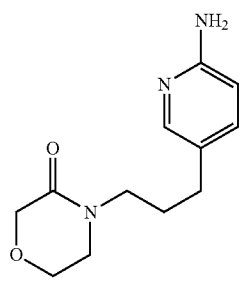

R-5

-continued

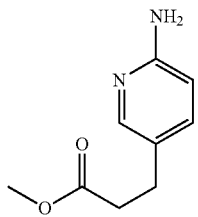

R-6

Reference Example 32

Intermediate S-1 was synthesized through the mesylation of intermediate R-1 synthesized in Reference Example 31, reaction with an amide derivative under basic conditions and subsequent deprotection.

[Formula 81]

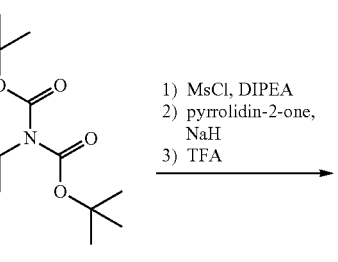

R-1

1) MsCl, DIPEA
2) pyrrolidin-2-one, NaH
3) TFA

→

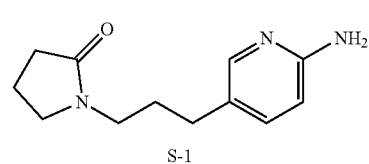

S-1

Intermediates S-2 and S-3 were each synthesized by the process of Reference Example 32 with the corresponding alcohol derivative, amide derivative, or sulfonamide derivative.

[Formula 82]

S-2

S-3

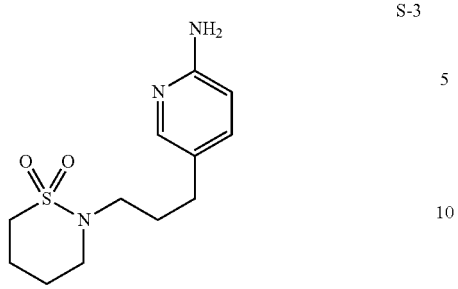

Reference Example 33

Intermediate T-1 was synthesized through basic hydrolysis of methyl 6-((tert-butoxycarbonyl)amino)nicotinate, condensation with morpholine, and deprotection.

[Formula 83]

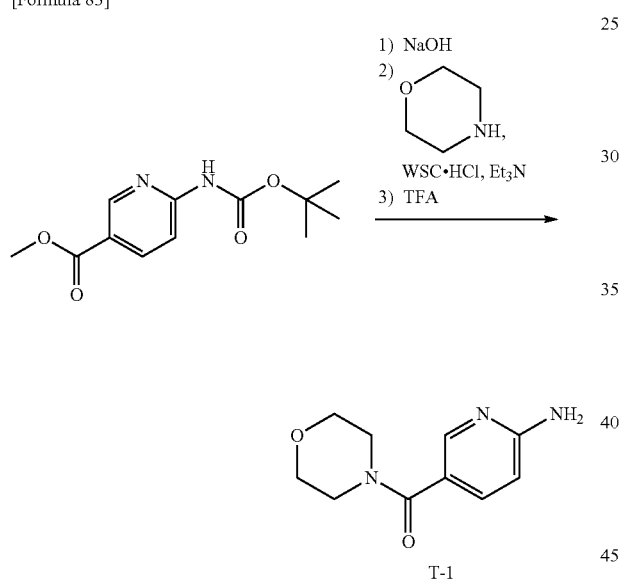

Intermediates T-2 to T-17 were each synthesized by the process of Reference Example 33 with the corresponding ester derivative synthesized by, for example, the process of Reference Example 31, or the corresponding carboxylic acid derivative and amine derivative. Appropriate protection and deprotection were performed as needed.

[Formula 84]

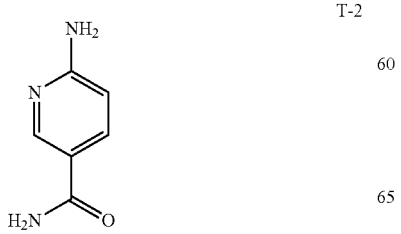

T-2

T-3

T-4

T-5

T-6

T-7

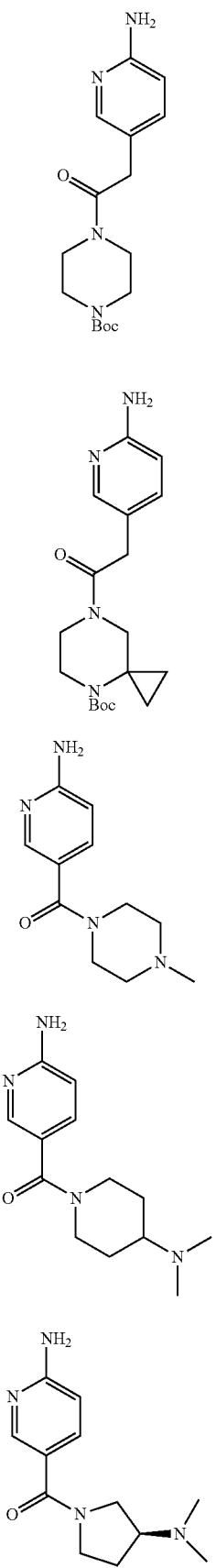
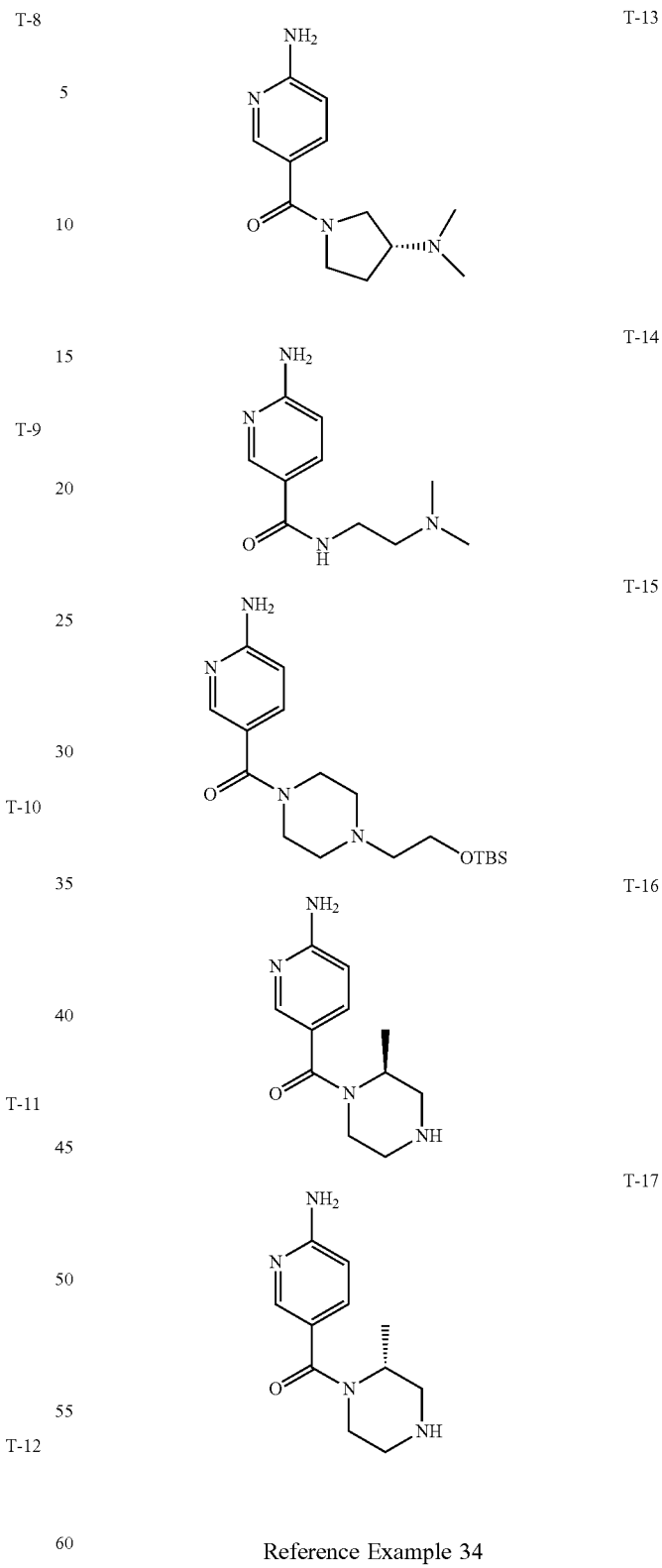
Reference Example 34
Intermediate U-1 was synthesized by oxidation of 5-((3-((tert-butyldimethylsilyl)oxy)propyl)thio)-2-nitropyridine synthesized by the process of Reference Example 15 with m-chloroperbenzoic acid and reduction with hydrogen in the presence of palladium hydroxide/activated carbon.

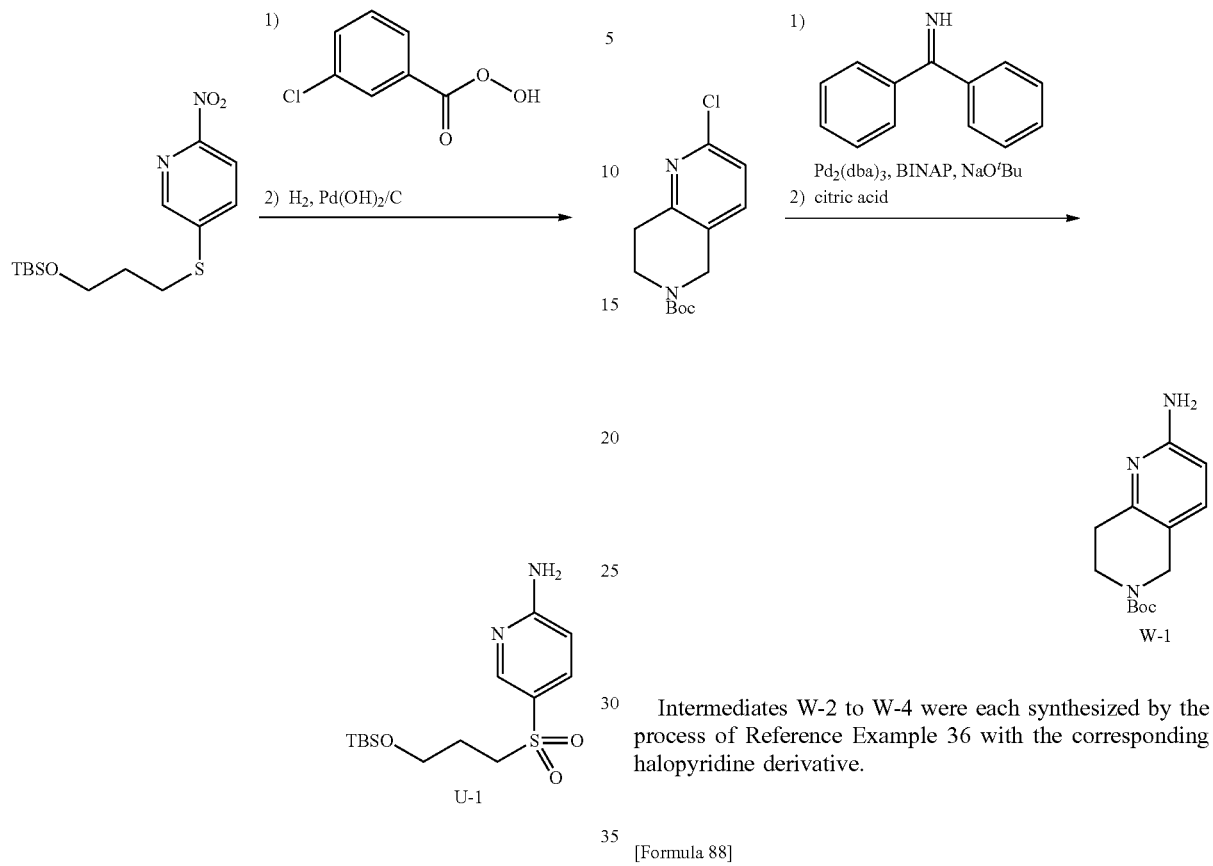

Reference Example 35

Intermediate V-1 was synthesized through the reaction of 5-amino-2-nitropyridine with sodium azide and orthoformate and subsequent reduction with hydrogen in the presence of palladium hydroxide/activated carbon.

[Formula 86]

Reference Example 36

Intermediate W-1 was synthesized through the reaction of tert-butyl 2-chloro-7,8-dihydro-1,6-naphthyridine-6(5H)-carboxylate with benzophenone imine and tert-butoxysodium in the presence of a Pd catalyst and deprotection.

Intermediates W-2 to W-4 were each synthesized by the process of Reference Example 36 with the corresponding halopyridine derivative.

[Formula 88]

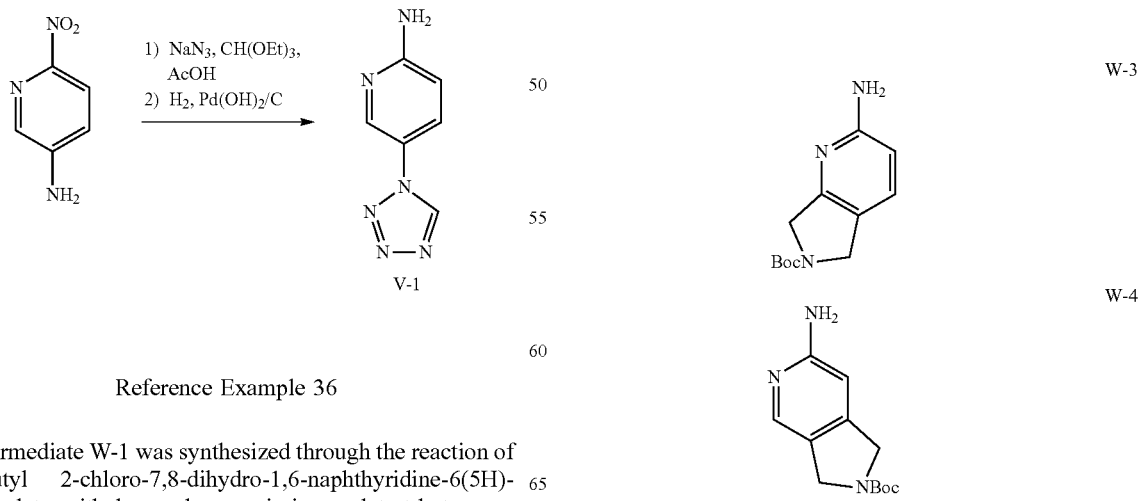

Example 1

Synthesis of 3-(4-formyl-2-methylthiopyrimidin-5-yl)-2-propynyl benzoate

[Formula 89]

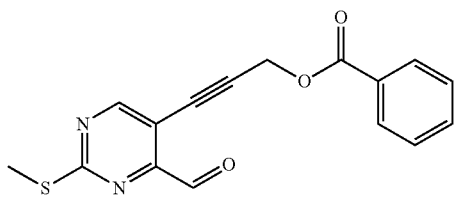

A solution of Pd(PhCN)$_2$Cl$_2$ (2.4 g, 6.4 mmol), copper iodide (0.82 g, 4.3 mmol), and [(t-Bu)$_3$P]HBF$_4$ (4 g, 13.9 mmol) in 1,4-dioxane (55 mL) was degassed and purged with argon, and diisopropylamine (18.5 mL, 128.8 mmol) was added to the solution at room temperature. The resultant reaction mixture was stirred at room temperature for five minutes. A solution of a mixture (25 g, crude product) of 5-bromo-2-methylsulfanylpyrimidine-4-carbaldehyde and (5-bromo-2-methylsulfanylpyrimidin-4-yl)methoxymethanol described in Reference Example 3 and propargyl benzoate (20 g, 128.8 mmol) in 1,4-dioxane (55 mL) was slowly added dropwise to the reaction mixture, and the reaction mixture was then stirred at room temperature for five hours. The reaction was monitored by LC/MS. After completion of the reaction, the reaction mixture was diluted with ethyl acetate (1 L). The mixture was subjected to suction filtration through Celite, and the Celite was washed with ethyl acetate. The filtrate was concentrated under reduced pressure, and the resultant crude product was directly used for the subsequent reaction.

Example 2

Synthesis of 6-((benzoyloxy)methyl)-2-(methylthio)pyrido[3,4-d]pyrimidine 7-oxide

[Formula 90]

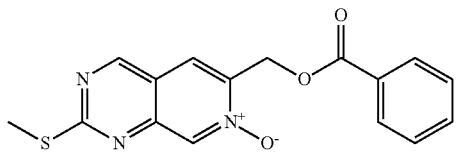

The crude product of 3-(4-formyl-2-methylthiopyrimidin-5-yl)-2-propynyl benzoate synthesized in Example 1 was dissolved in ethanol (500 mL), and hydroxylamine hydrochloride (8.3 g, 120 mmol) and sodium acetate (10 g, 120 mmol) were added to the solution at room temperature. The resultant reaction mixture was stirred at room temperature for six hours, and then diluted with ethanol (1 L). Potassium carbonate (27.8 g, 200 mmol) was added to the mixture, and the mixture was then stirred at 50° C. for three hours. The reaction was monitored by LC/MS. After completion of the reaction, the reaction mixture was subjected to suction filtration through Celite, and the Celite was washed with ethyl acetate. The filtrate was dried over anhydrous sodium sulfate, and solid was separated by filtration. The filtrate was concentrated under reduced pressure, and the resultant crude product was purified by silica gel column chromatography to yield the title compound (5.0 g, 16%).

Example 3

Synthesis of 8-chloro-2-methylthiopyrido[3,4-d]pyrimidin-6-yl benzoate

[Formula 91]

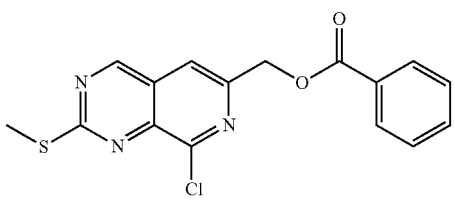

The 6-((benzoyloxy)methyl)-2-(methylthio)pyrido[3,4-d]pyrimidine 7-oxide synthesized in Example 2 (5.0 g, 15.3 mmol) was dissolved in dichloromethane (60 mL) and cooled to 0° C. Thionyl chloride (25 mL, 343 mmol) was added dropwise to the solution at 0° C., and the mixture was stirred at room temperature for 16 hours. The reaction was monitored by TLC. After completion of the reaction, the reaction mixture was concentrated under reduced pressure, followed by azeotropic distillation twice with toluene (20 mL), to remove thionyl chloride. The residue was roughly purified by neutral alumina column chromatography to yield the title compound (2.75 g, 52%).

Example 4

Synthesis of (R)-1-(2-(methylthio)-8-(((S)-tetrahydro-2H-pyran-3-yl)amino)pyrido[3,4-d]pyrimidin-6-yl)ethyl benzoate

[Formula 92]

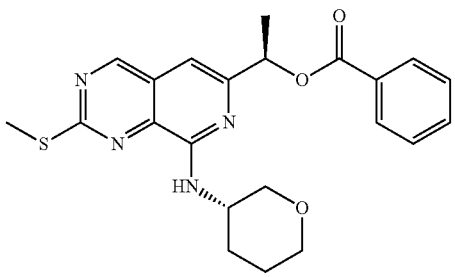

A mixture of (R)-1-(8-chloro-2-(methylthio)pyrido[3,4-d]pyrimidin-6-yl)ethyl benzoate synthesized by the process described in Example 3 (360 mg, 1.0 mmol), (S)-tetrahydro-2H-pyran-3-amine hydrochloride (206 mg, 1.5 mmol), and potassium carbonate (415 mg, 3.0 mmol) in 1,4-dioxane (4.0 mL) was stirred at 100° C. overnight. The reaction was monitored by TLC. After completion of the reaction, the reaction mixture was cooled to room temperature. The reaction mixture was diluted with water, and the mixture was extracted twice with ethyl acetate (10 mL). The resultant organic phase was washed with brine and dried over anhydrous magnesium sulfate. The solid was separated by filtration, and the filtrate was concentrated under reduced pressure. The resultant crude product was purified by silica gel column chromatography to yield the title compound (232 mg, 55%).

$^1$H-NMR (CDCl$_3$) δ: 8.97 (1H, s), 8.17-8.14 (2H, m), 7.62-7.57 (1H, m), 7.51-7.46 (2H, m), 6.87 (1H, s), 6.65 (1H, d, J=7.8 Hz), 6.10 (1H, q, J=6.7 Hz), 4.39-4.31 (1H, m), 4.08-4.03 (1H, m), 3.82-3.76 (1H, m), 3.70-3.64 (1H, m), 3.56-3.51 (1H, m), 2.65 (3H, s), 2.09-2.02 (1H, m), 1.89-1.78 (2H, m), 1.76-1.65 (4H, m)

LC/MS: (M+H)$^+$=425.2, C$_{22}$H$_{24}$N$_4$O$_3$S=424.16

Example 5

Synthesis of 2-methylthio-8-(propan-2-yl)aminopyrido[3,4-d]pyrimidin-6-ylmethanol

[Formula 93]

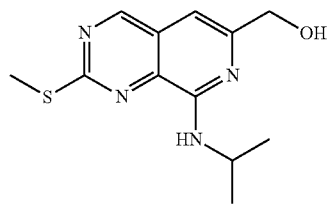

The 8-isopropylamino-2-methylthiopyrido[3,4-d]pyrimidine-6-yl benzoate synthesized by the process described in Example 4 (3.7 g, 10.0 mmol) was dissolved in methanol (20 mL) and THF (20 mL), and an aqueous solution (10 mL) of lithium hydroxide (0.96 g, 40 mmol) was added dropwise to the solution at room temperature. The resultant reaction mixture was stirred at room temperature for one hour. The reaction was monitored by LC/MS. After completion of the reaction, hydrochloric acid (2 mol/L) was added dropwise to the reaction mixture, to adjust the pH of the mixture to 7. The resultant solid was separated by filtration and dried under reduced pressure to yield the title compound (2.55 g, 96%).

Example 6

Synthesis of 2-methylthio-8-(propan-2-yl)aminopyrido[3,4-d]pyrimidine-6-carbaldehyde

[Formula 94]

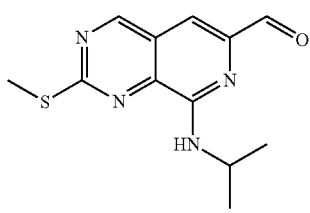

The 2-methylthio-8-(propan-2-yl)aminopyrido[3,4-d]pyrimidin-6-ylmethanol synthesized in Example 5 (3.1 g, 11.7 mmol) was dissolved in dichloromethane (30 mL) and the solution was stirred at 0° C. Dess-Martin Periodinane (15 g, 35.2 mmol) was gradually added to the solution at 0° C., and the reaction mixture was stirred at room temperature for three hours. The reaction was monitored by LC/MS. After completion of the reaction, the reaction was quenched by addition of an aqueous sodium thiosulfate solution for reduction of excess reagent. The aqueous phase was extracted three times with dichloromethane (50 mL). The resultant organic phases were combined together and dried over anhydrous sodium sulfate. The solid was separated by filtration, and the filtrate was then concentrated under reduced pressure. The residue was purified by silica gel column chromatography to yield the title compound (2.9 g, 94%).

Example 7

Synthesis of 6-difluoromethyl-2-methylthio-N-(propan-2-yl)pyrido[3,4-d]pyrimidine-8-amine

[Formula 95]

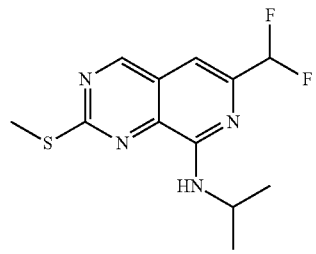

The 2-methylthio-8-(propan-2-yl)aminopyrido[3,4-d]pyrimidine-6-carbaldehyde synthesized in Example 6 (2.9 g, 11.1 mmol) was dissolved in dichloromethane (30 mL) and the solution was stirred at 0° C. DAST (7.1 g, 44.2 mmol) was gradually added to the solution at 0° C., and the reaction mixture was stirred at room temperature for three hours. The reaction was monitored by LC/MS. After completion of the reaction, the reaction was quenched by addition of saturated aqueous sodium carbonate solution (20 mL). The aqueous phase was extracted three times with dichloromethane (50 mL). The resultant organic phases were combined together and dried over anhydrous sodium sulfate. The solid was separated by filtration, and the filtrate was then concentrated under reduced pressure. The residue was purified by silica gel column chromatography to yield the title compound (2.37 g, 75%).

Compounds Int-1 to Int-8 were synthesized by the process described in Example 4 or Examples 5 to 7 in an appropriate order depending on the substituents.

TABLE 1
| Compound No. | Structure | NMR | (M + H)+ | Exact Mass |
|---|---|---|---|---|
| Int-1 | 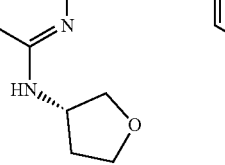 | 1H-NMR (CDCl3) δ: 8.99 (1H, s), 8.17-8.13 (2H, m), 7.63-7.56 (1H, m), 7.52-7.45 (2H, m), 6.90 (1H, s), 6.59 (1H, d, J = 6.3 Hz), 6.11 (1H, q, J = 6.7 Hz), 4.84-4.74 (1H, m), 4.11-4.00 (2H, m), 3.93-3.79 (2H, m), 2.64 (3H, s), 2.47-2.35 (1H, m), 2.06-1.95 (1H, m), 1.73 (3H, d, J = 6.8 Hz). | | |
| Int-2 | 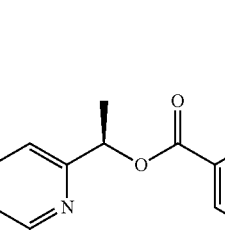 | 1H-NMR (CDCl3) δ: 8.98 (1H, s), 8.18-8.12 (2H, m), 7.63-7.56 (1H, m), 7.52-7.44 (2H, m), 6.87 (1H, s), 6.76-6.68 (1H, br m), 6.15-6.06 (1H, m), 3.98-3.55 (6H, m), 2.80-2.62 (4H, m), 2.12-2.01 (1H, m), 1.79-1.69 (4H, m). | | |
| Int-3 | 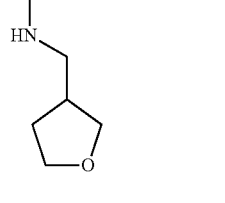 | 1H-NMR (CDCl3) δ: 9.01 (1H, s), 6.87 (1H, s), 6.42 (1H, d, J = 7.3 Hz), 4.39-4.27 (2H, m), 4.07-4.00 (2H, m), 3.66-3.57 (2H, m), 3.40 (3H, s), 2.66 (3H, s), 2.18-2.09 (2H, m), 1.73-1.59 (2H, m), 1.48 (3H, d, J = 6.8 Hz). | | |
| Int-4 | 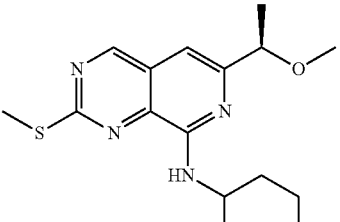 | | 453.3 | 452.19 |
| Int-5 | 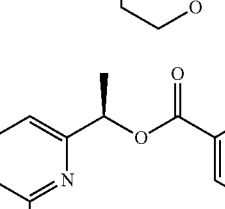 | | 453.3 | 452.19 |

TABLE 1-continued

| Compound No. | Structure | NMR | (M + H)+ | Exact Mass |
|---|---|---|---|---|
| Int-6 | 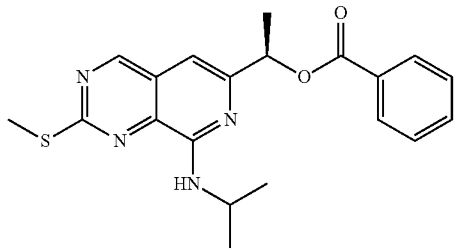 [SMILES: CSc1ncc2cc([C@@H](C)OC(=O)c3ccccc3)nc(NC(C)C)c2n1] | | 383.10 | 382.15 |
| Int-7 | 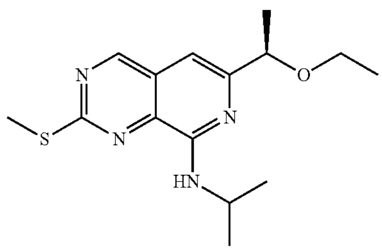 [SMILES: CCO[C@H](C)c1cc2cnc(SC)nc2c(NC(C)C)n1] | | 307.15 | 306.15 |
| Int-8 | 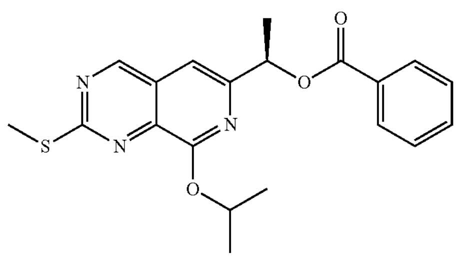 [SMILES: CSc1ncc2cc([C@@H](C)OC(=O)c3ccccc3)nc(OC(C)C)c2n1] | | 384.10 | 383.13 |

Example 8

Synthesis of (R)-1-(2-(methylsulfonyl)-8-(((S)-tetrahydro-2H-pyran-3-yl)amino)pyrido[3,4-d]pyrimidin-6-yl)ethyl benzoate

[Formula 96]

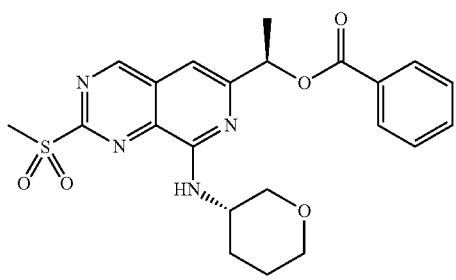

The (R)-1-(2-(methylthio)-8-(((S)-tetrahydro-2H-pyran-3-yl)amino)pyrido[3,4-d]pyrimidin-6-yl)ethyl benzoate synthesized in Example 4 (232 mg, 0.55 mmol) and Oxone® (672 mg, 1.09 mmol) were added to THF (2.7 mL) and water (2.7 mL) and the reaction mixture was stirred at room temperature overnight. The reaction was monitored by LC/MS. After completion of the reaction, saturated aqueous sodium hydrogen carbonate solution was slowly added to the reaction mixture, and the aqueous phase was extracted three times with ethyl acetate. The resultant organic phases were combined together and washed with saturated brine, and then dried over anhydrous magnesium sulfate. The solid was separated by filtration, and the filtrate was then concentrated under reduced pressure. The residue was purified by silica gel column chromatography to yield a crude product of the title compound (245 mg, 98%).

$^1$H-NMR (CDCl$_3$) δ: 9.30 (1H, s), 8.16 (2H, d, J=7.3 Hz), 7.65-7.60 (1H, m), 7.53-7.48 (2H, m), 7.02 (1H, s), 6.87 (1H, d, J=7.8 Hz), 6.13 (1H, q, J=6.7 Hz), 4.45-4.36 (1H, m), 4.08-4.04 (1H, m), 3.85-3.80 (1H, m), 3.67-3.60 (1H, m), 3.52-3.47 (1H, m), 3.41 (3H, s), 2.14-2.07 (1H, m), 1.90-1.74 (6H, m).

LC/MS: (M+H)$^+$=457.2, C$_{22}$H$_{24}$N$_4$O$_5$S=456.15

Example 9

Synthesis of (R)-1-(8-(1-methoxy-2-methylpropan-2-ylamino)-2-(methylsulfinyl)pyrido[3,4-d]pyrimidin-6-yl)ethyl benzoate

[Formula 97]

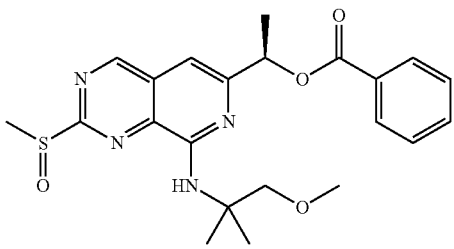

(R)-1-(8-(1-methoxy-2-methylpropan-2-ylamino)-2-(methylthio)pyrido[3,4-d]pyrimidin-6-yl)ethyl benzoate synthesized by the process described in Example 7 (1.9 g, 4.46 mmol) was dissolved in dichloromethane (30 mL) and the solution was stirred at 0° C. m-CPBA (0.767 g, 4.46 mmol) was gradually added to the solution at 0° C., and the reaction mixture was stirred at room temperature overnight. The reaction was monitored by LC/MS. After completion of the reaction, the reaction was quenched by addition of an aqueous sodium thiosulfate solution for reduction of excess reagent. The aqueous phase was extracted three times with dichloromethane (30 mL). The resultant organic phases were combined together and washed once with saturated aqueous sodium hydrogen carbonate solution (50 mL) and once with saturated brine (50 mL). The organic phase was dried over anhydrous sodium sulfate, and the solid was separated by filtration. The filtrate was then concentrated under reduced pressure, and the residue was purified by silica gel column chromatography to yield the title compound (1.9 g, 96%).

Compounds Int-9 to Int-16 were synthesized by the process described in Example 8 or 9.

TABLE 2

| Compound No. | Structure | (M + H)$^+$ | Exact Mass |
|---|---|---|---|
| Int-9 | 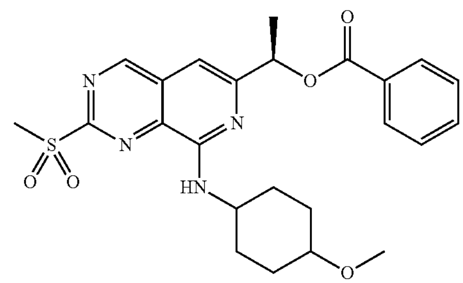 [SMILES: COC1CCC(Nc2nc([C@@H](C)OC(=O)c3ccccc3)cc3cnc(S(C)(=O)=O)nc23)CC1] | 485.3 | 484.18 |
| Int-10 | 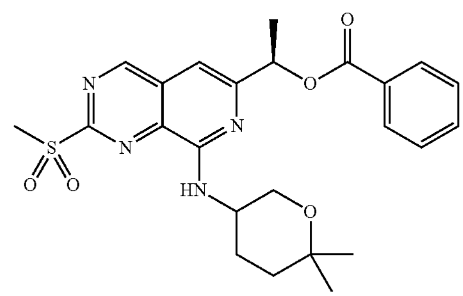 [SMILES: C[C@@H](OC(=O)c1ccccc1)c1cc2cnc(S(C)(=O)=O)nc2c(NC2CCC(C)(C)OC2)n1] | 485.3 | 484.18 |
| Int-11 | 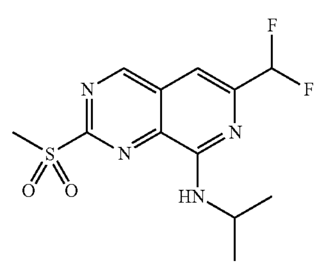 [SMILES: CC(C)Nc1nc(C(F)F)cc2cnc(S(C)(=O)=O)nc12] | 317.10 | 316.08 |

TABLE 2-continued

| Compound No. | Structure | (M + H)+ | Exact Mass |
|---|---|---|---|
| Int-12 | 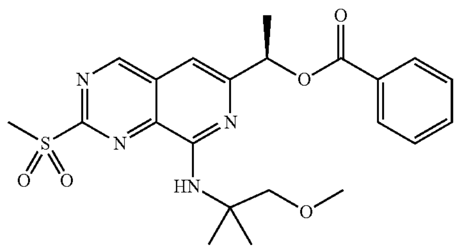 [SMILES: COCC(C)(C)Nc1nc([C@@H](C)OC(=O)c2ccccc2)cc2cnc(S(C)(=O)=O)nc12] | 459.15 | 458.16 |
| Int-13 | 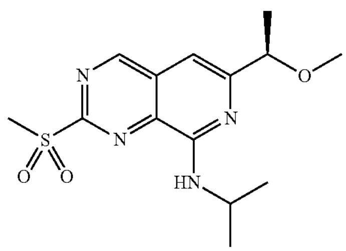 | 325.10 | 324.13 |
| Int-14 | 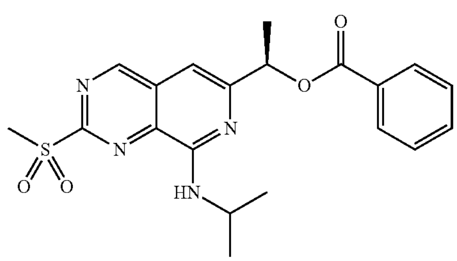 [SMILES: CC(C)Nc1nc([C@@H](C)OC(=O)c2ccccc2)cc2cnc(S(C)(=O)=O)nc12] | 415.10 | 414.14 |
| Int-15 | 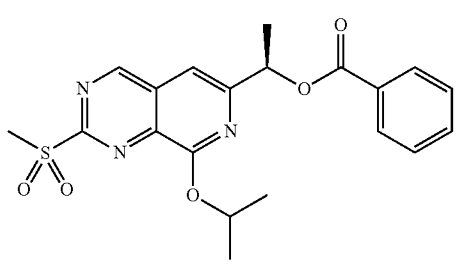 | 416.05<br>374.05 | 415.12 |
| Int-16 | 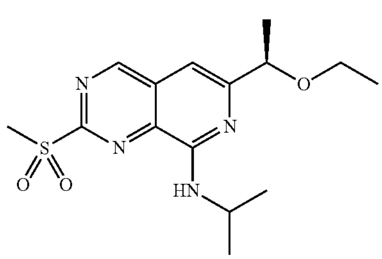 [SMILES: CCO[C@H](C)c1cc2cnc(S(C)(=O)=O)nc2c(NC(C)C)n1] | 339.15 | 338.14 |

Example 10

Synthesis of (R)-1-(5-chloro-2-(methylsulfonyl)-8-(((S)-tetrahydro-2H-pyran-3-yl)amino)pyrido[3,4-d]pyrimidin-6-yl)ethyl benzoate

[Formula 98]

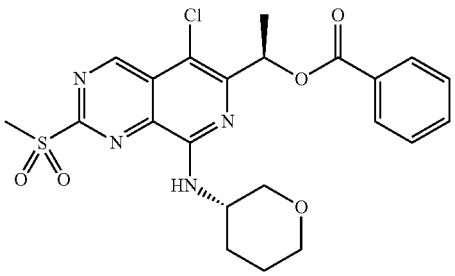

A mixture of (R)-1-(2-(methylsulfonyl)-8-(((S)-tetrahydro-2H-pyran-3-yl)amino)pyrido[3,4-d]pyrimidin-6-yl) ethyl benzoate synthesized in Example 8 (268 mg, 0.587 mmol) and N-chlorosuccinimide (96 mg, 0.72 mmol) in 1,2-dichloroethane (2.9 mL) was stirred at 65° C. overnight. The reaction was monitored by LC/MS. After completion of the reaction, the reaction mixture was cooled to room temperature. The reaction mixture was directly purified by silica gel column chromatography to yield the title compound (255 mg, 89%).

$^1$H-NMR (CDCl$_3$) δ: 9.70 (1H, s), 8.11-8.06 (2H, m), 7.60-7.53 (1H, m), 7.48-7.42 (2H, m), 6.90 (1H, d, J=7.8 Hz), 6.46 (1H, q, J=6.7 Hz), 4.28-4.18 (1H, m), 3.82 (1H, dd, J=11.5, 3.2 Hz), 3.76-3.69 (1H, m), 3.65-3.56 (1H, m), 3.45-3.37 (4H, m), 2.09-2.00 (1H, m), 1.88-1.61 (6H, m).

Compound Int-17 was synthesized by the process described in Example 10.

Example 11

Synthesis of tert-butyl 4-[6-(6-difluoromethyl-8-isopropylaminopyrido[3,4-d]pyrimidin-2-ylamino) pyridin-3-yl]piperazine-1-carboxylate

[Formula 99]

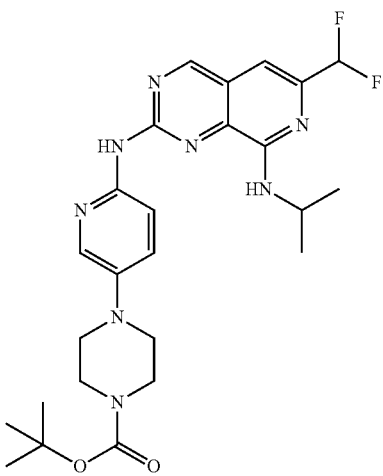

The tert-butyl 4-(6-aminopyridin-3-yl)piperazine-1-carboxylate synthesized in Reference Example 5 (88 mg, 0.316 mmol) was dissolved in THF (3.5 mL), and sodium hydride (22.8 mg, 0.57 mmol, 60%) was added to the solution at 0° C. and stirred for 10 minutes. To the suspension was added a solution of the (6-difluoromethyl-2-methanesulfonylpyrido[3,4-d]pyrimidine-8-yl)isopropylamine synthesized in Example 8 (Int-11, 100 mg, 0.316 mmol) in THF (3.5 mL) at room temperature and the reaction mixture was stirred at 35° C. for one hour. The reaction was monitored by TLC and LC/MS. After completion of the reaction, the reaction was quenched by addition of ice water (10 mL). The aqueous phase was extracted twice with ethyl acetate (25 mL). The resultant organic phases were combined together and washed with saturated brine, and the mixture was dried over anhydrous sodium sulfate. The solid was separated by filtration, and the filtrate was then concentrated under reduced pressure. The residue was purified by silica gel column chromatography to yield the title compound (56.7 mg, 35%).

TABLE 3

| Compound No. | Structure | (M + H)$^+$ | Exact Mass |
|---|---|---|---|
| Int-17 | 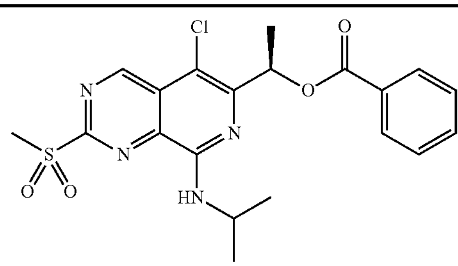 | 449.10 | 448.10 |

Example 12

Synthesis of 6-difluoromethyl-8-isopropyl-2-(5-piperazin-1-ylpyridin-2-yl)pyrido[3,4-d]pyrimidine-2,8-diamine (Compound 3)

[Formula 100]

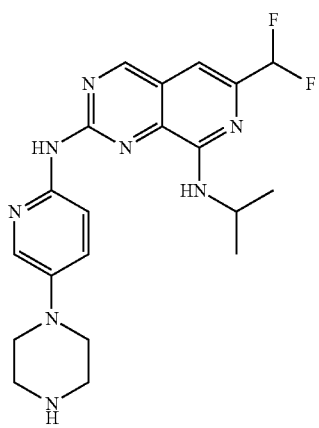

(3)

The tert-butyl 4-[6-(6-difluoromethyl-8-isopropylaminopyrido[3,4-d]pyrimidin-2-ylamino)pyridin-3-yl]piperazine-1-carboxylate synthesized in Example 11 (195 mg, 0.378 mmol) was dissolved in dichloromethane (5 mL) and stirred at 0° C. Hydrogen chloride (0.4 mL, 4 mol/L, 1,4-dioxane solution) was added dropwise to the solution and stirred at room temperature for 30 minutes. The reaction was monitored by LC/MS. After completion of the reaction, the reaction mixture was concentrated under reduced pressure. The resultant crude product was purified by fractionation HPLC (acetonitrile/water/TFA) to yield a TFA salt of the title compound (114 mg, purity: 99% or more). The TFA salts obtained by multiple reactions were combined and used in the next step.

The TFA salt (200 mg) was dissolved in methanol (0.625 mL) and dichloromethane (1.875 mL) and applied onto a strong cation exchange resin (SCX) column. The SCX column was washed with a solvent mixture of methanol and dichloromethane (1:3). The target compound was subsequently eluted from the SCX column with a solvent mixture of methanol and dichloromethane (1:3) containing 2.5% ammonia (2 mol/L, methanol solution). The eluate was concentrated under reduced pressure to yield the title compound (105 mg, purity: >99%).

Example 13

Synthesis of tert-butyl (R)-4-(6-(6-(benzoyloxy)ethyl-8-(1-methoxy-2-methylpropan-2-ylamino)pyrido[3,4-d]pyrimidin-2-ylamino)pyridin-3-yl)piperazine-1-carboxylate

[Formula 101]

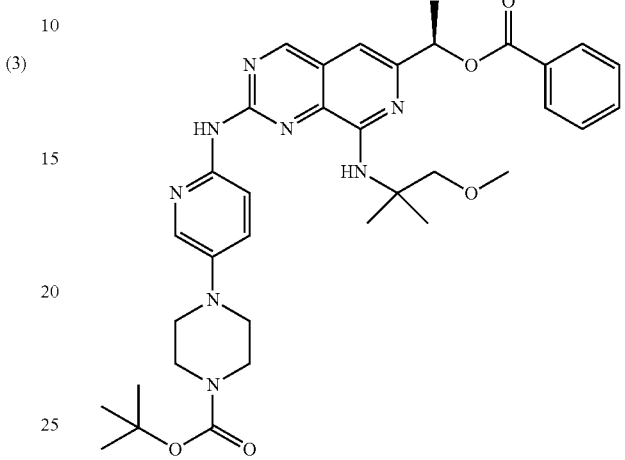

The (R)-1-(8-(1-methoxy-2-methylpropan-2-ylamino)-2-(methylsulfinyl)pyrido[3,4-d]pyrimidin-6-yl)ethyl benzoate synthesized in Example 9 (1.9 g, 4.3 mmol) and the tert-butyl 4-(6-aminopyridin-3-yl)piperazine-1-carboxylate synthesized in Reference Example 5 (3.59 g, 12.9 mmol) were suspended in toluene (30 mL) and the reaction mixture was stirred at 120° C. overnight. The reaction was monitored by LC/MS. The resultant reaction mixture was cooled to room temperature, and the solvent was removed through evaporation under reduced pressure. The residue was purified by silica gel column chromatography to yield the title compound (850 mg, 30%).

Example 14

Synthesis of (R)-1-(8-(1-methoxy-2-methylpropan-2-ylamino)-2-(5-(piperazin-1-yl)pyridin-2-ylamino)pyrido[3,4-d]pyrimidin-6-yl)ethanol (Compound 195)

[Formula 102]

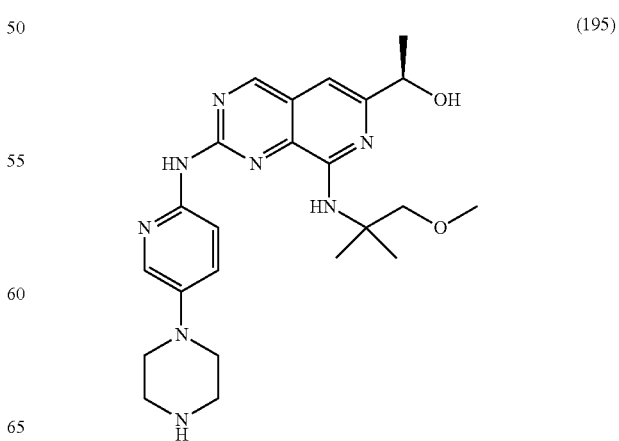

(195)

ide (124 mg, 5.2 mmol) was added to the solution. The resultant reaction mixture was stirred at room temperature overnight, and the reaction was monitored by LC/MS. After completion of the reaction, hydrogen chloride (4 mol/L, methanol solution) was added dropwise to the reaction mixture, to adjust the pH of the mixture to 7. The reaction mixture was concentrated under reduced pressure to yield a crude product. The crude product was used for the subsequent reaction without purification.

The crude product was dissolved in hydrogen chloride (20 mL, 4 mol/L, methanol solution) and stirred at room temperature for four hours. The reaction was monitored by LC/MS. After completion of the reaction, the reaction mixture was concentrated under reduced pressure. The residue was dissolved in methanol (30 mL), and concentrated aqueous ammonia (25%) was added dropwise to the solution, to adjust the pH of the solution to 10 or higher. Saturated brine (100 mL) was added to the solution, and the mixture was extracted three times with a solvent mixture of dichloromethane and methanol (9:1) (30 mL). The resultant organic phases were combined together and washed once with saturated brine (50 mL). The organic phase was dried over anhydrous sodium sulfate, and the solid was separated by filtration. The filtrate was concentrated under reduced pressure to yield a crude product of the title compound. The crude product was then washed with methanol to yield the title compound (470 mg, 80%).

Example 15

Synthesis of (S)-1-(4-(6-(((R)-1-hydroxyethyl)-8-(isopropylamino)pyrido[3,4-d]pyrimidin-2-yl)amino)pyridazin-3-yl)piperazin-1-yl)propan-2-ol (Compound 676)

[Formula 103]

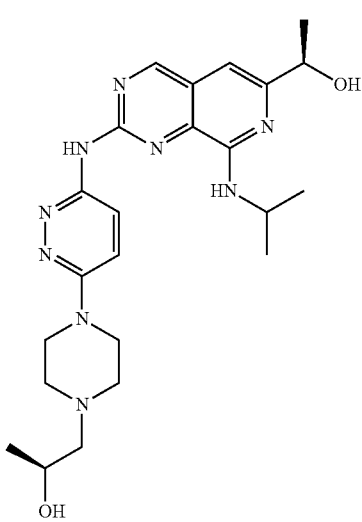

(676)

(R)-1-(8-(isopropylamino)-2-((6-(piperazin-1-yl)pyridazin-3-yl)amino)pyrido[3,4-d]pyrimidin-6-yl)ethanol synthesized by the process described in Example 14 (compound 261, 25 mg, 0.061 mmol) was dissolved in methanol (0.31 mL), and (S)-propylene oxide (3.5 mg, 0.061 mmol) was added to the solution. The resultant reaction mixture was stirred at 55° C. overnight, and the reaction was monitored by LC/MS. After completion of the reaction, the reaction mixture was concentrated under reduced pressure. The resultant crude product was purified by fractionation HPLC (acetonitrile/water/TFA) and applied onto a strong cation exchange resin (SCX) column. The SCX column was washed with methanol, and the target product was then eluted with ammonia (2 mol/L, methanol solution). The eluate was concentrated under reduced pressure to yield the title compound (19 mg).

Example 16

Synthesis of (R)-1-(8-(isopropylamino)-2-((6-(4-(oxetan-3-yl)piperazin-1-yl)pyridazin-3-yl)amino)pyrido[3,4-d]pyrimidin-6-yl)ethanol (Compound 682)

[Formula 104]

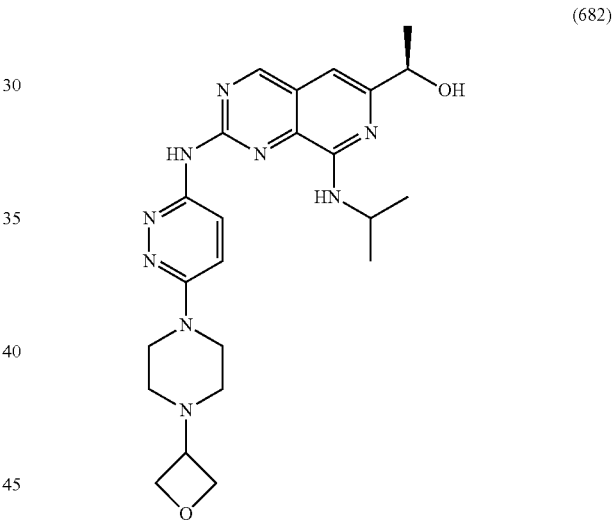

(682)

(R)-1-(8-(isopropylamino)-2-((6-(piperazin-1-yl)pyridazin-3-yl)amino)pyrido[3,4-d]pyrimidin-6-yl)ethanol synthesized by the process described in Example 14 (compound 261, 16.4 mg, 0.040 mmol) was dissolved in acetic acid (2.8 μL) and 1,2-dichloroethane (0.4 mL). To the mixture was added 3-oxetanone (2.8 μL, 0.048 mmol) and sodium triacetoxyborohydride (12.7 mg, 0.060 mmol). The resultant reaction mixture was stirred at 55° C. for two hours, and the reaction was monitored by LC/MS. After completion of the reaction, the reaction mixture was cooled to room temperature, and the reaction was quenched by addition of water. The reaction mixture was extracted with ethyl acetate, and the organic layer was concentrated under reduced pressure. The resultant crude product was then purified by amine-modified column chromatography (ethyl acetate/methanol) to yield the title compound (7.5 mg).

Example 17

Synthesis of (R)-3-(4-(6-((8-(isopropylamino)-6-(1-methoxyethyl)pyrido[3,4-d]pyrimidin-2-yl)amino)pyridazin-3-yl)piperazin-1-yl)propanoic acid (Compound 684)

[Formula 105]

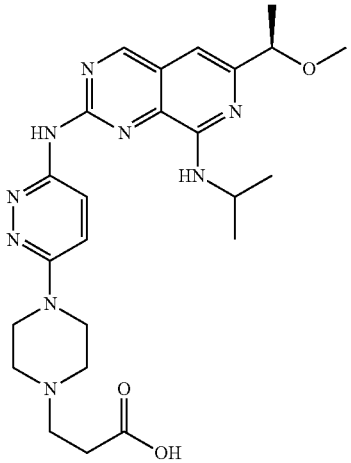

(684)

(R)—N8-isopropyl-6-(1-methoxyethyl)-N2-(6-(piperazin-1-yl)pyridazin-3-yl)pyrido[3,4-d]pyrimidine-2,8-diamine synthesized by the process described in Example 14 (compound 217, 29.6 mg, 0.07 mmol) was dissolved in methanol (0.35 mL), and methyl acrylate (6.3 μL, 0.07 mmol) was added to the solution. The resultant reaction mixture was stirred at 55° C. for two hours, and the reaction was monitored by LC/MS. After completion of the reaction, the reaction mixture was concentrated under reduced pressure, and the resultant crude product was roughly purified by silica gel column chromatography (ethyl acetate/heptane). The crude product was then dissolved in THF (0.56 mL) and methanol (0.56 mL), and 4M aqueous lithium hydroxide solution (0.028 mL, 0.112 mmol) was added to the solution. The resultant reaction mixture was stirred at room temperature overnight, and the reaction was monitored by LC/MS. After completion of the reaction, the reaction mixture was acidified with 2M aqueous hydrochloric acid solution and then adsorbed onto a strong cation exchange resin (SCX) column. The SCX column was washed with water and dichloromethane, and the target product was then eluted with ammonia (2 mol/L, methanol solution). The eluate was concentrated under reduced pressure to yield the title compound (27.5 mg).

Example 18

Synthesis of (R)-2-(4-(6-((8-(isopropylamino)-6-(1-methoxyethyl)pyrido[3,4-d]pyrimidin-2-yl)amino)pyridazin-3-yl)piperazin-1-yl)-2-methylpropanoic acid (Compound 678)

[Formula 106]

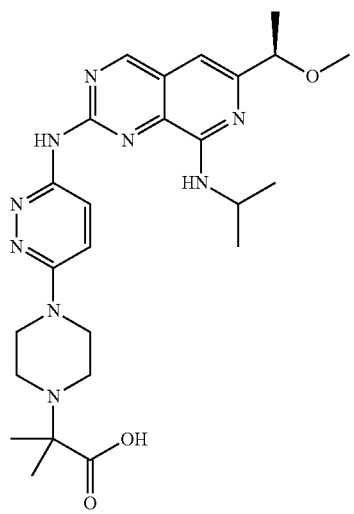

(678)

(R)—N8-isopropyl-6-(1-methoxyethyl)-N2-(6-(piperazin-1-yl)pyridazin-3-yl)pyrido[3,4-d]pyrimidine-2,8-diamine synthesized by the process described in Example 14 (compound 217, 42.3 mg, 0.10 mmol) was dissolved in acetonitrile (0.2 mL). To the mixture was added tert-butyl 2-bromo-2-methylpropanoate (22.4 μL, 0.12 mmol) and potassium carbonate (16.6 mg). The resultant reaction mixture was stirred at 85° C. overnight, and the reaction was monitored by LC/MS. After completion of the reaction, the reaction mixture was cooled to room temperature, and the reaction was quenched by addition of water. The reaction mixture was extracted with ethyl acetate, and the resultant crude product was briefly purified by silica gel column chromatography (ethyl acetate/heptane). The crude product was then dissolved in dichloromethane (1 mL), and trifluoroacetic acid (1 mL) was added to the solution. The resultant reaction mixture was stirred at room temperature for 24 hours, and the reaction was monitored by LC/MS. After completion of the reaction, the reaction mixture was concentrated under reduced pressure, and the resultant crude product was adsorbed onto a strong cation exchange resin (SCX) column. The SCX column was washed with methanol, and the target product was then eluted with ammonia (2 mol/L, methanol solution). The eluate was concentrated under reduced pressure to yield the title compound (8.5 mg).

Example 19

Compounds 1 to 1239 were synthesized by the processes described in Examples 11 to 18.

TABLE 4

| Compound No. | L | R¹ | R² | R³ | ![Y-Z/N=X with R⁴] |
|---|---|---|---|---|---|
| 1 | HN | cyclopentyl | CHF₂ | H | pyridin-2-yl-5-piperazin-1-yl |
| 2 | HN | piperidin-3-yl | CHF₂ | H | pyridin-2-yl-5-piperazin-1-yl |
| 3 | HN | isopropyl | CHF₂ | H | pyridin-2-yl-5-piperazin-1-yl |
| 4 | HN | tetrahydropyran-4-yl | CHF₂ | H | pyridin-2-yl-5-piperazin-1-yl |

TABLE 4-continued

| Compound No. | L | R¹ | R² | R³ | ![Y-Z/N=X-R⁴ ring] |
|---|---|---|---|---|---|
| 5 | N(CH₃) | cyclopentyl | CHF₂ | H | 6-(piperazin-1-yl)pyridin-3-yl |
| 6 | NH | cyclopentyl | C(CH₃)₂OH | H | 6-(piperazin-1-yl)pyridin-3-yl |
| 7 | O | isopropyl | CHF₂ | H | 6-(piperazin-1-yl)pyridin-3-yl |
| 8 | NH | cyclopentyl | CH(CH₃)OH | H | 6-(piperazin-1-yl)pyridin-3-yl |

TABLE 4-continued

| Compound No. | L | R¹ | R² | R³ | ![structure with Y-Z, N=X, R⁴] |
|---|---|---|---|---|---|
| 9 | HN (secondary amine linker) | isopropyl | C(CH₃)(OH)– | H | pyridine-piperazine |
| 10 | N-methyl amine linker | cyclopentyl | C(CH₃)(OH)– | H | pyridine-piperazine |
| 11 | N-methyl amine linker | tetrahydropyran-4-yl | C(CH₃)(OH)– | H | pyridine-piperazine |
| 12 | HN (secondary amine linker) | tetrahydropyran-4-yl | C(CH₃)(OH)– | H | pyridine-piperazine |

TABLE 4-continued

| Compound No. | L | R¹ | R² | R³ | ![structure with Y-Z, N=X, R⁴] |
|---|---|---|---|---|---|
| 13 | HN (secondary amine linker) | tert-butyl | CHF₂ | H | 6-(piperazin-1-yl)pyridin-3-yl |
| 14 | N-methyl amine linker | isopropyl | CHF₂ | H | 6-(piperazin-1-yl)pyridin-3-yl |
| 15 | HN (secondary amine linker) | CH₂CH₂OCH₃ (with gem-dimethyl) | CHF₂ | H | 6-(piperazin-1-yl)pyridin-3-yl |
| 16 | HN (secondary amine linker) | isopropyl | CH(OH)CH₃ | H | 6-(piperazin-1-yl)pyridin-3-yl |

TABLE 4-continued

| Compound No. | L | R¹ | R² | R³ | ![Y-Z/N=X-R⁴ ring] |
|---|---|---|---|---|---|
| 17 | -HN- | isopropyl | -C(CH₃)(OH)- (with stereochemistry) | H | 5-(piperazin-1-yl)pyridin-2-yl |
| 18 | -HN- | cyclopropyl | -CHF₂ | H | 5-(piperazin-1-yl)pyridin-2-yl |
| 19 | -HN- | -CH(CH₃)- | -CHF₂ | H | 5-(piperazin-1-yl)pyridin-2-yl |
| 20 | -HN- | -CH(CH₂CH₃)- | -CHF₂ | H | 5-(piperazin-1-yl)pyridin-2-yl |

TABLE 4-continued

| Compound No. | L | R¹ | R² | R³ | ![structure] |
|---|---|---|---|---|---|
| 21 | -HN- | cyclopropyl | -C(CH₃)(OH)- | H | 6-(piperazin-1-yl)pyridin-3-yl |
| 22 | -HN- | -CH₃ | -C(CH₃)(OH)- | H | 6-(piperazin-1-yl)pyridin-3-yl |
| 23 | -HN- | -CH(CH₂CH₃)- | -C(CH₃)(OH)- | H | 6-(piperazin-1-yl)pyridin-3-yl |
| 24 | -HN- | -C(CH₃)₃ | -C(CH₃)(OH)- | H | 6-(piperazin-1-yl)pyridin-3-yl |

TABLE 4-continued

| Compound No. | L | R¹ | R² | R³ | ![Y-Z/N=X-R⁴ structure] |
|---|---|---|---|---|---|
| 25 | HN (linker) | oxetan-3-yl | C(CH₃)₂OH | H | 6-(piperazin-1-yl)pyridin-3-yl |
| 26 | HN (linker) | phenyl | C(CH₃)₂OH | H | 6-(piperazin-1-yl)pyridin-3-yl |
| 27 | HN (linker) | 1H-pyrazol-3-yl | C(CH₃)₂OH | H | 6-(piperazin-1-yl)pyridin-3-yl |
| 28 | HN (linker) | CH(CH₃)CH₂OCH₃ | C(CH₃)₂OH | H | 6-(piperazin-1-yl)pyridin-3-yl |

TABLE 4-continued

| Compound No. | L | R¹ | R² | R³ | ![Y-Z/N=X-R⁴ ring] |
|---|---|---|---|---|---|
| 29 | -HN- | neopentyl-OMe | -C(CH₃)(OH)- | H | 5-(piperazin-1-yl)pyridin-2-yl |
| 30 | -HN- | -CH(CH₃)CH₂OMe | -CHF₂ | H | 5-(piperazin-1-yl)pyridin-2-yl |
| 31 | -HN- | neopentyl-OMe | -CHF₂ | H | 5-(piperazin-1-yl)pyridin-2-yl |
| 32 | -HN- | 1H-pyrazol-4-yl | -C(CH₃)(OH)- | H | 5-(piperazin-1-yl)pyridin-2-yl |

TABLE 4-continued

| Compound No. | L | R¹ | R² | R³ | ![Y-Z/N=X-R⁴ scaffold] |
|---|---|---|---|---|---|
| 33 | HN (linker) | oxetan-3-yl | CHF₂ | H | 5-(piperazin-1-yl)pyridin-2-yl |
| 34 | HN (linker) | isopropyl | C(=O)N(CH₃)₂ | H | 5-(piperazin-1-yl)pyridin-2-yl |
| 35 | HN (linker) | isopropyl | C(=O)CH₃ | H | 5-(piperazin-1-yl)pyridin-2-yl |
| 36 | HN (linker) | CH₂CHF₂ | C(CH₃)₂OH | H | 5-(piperazin-1-yl)pyridin-2-yl |

TABLE 4-continued

| Compound No. | L | R¹ | R² | R³ | ![Y-Z/N=X-R⁴ ring] |
|---|---|---|---|---|---|
| 37 | -HN< | -CH(CH₃)₂ | -CH(CH₃)OCH₃ | H | 5-(piperazin-1-yl)pyridin-2-yl |
| 38 | -HN< | -CH(CH₃)₂ | -CH(CH₃)OCH₃ (S) | H | 5-(piperazin-1-yl)pyridin-2-yl |
| 39 | -HN< | -CH(CH₃)₂ | -CH(CH₃)OCH₃ (R) | H | 5-(piperazin-1-yl)pyridin-2-yl |
| 40 | -HN< | -CH₂CF₃ | -C(CH₃)₂OH | H | 5-(piperazin-1-yl)pyridin-2-yl |

TABLE 4-continued

| Compound No. | L | R¹ | R² | R³ | ![Y-Z-X-R⁴ ring] |
|---|---|---|---|---|---|
| 41 | -HN-C(CH₃)- | -CH(CH₃)CH₂OH | -CH(CH₃)OH | H | pyridin-2-yl-5-(piperazin-1-yl) |
| 42 | -HN-C(CH₃)- | -CH(CH₃)₂ | -CHF₂ | H | pyridin-2-yl-5-(4-methylpiperazin-1-yl) |
| 43 | -HN-C(CH₃)- | -CH(CH₃)₂ | -CHF₂ | H | pyridin-2-yl-5-(morpholin-4-yl) |
| 44 | -HN-C(CH₃)- | -CH(CH₃)₂ | -CH₂OCH₃ | H | pyridin-2-yl-5-(piperazin-1-yl) |

TABLE 4-continued

| Compound No. | L | R¹ | R² | R³ | ![Y-Z-R⁴ / N=X] |
|---|---|---|---|---|---|
| 45 | -HN- | -C(CH₃)₂CH₂OH | -CH(OH)CH₃ | H | 5-(piperazin-1-yl)pyridin-2-yl |
| 46 | -HN- | -CH(CH₃)₂ | -CHF₂ | H | 5-(piperazin-1-yl)pyridin-2-yl |
| 47 | -HN- | -CH(CH₃)₂ | -CHF₂ | H | 5-(piperazin-1-ylmethyl)pyridin-2-yl |
| 48 | -HN- | -cyclobutyl | -CH(OH)CH₃ | H | 5-(piperazin-1-yl)pyridin-2-yl |

TABLE 4-continued

| Compound No. | L | R¹ | R² | R³ | ![Y-Z/N=X-R⁴ structure] |
|---|---|---|---|---|---|
| 49 | -HN< | -CH(CH₃)₂ | -CHF₂ | H | 6-(4-(2-hydroxyethyl)piperazin-1-yl)pyridin-3-yl |
| 50 | -HN< | -CH(CH₃)₂ | -CHF₂ | H | 6-(4-hydroxypiperidin-1-yl)pyridin-3-yl |
| 51 | -HN< | -CH(CH₃)₂ | -CHF₂ | H | 6-(4-(3-hydroxypropyl)piperidin-1-yl)pyridin-3-yl |
| 52 | -HN< | -CH(CH₃)₂ | -CHF₂ | H | 6-(3-aminopyrrolidin-1-yl)pyridin-3-yl |

TABLE 4-continued

| Compound No. | L | R¹ | R² | R³ | ⸺Y=Z⸺R⁴ / N=X |
|---|---|---|---|---|---|
| 53 | HN | isopropyl | CHF₂ | H | 5-(3-hydroxypyrrolidin-1-yl)pyridin-2-yl |
| 54 | HN | C(CH₃)(CF₃) | CH(CH₃)OH | H | 5-(piperazin-1-yl)pyridin-2-yl |
| 55 | HN | isopropyl | CHF₂ | F | 5-(piperazin-1-yl)pyridin-2-yl |
| 56 | HN | tetrahydropyran-4-yl | C(=O)CH₃ | H | 5-(piperazin-1-yl)pyridin-2-yl |

TABLE 4-continued

| Compound No. | L | R¹ | R² | R³ | ![Y-Z-X-R⁴ ring] |
|---|---|---|---|---|---|
| 57 | -HN- | cyclopentyl | -C(=O)CH₃ | H | 6-(piperazin-1-yl)pyridin-3-yl |
| 58 | -HN- | sec-butyl | -C(=O)CH₃ | H | 6-(piperazin-1-yl)pyridin-3-yl |
| 59 | -HN- | tert-butyl | -C(=O)CH₃ | H | 6-(piperazin-1-yl)pyridin-3-yl |
| 60 | -HN- | isopropyl | -CHF₂ | CH₃ | 6-(piperazin-1-yl)pyridin-3-yl |

TABLE 4-continued

| Compound No. | L | R¹ | R² | R³ | ![structure with Y-Z/N=X/R⁴] |
|---|---|---|---|---|---|
| 61 | -HN- | -CH(CH₃)₂ | -C(CH₃)₂OH | H | pyridine-piperidine-OH |
| 62 | -HN- | -CH(CH₃)₂ | -C(CH₃)₂CH₂OH | CH₃ | pyridine-piperazine-NH |
| 63 | -HN- | -CH(CH₃)₂ | -C(CH₃)(⫯⫯⫯OH) | F | pyridine-piperazine-NH |
| 64 | -HN- | -CH(CH₃)₂ | -C(CH₃)(▬OH) | F | pyridine-piperazine-NH |

TABLE 4-continued

| Compound No. | L | R¹ | R² | R³ | ![Y-Z/N=X-R⁴ structure] |
|---|---|---|---|---|---|
| 65 | -HN- | isopropyl | -C(CH₃)(OH)- (S) | CH₃ | 6-(piperazin-1-yl)pyridin-3-yl |
| 66 | -HN- | isopropyl | -C(CH₃)(OH)- (R) | CH₃ | 6-(piperazin-1-yl)pyridin-3-yl |
| 67 | -HN- | isopropyl | -CHF₂- | H | 2-fluoro-6-(piperazin-1-yl)pyridin-3-yl |
| 68 | -HN- | isopropyl | -C(=O)CH₃ | CH₃ | 6-(piperazin-1-yl)pyridin-3-yl |

TABLE 4-continued

| Compound No. | L | R¹ | R² | R³ | ![structure] |
|---|---|---|---|---|---|
| 69 | HN linker | benzyl | C(CH₃)(OH)– | H | 6-(piperazin-1-yl)pyridin-3-yl |
| 70 | HN linker | 1-phenylethyl | C(CH₃)(OH)– | H | 6-(piperazin-1-yl)pyridin-3-yl |
| 71 | HN linker | isopropyl | C(CH₃)(OH)– | H | 6-(4-methylpiperazin-1-yl)pyridin-3-yl |
| 72 | HN linker | isopropyl | C(CH₃)(OH)– | H | 6-morpholinopyridin-3-yl |

TABLE 4-continued

| Compound No. | L | R¹ | R² | R³ | ⟶Y—Z⟍R⁴ / N=X |
|---|---|---|---|---|---|
| 73 | HN | isopropyl | CHF₂ | H | pyridazine-piperazine(NH) |
| 74 | HN | isopropyl | C(CH₃)(OH) | H | pyridine-piperazine-CH₂CH₂OH |
| 75 | HN | isopropyl | C(CH₃)(OH) | H | pyridine-piperidine-CH₂CH₂CH₂OH |
| 76 | HN | isopropyl | C(CH₃)(OH) | H | pyridine-pyrrolidine-NH₂ |

TABLE 4-continued

| Compound No. | L | R¹ | R² | R³ | ![Y-Z/N=X-R⁴ structure] |
|---|---|---|---|---|---|
| 77 | HN | isopropyl | C(CH₃)(OH) | H | pyridine-pyrrolidine-OH |
| 78 | HN | isopropyl | C(CH₃)(OH) | H | pyridine-piperidine-NH |
| 79 | HN | isopropyl | C(CH₃)(OH) | H | pyridine-CH₂-piperazine-NH |
| 80 | HN | isopropyl | CHF₂ | H | pyridine-(N-methyl-oxopiperazine) |

TABLE 4-continued

| Compound No. | L | R¹ | R² | R³ | ![Y-Z/N=X-R⁴ structure] |
|---|---|---|---|---|---|
| 81 | -HN- | -CH(CH₃)₂ | -CHF₂ | H | 5-(2-(dimethylamino)ethoxy)pyridin-2-yl |
| 82 | -HN- | -CH(CH₃)₂ | -CHF₂ | H | pyridin-2-yl |
| 83 | -HN- | -CH(CH₃)₂ | -CHF₂ | H | 5-(3-oxopiperazin-1-yl)pyridin-2-yl |
| 84 | -HN- | -CH(CH₃)₂ | -CHF₂ | H | 5-(4-methyl-3-oxopiperazin-1-yl)pyridin-2-yl |
| 85 | -HN- | -CH(CH₃)₂ | -CHF₂ | H | 5-(ureido)pyridin-2-yl |

TABLE 4-continued

| Compound No. | L | R¹ | R² | R³ | ![Y-Z-X=N ring with R⁴] |
|---|---|---|---|---|---|
| 86 | -HN< | -CH(CH₃)₂ | -CHF₂ | H | 6-(acetylamino)pyridin-3-yl |
| 87 | -HN< | -CH(CH₃)₂ | -CHF₂ | H | 5-aminopyridin-2-yl |
| 88 | -HN< | -CH(CH₃)₂ | -CHF₂ | H | 6-(methylsulfonylamino)pyridin-3-yl |
| 89 | -HN< | -CH(CH₃)₂ | -CHF₂ | H | 6-(3-oxopiperazin-1-yl)pyridin-3-yl |

TABLE 4-continued

| Compound No. | L | R¹ | R² | R³ | ![structure](Y-Z, N=X, R⁴) |
|---|---|---|---|---|---|
| 90 | -HN- | isopropyl | -CHF₂ | H | pyridine-piperidine-COOH |
| 91 | -N(CH₃)- | isopropyl | -C(O)CH₃ | H | pyridine-piperazine-NH |
| 92 | -HN- | tetrahydrofuran-3-yl | -C(CH₃)(OH)- | H | pyridine-piperazine-NH |
| 93 | -HN- | tetrahydropyran-3-yl | -C(CH₃)(OH)- | H | pyridine-piperazine-NH |

TABLE 4-continued

| Compound No. | L | R¹ | R² | R³ | ![structure](Y-Z/N=X with R⁴) |
|---|---|---|---|---|---|
| 94 | -HN- | -CH(CH₃)₂ | -CHF₂ | H | 6-(morpholinomethyl)pyridin-3-yl |
| 95 | -HN- | -CH(CH₃)₂ | -CHF₂ | H | 6-(2-hydroxyacetamido)pyridin-3-yl |
| 96 | -HN- | -CH(CH₃)₂ | -CHF₂ | H | 6-carbamoylpyridin-3-yl |
| 97 | -HN- | -CH(CH₃)₂ | -CHF₂ | H | 6-(oxalamido)pyridin-3-yl |
| 98 | -HN- | -CH(CH₃)₂ | -CHF₂ | H | 6-(3-hydroxypropanamido)pyridin-3-yl |

TABLE 4-continued

| Compound No. | L | R¹ | R² | R³ | ![structure](Y-Z-X-N with R⁴) |
|---|---|---|---|---|---|
| 99 | HN (branched) | isopropyl | CHF₂ | H | 5-phenylpyridin-2-yl |
| 100 | HN (branched) | isopropyl | CHF₂ | H | 5-(pyridin-4-yl)pyridin-2-yl |
| 101 | HN (branched) | isopropyl | CHF₂ | Cl | 5-(piperazin-1-yl)pyridin-2-yl |
| 102 | HN (branched) | isopropyl | CHF₂ | H | 6-(3-methoxy-3-oxopropyl)pyridin-2-yl |

TABLE 4-continued

| Compound No. | L | R¹ | R² | R³ | ![structure] |
|---|---|---|---|---|---|
| 103 | HN | isopropyl | CHF₂ | H | 2-pyridyl with 5-O-CH₂CH₂-(2-oxopyrrolidin-1-yl) |
| 104 | HN | isopropyl | CHF₂ | H | 6-methylpyridin-2-yl |
| 105 | HN | 1-(1H-pyrazol-3-yl)ethyl | C(CH₃)₂OH | H | 6-(piperazin-1-yl)pyridin-3-yl |
| 106 | HN | 1-(1H-pyrazol-4-yl)ethyl | C(CH₃)₂OH | H | 6-(piperazin-1-yl)pyridin-3-yl |

TABLE 4-continued
| Compound No. | L | R¹ | R² | R³ | 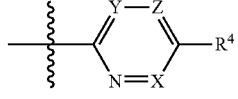 |
|---|---|---|---|---|---|
| 107 | 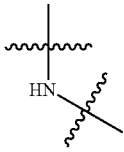 [SMILES: *N*] | 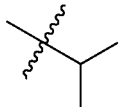 [SMILES: *C(C)C] | 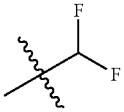 [SMILES: *C(F)F] | H |  |
| 108 | 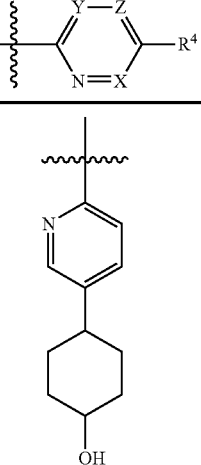 | 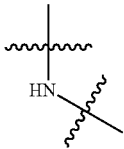 [SMILES: *N*] | 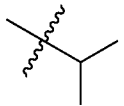 [SMILES: *C(C)C] | H | 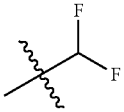 [SMILES: *C(F)F] |
| 109 |  | 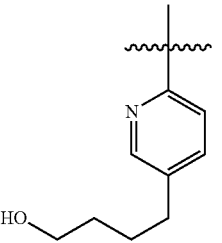 [SMILES: *c1ccc(CCCCO)cn1] | 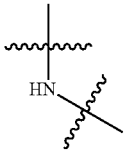 [SMILES: *N*] | H | 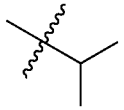 [SMILES: *C(C)C] |
| 110 | 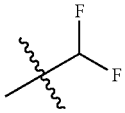 [SMILES: *C(F)F] |  | 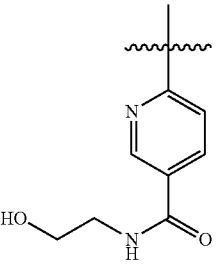 [SMILES: *c1ccc(C(=O)NCCO)cn1] | H | 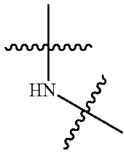 [SMILES: *N*] |
| 111 | 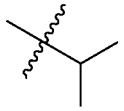 [SMILES: *C(C)C] | 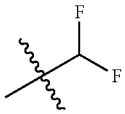 [SMILES: *C(F)F] |  | H | 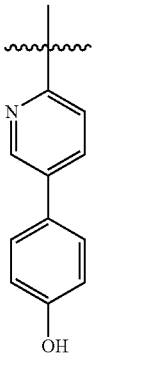 |

TABLE 4-continued

| Compound No. | L | R¹ | R² | R³ | ![Y-Z-R⁴ ring with N=X] |
|---|---|---|---|---|---|
| 112 | -HN- | isopropyl | -CHF₂ | H | pyridin-2-yl with 5-(3-hydroxypropylsulfonyl) |
| 113 | -HN- | isopropyl | -CHF₂ | H | pyridin-2-yl with 5-((1,1-dioxothiomorpholin-4-yl)methyl) |
| 114 | -HN- | isopropyl | -CHF₂ | H | pyridin-2-yl with 5-((4-(N,N-dimethylsulfamoyl)piperazin-1-yl)methyl) |
| 115 | -HN- | isopropyl | -CHF₂ | H | pyridin-2-yl with 5-((4-(methylsulfonyl)piperazin-1-yl)methyl) |

TABLE 4-continued

| Compound No. | L | R¹ | R² | R³ | ![](Y-Z/N=X-R⁴) |
|---|---|---|---|---|---|
| 116 | -HN- | isopropyl | -CHF₂ | H | pyridine-CH₂-piperazine-CH₂CF₃ |
| 117 | -HN- | isopropyl | -CHF₂ | H | pyridine-CH₂-piperazine-C(O)CH₃ |
| 118 | -HN- | isopropyl | -CHF₂ | H | pyridine-CH₂-piperidine-C(CH₃)₂OH |
| 119 | -HN- | isopropyl | -CHF₂ | H | pyridine-O-cyclohexyl-OH (trans) |

TABLE 4-continued

| Compound No. | L | R¹ | R² | R³ | ![structure](Y-Z/N=X with R⁴) |
|---|---|---|---|---|---|
| 120 | -HN< | -CH(CH₃)₂ | -CHF₂ | H | 5-(trans-4-hydroxycyclohexyloxy)pyridin-2-yl |
| 121 | -HN< | -CH(CH₃)₂ | -CHF₂ | H | 5-(2-carbamoylethyl)pyridin-2-yl |
| 122 | -HN< | -CH(CH₃)₂ | -CHF₂ | H | 5-(3-hydroxy-2,2-dimethylpropoxy)pyridin-2-yl |
| 123 | -HN< | -CH(CH₃)₂ | -CHF₂ | H | 5-[3-(2-oxopyrrolidin-1-yl)propoxy]pyridin-2-yl |
| 124 | -HN< | -CH(CH₃)₂ | -CHF₂ | H | 5-(acetamidomethyl)pyridin-2-yl |

TABLE 4-continued

| Compound No. | L | R¹ | R² | R³ | ![Y-Z/N=X-R⁴ structure] |
|---|---|---|---|---|---|
| 125 | HN | isopropyl | CHF₂ | H | 6-(piperidin-4-carboxamide-1-ylmethyl)pyridin-3-yl |
| 126 | HN | isopropyl | CHF₂ | H | 6-((3-hydroxyazetidin-1-yl)methyl)pyridin-3-yl |
| 127 | HN | isopropyl | CHF₂ | H | 6-((3-(hydroxymethyl)piperidin-1-yl)methyl)pyridin-3-yl |
| 128 | HN | isopropyl | CHF₂ | H | 6-((3-hydroxypiperidin-1-yl)methyl)pyridin-3-yl |

TABLE 4-continued

| Compound No. | L | R¹ | R² | R³ | ⟨Y—Z / N=X⟩—R⁴ |
|---|---|---|---|---|---|
| 129 | HN | isopropyl | CHF₂ | H | 6-(piperidin-1-ylmethyl)pyridine with 4-carboxylic acid |
| 130 | HN | isopropyl | CHF₂ | H | 6-(4-(dimethylamino)piperidin-1-ylmethyl)pyridine |
| 131 | HN | isopropyl | CHF₂ | H | 6-((3-oxopiperazin-1-yl)methyl)pyridine |
| 132 | HN | isopropyl | CHF₂ | H | 6-(pyridin-3-yl)acetamide |

TABLE 4-continued

| Compound No. | L | R¹ | R² | R³ | (structure with Y-Z, N=X, R⁴) |
|---|---|---|---|---|---|
| 133 | HN linker | isopropyl | CHF₂ | H | pyridin-3-yl-CH₂-COOH (2-substituted pyridine) |
| 134 | HN linker | isopropyl | CHF₂ | H | pyridin-3-yl-CH₂CH₂-OH |
| 135 | HN linker | isopropyl | CHF₂ | H | pyridin-3-yl-(CH₂)₃-C(O)NH₂ |
| 136 | HN linker | isopropyl | CHF₂ | H | pyridin-3-yl-(CH₂)₃-COOH |
| 137 | HN linker | isopropyl | CHF₂ | H | pyridin-3-yl-N(3-hydroxy-2-oxopiperidin-1-yl) |

TABLE 4-continued

| Compound No. | L | R¹ | R² | R³ | ![structure](Y-Z/N=X-R⁴) |
|---|---|---|---|---|---|
| 138 | -HN- | -CH(CH₃)₂ | -CHF₂ | H | 5-(NHC(O)NH₂-CH₂-)pyridin-2-yl |
| 139 | -HN- | -CH(CH₃)₂ | -CHF₂ | H | 5-(CH₃C(O)N(CH₃)-CH₂-)pyridin-2-yl |
| 140 | -HN- | -CH(CH₃)₂ | -CHF₂ | H | 5-(CH₃SO₂NH-CH₂-)pyridin-2-yl |
| 141 | -HN- | -CH(CH₃)₂ | -CHF₂ | H | 5-(CH₃SO₂N(CH₃)-CH₂-)pyrazin-2-yl |
| 142 | -HN- | -CH(CH₃)₂ | -CHF₂ | H | 5-((4-hydroxypiperidin-1-yl)methyl)pyridin-2-yl |

TABLE 4-continued

| Compound No. | L | R¹ | R² | R³ | ![structure](Y-Z/N=X-R⁴) |
|---|---|---|---|---|---|
| 143 | HN | isopropyl | CHF₂ | H | 6-pyridyl-CH₂-N(SO₂Me)-CH₂-(tetrahydropyran-4-yl) |
| 144 | HN | isopropyl | CHF₂ | H | 6-pyridyl-CH₂-N(COMe)-CH₂-(tetrahydropyran-4-yl) |
| 145 | HN | isopropyl | CHF₂ | H | 6-pyridyl-CH₂-N(COMe)-CH₂-((S)-tetrahydrofuran-2-yl) |
| 146 | HN | isopropyl | CHF₂ | H | 6-pyridyl-CH₂-N(COMe)-CH₂-((S)-tetrahydrofuran-2-yl) |

TABLE 4-continued

TABLE 4-continued

| Compound No. | L | R¹ | R² | R³ | ![](Y-Z / N=X with R⁴) |
|---|---|---|---|---|---|
| 151 | -HN- | isopropyl | -CHF₂ | H | pyridine substituted with -CH₂CH₂NHS(O)₂CH₃ |
| 152 | -HN- | isopropyl | -CHF₂ | H | pyridine substituted with -CH₂CH₂CH₂NHC(O)CH₃ |
| 153 | -HN- | isopropyl | -CHF₂ | H | pyridine substituted with -CH₂CH₂CH₂NHS(O)₂CH₃ |
| 154 | -HN- | isopropyl | -CHF₂ | H | pyridine substituted with -CH₂CH₂C(CH₃)₂OH |
| 155 | -HN- | isopropyl | -CHF₂ | H | pyridine substituted with -OCH₂CH₂OH |

TABLE 4-continued

| Compound No. | L | R¹ | R² | R³ | ![Y-Z/N=X ring with R⁴] |
|---|---|---|---|---|---|
| 156 | -HN- | isopropyl | -CHF₂ | H | pyridine substituted with -O-CH₂CH₂CH₂-OH |
| 157 | -HN- | isopropyl | -CHF₂ | H | 5-methylpyridin-2-yl |
| 158 | -HN- | isopropyl | -CHF₂ | H | pyridine linked via -CH₂-NH- to 5-methyl-4H-1,2,4-triazol-3-yl |
| 159 | -HN- | isopropyl | -CHF₂ | H | pyridine substituted with 1,1-dioxo-tetrahydro-2H-thiopyran-4-yl |
| 160 | -HN- | isopropyl | -CHF₂ | H | pyridine substituted with tetrahydro-2H-pyran-4-yl |

TABLE 4-continued

| Compound No. | L | R¹ | R² | R³ | ![Y-Z/N=X-R⁴ structure] |
|---|---|---|---|---|---|
| 161 | -HN- | isopropyl | -CHF₂ | H | pyridin-3-yl attached to tetrahydropyran-3-one |
| 162 | -HN- | isopropyl | -CHF₂ | H | pyridin-3-yl-CH₂-N(SO₂Me)(tetrahydrofuran-3-yl) |
| 163 | -HN- | isopropyl | -CHF₂ | H | pyrimidin-2-yl with piperazin-1-yl at 5-position |
| 164 | -HN- | isopropyl | -CHF₂ | H | pyridin-3-yl with 3-hydroxypropyl |

TABLE 4-continued

| Compound No. | L | R¹ | R² | R³ | (structure with Y—Z, N=X, R⁴) |
|---|---|---|---|---|---|
| 165 | HN | isopropyl | CHF₂ | H | 6-(1-(2-oxopyrrolidin-1-yl)methyl)pyridin-3-yl |
| 166 | HN | isopropyl | CHF₂ | H | 6-((3-oxomorpholin-4-yl)methyl)pyridin-3-yl |
| 167 | HN | isopropyl | CHF₂ | H | 6-(3-(2-oxopyrrolidin-1-yl)propyl)pyridin-3-yl |
| 168 | HN | isopropyl | CHF₂ | H | 6-(3-(3-oxomorpholin-4-yl)propyl)pyridin-3-yl |

TABLE 4-continued

| Compound No. | L | R¹ | R² | R³ | ![](Y-Z/N=X with R⁴) |
|---|---|---|---|---|---|
| 169 | -HN- | isopropyl | -CHF₂ | H | 6-(morpholine-4-carbonyl)pyridin-3-yl |
| 170 | -HN- | isopropyl | -CHF₂ | H | 6-(3-(1,1-dioxo-1,2-thiazinan-2-yl)propyl)pyridin-3-yl |
| 171 | -HN- | isopropyl | -CHF₂ | H | 6-(4-hydroxypiperidin-1-yl)pyridazin-3-yl |
| 172 | -HN- | isopropyl | -CH(OMe)CH₃ | H | 6-(morpholinomethyl)pyridin-3-yl |

TABLE 4-continued

| Compound No. | L | R¹ | R² | R³ | ![structure](Y-Z/N=X with R⁴) |
|---|---|---|---|---|---|
| 173 | HN linker | isopropyl | CHF₂ | H | 6-pyridyl-CH₂-N(1,4-oxazepan-5-one) |
| 174 | HN linker | isopropyl | CHF₂ | H | 6-pyridyl-CH₂-N(3,3-dimethylpiperazine) |
| 175 | HN linker | isopropyl | CHF₂ | H | 6-pyridyl-CH₂-N(4,7-diazaspiro[2.5] system) |
| 176 | HN linker | isopropyl | CH(OMe)CH₃ | H | 6-pyridyl-CH₂-N(3-oxopiperazine) |

TABLE 4-continued

| Compound No. | L | R¹ | R² | R³ | ![Y-Z/N=X-R⁴ structure] |
|---|---|---|---|---|---|
| 177 | HN | isopropyl | CHF₂ | H | 5-(piperidin-1-ylmethyl)pyridin-2-yl |
| 178 | HN | isopropyl | CHF₂ | H | 6-(1-acetylpiperidin-4-yl)pyridin-2-yl |
| 179 | HN | isopropyl | CHF₂ | H | 6-(1-(methylsulfonyl)piperidin-4-yl)pyridin-2-yl |
| 180 | HN | neopentyl-OMe | CH(OH)CH₃ | H | 5-(morpholinomethyl)pyridin-2-yl |

TABLE 4-continued

| Compound No. | L | R¹ | R² | R³ | ![](Y-Z / N=X with R⁴) |
|---|---|---|---|---|---|
| 181 | HN | isopropyl | CHF₂ | H | pyridin-2-yl-5-(3,3-dimethylpiperazin-1-yl) |
| 182 | HN | neopentyl methyl ether (CH₂C(CH₃)₂CH₂OMe) | C(CH₃)(OH)- | H | 5-((3-oxopiperazin-1-yl)methyl)pyridin-2-yl |
| 183 | HN | isopropyl | CHF₂ | H | 5-((4R)-4-hydroxy-2-oxopyrrolidin-1-yl)pyridin-2-yl |
| 184 | HN | isopropyl | CHF₂ | H | 5-((4S)-4-hydroxy-2-oxopyrrolidin-1-yl)pyridin-2-yl |

TABLE 4-continued

| Compound No. | L | R¹ | R² | R³ | ![Y-Z/N=X with R⁴] |
|---|---|---|---|---|---|
| 185 | -HN- | isopropyl | -CHF₂ (CF₂H with methyl) | H | 6-substituted pyridin-3-yl-CH₂-N(CH₃)-C(=O)-NH₂ |
| 186 | -HN- | isopropyl | -CHF₂ | H | 6-substituted pyridin-3-yl-CH₂-NH-C(=O)-NH-ethyl |
| 187 | -HN- | isopropyl | -CHF₂ | H | 6-substituted pyridin-3-yl-CH₂-NH-S(=O)₂-NH₂ |
| 188 | -HN- | isopropyl | -CHF₂ | H | 6-substituted pyridin-3-yl linked to 1-methylpyrazol-4-yl |
| 189 | -HN- | isopropyl | -CHF₂ | H | 6-substituted pyridin-3-yl-CH₂-N(pyrrolidine-2-carboxylic acid) |

TABLE 4-continued

| Compound No. | L | R¹ | R² | R³ | ![Y-Z/N=X-R⁴ ring] |
|---|---|---|---|---|---|
| 190 | -HN- | isopropyl | -CF₂H | H | pyridine-CH₂-N(pyrrolidine-COOH) |
| 191 | -HN- | isopropyl | -CF₂H | H | pyridazine-N(piperidine-C(CH₃)₂OH) |
| 192 | -HN- | isopropyl | -CH(OMe)CH₃ | H | pyridine-CH₂CH₂CH₂-N(morpholin-3-one) |
| 193 | -HN- | -C(CH₃)₂CH₂OMe | -CH(OH)CH₃ | H | pyridine-CH₂CH₂CH₂-N(morpholin-3-one) |

TABLE 4-continued

| Compound No. | L | R¹ | R² | R³ | ![structure with Y-Z-R⁴] |
|---|---|---|---|---|---|
| 194 | -HN- | isopropyl | -CHF₂ (CH with two F) | H | pyridine linked to piperidine-2-carboxylic acid via CH₂ |
| 195 | -HN- | -C(CH₃)₂CH₂OMe | -CH(OH)CH₃ | H | pyridine linked to piperazine |
| 196 | -HN- | -C(CH₃)₂CH₂OMe | -CH(OH)CH₃ | H | pyridine linked to 4-(2-hydroxypropan-2-yl)piperidine via CH₂ |
| 197 | -HN- | -C(CH₃)₂CH₂OMe | -CH(OH)CH₃ | H | pyridine linked to piperidine-4-carboxylic acid via CH₂ |

TABLE 4-continued

| Compound No. | L | R¹ | R² | R³ | ![Y-Z/N=X-R⁴ structure] |
|---|---|---|---|---|---|
| 198 | HN | neopentyl methyl ether | CH(OH)CH₃ | H | 6-(morpholin-3-one-4-ylmethyl)pyridin-3-yl |
| 199 | HN | isopropyl | CH(OMe)CH₃ | H | 6-(morpholin-3-one-4-ylmethyl)pyridin-3-yl |
| 200 | HN | isopropyl | CH(OMe)CH₃ | H | 6-{[4-(2-hydroxypropan-2-yl)piperidin-1-yl]methyl}pyridin-3-yl |
| 201 | HN | isopropyl | CH(OMe)CH₃ | H | 6-(4-hydroxypiperidin-1-yl)pyridazin-3-yl |

TABLE 4-continued

| Compound No. | L | R¹ | R² | R³ | ![Y-Z-X-R⁴ ring] |
|---|---|---|---|---|---|
| 202 | —HN— | neopentyl-OMe | CH(CH₃)OH | H | pyridazine-piperidine-OH |
| 203 | —HN— | isopropyl | CHF₂ | H | pyridine-dihydropyridinone |
| 204 | —HN— | neopentyl-OMe | CH(CH₃)OH | H | pyridine-morpholine |
| 205 | —HN— | isopropyl | CHF₂ | H | pyridine-CH₂-piperazinone |

TABLE 4-continued

| Compound No. | L | R¹ | R² | R³ | ![Y-Z/N=X-R⁴] |
|---|---|---|---|---|---|
| 206 | -HN- | neopentyl-OMe | -CH(CH₃)OH | H | pyridinyl-piperazinone |
| 207 | -HN- | isopropyl | -CH(CH₃)OMe | H | pyridinyl-piperazinone |
| 208 | -HN- | neopentyl-OMe | -CH(CH₃)OH | H | pyridinyl-O-CH₂CH₂-N(CH₃)₂ |
| 209 | -HN- | isopropyl | -CHF₂ | H | pyridinyl-pyrazole |

TABLE 4-continued

| Compound No. | L | R¹ | R² | R³ | (structure with Y-Z, X, R⁴) |
|---|---|---|---|---|---|
| 210 | HN | isopropyl | CHF₂-C | H | pyridine-pyrazole |
| 211 | HN | isopropyl | C(CH₃)F₂ | H | pyridine-tetrazole |
| 212 | HN | CH₂OCH₃ neopentyl | C(CH₃)(OH) | H | pyridazine-piperazine |
| 213 | HN | isopropyl | CHF₂-C | H | pyridine-(imidazolidin-2-one-methyl) |

TABLE 4-continued

| Compound No. | L | R¹ | R² | R³ | ![Y-Z-R⁴ ring with N=X] |
|---|---|---|---|---|---|
| 214 | HN | isopropyl | (S)-OMe methine | H | 5-(morpholin-4-yl)pyridin-2-yl |
| 215 | HN | neopentyl OMe | (S)-C(CH₃)₂OH | H | 5-(piperidin-4-yl)pyridin-2-yl |
| 216 | HN | neopentyl OMe | (S)-C(CH₃)₂OH | H | 6-(morpholin-4-yl)pyridazin-3-yl |
| 217 | HN | isopropyl | (S)-OMe methine | H | 6-(piperazin-1-yl)pyridazin-3-yl |

TABLE 4-continued

| Compound No. | L | R¹ | R² | R³ | [Y-Z/N=X ring with R⁴] |
|---|---|---|---|---|---|
| 218 | -HN- | isopropyl | -CHF₂ | H | 5-(2-oxopiperidin-4-yl)pyridin-2-yl |
| 219 | -HN- | isopropyl | -CHF₂ | H | 5-((2-oxotetrahydropyrimidin-1-yl)methyl)pyridin-2-yl |
| 220 | -HN- | isopropyl | -CH(OMe)CH₃ | H | 5-(piperazin-1-ylmethyl)pyridin-2-yl |
| 221 | -HN- | -C(CH₃)₂CH₂OMe | -CH(OH)CH₃ | H | 5-(piperazin-1-ylmethyl)pyridin-2-yl |

TABLE 4-continued

| Compound No. | L | R¹ | R² | R³ | ![structure](Y-Z/N=X with R⁴) |
|---|---|---|---|---|---|
| 222 | -HN- | -C(CH₃)₂CH₂OCH₃ | -CH(CH₃)CH(OH)- | H | 5-(carbamoylmethyl)pyridin-2-yl |
| 223 | -HN- | -CH(CH₃)₂ | -CH(CH₃)CH(OCH₃)- | H | 5-(2-hydroxyethyl)pyridin-2-yl |
| 224 | -HN- | -CH(CH₃)₂ | -CH(CH₃)CH(OCH₃)- | H | 5-(1-acetylpiperidin-4-yl)pyridin-2-yl |
| 225 | -HN- | -C(CH₃)₂CH₂OCH₃ | -CH(CH₃)CH(OH)- | H | 5-(1-acetylpiperidin-4-yl)pyridin-2-yl |

TABLE 4-continued

| Compound No. | L | R¹ | R² | R³ | ![Y-Z/N=X-R⁴ structure] |
|---|---|---|---|---|---|
| 226 | HN | isopropyl | CHF₂ | H | 6-pyridazinyl-N-(3-hydroxypiperidin-1-yl) |
| 227 | HN | isopropyl | CH(CH₃)OMe | H | 5-(2-dimethylaminoethoxy)pyridin-2-yl |
| 228 | HN | neopentyl-OMe (CH₂OMe on quaternary C) | CH(CH₃)OH | H | 5-(2-hydroxyethyl)pyridin-2-yl |
| 229 | HN | isopropyl | CH(CH₃)OH | H | 5-[3-(3-oxomorpholin-4-yl)propyl]pyridin-2-yl |

TABLE 4-continued

| Compound No. | L | R¹ | R² | R³ | ![structure](Y-Z-X-N with R⁴) |
|---|---|---|---|---|---|
| 230 | -HN- | isopropyl | CH(CH₃)OH | H | pyridine-piperazinone |
| 231 | -HN- | isopropyl | CH(CH₃)OMe | H | pyridine-CH₂C(O)NH₂ |
| 232 | -HN- | isopropyl | CH(CH₃)OMe | H | pyridine-piperidine |
| 233 | -HN- | isopropyl | CH(CH₃)OH | H | pyridine-CH₂-morpholine |

TABLE 4-continued

| Compound No. | L | R¹ | R² | R³ | (structure with Y-Z, N=X, R⁴) |
|---|---|---|---|---|---|
| 234 | HN | isopropyl | CH(CH₃)OH | H | pyridine-CH₂-piperazinone |
| 235 | HN | neopentyl-OMe | CH(CH₃)OH | H | pyridazine-NH-CH₂CH₂OH |
| 236 | HN | isopropyl | CHF₂ | H | pyridine-CH₂-piperidine-C(O)NHSO₂CH₃ |
| 237 | HN | isopropyl | CH(CH₃)OMe | H | pyridine-CH₂-piperazinone |

TABLE 4-continued

TABLE 4-continued

| Compound No. | L | R¹ | R² | R³ | [Y-Z-X-N ring with R⁴] |
|---|---|---|---|---|---|
| 243 | HN | neopentyl-OMe | C(CH₃)(OH) | H | pyridine-CH₂-piperazine-N-propyl |
| 244 | HN | neopentyl-OMe | C(CH₃)(OH) | H | pyridine-CH₂-piperazine-N-ethyl |
| 245 | HN | isopropyl | C(CH₃)(OH) | H | pyridine-O-CH₂CH₂-N(CH₃)₂ |
| 246 | HN | isopropyl | C(CH₃)(OMe) | H | pyridazine-CH₂-piperazine-NH |

TABLE 4-continued

| Compound No. | L | R¹ | R² | R³ | (structure with Y-Z, N=X, R⁴) |
|---|---|---|---|---|---|
| 247 | -HN- | isopropyl | -C(CH₃)(OH)- | Cl | pyridine-piperazinone |
| 248 | -HN- | -C(CH₃)₂CH₂OCH₃ | -C(CH₃)(OH)- | H | pyridine-CH₂-piperazinone |
| 249 | -HN- | isopropyl | -C(CH₃)(OMe)- | H | pyridazine-piperazine-CH₂CH₂OH |
| 250 | -HN- | tetrahydropyran-4-yl | -C(CH₃)(OH)- | H | pyridazine-piperazine |

TABLE 4-continued

| Compound No. | L | R¹ | R² | R³ | ![Y-Z/N=X-R⁴ header structure] |
|---|---|---|---|---|---|
| 251 | HN (linker) | (S)-tetrahydrofuran-3-yl | C(CH₃)(OH)- | H | 6-(piperazin-1-yl)pyridazin-3-yl |
| 252 | HN (linker) | (R)-tetrahydrofuran-3-yl | C(CH₃)(OH)- | H | 6-(piperazin-1-yl)pyridazin-3-yl |
| 253 | HN (linker) | (S)-tetrahydro-2H-pyran-3-yl | C(CH₃)(OH)- | H | 6-(piperazin-1-yl)pyridazin-3-yl |
| 254 | HN (linker) | (R)-tetrahydro-2H-pyran-3-yl | C(CH₃)(OH)- | H | 6-(piperazin-1-yl)pyridazin-3-yl |

TABLE 4-continued

| Compound No. | L | R¹ | R² | R³ | (structure with Y-Z, N=X, R⁴) |
|---|---|---|---|---|---|
| 255 | -HN- | tetrahydropyran-4-yl | -C(CH₃)(OH)H | H | 6-(piperazin-1-ylmethyl)pyridin-3-yl |
| 256 | -HN- | (R)-tetrahydropyran-3-yl | -C(CH₃)(OH)H | H | 6-(piperazin-1-ylmethyl)pyridin-3-yl |
| 257 | -HN- | (S)-tetrahydropyran-3-yl | -C(CH₃)(OH)H | H | 6-(piperazin-1-ylmethyl)pyridin-3-yl |
| 258 | -HN- | (S)-tetrahydrofuran-3-yl | -C(CH₃)(OH)H | H | 6-(piperazin-1-ylmethyl)pyridin-3-yl |

TABLE 4-continued

| Compound No. | L | R¹ | R² | R³ | ![Y-Z / N=X with R⁴] |
|---|---|---|---|---|---|
| 259 | -HN-C< | tetrahydrofuran-3-yl | -C(CH₃)(OH)H | H | 6-(piperazin-1-ylmethyl)pyridin-3-yl |
| 260 | -HN-C< | isopropyl | -C(CH₃)(OH)H | H | 6-(4-hydroxypiperidin-1-yl)pyridazin-3-yl |
| 261 | -HN-C< | isopropyl | -C(CH₃)(OH)H | H | 6-(piperazin-1-yl)pyridazin-3-yl |
| 262 | -HN-C< | isopropyl | -C(CH₃)(OH)H | H | 6-((3-oxopiperazin-1-yl)methyl)pyridin-3-yl |

TABLE 4-continued

| Compound No. | L | R¹ | R² | R³ | ![](Y-Z/N=X with R⁴) |
|---|---|---|---|---|---|
| 263 | -HN- | isopropyl | -C(CH₃)(OH)- | H | pyridine with -C(CH₃)₂CH₂NHCH₃ |
| 264 | -HN- | -C(CH₃)₂CH₂OCH₃ | -C(CH₃)(OH)- | H | pyridine with -C(CH₃)₂CH₂NHCH₃ |
| 265 | -HN- | -C(CH₃)₂CH₂OCH₃ | -C(CH₃)(OH)- | H | pyridine with -CH(CH₃)-piperazine |
| 266 | -HN- | isopropyl | -C(CH₃)(OCH₃)- | H | pyridine with -CH(CH₃)-piperazine |
| 267 | -HN- | isopropyl | -C(CH₃)(OCH₃)- | H | pyridine with N-(3-hydroxypiperidin-2-one) |

TABLE 4-continued

| Compound No. | L | R¹ | R² | R³ | ![Y-Z-R⁴ ring with N=X] |
|---|---|---|---|---|---|
| 268 | -HN- | neopentyl-OMe | -C(CH₃)(OH)- | H | pyridine-piperidinone-OH |
| 269 | -O- | isopropyl | -C(CH₃)(OH)- | H | pyridazine-piperazine |
| 270 | -HN- | isopropyl | -CH(OMe)CH₃ | H | pyridine-(S)-3-hydroxypyrrolidine-CH₂ |
| 271 | -HN- | isopropyl | -CH(OMe)CH₃ | H | pyridine-(S)-3-fluoropyrrolidine-CH₂ |

TABLE 4-continued

| Compound No. | L | R¹ | R² | R³ | ![Y-Z/N=X-R⁴ structure] |
|---|---|---|---|---|---|
| 272 | HN | isopropyl | OMe (stereo) | H | pyridine-CH₂-N(3-oxa-bicyclic) |
| 273 | HN | isopropyl | OMe (stereo) | H | pyridine-CH₂-N(1,4-oxazepane) |
| 274 | HN | isopropyl | OMe (stereo) | H | pyridine-CH₂-N(4-methoxypiperidine) |
| 275 | HN | isopropyl | OMe (stereo) | H | pyridine-CH₂-N(5,6,7,8-tetrahydroimidazo[1,2-a]pyrazine) |

TABLE 4-continued

| Compound No. | L | R¹ | R² | R³ | ![Y-Z-R⁴ ring with N=X] |
|---|---|---|---|---|---|
| 276 | -HN- | -iPr | -CH(CH₃)OMe | H | pyridine-CH₂-piperazine-CH₂CH₂F |
| 277 | -HN- | -iPr | -CH(CH₃)OMe | H | pyridine-CH₂-(2-methyl-4,5,6,7-tetrahydro-3H-imidazo[4,5-c]pyridine) |
| 278 | -HN- | -iPr | -CH(CH₃)OMe | H | pyridine-CH₂-piperidine-C(O)NHMe |
| 279 | -HN- | -iPr | -CH(CH₃)OMe | H | pyridine-CH₂-(3,3-dimethylmorpholine) |

TABLE 4-continued
| Compound No. | L | R¹ | R² | R³ | ![Y-Z/N=X-R⁴ template] |
|---|---|---|---|---|---|
| 280 |  | 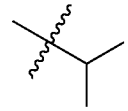 [SMILES: *C(C)C] | 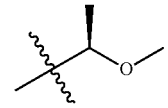 | H |  |
| 281 | 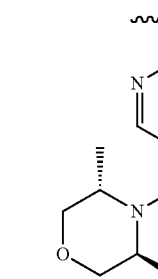 | 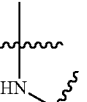 | 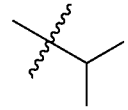 [SMILES: *C(C)C] | H | 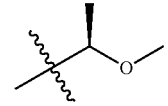 [SMILES: *[C@@H](C)OC] |
| 282 |  |  | 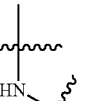 | H | 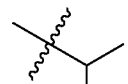 |
| 283 | 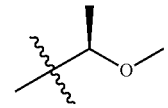 [SMILES: *[C@@H](C)OC] |  |  | H | 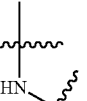 |

TABLE 4-continued

| Compound No. | L | R¹ | R² | R³ | ⟨Y-Z / N=X⟩-R⁴ |
|---|---|---|---|---|---|
| 284 | HN | (tetrahydrofuran-3-yl)methyl | CH(OH)CH₃ | H | 6-(piperazin-1-yl)pyridazin-3-yl |
| 285 | HN | tetrahydropyran-4-yl | CH(OCH₃)CH₃ | H | 6-(piperazin-1-yl)pyridazin-3-yl |
| 286 | HN | isopropyl | CH(OCH₃)CH₃ | H | 6-(3-hydroxypiperidin-1-yl)pyridazin-3-yl |
| 287 | HN | isopropyl | CH(OCH₃)CH₃ | H | 6-(2-(pyrrolidin-1-yl)ethoxy)pyridin-3-yl |

TABLE 4-continued

| Compound No. | L | R¹ | R² | R³ | ![Y-Z-X-N ring with R⁴] |
|---|---|---|---|---|---|
| 288 | -HN- | isopropyl | -CH(OMe)- | H | pyridine-O-CH₂CH₂-NHMe |
| 289 | -HN- | isopropyl | -CH(OMe)- | H | pyridine-O-(piperidin-4-yl) |
| 290 | -HN- | isopropyl | -CH(OMe)- | H | pyridine-O-(pyrrolidin-3-yl) |
| 291 | -HN- | tetrahydropyran-4-yl | -CH(OMe)- | H | pyridine-CH₂-(piperazin-1-yl) |

TABLE 4-continued

| Compound No. | L | R¹ | R² | R³ | ![Y-Z/N=X-R⁴ structure] |
|---|---|---|---|---|---|
| 292 | -HN- | neopentyl-OMe | -CH(OH)CH₃ | H | pyridine-CH₂-N-[(3S)-3-fluoropyrrolidinyl] |
| 293 | -HN- | neopentyl-OMe | -CH(OH)CH₃ | H | pyridine-CH₂-N-[1,4-oxazepanyl] |
| 294 | -HN- | neopentyl-OMe | -CH(OH)CH₃ | H | pyridine-CH₂-N-(4-methoxypiperidinyl) |
| 295 | -HN- | neopentyl-OMe | -CH(OH)CH₃ | H | pyridine-CH₂-N-(5,6,7,8-tetrahydroimidazo[1,2-a]pyrazinyl) |

TABLE 4-continued

| Compound No. | L | R¹ | R² | R³ | ![structure](Y-Z / N=X with R⁴) |
|---|---|---|---|---|---|
| 296 | -HN- | -C(CH₃)₂CH₂OCH₃ | -C(CH₃)(OH)- | H | pyridinyl-CH₂-(2-methyl-4,5,6,7-tetrahydro-3H-imidazo[4,5-c]pyridin-5-yl) |
| 297 | -HN- | -C(CH₃)₂CH₂OCH₃ | -C(CH₃)(OH)- | H | pyridinyl-CH₂-(1-(N-methylcarbamoyl)piperidin-4-yl) |
| 298 | -HN- | -C(CH₃)₂CH₂OCH₃ | -C(CH₃)(OH)- | H | pyridinyl-CH₂-(3,3-dimethylmorpholin-4-yl) |
| 299 | -HN- | -C(CH₃)₂CH₂OCH₃ | -C(CH₃)(OH)- | H | pyridinyl-CH₂-(4-(2,2-difluoroethyl)piperazin-1-yl) |

TABLE 4-continued

| Compound No. | L | R¹ | R² | R³ | ![Y-Z ring with R⁴] |
|---|---|---|---|---|---|
| 300 | HN | tetrahydropyran (dashed wedge) | OMe (solid wedge) | H | pyridine-CH₂-piperazine |
| 301 | HN | tetrahydropyran (solid wedge) | OMe (solid wedge) | H | pyridine-CH₂-piperazine |
| 302 | HN | tetrahydrofuran (dashed wedge) | OMe (solid wedge) | H | pyridine-CH₂-piperazine |
| 303 | HN | tetrahydrofuran (solid wedge) | OMe (solid wedge) | H | pyridine-CH₂-piperazine |

TABLE 4-continued

| Compound No. | L | R¹ | R² | R³ | ![Y-Z/N=X-R⁴ ring] |
|---|---|---|---|---|---|
| 304 | -HN- | (S)-tetrahydropyran-3-yl | (R)-CH(OMe)- | H | 6-(piperazin-1-yl)pyridazin-3-yl |
| 305 | -HN- | (R)-tetrahydropyran-3-yl | (R)-CH(OMe)- | H | 6-(piperazin-1-yl)pyridazin-3-yl |
| 306 | -HN- | (S)-tetrahydrofuran-3-yl | (R)-CH(OMe)- | H | 6-(piperazin-1-yl)pyridazin-3-yl |
| 307 | -HN- | (R)-tetrahydrofuran-3-yl | (R)-CH(OMe)- | H | 6-(piperazin-1-yl)pyridazin-3-yl |

TABLE 4-continued

| Compound No. | L | R¹ | R² | R³ | ![Y-Z-X-R⁴ ring] |
|---|---|---|---|---|---|
| 308 | -HN- | 2-carboxycyclohexyl | -CH(OH)CH₃ | H | 6-(piperazin-1-yl)pyridazin-3-yl |
| 309 | -HN- | 2-carboxycyclopentyl | -CH(OH)CH₃ | H | 6-(piperazin-1-yl)pyridazin-3-yl |
| 310 | -HN- | isopropyl | -CH(OEt)CH₃ | H | 6-(piperazin-1-yl)pyridazin-3-yl |
| 311 | -HN- | isopropyl | -CH(OMe)CH₃ | H | 6-(piperidin-4-yl)pyridazin-3-yl |

TABLE 4-continued

| Compound No. | L | R¹ | R² | R³ | |
|---|---|---|---|---|---|
| 312 | -HN- | -CH₂-(tetrahydropyran-4-yl) | -CH(OH)CH₃ | H | 6-(piperazin-1-ylmethyl)pyridin-3-yl |
| 313 | -HN- | -CH₂-(tetrahydropyran-4-yl) | -CH(OH)CH₃ | H | 6-(piperazin-1-yl)pyridazin-3-yl |
| 314 | -HN- | -CH₂-(1,1-dioxo-tetrahydrothiopyran-4-yl) | -CH(OH)CH₃ | H | 6-(piperazin-1-ylmethyl)pyridin-3-yl |
| 315 | -HN- | -C(CH₃)₂COOH | -CH(OH)CH₃ | H | 6-(piperazin-1-yl)pyridazin-3-yl |

TABLE 4-continued

| Compound No. | L | R¹ | R² | R³ | ![Y-Z-R⁴ with N=X ring] |
|---|---|---|---|---|---|
| 316 | -HN- | 1-carboxycyclopentyl | -C(CH₃)(OH)- | H | pyridazine-piperazine |
| 317 | -HN- | tetrahydropyran-4-yl | -C(CH₃)(OH)- | H | pyridazine-piperidine |
| 318 | -HN- | isopropyl | -C(CH₃)(OH)- | H | pyridazine-piperidine |
| 319 | -HN- | isopropyl | -C(CH₃)(OH)- | H | pyridine-(3-oxo-4-formyl-piperazine) |

TABLE 4-continued

| Compound No. | L | R¹ | R² | R³ | ![structure](Y-Z, N=X, R⁴) |
|---|---|---|---|---|---|
| 320 | HN | tetrahydrofuran-3-ylmethyl | CH(CH₃)OMe | H | 6-(piperazin-1-ylmethyl)pyridin-3-yl |
| 321 | HN | tetrahydrofuran-3-ylmethyl | CH(CH₃)OMe | H | 6-(piperazin-1-yl)pyridazin-3-yl |
| 322 | HN | 1,1-dioxo-tetrahydro-2H-thiopyran-4-yl | C(CH₃)₂OH | H | 6-(piperazin-1-yl)pyridazin-3-yl |
| 323 | HN | tetrahydrofuran-3-ylmethyl | C(CH₃)₂OH | H | 6-(piperazin-1-ylmethyl)pyridin-3-yl |

TABLE 4-continued

| Compound No. | L | R¹ | R² | R³ | ![Y-Z/N=X-R⁴ structure] |
|---|---|---|---|---|---|
| 324 | HN | 2-carboxycyclopentyl | CH(CH₃)OH | H | 6-(piperazin-1-ylmethyl)pyridin-3-yl |
| 325 | HN | 1-carboxycyclopentyl | CH(CH₃)OH | H | 6-(piperazin-1-ylmethyl)pyridin-3-yl |
| 326 | HN | tetrahydro-2H-pyran-4-yl | CH(CH₃)OH | Cl | 6-(piperazin-1-ylmethyl)pyridin-3-yl |
| 327 | HN | –C(CH₃)₂CH₂COOH | CH(CH₃)OH | H | 6-(piperazin-1-yl)pyridazin-3-yl |

TABLE 4-continued

| Compound No. | L | R¹ | R² | R³ | ![structure](Y-Z-X-N with R⁴) |
|---|---|---|---|---|---|
| 328 | -HN- | isopropyl | -C(=O)CH₃ | H | 6-(piperazin-1-yl)pyridazin-3-yl |
| 329 | -HN- | isopropyl | -C(=O)CH₃ | H | 6-(piperazin-1-ylmethyl)pyridin-3-yl |
| 330 | -HN- | tetrahydropyran-4-yl | -C(=O)CH₃ | H | 6-(piperazin-1-yl)pyridazin-3-yl |
| 331 | -HN- | isopropyl | -CH(CH₃)OCH₃ | H | [3,3'-bipyridin]-6-yl |

TABLE 4-continued

| Compound No. | L | R¹ | R² | R³ | [Y-Z / N=X-R⁴ ring] |
|---|---|---|---|---|---|
| 332 | -HN- | isopropyl | -CH(OMe)CH₃ | H | 5-(piperidin-3-yl)pyridin-2-yl |
| 333 | -HN- | -C(CH₃)₂CH₂OMe | -CH(OH)CH₃ | H | 5-(piperidin-3-yl)pyridin-2-yl |
| 334 | -HN- | isopropyl | -CH(OMe)CH₃ | H | 6-(3-hydroxypyrrolidin-1-yl)pyridazin-3-yl |
| 335 | -HN- | isopropyl | -CH(OMe)CH₃ | H | 6-[4-(hydroxyacetyl)piperazin-1-yl]pyridazin-3-yl |

TABLE 4-continued

| Compound No. | L | R¹ | R² | R³ | ![Y-Z/N=X-R⁴] |
|---|---|---|---|---|---|
| 336 | HN | isopropyl | CH(CH₃)OMe | H | pyridazine-NH-piperidine |
| 337 | HN | tetrahydropyran-4-yl | C(CH₃)₂OH | Cl | pyridazine-piperazine |
| 338 | HN | trans-4-carboxycyclohexyl | C(CH₃)₂OH | H | pyridazine-piperazine |
| 339 | HN | trans-4-carboxycyclohexyl | CH(CH₃)OMe | H | pyridazine-piperazine |

TABLE 4-continued

| Compound No. | L | R¹ | R² | R³ | ![structure](Y-Z/N=X-R⁴) |
|---|---|---|---|---|---|
| 340 | -HN- | cyclohexyl-OH (trans) | -C(CH₃)(H)OH | H | pyridazine-piperazine |
| 341 | -HN- | cyclohexyl-OH (trans) | -C(CH₃)(H)OMe | H | pyridazine-piperazine |
| 342 | -HN- | cyclohexyl-COOH (trans) | -C(CH₃)(H)OH | H | pyridine-CH₂-piperazine |
| 343 | -HN- | cyclohexyl-COOH (trans) | -C(CH₃)(H)OMe | H | pyridine-CH₂-piperazine |

TABLE 4-continued

| Compound No. | L | R¹ | R² | R³ | ![structure] |
|---|---|---|---|---|---|
| 344 | -HN- | trans-4-hydroxycyclohexyl | -CH(CH₃)CH(OH)- | H | 6-(piperazin-1-ylmethyl)pyridin-3-yl |
| 345 | -HN- | trans-4-hydroxycyclohexyl | -CH(CH₃)CH(OMe)- | H | 6-(piperazin-1-ylmethyl)pyridin-3-yl |
| 346 | -HN- | tetrahydro-2H-pyran-3-yl | -CH(CH₃)CH(OH)- | H | 6-(3-oxopiperazin-1-yl)pyridin-3-yl |
| 347 | -HN- | (S)-tetrahydro-2H-pyran-3-yl | -CH(CH₃)CH(OH)- | H | 6-(3-oxopiperazin-1-yl)pyridin-3-yl |

TABLE 4-continued

| Compound No. | L | R¹ | R² | R³ | ![Y-Z/N=X-R⁴ ring] |
|---|---|---|---|---|---|
| 348 | HN | tetrahydrofuran-3-yl | CH(CH₃)OH | H | 5-(2-oxopiperazin-1-yl)pyridin-2-yl |
| 349 | HN | tetrahydrofuran-3-yl | CH(CH₃)OH | H | 5-(2-oxopiperazin-1-yl)pyridin-2-yl |
| 350 | HN | tetrahydropyran-4-yl | CH(CH₃)OH | H | 5-(2-oxopiperazin-1-yl)pyridin-2-yl |
| 351 | HN | tetrahydropyran-3-yl | CH(CH₃)OH | H | 5-(4-formyl-2-oxopiperazin-1-yl)pyridin-2-yl |

TABLE 4-continued

| Compound No. | L | R¹ | R² | R³ | ![](Y-Z / N=X with R⁴) |
|---|---|---|---|---|---|
| 352 | -HN- | (3-tetrahydropyranyl) | -C(CH₃)(OH)- | H | 6-pyridyl-3-(3-oxo-4-formyl-piperazin-1-yl) |
| 353 | -HN- | (3-tetrahydrofuranyl) | -C(CH₃)(OH)- | H | 6-pyridyl-3-(3-oxo-4-formyl-piperazin-1-yl) |
| 354 | -HN- | (3-tetrahydrofuranyl) | -C(CH₃)(OH)- | H | 6-pyridyl-3-(3-oxo-4-formyl-piperazin-1-yl) |
| 355 | -HN- | (4-tetrahydropyranyl) | -C(CH₃)(OH)- | H | 6-pyridyl-3-(3-oxo-4-formyl-piperazin-1-yl) |

TABLE 4-continued

| Compound No. | L | R¹ | R² | R³ | ![structure](Y-Z/N=X-R⁴) |
|---|---|---|---|---|---|
| 356 | HN | isopropyl | (S)-OMe | H | pyridazinyl-piperazinone |
| 357 | HN | isopropyl | (S)-OMe | H | pyridazinyl-NH-pyrrolidine |
| 358 | HN | tetrahydropyran-4-ylmethyl | (S)-OMe | H | pyridazinyl-piperazine |
| 359 | HN | 1,1-dioxo-tetrahydrothiopyran-4-yl | (S)-OMe | H | pyridazinyl-piperazine |

TABLE 4-continued

| Compound No. | L | R¹ | R² | R³ | ![Y-Z-R⁴ ring with N=X] |
|---|---|---|---|---|---|
| 360 | -HN- | 4-tetrahydropyranyl-CH₂- | -CH(OMe)- | H | 6-(piperazin-1-ylmethyl)pyridin-3-yl |
| 361 | -HN- | 4-(1,1-dioxidotetrahydro-2H-thiopyran-4-yl)- | -CH(OMe)- | H | 6-(piperazin-1-ylmethyl)pyridin-3-yl |
| 362 | -HN- | isopropyl | -CH(OMe)- | H | 6-(3-oxopiperazin-1-yl)pyridazin-3-yl |
| 363 | -HN- | isopropyl | -CH(OMe)- | H | 5-(piperazin-1-yl)pyrazin-2-yl |

TABLE 4-continued

| Compound No. | L | R¹ | R² | R³ | ![Y-Z-R⁴ ring with N=X] |
|---|---|---|---|---|---|
| 364 | HN linker | tetrahydropyran-4-yl | CHF₂ | H | 6-(piperazin-1-ylmethyl)pyridin-3-yl |
| 365 | HN linker | tetrahydropyran-4-yl | CHF₂ | H | 6-(piperazin-1-yl)pyridazin-3-yl |
| 366 | HN linker | tetrahydropyran-3-yl | CHF₂ | H | 6-(2-(dimethylamino)ethoxy)pyridin-3-yl |
| 367 | HN linker | (3S)-tetrahydropyran-3-yl | CH(OH)CH₃ | Cl | 6-(piperazin-1-yl)pyridazin-3-yl |

TABLE 4-continued

| Compound No. | L | R¹ | R² | R³ | ![structure] |
|---|---|---|---|---|---|
| 368 | HN | cyclohexyl-OH (trans) | CH(CH₃)OH | Cl | pyridazine-piperazine |
| 369 | HN | tetrahydropyran-3-yl | CH(CH₃)OH | Cl | pyridine-CH₂-piperazine |
| 370 | HN | cyclohexyl-OH (trans) | CH(CH₃)OH | Cl | pyridine-CH₂-piperazine |
| 371 | HN | isopropyl | CH(CH₃)OMe | H | pyridazine-(S)-2-methylpiperazine |

TABLE 4-continued

| Compound No. | L | R¹ | R² | R³ | ![Y-Z/N=X-R⁴ structure] |
|---|---|---|---|---|---|
| 372 | -HN- | isopropyl | (S)-OMe methine | H | 6-(3-methylpiperazin-1-yl)pyridazin-3-yl |
| 373 | -HN- | neopentyl-OMe | OH methine | H | 5-(piperazin-1-yl)pyrazin-2-yl |
| 374 | -HN- | isopropyl | (S)-OMe methine | H | 5-(piperazin-1-yl)pyrimidin-2-yl |
| 375 | -HN- | neopentyl-OMe | OH methine | H | 5-(piperazin-1-yl)pyrimidin-2-yl |

TABLE 4-continued

| Compound No. | L | R¹ | R² | R³ | ![Y-Z/N=X-R⁴ structure] |
|---|---|---|---|---|---|
| 376 | HN | tetrahydropyran-3-yl | CH(CH₃)OMe | H | pyridazinyl-4,7-diazaspiro[2.5]octane |
| 377 | HN | isopropyl | CH(CH₃)OMe | H | pyridinyl-C(O)N(Me)-piperidine |
| 378 | HN | tetrahydropyran-3-yl | CH(CH₃)OMe | H | pyridinyl-CH₂-4,7-diazaspiro[2.5]octane |
| 379 | HN | isopropyl | C(CH₃)OH | H | pyridazinyl-4,7-diazaspiro[2.5]octane |

TABLE 4-continued

| Compound No. | L | R¹ | R² | R³ | ![Y-Z-R⁴ ring with N=X] |
|---|---|---|---|---|---|
| 380 | HN (secondary amine linker) | (S)-tetrahydropyran-3-yl | CHF₂ | H | 6-methyl-pyridin-3-yl-CH₂-piperazine |
| 381 | HN | (S)-tetrahydropyran-3-yl | CHF₂ | H | 6-(piperazin-1-yl)pyridazin-3-yl |
| 382 | HN | (S)-tetrahydropyran-3-yl | CHF₂ | H | 6-methyl-pyridin-3-yl-O-CH₂CH₂-N(CH₃)₂ |
| 383 | HN | trans-4-carboxycyclohexyl | CHF₂ | H | 6-methyl-pyridin-3-yl-CH₂-piperazine |

TABLE 4-continued

| Compound No. | L | R¹ | R² | R³ | ![Y-Z/N=X-R⁴ structure] |
|---|---|---|---|---|---|
| 384 | HN | cyclohexyl-COOH | CHF₂ | H | pyridazine-piperazine |
| 385 | HN | cyclohexyl-COOH | CHF₂ | H | pyridine-O-CH₂CH₂-N(CH₃)₂ |
| 386 | HN | cyclohexyl-OH | CHF₂ | H | pyridine-CH₂-piperazine |
| 387 | HN | cyclohexyl-OH | CHF₂ | H | pyridazine-piperazine |

TABLE 4-continued

| Compound No. | L | R¹ | R² | R³ | ![structure](Y-Z / N=X-R⁴) |
|---|---|---|---|---|---|
| 388 | HN | cyclohexyl-OH (trans) | CHF₂ | H | pyridine with OCH₂CH₂N(CH₃)₂ |
| 389 | HN | isopropyl | CH(OMe)Me | H | pyridine with piperazine-C(=O) |
| 390 | HN | cyclohexyl-C(=O)OMe (trans) -CH₂- | CH(OMe)Me | H | pyridine with CH₂-piperazine |
| 391 | N(Me) | isopropyl | CH(OMe)Me | H | pyridine with CH₂-piperazine |

TABLE 4-continued

| Compound No. | L | R¹ | R² | R³ | ![Y-Z/N=X-R⁴ ring] |
|---|---|---|---|---|---|
| 392 | -HN- | isobutyl (CH₂CH(CH₃)₂) branched | -CH(CH₃)OCH₃ | H | 6-(piperazin-1-ylmethyl)pyridin-3-yl |
| 393 | -HN- | -CH₂CH₂-(2-oxoimidazolidin-1-yl) | -CH(CH₃)OCH₃ | H | 6-(piperazin-1-ylmethyl)pyridin-3-yl |
| 394 | -HN- | -C(CH₃)₂CH₂OCH₃ | -CH(CH₃)OCH₃ | H | 6-(piperazin-1-ylmethyl)pyridin-3-yl |
| 395 | -HN- | 4-methoxycyclohexyl | -CH(CH₃)OCH₃ | H | 6-(piperazin-1-ylmethyl)pyridin-3-yl |

TABLE 4-continued

| Compound No. | L | R¹ | R² | R³ | ![Y-Z/N=X-R⁴] |
|---|---|---|---|---|---|
| 396 | -HN- | oxetan-3-ylmethyl | -CH(OMe)CH₃ | H | 6-(piperazin-1-ylmethyl)pyridin-3-yl |
| 397 | -HN- | 3-hydroxycyclohexyl | -CH(OMe)CH₃ | H | 6-(piperazin-1-ylmethyl)pyridin-3-yl |
| 398 | -HN- | (tetrahydro-2H-pyran-2-yl)methyl | -CH(OMe)CH₃ | H | 6-(piperazin-1-ylmethyl)pyridin-3-yl |
| 399 | -HN- | piperidin-4-yl | -CH(OMe)CH₃ | H | 6-(piperazin-1-ylmethyl)pyridin-3-yl |

TABLE 4-continued

| Compound No. | L | R¹ | R² | R³ | ⁂-Y=Z/N=X-R⁴ |
|---|---|---|---|---|---|
| 400 | -HN- | (tetrahydropyran-yl-methyl) | -CH(OMe)- | H | 6-(piperazin-1-ylmethyl)pyridin-3-yl |
| 401 | -HN- | 4-cyanophenyl | -CH(OMe)- | H | 6-(piperazin-1-ylmethyl)pyridin-3-yl |
| 402 | -HN- | (3-hydroxycyclohexyl)methyl | -CH(OMe)- | H | 6-(piperazin-1-ylmethyl)pyridin-3-yl |
| 403 | -HN- | (5-oxopyrrolidin-2-yl)methyl | -CH(OMe)- | H | 6-(piperazin-1-ylmethyl)pyridin-3-yl |

TABLE 4-continued

| Compound No. | L | R¹ | R² | R³ | ![Y-Z-R⁴ ring with N=X] |
|---|---|---|---|---|---|
| 404 | -HN- | isopropyl-tetrahydrofuran | -CH(CH₃)OMe | H | 6-(piperazin-1-ylmethyl)pyridin-3-yl |
| 405 | -HN- | 1-acetylpiperidin-3-yl | -CH(CH₃)OMe | H | 6-(piperazin-1-ylmethyl)pyridin-3-yl |
| 406 | -HN- | (5-oxopyrrolidin-3-yl)methyl | -CH(CH₃)OMe | H | 6-(piperazin-1-ylmethyl)pyridin-3-yl |
| 407 | -HN- | 1-methylpiperidin-3-yl | -CH(CH₃)OMe | H | 6-(piperazin-1-ylmethyl)pyridin-3-yl |

TABLE 4-continued

| Compound No. | L | R¹ | R² | R³ | ![](Y-Z / N=X with R⁴) |
|---|---|---|---|---|---|
| 408 | -HN- | -CH₂-(tetrahydrofuran-2-yl) | -CH(OMe)- | H | 6-(piperazin-1-ylmethyl)pyridin-3-yl |
| 409 | -HN- | -CH(CH₃)-(tetrahydrofuran-2-yl) | -CH(OMe)- | H | 6-(piperazin-1-ylmethyl)pyridin-3-yl |
| 410 | -HN- | 2,2-dimethyltetrahydro-2H-pyran-4-yl | -CH(OMe)- | H | 6-(piperazin-1-ylmethyl)pyridin-3-yl |
| 411 | -HN- | -CH₂-(tetrahydrofuran-2-yl) | -CH(OMe)- | H | 6-(piperazin-1-ylmethyl)pyridin-3-yl |

TABLE 4-continued

| Compound No. | L | R¹ | R² | R³ | ⸺Y=Z⸺R⁴ / N=X |
|---|---|---|---|---|---|
| 412 | HN | 3-cyanophenyl | CH(OMe)- | H | 6-(piperazin-1-ylmethyl)pyridin-3-yl |
| 413 | HN | 1-(hydroxymethyl)cyclopentyl | CH(OMe)- | H | 6-(piperazin-1-ylmethyl)pyridin-3-yl |
| 414 | HN | 2-(2-oxopyrrolidin-1-yl)ethyl | CH(OMe)- | H | 6-(piperazin-1-ylmethyl)pyridin-3-yl |
| 415 | HN | 2-oxo-3-oxa-1-azabicyclo substituent | CH(OMe)- | H | 6-(piperazin-1-ylmethyl)pyridin-3-yl |

TABLE 4-continued

| Compound No. | L | R¹ | R² | R³ | ⟨Y-Z⟩(R⁴) with N=X |
|---|---|---|---|---|---|
| 416 | -HN- | 5-(6-oxo-1,6-dihydropyridin-3-yl)methyl | -CH(OMe)- | H | 6-(piperazin-1-ylmethyl)pyridin-3-yl |
| 417 | -HN- | cyclopentyl | -CH(OMe)- | H | 6-(piperazin-1-ylmethyl)pyridin-3-yl |
| 418 | -HN- | neopentyl (3,3-dimethylbutyl) | -CH(OMe)- | H | 6-(piperazin-1-ylmethyl)pyridin-3-yl |
| 419 | -HN- | 4-(2-oxopyrrolidin-3-yl) | -CH(OMe)- | H | 6-(piperazin-1-ylmethyl)pyridin-3-yl |

TABLE 4-continued

| Compound No. | L | R¹ | R² | R³ | ![Y-Z/N=X-R⁴ structure] |
|---|---|---|---|---|---|
| 420 | -HN- | 4-methyltetrahydropyran-4-yl | -CH(OMe)CH₃ | H | 6-(piperazin-1-ylmethyl)pyridin-3-yl |
| 421 | -HN- | 5-(2-oxopiperidinyl) | -CH(OMe)CH₃ | H | 6-(piperazin-1-ylmethyl)pyridin-3-yl |
| 422 | -HN- | 4-(2-oxopiperidinyl) | -CH(OMe)CH₃ | H | 6-(piperazin-1-ylmethyl)pyridin-3-yl |
| 423 | -HN- | sec-pentyl (3-methylpent-2-yl) | -CH(OMe)CH₃ | H | 6-(piperazin-1-ylmethyl)pyridin-3-yl |

TABLE 4-continued

| Compound No. | L | R¹ | R² | R³ | ![structure](Y-Z/N=X with R⁴) |
|---|---|---|---|---|---|
| 424 | -HN- | 4-hydroxycyclohexyl | -CHF₂ | H | 6-(piperazin-1-ylmethyl)pyridin-2-yl |
| 425 | -HN- | 4-hydroxycyclohexyl | -CHF₂ | H | 6-(piperazin-1-yl)pyridazin-3-yl |
| 426 | -HN- | 4-hydroxycyclohexyl | -CHF₂ | H | 6-(2-(dimethylamino)ethoxy)pyridin-3-yl |
| 427 | -HN- | 3-hydroxycyclopentyl | -CH(OMe)CH₃ | H | 6-(piperazin-1-ylmethyl)pyridin-2-yl |

TABLE 4-continued

| Compound No. | L | R¹ | R² | R³ | ![Y-Z/N=X-R⁴ structure] |
|---|---|---|---|---|---|
| 428 | -HN- | -CH₂CH₂-(tetrahydropyran-4-yl) | -CH(OMe)- | H | 6-(piperazin-1-ylmethyl)pyridin-3-yl |
| 429 | -HN- | -CH₂CH₂-(tetrahydrofuran-2-yl) | -CH(OMe)- | H | 6-(piperazin-1-ylmethyl)pyridin-3-yl |
| 430 | -HN- | -CH₂CH₂-(tetrahydropyran-2-yl) | -CH(OMe)- | H | 6-(piperazin-1-ylmethyl)pyridin-3-yl |
| 431 | -HN- | -CH₂CH₂-(tetrahydropyran-3-yl) | -CH(OMe)- | H | 6-(piperazin-1-ylmethyl)pyridin-3-yl |

TABLE 4-continued

| Compound No. | L | R¹ | R² | R³ | ![](Y-Z/N=X-R⁴) |
|---|---|---|---|---|---|
| 432 | -HN- | 2,2-dimethyltetrahydropyran-5-yl | -CH(OMe)- | H | 6-(piperazin-1-ylmethyl)pyridin-3-yl |
| 433 | -HN- | 4-(hydroxymethyl)tetrahydropyran-4-yl | -CH(OMe)- | H | 6-(piperazin-1-ylmethyl)pyridin-3-yl |
| 434 | -HN- | 1-(hydroxymethyl)cyclohexyl | -CH(OMe)- | H | 6-(piperazin-1-ylmethyl)pyridin-3-yl |
| 435 | -HN- | (4-carboxycyclohexyl)methyl | -CH(OMe)- | H | 6-(piperazin-1-ylmethyl)pyridin-3-yl |

TABLE 4-continued

| Compound No. | L | R¹ | R² | R³ | ⁝—Y=Z / N=X—R⁴ |
|---|---|---|---|---|---|
| 436 | HN (branched linker) | methyl-cyclohexyl with methyl and COOH | CH(OMe)- | H | pyridine-CH2-piperazine (NH) |
| 437 | HN (branched linker) | methyl-cyclohexyl with methyl and COOH | CH(OMe)- | H | pyridine-CH2-piperazine (NH) |
| 438 | HN (branched linker) | isopropyl | CHF2 | H | pyridine-N(3,3-dimethyl-2-oxopiperazin-1-yl) |
| 439 | HN (branched linker) | tetrahydropyran-4-yl | CHF2 | H | pyridine-N(3,3-dimethyl-2-oxopiperazin-1-yl) |

TABLE 4-continued

| Compound No. | L | R¹ | R² | R³ | ![Y-Z/N=X-R⁴ header structure] |
|---|---|---|---|---|---|
| 440 | -HN- | isopropyl | -C(CH₃)(OH)H (R) | H | 5-(3,3-dimethyl-2-oxopiperazin-1-yl)pyridin-2-yl |
| 441 | -HN- | tetrahydropyran-4-yl | -C(CH₃)(OH)H (R) | H | 5-(3,3-dimethyl-2-oxopiperazin-1-yl)pyridin-2-yl |
| 442 | -HN- | trans-4-carboxycyclohexyl | -CHF₂ | H | 5-(3,3-dimethyl-2-oxopiperazin-1-yl)pyridin-2-yl |
| 443 | -HN- | trans-4-hydroxycyclohexyl | -CHF₂ | H | 5-(3,3-dimethyl-2-oxopiperazin-1-yl)pyridin-2-yl |

TABLE 4-continued

| Compound No. | L | R¹ | R² | R³ | ![Y-Z/N=X-R⁴ structure] |
|---|---|---|---|---|---|
| 444 | HN< | isopropyl | (S)-CH(CH₃)OMe | H | 1-(pyridin-3-yl)-3,3-dimethylpiperazin-2-one |
| 445 | HN< | cycloheptyl | CH(CH₃)OMe | H | 5-(piperazin-1-ylmethyl)pyridin-2-yl |
| 446 | HN< | 4-fluorophenyl | CH(CH₃)OMe | H | 5-(piperazin-1-ylmethyl)pyridin-2-yl |
| 447 | HN< | 3-fluorophenyl | CH(CH₃)OMe | H | 5-(piperazin-1-ylmethyl)pyridin-2-yl |

TABLE 4-continued

| Compound No. | L | R¹ | R² | R³ | ![Y-Z-R⁴ ring with N=X] |
|---|---|---|---|---|---|
| 448 | -HN- | 4-carboxyphenyl | -CH(CH₃)OCH₃ | H | 6-(piperazin-1-ylmethyl)pyridin-3-yl (attached at 2-position) |
| 449 | -HN- | 3-carboxyphenyl | -CH(CH₃)OCH₃ | H | 6-(piperazin-1-ylmethyl)pyridin-3-yl |
| 450 | -HN- | 4-methoxyphenyl | -CH(CH₃)OCH₃ | H | 6-(piperazin-1-ylmethyl)pyridin-3-yl |
| 451 | -HN- | 3-methoxyphenyl | -CH(CH₃)OCH₃ | H | 6-(piperazin-1-ylmethyl)pyridin-3-yl |

TABLE 4-continued

| Compound No. | L | R¹ | R² | R³ | ![structure] |
|---|---|---|---|---|---|
| 452 | HN | isopropyl | CH(CH₃)OCH₃ | H | pyridazine-piperidine-NHCH₃ |
| 453 | HN | isopropyl | CH(CH₃)OCH₃ | H | pyridine-1,4-diazepane |
| 454 | HN | 3,3,5-trimethyl-5-hydroxycyclohexylmethyl | CH(CH₃)OCH₃ | H | pyridine-CH₂-piperazine |
| 455 | HN | 3-hydroxyadamantyl | CH(CH₃)OCH₃ | H | pyridine-CH₂-piperazine |

TABLE 4-continued

| Compound No. | L | R¹ | R² | R³ | ![Y-Z-R4 structure] |
|---|---|---|---|---|---|
| 456 | -S- | isopropyl | -CH(CH₃)OMe | H | pyridine-CH₂-piperazine |
| 457 | -NH- | isopropyl | -CH(CH₃)OMe | H | pyridine-O-CH₂-(1-aminocyclopropyl) |
| 458 | -NH- | isopropyl | -CH(CH₃)OMe | H | pyridine-O-CH₂-C(CH₃)₂-NH₂ |
| 459 | -NH- | isopropyl | -CH(CH₃)OMe | H | pyridine-O-(3-fluoropiperidin-4-yl) |

TABLE 4-continued

| Compound No. | L | R¹ | R² | R³ | ![Y-Z/N=X-R⁴ structure] |
|---|---|---|---|---|---|
| 460 | HN | isopropyl | CH(CH₃)OMe | H | pyridine-O-(3-fluoropiperidin-4-yl) |
| 461 | HN | isopropyl | CH(CH₃)OMe | H | pyridine-OCH₂-(1-methylaminocyclopropyl) |
| 462 | HN | isopropyl | CH(CH₃)OMe (stereo) | H | pyridine-(3S-methyl-2-oxopiperazin-1-yl) |
| 463 | HN | isopropyl | CH(CH₃)OMe (stereo) | H | pyridine-(3R-methyl-2-oxopiperazin-1-yl) |

TABLE 4-continued

| Compound No. | L | R¹ | R² | R³ | ![structure](Y-Z-X-N with R⁴) |
|---|---|---|---|---|---|
| 464 | HN | cyclohexyl-O-iPr | CH(CH₃)OMe | H | pyridine-CH₂-piperazine |
| 465 | HN | CH₂-(3,3-difluorocyclobutyl) | CH(CH₃)OMe | H | pyridine-CH₂-piperazine |
| 466 | HN | iPr | CH(CH₃)OMe | H | pyridine-(3-fluoro-4-amino-piperidine) |
| 467 | HN | iPr | CH(CH₃)OMe | H | pyridine-(3-fluoro-4-amino-piperidine) |

TABLE 4-continued

| Compound No. | L | R¹ | R² | R³ | ![Y-Z/N=X-R⁴ structure] |
|---|---|---|---|---|---|
| 468 | -HN- | 4-oxepanyl | -CH(CH₃)OCH₃ | H | 6-(5-(piperazin-1-ylmethyl)pyridin-2-yl) |
| 469 | -HN- | isopropyl | -CH(CH₃)OCH₃ | H | 6-(5-(4-fluoropiperidin-1-yl)pyridin-2-yl) |
| 470 | -HN- | isopropyl | -CH(CH₃)OCH₃ | H | 6-(5-(4,4-difluoropiperidin-1-yl)pyridin-2-yl) |
| 471 | -HN- | isopropyl | -CH(CH₃)OCH₃ | H | 6-(6-(2-(dimethylamino)ethoxy)pyridazin-3-yl) |

TABLE 4-continued

| Compound No. | L | R¹ | R² | R³ | (Y-Z/N=X with R⁴) |
|---|---|---|---|---|---|
| 472 | -HN- | isopropyl | -CH(CH₃)OMe | H | pyridine-CH₂-(4-fluoropiperidin-1-yl) |
| 473 | -HN- | isopropyl | -CH(CH₃)OMe | H | pyridine-O-(3,3-difluoropiperidin-4-yl) |
| 474 | -HN- | isopropyl | -CH(CH₃)OH | H | pyridazine-O-CH₂CH₂-N(CH₃)₂ |
| 475 | -HN- | bicyclo[1.1.1]pentane-COOH | -CH(CH₃)OMe | H | pyridine-CH₂-(piperazin-1-yl) |

TABLE 4-continued

| Compound No. | L | R¹ | R² | R³ | ![structure](Y-Z/N=X-R⁴) |
|---|---|---|---|---|---|
| 476 | HN | isopropyl | methoxymethyl | H | pyridine-2,6-diazaspiro[3.3]heptane |
| 477 | HN | isopropyl | methoxymethyl | H | pyridine-2-azaspiro[3.5]nonane |
| 478 | HN | isopropyl | methoxymethyl | H | pyridine-2,5-diazaspiro[3.3]heptane |
| 479 | HN | isopropyl | methoxymethyl | H | pyridine-2,6-diazaspiro[3.4]octane |

TABLE 4-continued

| Compound No. | L | R¹ | R² | R³ | ![Y-Z/N=X-R⁴ structure] |
|---|---|---|---|---|---|
| 480 | HN linker | isopropyl | methoxy (stereo) | H | pyridine-azaspiro[3.3]heptane |
| 481 | HN linker | isopropyl | methoxy (stereo) | H | pyridine-2-oxa-7-azaspiro[3.5]nonane |
| 482 | HN linker | isopropyl | methoxy (stereo) | H | pyridine-2,7-diazaspiro[3.5]nonane |
| 483 | HN linker | isopropyl | methoxy (stereo) | H | pyridine-O-azaspiro[3.3]heptane |

TABLE 4-continued

| Compound No. | L | R¹ | R² | R³ | ![Y-Z/N=X-R⁴ structure] |
|---|---|---|---|---|---|
| 484 | HN linker | isopropyl | methoxymethyl (stereo) | H | pyridine-azaspiro[3.3]heptane-NH₂ |
| 485 | HN linker | isopropyl | methoxymethyl (stereo) | H | pyridine-NH-azaspiro[3.3]heptane |
| 486 | HN linker | isopropyl | methoxymethyl (stereo) | H | pyridine-diazaspiro |
| 487 | HN linker | isopropyl | methoxymethyl (stereo) | H | pyridine-O-CH₂-CHF-CH₂-N(CH₃)₂ |

TABLE 4-continued

| Compound No. | L | R¹ | R² | R³ | ![](Y-Z-X-N ring with R⁴) |
|---|---|---|---|---|---|
| 488 | HN (branched) | isopropyl | CH(CH₃)OMe | H | pyridazine-N(4-methyl-1,4-diazepan-1-yl) |
| 489 | HN (branched) | isopropyl | CH(CH₃)OMe | H | pyridazine-(4-(dimethylamino)piperidin-1-yl) |
| 490 | HN (branched) | isopropyl | CH(CH₃)OH | H | pyridazine-(4-methyl-1,4-diazepan-1-yl) |
| 491 | HN (branched) | isopropyl | CH(CH₃)OH | H | pyridazine-(4-(dimethylamino)piperidin-1-yl) |

TABLE 4-continued

| Compound No. | L | R¹ | R² | R³ | ![Y-Z/N=X-R⁴ structure] |
|---|---|---|---|---|---|
| 492 | -HN-C(CH₃)< | -CH(CH₃)₂ | -CH(CH₃)-OMe | H | 5-(2-oxo-1,4-diazepan-1-yl)pyridin-2-yl |
| 493 | -HN-C(CH₃)< | -CH(CH₃)₂ | -CH(CH₃)-OMe | H | 6-((1,4-diazepan-1-yl)methyl)pyridin-3-yl |
| 494 | -HN-C(CH₃)< | -CH(CH₃)₂ | -CH(CH₃)-OMe | H | 6-((4-hydroxypiperidin-1-yl)methyl)pyridin-3-yl |
| 495 | -HN-C(CH₃)< | -CH(CH₃)₂ | -CH(CH₃)-OMe | H | 6-(1,4-diazepan-1-yl)pyridazin-3-yl |

TABLE 4-continued

| Compound No. | L | R¹ | R² | R³ | ![Y-Z/N=X-R⁴ structure] |
|---|---|---|---|---|---|
| 496 | -HN- | isopropyl | -CH(OH)CH₃ | H | pyridazine-N-(1,4-diazepane) |
| 497 | -HN- | isopropyl | -CH(OH)CH₃ | H | pyridazine-N-(4-methylamino-piperidine) |
| 498 | -HN- | isopropyl | -CH(OMe)CH₃ | H | pyridine-N-(imidazolidin-2-one) |
| 499 | -HN- | isopropyl | -CH(OMe)CH₃ | H | pyridine-N-(1,4-diazepan-2-one) |

TABLE 4-continued

| Compound No. | L | R¹ | R² | R³ | ![structure](Y-Z, R⁴) |
|---|---|---|---|---|---|
| 500 | -HN- | -iPr | -CH(OMe)- | H | pyridine-piperazine bicyclic (3,8-diazabicyclo) |
| 501 | -HN- | -iPr | -CH(OMe)- | H | pyridine-piperazine bicyclic (3,8-diazabicyclo) |
| 502 | -HN- | -iPr | -CH(OMe)- | H | pyridine-bicyclic-NH₂ |
| 503 | -HN- | -iPr | -CH(OMe)- | H | pyridine-bicyclic-NHMe |

TABLE 4-continued

| Compound No. | L | R¹ | R² | R³ | ![Y-Z / N=X with R⁴] |
|---|---|---|---|---|---|
| 504 | HN | isopropyl | CH(CH₃)OMe | H | pyridine-O-azabicyclo[2.2.1] |
| 505 | HN | isopropyl | CH(CH₃)OMe | H | pyridine-O-CH₂-(1-aminocyclobutyl) |
| 506 | HN | isopropyl | C(CH₃)(OH) | H | pyridine-(3-methyl-2-oxopiperazin-1-yl) |
| 507 | HN | isopropyl | C(CH₃)(OH) | H | pyridine-(3-methyl-2-oxopiperazin-1-yl) |

TABLE 4-continued

| Compound No. | L | R¹ | R² | R³ | ![](Y-Z/N=X-R⁴) |
|---|---|---|---|---|---|
| 508 | -HN- | -CH(CH₃)₂ | -CH(OMe)CH₃ | H | 6-[[4-(2-hydroxyethyl)piperazin-1-yl]methyl]pyridin-3-yl |
| 509 | -HN- | -CH(CH₃)₂ | -CH(OMe)CH₃ | H | 6-[2-fluoro-3-(methylamino)propoxy]pyridin-3-yl |
| 510 | -HN- | -CH(CH₃)₂ | -CH(OH)CH₃ | H | 6-[4-(2-hydroxyethyl)piperazin-1-yl]pyridazin-3-yl |
| 511 | -HN- | -CH(CH₃)₂ | -CH(OMe)CH₃ | H | 6-(7-oxo-2,6-diazaspiro[3.4]octan-6-yl)pyridin-3-yl |

TABLE 4-continued

| Compound No. | L | R¹ | R² | R³ | ![Y-Z ring with R⁴] |
|---|---|---|---|---|---|
| 512 | -HN- | isopropyl | -CH(OMe)- (stereo) | H | pyridine-azaspiro[3.3]heptane-NHMe |
| 513 | -HN- | spiro[3.3]heptane-COOH | -CH(OMe)- | H | pyridine-CH₂-piperazine |
| 514 | -HN- | isopropyl | -CH(OMe)- | H | pyridine-(dimethyl-oxo-diazepane) |
| 515 | -HN- | isopropyl | -CH(OMe)- | H | pyridine-CH₂-(cyclopropane-fused piperazine) |

TABLE 4-continued

| Compound No. | L | R¹ | R² | R³ | ![structure](Y-Z-X-N with R⁴) |
|---|---|---|---|---|---|
| 516 | HN | isopropyl | C(CH₃)(OH) | H | 6-(4,7-diazaspiro[2.5]octan-7-ylmethyl)pyridin-3-yl |
| 517 | HN | isopropyl | CH(CH₃)OH | H | 6-(3-hydroxypiperidin-1-yl)pyridazin-3-yl |
| 518 | HN | isopropyl | CH(CH₃)OMe | H | 6-(2-oxo-2-(piperazin-1-yl)ethyl)pyridin-3-yl |
| 519 | HN | isopropyl | CH(CH₃)OH | H | 6-(2-oxo-2-(piperazin-1-yl)ethyl)pyridin-3-yl |

TABLE 4-continued

| Compound No. | L | R¹ | R² | R³ | ![Y-Z-X-N ring with R⁴] |
|---|---|---|---|---|---|
| 520 | -HN- | isopropyl | -C(CH₃)(OH)- (stereo) | H | pyridazine-piperidine-morpholine |
| 521 | -HN- | isopropyl | -C(CH₃)(OH)- (stereo) | H | pyridine-(1,4-diazepan-2-one) |
| 522 | -HN- | isopropyl | -C(CH₃)(OH)- (stereo) | H | pyridine-(1,4-diazepan-5-one) |
| 523 | -HN- | isopropyl | -C(CH₃)(OMe)- (stereo) | H | pyridazine-(2-azaspiro[3.3]heptane with OH) |

TABLE 4-continued

| Compound No. | L | R¹ | R² | R³ | ![Y-Z/N=X-R⁴ structure] |
|---|---|---|---|---|---|
| 524 | -HN- | isopropyl | -C(CH₃)(OH)- | H | pyridazine-azaspiro[3.3]heptane-OH |
| 525 | -HN- | isopropyl | -C(CH₃)(OMe)- | H | pyridine-diazabicyclic amine |
| 526 | -HN- | isopropyl | -C(CH₃)(OMe)- | H | pyridine-O-(CH₂)₃-NHMe |
| 527 | -HN- | isopropyl | -C(CH₃)(OMe)- | H | pyridazine-O-(CH₂)₃-NHMe |
| 528 | -HN- | isopropyl | -C(CH₃)(OH)- | H | pyridine-O-(CH₂)₃-NHMe |

TABLE 4-continued

| Compound No. | L | R¹ | R² | R³ | ![Y-Z/N=X-R⁴ ring] |
|---|---|---|---|---|---|
| 529 | HN (branched) | isopropyl | CH(OH)CH₃ | H | pyridine-O-CH₂CH₂-NH-CH₃ |
| 530 | HN (branched) | isopropyl | CH(OH)CH₃ | H | pyridazine-O-CH₂CH₂CH₂-NH-CH₃ |
| 531 | HN (branched) | isopropyl | CH(OMe)CH₃ | H | pyridazine-N-methylpiperazine |
| 532 | HN (branched) | isopropyl | CH(OH)CH₃ | H | pyridazine-N-methylpiperazine |

TABLE 4-continued

| Compound No. | L | R¹ | R² | R³ | ![Y-Z/N=X-R⁴ header] |
|---|---|---|---|---|---|
| 533 | HN | isopropyl | OMe (wedge) | H | pyridine-piperazine-2,5-dione |
| 534 | HN | isopropyl | OMe (wedge) | H | pyridine-CH₂-3,3-dimethylpiperazine |
| 535 | HN | isopropyl | OMe (wedge) | H | pyridine-CH₂-spirocyclopropyl piperazine |
| 536 | HN | isopropyl | OH (wedge) | H | pyridine-CH₂-3,3-dimethylpiperazine |

TABLE 4-continued

| Compound No. | L | R¹ | R² | R³ | ![Y-Z/N=X-R⁴ ring] |
|---|---|---|---|---|---|
| 537 | HN | isopropyl | (R)-CH(CH₃)OH | H | pyridine-CH₂-(4,4-cyclopropane-piperazine) |
| 538 | HN | isopropyl | (R)-CH(CH₃)OH | H | pyridine-N(CH₃)-C(O)-CH₂-NH₂ |
| 539 | HN | isopropyl | (R)-CH(CH₃)OH | H | pyridine-NH-CH₂-C(O)-NH-CH₃ |
| 540 | HN | isopropyl | (R)-CH(CH₃)OH | H | pyridazine-(3-oxopiperazine) |

TABLE 4-continued

| Compound No. | L | R¹ | R² | R³ | (structure with Y-Z, N-X, R⁴) |
|---|---|---|---|---|---|
| 541 | -HN- | isopropyl | -C(CH₃)(OH)- | H | pyridazine-O-piperidine |
| 542 | -HN- | isopropyl | -C(CH₃)(OMe)- | H | pyridine-N(dimethyl-caprolactam) |
| 543 | -HN- | isopropyl | -C(CH₃)(OH)- | H | pyridine-N(dimethyl-caprolactam) |
| 544 | -HN- | isopropyl | -C(CH₃)(OH)- | H | pyridazine-O-pyrrolidine |

TABLE 4-continued

| Compound No. | L | R¹ | R² | R³ | (heterocycle) |
|---|---|---|---|---|---|
| 545 | -HN- | isopropyl | -CH(CH₃)OH | H | pyridazinyl-O-(4-fluoropyrrolidin-3-yl) |
| 546 | -HN- | isopropyl | -CH(CH₃)OH | H | pyridazinyl-O-(azetidin-3-yl) |
| 547 | -HN- | isopropyl | -CH(CH₃)OH | H | pyridazinyl-O-(4-fluoropiperidin-3-yl) |
| 548 | -HN- | isopropyl | -CH(CH₃)OH | H | pyridyl-CH₂-(4-methylpiperazin-1-yl) |

TABLE 4-continued

| Compound No. | L | R¹ | R² | R³ | ![Y-Z/N=X-R⁴ ring] |
|---|---|---|---|---|---|
| 549 | HN | iPr | CH(CH₃)OH | H | 6-pyridyl-CH₂-N(piperidin-4-yl-C(CH₃)₂OH) |
| 550 | HN | iPr | CH(CH₃)OH | H | 6-pyridyl-O-CH₂CH₂-N(piperazin-2-one) |
| 551 | HN | iPr | CH(CH₃)OMe | H | pyridazinyl-O-CH₂CH₂-NHMe |
| 552 | HN | iPr | CH(CH₃)OH | H | pyridazinyl-O-CH₂CH₂-NHMe |

TABLE 4-continued
| Compound No. | L | R¹ | R² | R³ | ![Y-Z/N=X-R⁴ ring] |
|---|---|---|---|---|---|
| 553 | 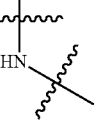 | 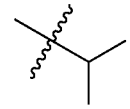 [SMILES: *C(C)C] |  | H |  |
| 554 | 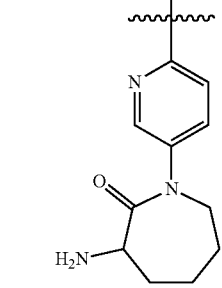 | 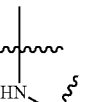 | 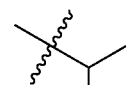 | H | 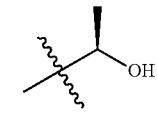 [SMILES: *[C@@H](C)O] |
| 555 |  | 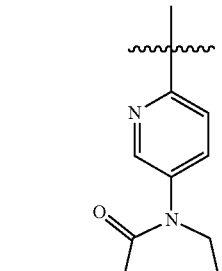 | 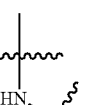 | H | 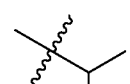 |
| 556 | 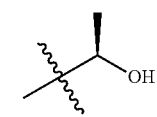 [SMILES: *[C@@H](C)O] |  | 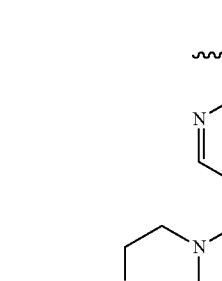 | H |  |

TABLE 4-continued

| Compound No. | L | R¹ | R² | R³ | ![Y-Z/N=X-R⁴ structure] |
|---|---|---|---|---|---|
| 557 | HN | isopropyl | (S)-OMe | H | pyridine-OCH₂C(O)-piperazine |
| 558 | HN | isopropyl | OH | H | pyridine-hexahydropyrrolo[3,4-b]pyrrol-2(1H)-one |
| 559 | HN | isopropyl | OH | H | pyridine-OCH₂C(O)-piperazine |
| 560 | HN | isopropyl | (S)-OMe | H | pyridazine-(4-amino-4-methylpiperidine) |

TABLE 4-continued
| Compound No. | L | R¹ | R² | R³ | ![Y-Z/N=X with R⁴] |
|---|---|---|---|---|---|
| 561 |  | 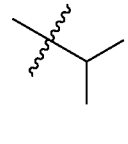 [SMILES: *C(C)C] | 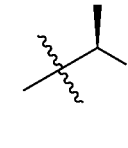 | H | 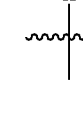 |
| 562 | 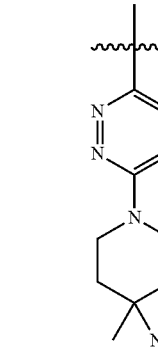 |  | 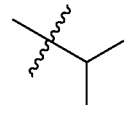 [SMILES: *C(C)C] | H | 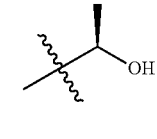 [SMILES: *[C@@H](C)O] |
| 563 |  | 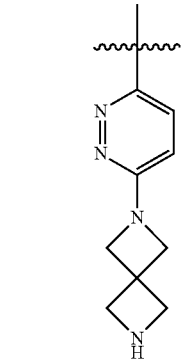 [SMILES: *c1ccc(N2CC3(CNC3)C2)cn1] | 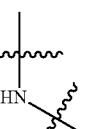 | H | 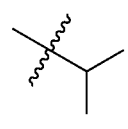 [SMILES: *C(C)C] |
| 564 | 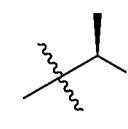 | 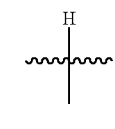 | 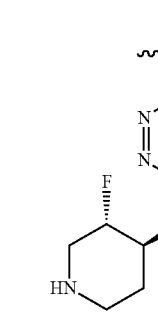 | H | 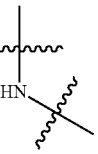 |

TABLE 4-continued

| Compound No. | L | R¹ | R² | R³ | ![Y-Z/N=X-R⁴ ring] |
|---|---|---|---|---|---|
| 565 | HN | isopropyl | CH(OH)CH₃ | H | 5-(piperidin-3-yloxy)pyridin-2-yl |
| 566 | HN | isopropyl | CH(OH)CH₃ | H | 5-(pyrrolidin-3-yloxy)pyridin-2-yl |
| 567 | HN | isopropyl | CH(OH)CH₃ | H | 5-((3-fluoropiperidin-4-yl)oxy)pyridin-2-yl |
| 568 | HN | isopropyl | CH(OH)CH₃ | H | 5-(azetidin-3-yloxy)pyridin-2-yl |
| 569 | HN | isopropyl | CH(OH)CH₃ | H | 5-((3-fluoropiperidin-4-yl)oxy)pyridin-2-yl |

TABLE 4-continued

| Compound No. | L | R¹ | R² | R³ | ![Y-Z-R⁴ ring with N=X] |
|---|---|---|---|---|---|
| 570 | -HN- | isopropyl | -C(CH₃)(OH)- | H | pyridine-OCH₂-azetidine |
| 571 | -HN- | isopropyl | -C(CH₃)(OH)- | H | pyridine-O-piperidine |
| 572 | -HN- | isopropyl | -C(CH₃)(OH)- | H | pyridine-O-pyrrolidine |
| 573 | -HN- | isopropyl | -C(CH₃)(OH)- | H | pyridazine-N-(2,6-diazaspiro[3.3]heptane) |

TABLE 4-continued

| Compound No. | L | R¹ | R² | R³ | ![Y-Z/N=X-R⁴ structure] |
|---|---|---|---|---|---|
| 574 | HN | isopropyl | CH(CH₃)OH | H | pyridazine-2,6-diazaspiro[3.4]octane-NH |
| 575 | HN | isopropyl | CH(CH₃)OH | H | pyridazine-2,7-diazaspiro[3.5]nonane-NH |
| 576 | HN | isopropyl | CH(CH₃)OH | H | pyridazine-2-azaspiro[3.3]heptane-NH₂ |
| 577 | HN | isopropyl | CH(CH₃)OH | H | pyridine-O-piperidine-F |

TABLE 4-continued

| Compound No. | L | R¹ | R² | R³ | ![structure](Y-Z/N=X-R⁴) |
|---|---|---|---|---|---|
| 578 | HN | iPr | C(CH₃)(OH) (stereo) | H | pyridin-2-yl with 5-OCH₂-(3-fluoroazetidin-3-yl) |
| 579 | HN | iPr | C(CH₃)(OH) (stereo) | H | pyridazin-3-yl with 6-OCH₂-(azetidin-3-yl) |
| 580 | HN | iPr | C(CH₃)(OH) (stereo) | H | pyridin-2-yl with 5-S-CH₂CH₂-N(CH₃)₂ |
| 581 | HN | iPr | C(CH₃)(OH) (stereo) | H | *faster isomer; pyridazin-3-yl with 6-(3-hydroxypiperidin-1-yl)* |

TABLE 4-continued

| Compound No. | L | R¹ | R² | R³ | ![Y-Z / N=X - R⁴ structure] |
|---|---|---|---|---|---|
| 582 | HN-linker | isopropyl | C(CH₃)(OH)- | H | *later isomer; pyridazine-N-piperidin-3-ol |
| 583 | HN-linker | isopropyl | C(CH₃)(OH)- | H | pyridine-N-(3-aminopyrrolidin-2-one) |
| 584 | HN-linker | isopropyl | C(CH₃)(OH)- | H | pyridine-N-(4-isopropyl-piperazin-2-one) |
| 585 | HN-linker | isopropyl | C(CH₃)(OH)- | H | pyridazine-N-(4-isopropylpiperazine) |

TABLE 4-continued

| Compound No. | L | R¹ | R² | R³ | ![Y-Z-R⁴ ring with N=X] |
|---|---|---|---|---|---|
| 586 | -HN- | isopropyl | -C(CH₃)(OH)H | H | pyridazine-piperazine-N-isobutyl |
| 587 | -HN- | isopropyl | -C(CH₃)(OH)H | H | pyridazine-piperazine-N-neopentyl |
| 588 | -HN- | isopropyl | -C(CH₃)(OH)H | H | pyridazine-piperazine-N-CH(CH₃)CH₂OH |

TABLE 4-continued

| Compound No. | L | R¹ | R² | R³ | ![Y-Z/N=X-R⁴ structure] |
|---|---|---|---|---|---|
| 589 | HN | 2,2-dimethyltetrahydropyran-5-yl | CH(CH₃)OH | H | pyridazin-3-yl-(4-hydroxypiperidin-1-yl) |
| 590 | HN | 4-methoxycyclohexyl | CH(CH₃)OH | H | pyridazin-3-yl-(4-hydroxypiperidin-1-yl) |
| 591 | HN | isopropyl | CH(CH₃)OMe | H | 5-(3-amino-2-oxopiperidin-1-yl)pyridin-2-yl |
| 592 | HN | 4-methoxycyclohexyl | CH(CH₃)OH | H | 5-(2-(methylamino)ethoxy)pyridin-2-yl |

TABLE 4-continued

| Compound No. | L | R¹ | R² | R³ | ![Y-Z-X-R⁴ ring] |
|---|---|---|---|---|---|
| 593 | HN | isopropyl | CH(OH)CH₃ | H | 5-(3-amino-2-oxopiperidin-1-yl)pyridin-2-yl |
| 594 | HN | isopropyl | CH(OCH₃)CH₃ | H | 6-(4-methyl-4-(methylamino)piperidin-1-yl)pyridazin-3-yl |
| 595 | HN | tetrahydro-2H-pyran-3-yl | CH(OH)CH₃ | H | 6-(4-hydroxypiperidin-1-yl)pyridazin-3-yl |
| 596 | HN | isopropyl | CH(OH)CH₃ | H | 5-(4-isobutyl-2-oxopiperazin-1-yl)pyridin-2-yl |

TABLE 4-continued

| Compound No. | L | R¹ | R² | R³ | ![Y-Z/N=X-R⁴ structure] |
|---|---|---|---|---|---|
| 597 | -HN-C(CH₃)₂- | isopropyl | -C(CH₃)(OH)- (with stereochemistry) | H | pyridinyl-piperazinone-N-CH₂CH₂OH |
| 598 | -HN-C(CH₃)₂- | isopropyl | -C(CH₃)(OH)- (with stereochemistry) | H | pyridinyl-piperazinone-N-CH(CH₃)CH₂OH |
| 599 | -HN-C(CH₃)₂- | isopropyl | -C(CH₃)(OMe)- (with stereochemistry) | H | pyridazinyl-piperazine-N-tBu |

TABLE 4-continued

| Compound No. | L | R¹ | R² | R³ | ![Y-Z / N=X / R⁴ structure] |
|---|---|---|---|---|---|
| 600 | -HN- | 2,2-dimethyltetrahydropyran-5-yl | -C(CH₃)(OH)- | H | pyridin-2-yl with 5-O-CH₂CH₂-N(CH₃)₂ |
| 601 | -HN- | isopropyl | -C(CH₃)(OH)- | H | pyridazin-3-yl with 6-(4-methyl-4-methylamino-piperidin-1-yl) |
| 602 | -HN- | isopropyl | -C(CH₃)(OH)- | H | pyridazin-3-yl with 6-(4-cyclobutyl-piperazin-1-yl) |
| 603 | -HN- | isopropyl | -C(CH₃)(OH)- | H | pyridin-2-yl with 5-(4-neopentyl-3-oxo-piperazin-1-yl) |

TABLE 4-continued

| Compound No. | L | R¹ | R² | R³ | ![structure] |
|---|---|---|---|---|---|
| 604 | HN | isopropyl | CH(OH)CH₃ | H | pyridazine-piperazine-tBu |
| 605 | HN | isopropyl | CH(OH)CH₃ | H | pyridine-piperidinone-NH₂ |
| 606 | HN | isopropyl | CH(OH)CH₃ | H | pyridazine-azaspiro-NHMe |

TABLE 4-continued

| Compound No. | L | R¹ | R² | R³ | ![structure](Y-Z-X-N ring with R⁴) |
|---|---|---|---|---|---|
| 607 | -HN- | -CH(CH₃)₂ | -CH(OH)CH₃ | H | pyridazine-piperidine with 3-F, 4-OH (trans) |
| 608 | -NH- | -CH(CH₃)₂ | -CH(OH)CH₃ | H | pyridazine-piperidine with 3-F, 4-OH |
| 609 | -HN- | -CH(CH₃)₂ | -CH(OH)CH₃ | H | pyridazine-piperidine with 3-F, 4-NHMe |
| 610 | -HN- | -CH(CH₃)₂ | -CH(OH)CH₃ | H | pyridazine-piperidine with 3-F, 4-NHMe |

TABLE 4-continued

| Compound No. | L | R¹ | R² | R³ | ![Y-Z-R⁴ ring] |
|---|---|---|---|---|---|
| 611 | HN | isopropyl | CH(OH)CH₃ | H | pyridazine-azaspiro[3.3]heptane-N(CH₃)₂ |
| 612 | HN | 4-methylcyclohexyl | CH(OH)CH₃ | H | pyridine-piperazinone |
| 613 | HN | isopropyl | CH(OH)CH₃ | H | pyridazine-piperazinone |
| 614 | HN | isopropyl | CH(OH)CH₃ | H | pyridazine-S-CH₂CH₂-N(CH₃)₂ |

TABLE 4-continued
| Compound No. | L | R¹ | R² | R³ |  |
|---|---|---|---|---|---|
| 615 | 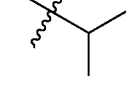 | 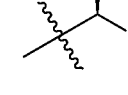 |  | H | 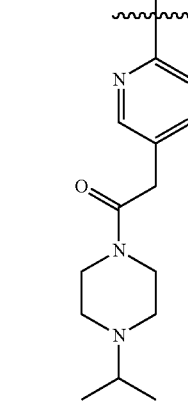 |
| 616 |  | 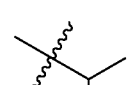 | 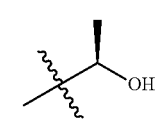 [SMILES: *[C@@H](C)O] | H |  |
| 617 | 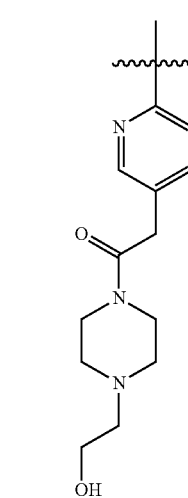 |  |  | H |  |

TABLE 4-continued

| Compound No. | L | R¹ | R² | R³ | ![Y-Z/N=X-R⁴ structure] |
|---|---|---|---|---|---|
| 618 | HN linker | isopropyl | CH(CH₃)OH | H | pyridazine-piperidine(F,NH₂) |
| 619 | HN linker | isopropyl | CH(CH₃)OH | H | pyridazine-piperidine(F,NH₂) |
| 620 | HN linker | isopropyl | CH(CH₃)OH | H | pyridazine-2,6-diazaspiro[3.4]octan-7-one |
| 621 | HN linker | isopropyl | CH(CH₃)OH | H | pyridazine-piperidine(F,N(CH₃)₂) |

US 10,124,004 B2

TABLE 4-continued

| Compound No. | L | R¹ | R² | R³ | ![Y-Z-R⁴ ring with N=X] |
|---|---|---|---|---|---|
| 622 | HN | isopropyl | CH(CH₃)OH | H | pyridazine-piperidine with F and N(CH₃)₂ |
| 623 | HN | isopropyl | CH(CH₃)OH | H | pyridine-bicyclic lactam |
| 624 | HN | trans-4-methylcyclohexyl | CH(CH₃)OH | H | pyridine-piperazinone |
| 625 | HN | isopropyl | CH(CH₃)OH | H | pyridazine-piperazine-CH₂C(CH₃)₂OH |

TABLE 4-continued

| Compound No. | L | R¹ | R² | R³ | ![structure](Y-Z/N=X with R⁴) |
|---|---|---|---|---|---|
| 626 | HN | isopropyl | C(CH₃)(OH)- | H | pyridine-CH₂-piperazine-CH₂C(CH₃)₂OH |
| 627 | HN | isopropyl | C(CH₃)(OH)- | H | pyridine-piperazinone-CH₂C(CH₃)₂OH |
| 628 | HN | 4-methoxycyclohexyl | C(CH₃)(OH)- | H | pyridine-O-CH₂CH₂-N(CH₃)₂ |
| 629 | HN | tetrahydropyran-3-yl | C(CH₃)(OH)- | H | pyridine-O-CH₂CH₂-N(CH₃)₂ |

TABLE 4-continued

TABLE 4-continued

| Compound No. | L | R¹ | R² | R³ | ![Y-Z/N=X-R⁴ header structure] |
|---|---|---|---|---|---|
| 634 | -HN- | 2,2-dimethyltetrahydropyran-5-yl | -C(CH₃)(OH)- | H | 6-substituted pyridin-3-yl-O-CH₂CH₂-NH-CH₃ |
| 635 | -HN- | tetrahydropyran-3-yl | -C(CH₃)(OH)- | H | 6-substituted pyridin-3-yl-O-CH₂CH₂-NH-CH₃ |
| 636 | -HN- | isopropyl | -C(CH₃)(OH)- | H | 6-substituted pyridin-3-yl-(2-oxopiperazin-1-yl) with N-CH₂CH(OH)CH₃ |

TABLE 4-continued

| Compound No. | L | R¹ | R² | R³ | ![Y-Z/N=X-R⁴ structure] |
|---|---|---|---|---|---|
| 637 | HN | isopropyl | CH(OH)CH₃ | H | pyridazine-piperazine-CH₂CH(OH)CH₃ |
| 638 | HN | isopropyl | CH(OH)CH₃ | H | pyridine-CH₂-piperazine-CH₂CH(OH)CH₃ |
| 639 | HN | 2,2-dimethyltetrahydropyran-5-yl | CH(OH)CH₃ | H | pyridazine-piperazine-N-CH₃ |
| 640 | HN | tetrahydropyran-3-yl | CH(OH)CH₃ | H | pyridazine-piperazine-N-CH₃ |

TABLE 4-continued

| Compound No. | L | R¹ | R² | R³ | ![Y-Z/N=X-R⁴ header] |
|---|---|---|---|---|---|
| 641 | HN | 4-methoxycyclohexyl | C(CH₃)(OH)- | H | 6-(4-methylpiperazin-1-yl)pyridazin-3-yl |
| 642 | HN | isopropyl | C(CH₃)(OH)- | H | 6-(1-oxohexahydropyrrolo[1,2-a]pyrazin-2(1H)-yl)pyridin-3-yl |
| 643 | HN | isopropyl | C(CH₃)(OH)- | H | 6-(5-(2-hydroxy-2-methylpropyl)-2-oxo-1,4-diazepan-1-yl)pyridin-3-yl |
| 644 | HN | isopropyl | C(CH₃)(OH)- | H | 6-((4-(1-hydroxypropan-2-yl)piperazin-1-yl)methyl)pyridin-3-yl |

TABLE 4-continued

| Compound No. | L | R¹ | R² | R³ | ![Y-Z/N=X-R⁴ structure] |
|---|---|---|---|---|---|
| 645 | HN | (3-tetrahydropyran-3-yl) | CH(CH₃)OH | H | 6-(pyridin-3-yloxy)-3-fluoropiperidine-pyridyl |
| 646 | HN | 4-methoxycyclohexyl | CH(CH₃)OH | H | 6-(pyridin-3-yloxy)-3-fluoropiperidine-pyridyl |
| 647 | HN | 2,2-dimethyltetrahydropyran-5-yl | CH(CH₃)OH | H | 6-(pyridin-3-yloxy)-3-fluoropiperidine-pyridyl |
| 648 | HN | isopropyl-CH | CH(CH₃)OH | H | pyridazinyl-2,8-diazaspiro[4.5]decan-1-one |

TABLE 4-continued

| Compound No. | L | R¹ | R² | R³ | ![Y-Z/N=X structure with R⁴] |
|---|---|---|---|---|---|
| 649 | -HN- | 2,2-dimethyltetrahydropyran-5-yl | -CH(CH₃)OH | H | 6-(2-oxopiperazin-1-yl)pyridin-3-yl |
| 650 | -HN- | 4-methoxycyclohexyl | -CH(CH₃)OH | H | 6-(2-oxopiperazin-1-yl)pyridin-3-yl |
| 651 | -HN- | isopropyl (tert-butyl-like) | -CH(CH₃)OH | H | 6-(2-hydroxyacetyl)-5,6,7,8-tetrahydro-1,6-naphthyridin-2-yl |
| 652 | -HN- | trans-4-methylcyclohexyl | -CH(CH₃)OH | H | 6-(2-hydroxyacetyl)-5,6,7,8-tetrahydro-1,6-naphthyridin-2-yl |

TABLE 4-continued

| Compound No. | L | R¹ | R² | R³ | ![](Y-Z ring with R⁴) |
|---|---|---|---|---|---|
| 653 | HN | 1,4-cyclohexyl | CH(CH₃)OH | H | 2,3,4-tetrahydro-1,6-naphthyridine with N-C(O)CH₂OH |
| 654 | HN | 4,4-dimethylcyclohexyl | CH(CH₃)OH | H | 2,3,4-tetrahydro-1,6-naphthyridine with N-C(O)CH₂OH |
| 655 | HN | isopropyl | CH(CH₃)OH | H | 2,3,4-tetrahydro-2,7-naphthyridine with N-C(O)CH₂OH |
| 656 | HN | isopropyl | CH(CH₃)OH | H | 2,3-dihydro-1H-pyrrolo[3,4-b]pyridine with N-C(O)CH₂OH |

TABLE 4-continued
| Compound No. | L | R¹ | R² | R³ | ![](Y-Z/N=X-R⁴) |
|---|---|---|---|---|---|
| 657 | 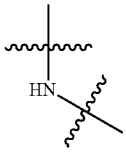 [SMILES: *N*] | 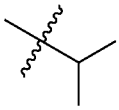 [SMILES: *C(C)C] | 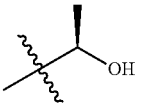 [SMILES: *[C@@H](C)O] | H |  |
| 658 | 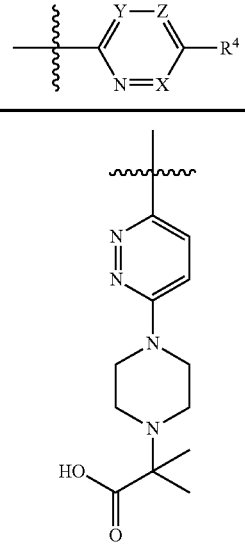 | 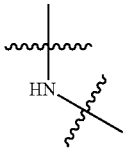 [SMILES: *N*] | 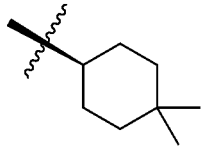 | H | 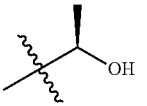 [SMILES: *[C@@H](C)O] |
| 659 |  | 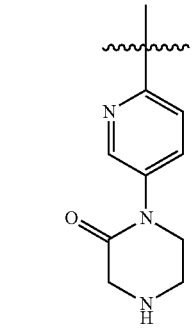 [SMILES: *c1ccc(N2CCNCC2=O)cn1] | 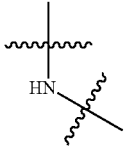 [SMILES: *N*] | H | 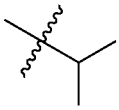 [SMILES: *C(C)C] |

TABLE 4-continued

| Compound No. | L | R¹ | R² | R³ | ![Y-Z-R⁴ ring] |
|---|---|---|---|---|---|
| 660 | HN | isopropyl | CH(CH₃)OH | H | pyridazine-piperidine-CH₂OH |
| 661 | HN | isopropyl | CH(CH₃)OH | H | pyridazine-(3S)-hydroxypyrrolidine |
| 662 | HN | isopropyl | CH(CH₃)OH | H | pyridazine-(3R)-hydroxypyrrolidine |
| 663 | HN | isopropyl | CH(CH₃)OH | H | pyridazine-pyrrolidine-CH₂OH |

TABLE 4-continued

| Compound No. | L | R¹ | R² | R³ | ![Y-Z/N=X-R⁴ structure] |
|---|---|---|---|---|---|
| 664 | HN | isopropyl | CH(OH)CH₃ | H | pyridazine-piperidine (3,3-dimethyl-4-hydroxy) |
| 665 | HN | isopropyl | CH(OH)CH₃ | H | pyridine-(methyl-oxo-diazepane) |
| 666 | HN | isopropyl | CH(OH)CH₃ | H | pyridazine-azetidine (3-hydroxy) |
| 667 | HN | isopropyl | CH(OH)CH₃ | H | pyridazine-azetidine (3-hydroxymethyl) |

TABLE 4-continued

| Compound No. | L | R¹ | R² | R³ | ![structure] |
|---|---|---|---|---|---|
| 668 | HN | isopropyl | CH(OH)CH₃ | H | pyridazine-azetidine-CH₂OH |
| 669 | HN | isopropyl | CH(OH)CH₃ | H | pyridine-CH₂-C(O)-(4-cyclopropyl-piperazine) |
| 670 | HN | isopropyl | tetrahydrofuran-2-yl *faster isomer | H | pyridine-piperazinone |
| 672 | HN | isopropyl | tetrahydrofuran-2-yl *later isomer | H | pyridine-piperazinone |

TABLE 4-continued

| Compound No. | L | R¹ | R² | R³ | ![Y-Z ring with R⁴] |
|---|---|---|---|---|---|
| 673 | HN | isopropyl | CH(CH₃)OH | H | pyridine-O-(3-fluoropyrrolidin-4-yl) |
| 674 | HN | isopropyl | CH(CH₃)OH | H | pyridine-CH₂-piperazine-CH₂-CH(OH)CH₃ |
| 675 | HN | isopropyl | CH(CH₃)OH | H | pyridine-CH₂-piperazine-CH₂-CH(OH)CH₃ |
| 676 | HN | isopropyl | CH(CH₃)OH | H | pyridazine-piperazine-CH₂-CH(OH)CH₃ |

TABLE 4-continued

| Compound No. | L | R¹ | R² | R³ | ![structure] |
|---|---|---|---|---|---|
| 677 | HN | iPr | CH(CH₃)OH | H | pyridazine-piperazine-CH₂CH(OH)CH₃ |
| 678 | HN | iPr | CH(CH₃)OMe | H | pyridazine-piperazine-C(CH₃)₂COOH |
| 679 | HN | iPr | CH(CH₃)OMe | H | pyridine-CH₂-piperazine-C(CH₃)₂COOH |

TABLE 4-continued

| Compound No. | L | R¹ | R² | R³ | ![Y-Z-R⁴ ring structure] |
|---|---|---|---|---|---|
| 680 | -HN- branched | isopropyl | -C(CH₃)(OMe)- | H | pyridazine-piperazine-oxetane |
| 681 | -HN- branched | isopropyl | -C(CH₃)(OMe)- | H | pyridine-CH₂-piperazine-oxetane |
| 682 | -HN- branched | isopropyl | -C(CH₃)(OH)- | H | pyridazine-piperazine-oxetane |
| 683 | -HN- branched | isopropyl | -C(CH₃)(OH)- | H | pyridine-CH₂-piperazine-oxetane |

TABLE 4-continued

| Compound No. | L | R¹ | R² | R³ | ![Y-Z-R⁴/N=X structure] |
|---|---|---|---|---|---|
| 684 | -HN- | isopropyl | -CH(CH₃)OMe | H | pyridazine-piperazine-CH₂CH₂COOH |
| 685 | -HN- | isopropyl | -CH(CH₃)OMe | H | pyridine-CH₂-piperazine-CH₂CH₂COOH |
| 686 | -HN- | isopropyl | -CH(CH₃)OH | H | pyridine-azepanone |
| 687 | -HN- | isopropyl | -CH(CH₃)OH | H | pyridazine-azabicyclo-OH |

TABLE 4-continued

| Compound No. | L | R¹ | R² | R³ | ![Y-Z structure with R⁴] |
|---|---|---|---|---|---|
| 688 | HN linker | isopropyl | C(CH₃)(OH)H | H | pyridazine-piperidine-CH₂OH with methyl |
| 689 | HN linker | *faster isomer, 2,2-dimethyltetrahydropyran | C(CH₃)(OH)H | H | pyridine-O-CH₂CH₂-N(CH₃)₂ |
| 690 | HN linker | *later isomer, 2,2-dimethyltetrahydropyran | C(CH₃)(OH)H | H | pyridine-O-CH₂CH₂-N(CH₃)₂ |
| 691 | HN linker | CH₂-tetrahydropyran-3-yl | C(CH₃)(OH)H | H | pyridine-piperazinone |

TABLE 4-continued

| Compound No. | L | R¹ | R² | R³ | (structure with Y-Z, N=X, R⁴) |
|---|---|---|---|---|---|
| 692 | HN | 2,2-dimethyltetrahydropyran-4-yl | CH(OH)CH₃ | H | 5-(2-oxopiperazin-1-yl)pyridin-2-yl |
| 693 | HN | isopropyl | CH(OH)CH₃ | H | 5,6,7,8-tetrahydro-1,6-naphthyridin-2-yl |
| 694 | HN | isopropyl | CH(OH)CH₃ | H | 5,6,7,8-tetrahydro-2,7-naphthyridin-3-yl |
| 695 | HN | isopropyl | CH(OH)CH₃ | H | 6,7-dihydro-5H-pyrrolo[3,4-b]pyridin-2-yl |
| 696 | HN | tert-butyl | CH(OMe)CH₃ | H | 6-(2,6-diazaspiro[3.3]heptan-2-yl)pyridazin-3-yl |

TABLE 4-continued

| Compound No. | L | R¹ | R² | R³ | ![structure](Y-Z, X, R⁴ ring) |
|---|---|---|---|---|---|
| 697 | HN linker | isopropyl | CH(CH₃)OMe | H | pyridine-CH₂-piperazine-(CH₂)₃-COOH |
| 698 | HN linker | isopropyl | CH(CH₃)F | H | pyridazine-piperazine-NH |
| 699 | HN linker | isopropyl | CH(CH₃)OMe | H | pyridazine-piperazine-(CH₂)₃-COOH |
| 700 | HN linker | isopropyl | CH(CH₃)OH | H | pyridine-CH₂-piperazine-C(CH₃)₂-CH₂OH |

TABLE 4-continued

| Compound No. | L | R¹ | R² | R³ | (structure with Y-Z, N=X, R⁴) |
|---|---|---|---|---|---|
| 701 | -HN- | isopropyl | -C(CH₃)(OH)CH₃ (with stereochemistry) | H | 6-piperazinyl-pyridazin-3-yl, piperazine N-substituted with -C(CH₃)₂CH₂OH |
| 702 | -HN- | isopropyl | -C(CH₃)(OH)CH₃ (with stereochemistry) | H | 6-[4-(carboxymethoxy)piperidin-1-yl]pyridazin-3-yl |
| 703 | -HN- | isopropyl | -C(CH₃)(OH)CH₃ (with stereochemistry) | Cl | 6-[4-(carboxymethoxy)piperidin-1-yl]pyridazin-3-yl |

TABLE 4-continued

| Compound No. | L | R¹ | R² | R³ | ![Y-Z / N=X ring with R⁴] |
|---|---|---|---|---|---|
| 704 | -HN- | -CH(CH₃)₂ | -C(CH₃)(OH)- (with stereochem) | H | *later isomer; pyridazine-N-piperidine with 3-methyl, 4-OH (trans stereochem) |
| 705 | -HN- | -CH(CH₃)₂ | -C(CH₃)(OH)- (with stereochem) | H | *faster isomer; pyridazine-N-piperidine with 3-methyl, 4-OH (trans stereochem) |
| 706 | -HN- | -CH(CH₃)₂ | -C(CH₃)(OH)- (with stereochem) | H | pyridazine-morpholine (2-yl) |
| 707 | -HN- | -CH(CH₃)₂ | -C(CH₃)(OH)- (with stereochem) | H | pyridazine-N-azetidine with 3-F, 3-CH₂OH |

TABLE 4-continued

| Compound No. | L | R¹ | R² | R³ | ![Y-Z/N=X-R⁴ ring] |
|---|---|---|---|---|---|
| 708 | HN | isopropyl | CH(CH₃)OH | H | 6-pyridyl-O-(3-fluoro-4-piperidinyl) |
| 709 | HN | tert-butyl | CH(CH₃)OMe | H | pyridazinyl-piperazine |
| 710 | HN | neopentyl | CH(CH₃)OMe | H | pyridazinyl-piperazine |
| 711 | HN | 4-methoxycyclohexyl | CH(CH₃)OMe | H | pyridazinyl-piperazine |

TABLE 4-continued

| Compound No. | L | R¹ | R² | R³ | ![Y-Z/N=X-R⁴ structure] |
|---|---|---|---|---|---|
| 712 | HN (linker) | cyclopentyl | CH(CH₃)OMe | H | pyridazine-piperazine |
| 713 | HN (linker) | isopropyl | tetrahydrofuran-2-yl *later isomer | H | pyridazine-piperazine |
| 714 | HN (linker) | isopropyl | tetrahydrofuran-2-yl *faster isomer | H | pyridazine-piperazine |
| 715 | HN (linker) | isopropyl | CH(CH₃)OMe | H | 3-fluoropyridine-piperazin-2-one |

TABLE 4-continued

| Compound No. | L | R¹ | R² | R³ | ⸺Y═Z⸺R⁴ ／N═X＼ |
|---|---|---|---|---|---|
| 716 | -HN< | -iPr | -C(CH₃)(OH)H | H | 5-(3-oxopiperazin-1-yl)pyrimidin-2-yl |
| 717 | -HN< | -iPr | -C(CH₃)(OH)H | H | 6-{[2-({2-methoxy-2-oxoethyl}amino)ethyl]amino}pyridin-3-yl |
| 718 | -HN< | -iPr | -CH(CH₃)F | H | 6-(piperazin-1-yl)pyridazin-3-yl |
| 719 | -HN< | tetrahydro-2H-pyran-3-yl | -C(CH₃)(OH)H | Cl | 5-[2-(dimethylamino)ethoxy]pyridin-2-yl |

TABLE 4-continued

| Compound No. | L | R¹ | R² | R³ | ![Y-Z/N=X-R⁴ structure] |
|---|---|---|---|---|---|
| 720 | -HN- | isopropyl | -C(CH₃)(OH)- | H | pyridine-diazepanone with (S)-2-hydroxypropyl |
| 721 | -HN- | isopropyl | -C(CH₃)(OH)- | H | pyridine-diazepanone with (S)-2-hydroxypropyl |
| 722 | -HN- | isopropyl | -C(CH₃)(OH)- | H | pyridazine-piperidine-NH-isopropyl |

TABLE 4-continued

| Compound No. | L | R¹ | R² | R³ | ![Y-Z/N=X-R⁴ structure] |
|---|---|---|---|---|---|
| 723 | HN | isopropyl | CH(CH₃)OH | H | pyridazine-N-piperidine-spirocyclopropane-OH |
| 724 | HN | isopropyl | CH(CH₃)OH | H | *faster isomer; pyridazine-N-piperidine-spirocyclopropane-OH |
| 725 | HN | isopropyl | CH(CH₃)OH | H | *later isomer; pyridazine-N-piperidine-spirocyclopropane-OH |
| 726 | HN | 4,4-dimethylcyclohexyl | CH(CH₃)OMe | H | pyridazine-N-piperazine-NH |

TABLE 4-continued

| Compound No. | L | R¹ | R² | R³ | ![structure](Y-Z / N=X -R⁴) |
|---|---|---|---|---|---|
| 727 | HN | 2,2-dimethyltetrahydropyran-5-yl | (methoxy)methyl (stereo) | H | pyridazin-3-yl-piperazine |
| 728 | S | isopropyl | (methoxy)methyl (stereo) | H | pyridazin-3-yl-piperazine |
| 729 | HN | isopropyl | tetrahydrofuran-2-yl *later isomer | H | 5-(piperazin-1-ylmethyl)pyridin-2-yl |
| 730 | HN | isopropyl | tetrahydrofuran-2-yl *faster isomer | H | 5-(piperazin-1-ylmethyl)pyridin-2-yl |

TABLE 4-continued

| Compound No. | L | R¹ | R² | R³ | ![](Y-Z/N=X-R⁴) |
|---|---|---|---|---|---|
| 731 | HN | isopropyl | CH(OH)CH₃ | H | pyridine-pyrazinone |
| 732 | HN | isopropyl | CH(OH)CH₃ | H | pyridine-isopropyl piperazinone |
| 733 | HN | isopropyl | CH(OH)CH₃ | H | pyridine-spirocyclopropyl piperazinone |
| 734 | HN | isopropyl | C(O)CH₃ | H | pyridine-O-CH₂CH₂-N(CH₃)₂ |

TABLE 4-continued

| Compound No. | L | R¹ | R² | R³ | ![Y-Z-R⁴ ring structure] |
|---|---|---|---|---|---|
| 735 | HN linker | isopropyl | CH(CH₃)OH | H | pyridine-morpholine *faster isomer |
| 736 | HN linker | isopropyl | CH(CH₃)OH | H | pyridine-morpholine *later isomer |
| 737 | HN linker | isopropyl | CH(CH₃)OH | H | pyridine-O-cyclohexyl-NHMe |
| 738 | HN linker | isopropyl | CH(CH₃)OH | H | pyridine-O-cyclohexyl-NHMe |

TABLE 4-continued

| Compound No. | L | R¹ | R² | R³ | ![Y-Z/N=X-R⁴ ring] |
|---|---|---|---|---|---|
| 739 | HN | isopropyl | CH(OH)CH₃ | H | pyridine-O-cyclopentyl-NHMe (trans) |
| 740 | HN | isopropyl | CH(OH)CH₃ | H | pyridine-O-cyclohexyl-NMe₂ (trans) |
| 741 | HN | isopropyl | CH(OH)CH₃ | H | pyridine-O-cyclohexyl-NMe₂ (cis) |
| 742 | HN | isopropyl | CH(OH)CH₃ | H | pyridine-O-cyclopentyl-NMe₂ (trans) |

TABLE 4-continued

| Compound No. | L | R¹ | R² | R³ | ![structure](Y-Z/N=X-R⁴) |
|---|---|---|---|---|---|
| 743 | -NH- | isopropyl | -C(=O)CH₃ (acetyl) | H | pyridin-2-yl substituted with 3-oxopiperazin-1-yl at 5-position |
| 744 | -S- | isopropyl | -C(CH₃)(OH)- | H | pyridin-2-yl substituted with 3-oxopiperazin-1-yl at 5-position |
| 745 | -NH- | isopropyl | -C(CH₃)(OH)- | H | pyridazin-3-yl substituted with 4-acetylpiperazin-1-yl at 6-position |
| 746 | -NH- | isopropyl | -C(CH₃)(OH)- | H | pyridazin-3-yl substituted with 4-isobutyryl-piperazin-1-yl at 6-position |

TABLE 4-continued

| Compound No. | L | R¹ | R² | R³ | ![Y-Z-X-R⁴ ring] |
|---|---|---|---|---|---|
| 747 | -HN- | -CH(CH₃)₂ | -CH(CH₃)OMe | H | 6-(4-(isobutyryl)piperazin-1-yl)pyridazin-3-yl |
| 748 | -HN- | -CH(CH₃)₂ | -CH(CH₃)OMe | H | 6-(4-(isopropoxycarbonyl)piperazin-1-yl)pyridazin-3-yl |
| 749 | -HN- | -CH(CH₃)₂ | -CH(CH₃)OH | H | 2-methyl-3-(3-oxopiperazin-1-yl)pyridin-6-yl |
| 750 | -HN- | -CH(CH₃)₂ | -CH(CH₃)OH | Cl | 5-(2-oxo-1,4-diazepan-1-yl)pyridin-2-yl |

TABLE 4-continued

| Compound No. | L | R¹ | R² | R³ | ![Y-Z-R⁴ ring with N=X] |
|---|---|---|---|---|---|
| 751 | -HN- | 3-tetrahydropyranyl | -C(CH₃)(OH)- | Cl | 5-(2-oxopiperazin-1-yl)pyridin-2-yl |
| 752 | -HN- | -C(CH₃)₂CH₂OCH₃ (S) | -C(CH₃)(OH)- | H | 5-(2-oxopiperazin-1-yl)pyridin-2-yl |
| 753 | -HN- | isopropyl | -C(CH₃)(OH)- | Cl | 6-(4-hydroxypiperidin-1-yl)pyridazin-3-yl |
| 754 | -HN- | -C(CH₃)₂CH₂OCH₃ (S) | -C(CH₃)(OH)- | H | 5-(2-(dimethylamino)ethoxy)pyridin-2-yl |

TABLE 4-continued

| Compound No. | L | R¹ | R² | R³ | ![Y-Z/N=X-R⁴ ring] |
|---|---|---|---|---|---|
| 755 | -HN- | (3-tetrahydropyran-yl) | -CH(OH)CH₃ | Cl | 5-(2-(methylamino)ethoxy)pyridin-2-yl |
| 756 | -HN- | -CH(CH₃)CH₂OCH₃ | -CH(OH)CH₃ | Cl | 5-(2-oxopiperazin-1-yl)pyridin-2-yl |
| 757 | -HN- | -CH(CH₃)CH₂OCH₃ | -CH(OH)CH₃ | H | 5-(2-(methylamino)ethoxy)pyridin-2-yl |
| 758 | -HN- | -CH(CH₃)CH₂OCH₃ | -CH(OH)CH₃ | Cl | 5-(2-(methylamino)ethoxy)pyridin-2-yl |

TABLE 4-continued

| Compound No. | L | R¹ | R² | R³ | ![Y-Z-X-N structure with R⁴] |
|---|---|---|---|---|---|
| 759 | -HN- | -CH(CH₃)CH₂OMe | -C(CH₃)(OH)- | Cl | pyridazine-piperidine-OH |
| 760 | -HN- | -CH(CH₃)CH₂OMe | -C(CH₃)(OH)- | H | pyridazine-piperidine-OH |
| 761 | -HN- | -CH(iPr) | -C(CH₃)(OH)- | H | pyridazine-piperidine-OMe |
| 762 | -HN- | tetrahydropyran-3-yl | -C(CH₃)(OH)- | H | pyridazine-piperidine-OMe |

TABLE 4-continued

| Compound No. | L | R¹ | R² | R³ | ![Y-Z-R⁴/N=X structure] |
|---|---|---|---|---|---|
| 763 | -HN- | isopropyl | tetrahydrofuran-3-yl | H | 5-(2-oxopiperazin-1-yl)pyridin-2-yl |
| 764 | -HN- | isopropyl | (R)-2-hydroxypropan-2-yl with stereochemistry | H | 5-(2-(trifluoromethyl)piperazin-1-yl)pyridin-2-yl |
| 765 | -HN- | isopropyl | (R)-2-hydroxypropan-2-yl with stereochemistry | H | 5-((S)-3-isopropyl-2-oxopiperazin-1-yl)pyridin-2-yl |
| 766 | -HN- | isopropyl | (R)-2-hydroxypropan-2-yl with stereochemistry | H | 5-((R)-3-isopropyl-2-oxopiperazin-1-yl)pyridin-2-yl |

TABLE 4-continued

| Compound No. | L | R¹ | R² | R³ | ![Y-Z/N=X-R⁴ structure] |
|---|---|---|---|---|---|
| 767 | —HN— | isopropyl | —C(CH₃)(OH)— | H | pyridazine-piperazine-C(O)O-iPr |
| 768 | —HN— | isopropyl | —C(CH₃)(OH)— | H | pyridine-NHC(O)-piperidin-4-yl |
| 769 | —HN— | isopropyl | —C(CH₃)(OH)— | H | pyridine-NHC(O)-piperidin-3-yl |
| 770 | —HN— | isopropyl | —C(CH₃)(OH)— | H | pyridine-CH₂-piperidine-4-COOH |

TABLE 4-continued

| Compound No. | L | R¹ | R² | R³ | ![Y-Z/N=X-R⁴ structure] |
|---|---|---|---|---|---|
| 771 | HN | bicyclopentyl | C(CH₃)(OH) | H | pyridyl-piperazinone |
| 772 | HN | isopropyl | C(CH₃)(OH) | H | pyridyl-O-cyclopentyl-NH₂ |
| 773 | HN | isopropyl | *faster isomer tetrahydrofuranyl | H | pyridyl-piperazinone |
| 774 | HN | isopropyl | *later isomer tetrahydrofuranyl | H | pyridyl-piperazinone |

TABLE 4-continued

| Compound No. | L | R¹ | R² | R³ | ⁀Y—Z⁀<br>⁀N=X⁀R⁴ |
|---|---|---|---|---|---|
| 775 | HN | isopropyl | CH(CH₃)OH | H | 5-[(2S)-2-(trifluoromethyl)piperazin-1-yl]pyridin-2-yl<br>*faster isomer |
| 776 | HN | isopropyl | CH(CH₃)OH | H | 5-[(2R)-2-(trifluoromethyl)piperazin-1-yl]pyridin-2-yl<br>*later isomer |
| 777 | HN | isopropyl | CH(CH₃)OH | H | 5-[3-(trifluoromethyl)piperazin-1-yl]pyridin-2-yl |
| 778 | HN | tetrahydropyran-3-yl | CH(CH₃)OH | H | 5,6,7,8-tetrahydro-1,6-naphthyridin-2-yl |

TABLE 4-continued

| Compound No. | L | R¹ | R² | R³ | ![Y-Z/N=X-R⁴ ring] |
|---|---|---|---|---|---|
| 779 | HN | isopropyl | 3-methyloxetan-3-yl | H | 5-(2-oxopiperazin-1-yl)pyridin-2-yl |
| 780 | HN | isopropyl | (S)-1-hydroxyethyl (with methyl) | H | 4-methyl-5-(2-oxopiperazin-1-yl)pyridin-2-yl |
| 781 | HN | tetrahydropyran-3-yl | (S)-1-hydroxyethyl (with methyl) | H | 5-(1-(dimethylamino)propan-2-yloxy)pyridin-2-yl |
| 782 | HN | tetrahydropyran-3-yl | (S)-1-hydroxyethyl (with methyl) | H | 5-((pyrrolidin-2-yl)methoxy)pyridin-2-yl |

TABLE 4-continued

TABLE 4-continued

| Compound No. | L | R¹ | R² | R³ | |
|---|---|---|---|---|---|
| 787 | | | | H | |
| 788 | | | | H | |
| 789 | | | | H | |
| 790 | | | | H | |

TABLE 4-continued

| Compound No. | L | R¹ | R² | R³ | ![Y-Z/N=X-R⁴ header structure] |
|---|---|---|---|---|---|
| 791 | -HN- | t-Bu | -C(CH₃)(OH)- | H | pyridazine-piperazine(NH) |
| 792 | -HN- | i-Pr | -C(CH₃)(OH)- | H | pyridazine-piperidine-4-COOH |
| 793 | -HN- | i-Pr | -C(CH₃)(OH)- | H | pyridazine-piperidine-3-COOH |
| 794 | -HN- | sec-Bu | -C(CH₃)(OH)- | H | pyridazine-piperidine-4-C(CH₃)₂COOH |

TABLE 4-continued

| Compound No. | L | R¹ | R² | R³ | ![Y-Z-X-N ring with R⁴] |
|---|---|---|---|---|---|
| 795 | -HN- | -C(CH₃)₃ | -CH(OH)CH₃ | H | pyridine-N-(2-oxopiperazin-1-yl) |
| 796 | -HN- | -CH(CH₃)₂ | -CH(OH)CH₃ | H | pyridine-piperidine-C(CH₃)₂COOH |
| 797 | -HN- | -CH(CH₃)₂ | -CH(OH)CH₃ | H | pyridazine-piperidine-CH₂COOH |
| 798 | -HN- | -CH(CH₃)₂ | -CH(OH)CH₃ | H | pyridine-morpholine |

TABLE 4-continued

| Compound No. | L | R¹ | R² | R³ | ![Y-Z/N=X-R⁴ structure] |
|---|---|---|---|---|---|
| 799 | -HN< | -CH(CH₃)₂ | -C(CH₃)(OH)- | H | 5-(((1S,2R)-2-(methylamino)cyclopentyl)oxy)pyridin-2-yl |
| 800 | -HN< | tetrahydro-2H-pyran-3-yl | -C(CH₃)(OH)- | H | 5-(azetidin-3-ylmethoxy)pyridin-2-yl |
| 801 | -HN< | -CH(CH₃)₂ | -C(CH₃)(OH)- | H | 5-(((1S,2R)-2-(methylamino)cyclopentyl)oxy)pyridin-2-yl |
| 802 | -HN< | tetrahydro-2H-pyran-3-yl | -C(CH₃)(OH)- | H | 5-(azetidin-2-ylmethoxy)pyridin-2-yl |

TABLE 4-continued

| Compound No. | L | R¹ | R² | R³ | ![structure] |
|---|---|---|---|---|---|
| 803 | HN | tetrahydropyran-3-yl | C(CH₃)(OH)- | H | pyridine with pyrrolidin-3-yloxy |
| 804 | HN | isopropyl | C(CH₃)(OH)- | H | pyridine with 3-oxomorpholin-4-yl |
| 805 | HN | tetrahydropyran-3-yl | C(CH₃)(OH)- | H | pyridine with pyrrolidin-3-yloxy |
| 806 | HN | tetrahydropyran-3-yl | CHF₂-C(CH₃)- | H | pyridine with piperidine-4-carboxylic acid via CH₂ |

TABLE 4-continued

| Compound No. | L | R¹ | R² | R³ | ![structure](Y-Z/N=X-R⁴) |
|---|---|---|---|---|---|
| 807 | -HN- | isopropyl | tetrahydropyran-3-yl | H | 5-(2-oxopiperazin-1-yl)pyridin-2-yl |
| 808 | -HN- | isopropyl | 2-hydroxypropan-2-yl with methyl | H | 5-(1-(piperidin-4-yl)-1H-pyrazol-4-yl)pyridin-2-yl |
| 809 | -HN- | isopropyl | 2-hydroxypropan-2-yl with methyl | H | *faster isomer; 5-(4-((S)-1-hydroxypropan-2-yl)-7-oxo-1,4-diazepan-1-yl)pyridin-2-yl |

TABLE 4-continued

| Compound No. | L | R¹ | R² | R³ | ![Y-Z/N=X-R⁴ structure] |
|---|---|---|---|---|---|
| 810 | HN | isopropyl | C(CH₃)(OH)- | H | *later isomer; pyridine-piperazinone-CH(CH₃)CH₂OH |
| 811 | HN | isopropyl | C(CH₃)(OH)- | H | pyridine-diazepanone-CH₂CH₂OH |
| 812 | HN | sec-butyl | C(CH₃)(OH)- | H | pyridine-piperazinone-NH |
| 813 | HN | n-butyl | C(CH₃)(OH)- | H | pyridine-piperazinone-NH |

TABLE 4-continued

| Compound No. | L | R¹ | R² | R³ | ![Y-Z-R⁴ ring with N=X] |
|---|---|---|---|---|---|
| 814 | HN | (propyl) | OH (with methyl, stereo) | H | 5-(2-oxopiperazin-1-yl)pyridin-2-yl |
| 815 | HN | isopropyl | OH (with methyl, stereo) | Cl | 3-(2-oxopiperazin-1-yl)-2-methylpyridin-6-yl |
| 816 | HN | (ethyl/propyl) | OMe (with methyl, stereo) | H | 5-(piperazin-1-ylmethyl)pyridin-2-yl |
| 817 | HN | (ethyl/propyl) | OMe (with methyl, stereo) | H | 6-(piperazin-1-yl)pyridazin-3-yl |

TABLE 4-continued

| Compound No. | L | R¹ | R² | R³ | ![Y-Z/N=X-R⁴ structure] |
|---|---|---|---|---|---|
| 818 | HN | (propyl) | CH(CH₃)OMe | H | pyridine-CH₂-piperazine |
| 819 | HN | (propyl) | CH(CH₃)OMe | H | pyridazine-piperazine |
| 820 | HN | (ethyl) | CHF₂ | H | pyridine-piperazinone |
| 821 | HN | (propyl) | CHF₂ | H | pyridine-piperazinone |

TABLE 4-continued

| Compound No. | L | R¹ | R² | R³ | ![structure](Y-Z/N=X with R⁴) |
|---|---|---|---|---|---|
| 822 | -HN- | 4-tetrahydropyranyl | -CF₂H (gem-difluoro) | H | 6-(3-oxopiperazin-1-yl)pyridin-3-yl |
| 823 | -HN- | (tetrahydropyran-4-yl)methyl | -CHF₂ | H | 6-(3-oxopiperazin-1-yl)pyridin-3-yl |
| 824 | -HN- | isopropyl | tetrahydrofuran-3-yl | H | 2-methyl-6-(3-oxopiperazin-1-yl)pyridin-3-yl |
| 825 | -HN- | isopropyl | -CH(OH)CH₃ | H | 6-(hexahydropyrrolo[1,2-a]pyrazin-2(1H)-one-yl)pyridin-3-yl |

TABLE 4-continued

| Compound No. | L | R¹ | R² | R³ | ![Y-Z / N=X-R⁴ ring] |
|---|---|---|---|---|---|
| 826 | -HN- | isobutyl | -C(CH₃)(OH)- | H | pyridinyl-piperazinone |
| 827 | -HN- | isobutyl | -C(CH₃)(OH)- | H | pyridazinyl-piperazine |
| 828 | -HN- | isopropyl | -C(CH₃)(OH)- | H | pyridazinyl-piperidine-CH₂CH₂COOH |
| 829 | -HN- | isopropyl | -C(CH₃)(OH)- | H | pyridinyl-piperidine-CH₂COOH |

TABLE 4-continued

| Compound No. | L | R¹ | R² | R³ | ![](Y-Z / N=X with R⁴) |
|---|---|---|---|---|---|
| 830 | -HN- | t-Bu | -C(CH₃)(OH)- (stereo) | H | 6-(1-(carboxymethyl)piperidin-4-yl)pyridin-3-yl |
| 831 | -HN- | i-Pr | -C(CH₃)(OH)- (stereo) | H | 6-(trans-4-carboxycyclohexyloxy)pyridin-3-yl |
| 832 | -HN- | i-Pr | -C(CH₃)(OH)- (stereo) | H | 6-(trans-4-carboxycyclohexyloxy)pyridin-3-yl |

TABLE 4-continued

| Compound No. | L | R¹ | R² | R³ | ![Y-Z-R⁴ ring with N=X] |
|---|---|---|---|---|---|
| 833 | -HN- | isopropyl | -CH(OH)CH₃ | H | pyridine-piperazinone-CH₂COOH |
| 834 | -HN- | tert-butyl | -CH(OH)CH₃ | H | pyridine-piperidine-C(CH₃)₂COOH |
| 835 | -HN- | isopropyl | -CH(OH)CH₃ | H | pyridine-piperidine-3-COOH |

TABLE 4-continued

| Compound No. | L | R¹ | R² | R³ | (structure with Y—Z, N=X, R⁴) |
|---|---|---|---|---|---|
| 836 | -HN- | isopropyl | -C(CH₃)(OH)- | H | pyridine-piperidine-COOH |
| 837 | -HN- | tert-butyl | -C(CH₃)(OH)- | H | pyridine-CH₂-piperidine-COOH |
| 838 | -HN- | isopropyl | -C(CH₃)(OCH₃)- | H | pyridine-NHC(O)-piperidine |
| 839 | -HN- | trans-4-methylcyclohexyl | -C(CHF₂)- | H | pyridine-CH₂-piperidine-COOH |

TABLE 4-continued

| Compound No. | L | R¹ | R² | R³ | ![](Y-Z / N=X with R⁴) |
|---|---|---|---|---|---|
| 840 | -HN- | -CH₂-(tetrahydropyran-4-yl) | -CHF₂ | Cl | 5-(2-oxopiperazin-1-yl)pyridin-2-yl |
| 841 | -HN- | -CH(CH₃)₂ | -CH(CH₃)OH | Cl | 5-[4-(2-hydroxyethyl)-1,4-diazepan-1-yl, 5-oxo]pyridin-2-yl |
| 842 | -HN- | -CH(CH₃)₂ | -CH(CH₃)OMe | Cl | 5-(piperazine-1-carbonyl)pyridin-2-yl |
| 843 | -HN- | -C(CH₃)₂-CH₂CH₃ | -CH(CH₃)OH | H | 5-{[4-(2-hydroxyethyl)piperazin-1-yl]methyl}pyridin-2-yl |

TABLE 4-continued

| Compound No. | L | R¹ | R² | R³ | ![structure] |
|---|---|---|---|---|---|
| 844 | -HN- | n-butyl | -C(CH₃)(OH)- | H | 6-[4-(2-hydroxyethyl)piperazin-1-ylmethyl]pyridin-3-yl |
| 845 | -HN- | n-pentyl | -C(CH₃)(OH)- | H | 6-[4-(2-hydroxyethyl)piperazin-1-ylmethyl]pyridin-3-yl |
| 846 | -HN- | isobutyl | -C(CH₃)(OH)- | H | 6-[4-(2-hydroxyethyl)piperazin-1-ylmethyl]pyridin-3-yl |
| 847 | -HN- | (tetrahydropyran-4-yl)methyl | -C(CH₃)(OH)- | H | 6-[4-(2-hydroxyethyl)piperazin-1-ylmethyl]pyridin-3-yl |

TABLE 4-continued

| Compound No. | L | R¹ | R² | R³ | ![Y-Z/N=X-R⁴ ring] |
|---|---|---|---|---|---|
| 848 | -HN- | t-Bu | -C(CH₃)(OH)- (with stereochemistry) | H | 5-(3-oxopiperazin-1-yl)pyridin-2-yl |
| 849 | -HN- | tetrahydropyran-3-yl | -CHF₂ | H | 5-(3-oxopiperazin-1-yl)pyridin-2-yl |
| 850 | -HN- | i-Pr | -CHF₂ | Cl | 5-(3-oxopiperazin-1-yl)pyridin-2-yl |
| 851 | -HN- | i-Pr | -CHF₂ | Cl | 2-methyl-5-(3-oxopiperazin-1-yl)pyridin-6-yl |

TABLE 4-continued

| Compound No. | L | R¹ | R² | R³ | ![Y-Z/N=X-R⁴ structure] |
|---|---|---|---|---|---|
| 852 | -HN- | propyl | -CH(OMe)- | H | 6-pyridyl-CH₂-piperazine-N-CH₂CH₂OH |
| 853 | -HN- | butyl | -CH(OMe)- | H | 6-pyridyl-CH₂-piperazine-N-CH₂CH₂OH |
| 854 | -HN- | butyl | -CH(OMe)- | H | 6-pyridyl-CH₂-piperazine-NH |
| 855 | -HN- | butyl | -CH(OMe)- | H | pyridazine-piperazine-NH |

TABLE 4-continued

| Compound No. | L | R¹ | R² | R³ | ![Y-Z/N=X-R⁴ structure] |
|---|---|---|---|---|---|
| 856 | HN | tetrahydropyran-3-yl | CHF₂ | H | pyridine-CH₂-piperazinone |
| 857 | HN | n-propyl | CH(CH₃)OMe | H | pyridine-CH₂-diazabicycloheptane |
| 858 | HN | n-propyl | CH(CH₃)OMe | H | pyridazine-diazabicycloheptane |
| 859 | HN | isopropyl | CH(CH₃)OMe | H | pyridazine-diazabicycloheptane |

TABLE 4-continued

| Compound No. | L | R¹ | R² | R³ | ![Y-Z/N=X-R⁴ structure] |
|---|---|---|---|---|---|
| 860 | -HN< | 3-tetrahydropyranyl | -CH(CH₃)OCH₃ | H | 6-[4-(2-hydroxyethyl)piperazin-1-ylmethyl]pyridin-3-yl |
| 861 | -HN< | isobutyl (CH₂CH(CH₃)₂) | -CH(CH₃)OCH₃ | H | 6-(piperazin-1-ylmethyl)pyridin-3-yl |
| 862 | -HN< | isobutyl | -CH(CH₃)OCH₃ | H | 6-(piperazin-1-yl)pyridazin-3-yl |
| 863 | -HN< | isopropyl-CH₂ (neopentyl-like) | -CH(CH₃)OH | H | 6-[2-(trifluoromethyl)piperazin-1-yl]pyridazin-3-yl |

TABLE 4-continued

| Compound No. | L | R¹ | R² | R³ | ![Y-Z/N=X-R⁴ ring] |
|---|---|---|---|---|---|
| 864 | HN | isopropyl | C(CH₃)(OH)- | H | pyridine-O-(4-fluoropiperidin-3-yl) |
| 865 | HN | isopropyl | C(CH₃)(OH)- | H | *faster isomer; pyridine-(morpholin-3-yl) |
| 866 | HN | isopropyl | C(CH₃)(OH)- | H | *later isomer; pyridine-(morpholin-3-yl) |
| 867 | HN | isopropyl | C(CH₃)(OH)- | H | pyridine-O-CH₂CH₂-NH-SO₂CH₃ |

TABLE 4-continued

| Compound No. | L | R¹ | R² | R³ | ![structure](Y-Z / N=X with R⁴) |
|---|---|---|---|---|---|
| 868 | -N(Me)- | 3-tetrahydropyranyl | -C(Me)(OH)- | H | 6-(2-(methylamino)ethoxy)pyridin-3-yl |
| 869 | -NH- | 3-methyl-tetrahydropyran-3-yl (*faster isomer) | -C(Me)(OH)- | H | 6-(2-(methylamino)ethoxy)pyridin-3-yl |
| 870 | -NH- | 3-methyl-tetrahydropyran-3-yl (*later isomer) | -C(Me)(OH)- | H | 6-(2-(methylamino)ethoxy)pyridin-3-yl |
| 871 | -N(Me)- | isopropyl | -C(Me)(OH)- | H | 6-(3-oxopiperazin-1-yl)pyridin-3-yl |

TABLE 4-continued

| Compound No. | L | R¹ | R² | R³ | ![structure] |
|---|---|---|---|---|---|
| 872 | -N(Me)- | 3-tetrahydropyranyl | -CH(CH₃)OH | H | 5-(3-oxopiperazin-1-yl)pyridin-2-yl |
| 873 | -NH- | 4-tetrahydropyranyl | -CH(CH₃)OMe | H | 5-(piperidin-4-yloxy)pyridin-2-yl |
| 874 | -NH- | 3-tetrahydropyranyl | -CH(CH₃)OMe | H | 5-(piperidin-4-yloxy)pyridin-2-yl |
| 875 | -NH- | isopropyl | 3-tetrahydrofuranyl (*faster isomer) | H | 2-methyl-3-(3-oxopiperazin-1-yl)pyridin-6-yl |

*faster isomer

TABLE 4-continued

TABLE 4-continued

| Compound No. | L | R¹ | R² | R³ | ![Y-Z-X-R⁴ structure] |
|---|---|---|---|---|---|
| 880 | -HN- | (S)-tetrahydropyran-3-yl | 3-methyloxetan-3-yl | H | 6-(piperazin-1-yl)pyridazin-3-yl |
| 881 | -HN- | isopropyl | tetrahydrofuran-3-yl | H | 6-(piperazin-1-ylmethyl)pyridin-3-yl |
| 882 | -HN- | (S)-tetrahydropyran-3-yl | tetrahydrofuran-3-yl | H | 6-(piperazin-1-ylmethyl)pyridin-3-yl |
| 883 | -HN- | isopropyl | 3-methyloxetan-3-yl | H | 6-(piperazin-1-ylmethyl)pyridin-3-yl |

TABLE 4-continued

| Compound No. | L | R¹ | R² | R³ | ![](Y-Z/N=X-R⁴) |
|---|---|---|---|---|---|
| 884 | HN | tetrahydropyran-3-yl | 3-methyloxetan-3-yl | H | 5-(piperazin-1-ylmethyl)pyridin-2-yl |
| 885 | HN | isopropyl | tetrahydrofuran-3-yl | H | 1,2,3,4-tetrahydro-1,6-naphthyridin-6-yl |
| 886 | HN | tetrahydropyran-3-yl | tetrahydrofuran-3-yl | H | 1,2,3,4-tetrahydro-1,6-naphthyridin-6-yl |
| 887 | HN | isopropyl | 3-methyloxetan-3-yl | H | 1,2,3,4-tetrahydro-1,6-naphthyridin-6-yl |
| 888 | HN | tetrahydropyran-3-yl | 3-methyloxetan-3-yl | H | 1,2,3,4-tetrahydro-1,6-naphthyridin-6-yl |

TABLE 4-continued

| Compound No. | L | R¹ | R² | R³ | ![Y-Z/N=X-R⁴ structure] |
|---|---|---|---|---|---|
| 889 | -HN- | isopropyl | tetrahydrofuran-3-yl | H | 6-[4-(carboxymethyl)-2-(trifluoromethyl)piperazin-1-yl]pyridin-3-yl |
| 890 | -HN- | isopropyl | 3-methyloxetan-3-yl | H | 6-[4-(carboxymethyl)-2-(trifluoromethyl)piperazin-1-yl]pyridin-3-yl |
| 891 | -HN- | isopropyl | (1S)-1-methoxyethyl | H | 6-[4-(carboxymethyl)-2-(trifluoromethyl)piperazin-1-yl]pyridin-3-yl |

TABLE 4-continued

| Compound No. | L | R¹ | R² | R³ | ![Y-Z-R⁴ ring with N=X] |
|---|---|---|---|---|---|
| 892 | -HN- | isopropyl | -C(CH₃)(OH)- (stereo) | H | pyridine-piperazine with CF₃ substituent, N-CH₂COOH |
| 893 | -HN- | isopropyl | -C(CH₃)(OMe)- (stereo) | H | pyridine-piperidine-3-carboxylic acid |
| 894 | -HN- | isopropyl | -C(CH₃)(OMe)- (stereo) | H | pyridine-(2-oxopiperazine)-N-CH₂COOH |

TABLE 4-continued

| Compound No. | L | R¹ | R² | R³ | ![structure](Y-Z-X-N with R⁴) |
|---|---|---|---|---|---|
| 895 | -HN- | isopropyl | -C(CH₃)(OH)- | H | pyridinyl-piperazinone-CH(CH₃)COOH |
| 896 | -HN- | isopropyl | -C(CH₃)(OH)- | H | pyridazinyl-(3-trifluoromethyl)piperazine |
| 897 | -HN- | isopropyl | -C(CH₃)(OMe)- | H | pyridinyl-piperazinone-CH(CH₃)COOH |

TABLE 4-continued

| Compound No. | L | R¹ | R² | R³ | ![Y-Z/N=X-R⁴ structure] |
|---|---|---|---|---|---|
| 898 | -HN- | isopropyl | -C(CH₃)(OH)- | H | pyridazinyl-tetrahydroimidazo[1,2-a]pyrazine |
| 899 | -HN- | isopropyl | -C(CH₃)(OH)- | H | pyridinyl-(3-oxopiperazinyl)-CH₂CN |
| 900 | -HN- | isopropyl | -C(CH₃)(OH)- | H | pyridinyl-(3-oxopiperazinyl)-CH₂C(O)NH₂ |

TABLE 4-continued

| Compound No. | L | R¹ | R² | R³ | ![Y-Z-R⁴ ring with N=X] |
|---|---|---|---|---|---|
| 901 | -HN- | isopropyl | -C(CH₃)(OH)- (with stereochemistry) | H | pyridazine-piperazine-CH₂CN |
| 902 | -HN- | isopropyl | -C(CH₃)(OH)- | H | pyridazine-piperazine-CH(CH₃)CN |
| 903 | -HN- | 3-methyltetrahydropyran-3-yl | -C(CH₃)(OH)- | H | pyridine-piperazinone |
| 904 | -N(CH₃)- | isopropyl | -C(CH₃)(OH)- | H | pyridine-(1,4-diazepan-2-one) |

TABLE 4-continued

| Compound No. | L | R¹ | R² | R³ | ![Y-Z/N=X with R⁴] |
|---|---|---|---|---|---|
| 905 | -HN- | isopropyl | -CH(CH₃)OH | H | 2-(tetrahydro-1,6-naphthyridin-6-yl) substituted with N,N-dimethylglycinoyl |
| 906 | -HN- | isopropyl | -CH(CH₃)OMe | H | pyridazinyl-piperazinyl-CH₂CN |
| 907 | -HN- | isopropyl | -CH(CH₃)OMe | H | pyridazinyl-piperazinyl-CH(CH₃)CN |
| 908 | -HN- | isopropyl | -CH(CH₃)OMe | H | pyridazinyl-piperazinyl-CH₂C(O)NH₂ |

TABLE 4-continued

| Compound No. | L | R¹ | R² | R³ | ![Y-Z/N=X with R⁴] |
|---|---|---|---|---|---|
| 909 | -HN- | tert-butyl | -C(O)CH₃ | H | pyridazine-piperazine |
| 910 | -HN- | n-propyl | -C(O)CH₃ | H | pyridine-CH₂-piperazine |
| 911 | -HN- | n-butyl | -C(O)CH₃ | H | pyridine-CH₂-piperazine |
| 912 | -HN- | isobutyl | -C(O)CH₃ | H | pyridine-CH₂-piperazine |

TABLE 4-continued

| Compound No. | L | R¹ | R² | R³ | ![structure] |
|---|---|---|---|---|---|
| 913 | HN | C(CH₃)₂CH₂OH | CH(OMe)CH₃ | H | 6-(4-(2-hydroxyethyl)piperazin-1-ylmethyl)pyridin-3-yl |
| 914 | HN | CH(CH₃)CH₂OH | CH(OMe)CH₃ | H | 6-(4-(2-hydroxyethyl)piperazin-1-ylmethyl)pyridin-3-yl |
| 915 | HN | CH(CH₃)CH₂OH | CH(OMe)CH₃ | H | 6-(4-(2-hydroxyethyl)piperazin-1-ylmethyl)pyridin-3-yl |
| 916 | HN | CH(CH₃)CH₂OMe | CH(OMe)CH₃ | H | 6-(4-(2-hydroxyethyl)piperazin-1-ylmethyl)pyridin-3-yl |

TABLE 4-continued

| Compound No. | L | R¹ | R² | R³ | ![structure](Y-Z-X-N ring with R⁴) |
|---|---|---|---|---|---|
| 917 | -HN- | 4-hydroxycyclohexyl | -CH(CH₃)OMe | H | 6-{[4-(2-hydroxyethyl)piperazin-1-yl]methyl}pyridin-3-yl |
| 918 | -HN- | (tetrahydro-2H-pyran-4-yl)methyl | -CH(CH₃)OMe | H | 6-{[4-(2-hydroxyethyl)piperazin-1-yl]methyl}pyridin-3-yl |
| 919 | -HN- | sec-butyl | -CH(CH₃)OMe | H | 6-(piperazin-1-yl)pyridin-3-yl |
| 920 | -HN- | pentan-2-yl | -CH(CH₃)OMe | H | 6-(piperazin-1-yl)pyridin-3-yl |

TABLE 4-continued

TABLE 4-continued

| Compound No. | L | R¹ | R² | R³ | ![Y-Z/N=X-R⁴ structure] |
|---|---|---|---|---|---|
| 925 | -HN- | isopropyl | -CH(OMe)- (stereo) | H | 2-methyl-5-(piperazin-1-yl)pyridin-... |
| 926 | -HN- | isopropyl | -C(CH₃)(OH)- (stereo) | H | 5-(4-hydroxy-2-oxopiperidin-1-yl)pyridin-2-yl |
| 927 | -HN- | (tetrahydropyran-4-yl)methyl | -CH(OMe)- (stereo) | H | 5-(piperidin-4-yloxy)pyridin-2-yl |
| 928 | -HN- | 1-(tetrahydropyran-4-yl)ethyl | -CH(OMe)- (stereo) | H | 5-((piperazin-1-yl)methyl)pyridin-2-yl |

TABLE 4-continued

| Compound No. | L | R¹ | R² | R³ | ![structure header] |
|---|---|---|---|---|---|
| 929 | HN | iPr | CH(CH₃)OH | H | 2-(hydroxyethyl)-5,6,7,8-tetrahydro-1,6-naphthyridin-2-yl |
| 930 | HN | iPr | CH(CH₃)OH | H | 6-(2-(methylamino)ethyl)-5,6,7,8-tetrahydro-1,6-naphthyridin-2-yl |
| 931 | HN | iPr | CH(CH₃)OH | H | 6-((S)-2-amino-3-methylbutanoyl)-5,6,7,8-tetrahydro-1,6-naphthyridin-2-yl |
| 932 | HN | iPr | CH(CH₃)OH | H | 6-(piperidine-4-carbonyl)-5,6,7,8-tetrahydro-1,6-naphthyridin-2-yl |

TABLE 4-continued

TABLE 4-continued

| Compound No. | L | R¹ | R² | R³ | (Y-Z/N=X-R⁴ ring) |
|---|---|---|---|---|---|
| 937 | -HN- | isopropyl | -C(CH₃)(OH)- (with stereo) | H | 6-(piperazin-1-yl)pyridazin-3-yl with N-CH₂C(O)NH₂ on piperazine |
| 938 | -HN- | tetrahydropyran-3-yl | *faster isomer, tetrahydrofuran-3-yl | H | 6-(piperazin-1-yl)pyridazin-3-yl |
| 939 | -HN- | tetrahydropyran-3-yl | *later isomer, tetrahydrofuran-3-yl | H | 6-(piperazin-1-yl)pyridazin-3-yl |
| 940 | -HN- | tetrahydropyran-3-yl | *faster isomer, tetrahydrofuran-3-yl | H | 6-(piperazin-1-ylmethyl)pyridin-3-yl |

TABLE 4-continued

| Compound No. | L | R¹ | R² | R³ | ![](Y-Z ring with R⁴) |
|---|---|---|---|---|---|
| 941 | -HN- | tetrahydropyran-3-yl | tetrahydrofuran-3-yl *later isomer | H | 6-(piperazin-1-ylmethyl)pyridin-3-yl |
| 942 | -HN- | tetrahydropyran-3-yl | tetrahydrofuran-3-yl *faster isomer | H | 5,6,7,8-tetrahydro-1,6-naphthyridin-2-yl |
| 943 | -HN- | tetrahydropyran-3-yl | tetrahydrofuran-3-yl *later isomer | H | 5,6,7,8-tetrahydro-1,7-naphthyridin-2-yl |
| 944 | -HN- | n-propyl | CH(OH)CH₃ | H | 5,6,7,8-tetrahydro-1,6-naphthyridin-2-yl |
| 945 | -HN- | n-propyl | 3-methyloxetan-3-yl | H | 6-(piperazin-1-yl)pyridazin-3-yl |

TABLE 4-continued

| Compound No. | L | R¹ | R² | R³ | ⌇—⟨Y=Z⟩—R⁴ (N=X) |
|---|---|---|---|---|---|
| 946 | HN | (alkyl) | tetrahydrofuran-3-yl | H | pyridazine-piperazine |
| 947 | HN | (alkyl) | 3-methyloxetan-3-yl | H | 5,6,7,8-tetrahydro-1,7-naphthyridine |
| 948 | HN | (alkyl) | tetrahydrofuran-3-yl | H | 5,6,7,8-tetrahydro-1,7-naphthyridine |
| 949 | HN | isopropyl | CH(CH₃)OH | H | pyridine-CH₂-1,2,4-triazole |
| 950 | HN | isopropyl | CH(CH₃)OH | H | pyridine-CH₂-piperidine |

TABLE 4-continued

| Compound No. | L | R¹ | R² | R³ | ![structure](Y-Z, N=X, R⁴) |
|---|---|---|---|---|---|
| 951 | HN | isopropyl | OH (stereo) | H | pyridine-CH₂-piperidine-N-CH₂CH₂OH |
| 952 | HN | CH₂-tetrahydropyran-4-yl | OH (stereo) | H | pyridine-CH₂-piperidine (NH) |
| 953 | HN | CH₂-tetrahydropyran-4-yl | OH (stereo) | H | pyridine-CH₂-piperidine-N-CH₂CH₂OH |
| 954 | HN | isopropyl | OH (stereo) | H | 1,2,3,4-tetrahydro-1,6-naphthyridine-N-CH₂CH₂N(CH₃)₂ |

TABLE 4-continued

| Compound No. | L | R¹ | R² | R³ | ![](Y-Z / N=X - R⁴) |
|---|---|---|---|---|---|
| 955 | -HN- | isopropyl | -C(CH₃)(OH)- (S) | H | 3-substituted 5,6,7,8-tetrahydro-1,7-naphthyridine with N-(2-(2-oxopyrrolidin-1-yl)ethyl) |
| 956 | -HN- | tetrahydropyran-3-yl | -CH(OMe)- | H | 6-(piperidin-4-yl)pyridin-3-yl |
| 957 | -HN- | tetrahydropyran-3-yl | -CH(OH)- | H | 6-(piperidin-4-yl)pyridin-3-yl |
| 958 | -HN- | isopropyl | -CH(OH)- | H | 6-(1-methyl-1H-imidazol-5-yl)pyridin-3-yl |

TABLE 4-continued

| Compound No. | L | R¹ | R² | R³ | ⟨structure with Y-Z, N=X, R⁴⟩ |
|---|---|---|---|---|---|
| 959 | -HN- | -CH₂CH₂CH₃ (propyl) | -C(CH₃)₂-CH(OH)CH₃ | H | pyridin-2-yl linked to 1-methylimidazol-5-yl |
| 960 | -HN- | isopropyl | -C(CH₃)₂-CH(OH)CH₃ | H | pyridazine-piperazine-CH₂C(O)NHCH₃ |
| 961 | -HN- | isopropyl | -C(CH₃)₂-CH(OH)CH₃ | H | pyridine-(3-oxopiperazine)-CH₂C(O)NHCH₃ |

TABLE 4-continued

| Compound No. | L | R¹ | R² | R³ | ![](Y-Z / N=X with R⁴) |
|---|---|---|---|---|---|
| 962 | -HN- | -iPr | -C(CH₃)(OH)- (stereo) | H | pyridine-piperazinone-CH₂C(O)N(CH₃)₂ |
| 963 | -HN- | -iPr | -C(CH₃)(OH)- (stereo) | H | pyridazine-piperazine-CH₂CF₃ |
| 964 | -HN- | -iPr | -C(CH₃)(OH)- (stereo) | H | pyridazine-tetrahydroimidazo[1,5-a]pyrazine |

TABLE 4-continued

| Compound No. | L | R¹ | R² | R³ | ![Y-Z/N=X-R⁴ structure] |
|---|---|---|---|---|---|
| 965 | -HN- | isopropyl | -C(CH₃)(OH)H | H | pyridine-CH₂-N(imidazole with methyl and COOH) |
| 966 | -HN- | isopropyl | -C(CH₃)(OH)H | H | pyridazine-piperazine-CH₂-C(O)-pyrrolidine |
| 967 | -HN- | isopropyl | -C(CH₃)(OH)H | H | pyridazine-piperazine-CH₂-C(O)-morpholine |

TABLE 4-continued

| Compound No. | L | R¹ | R² | R³ | ![Y-Z/X-R⁴ ring] |
|---|---|---|---|---|---|
| 968 | –HN– | isopropyl | –CH(OH)CH₃ | H | pyridazine-piperazine-CH₂C(O)NH-isopropyl |
| 969 | –HN– | isopropyl | –CH(OCH₃)CH₃ | H | pyridine-CH₂-piperazine-CH₂CN |
| 970 | –HN– | isopropyl | –CH(OCH₃)CH₃ | H | pyridine-CH₂-piperazine-CH₂C(O)NH₂ |
| 971 | –HN– | isopropyl | –CH(OCH₃)CH₃ | H | pyridine-CH₂-piperazine-CH₂C(O)NHCH₃ |

TABLE 4-continued

| Compound No. | L | R¹ | R² | R³ | ![Y-Z/N=X/R⁴ structure] |
|---|---|---|---|---|---|
| 972 | HN | isopropyl | CH(OMe)— | H | 6-pyridyl-CH₂-piperazine-CH₂-C(O)N(Me)₂ |
| 973 | HN | isobutyl | C(O)CH₃ | H | 6-pyridyl-CH₂-piperazine-CH₂CH₂OH |
| 974 | HN | n-butyl | C(O)CH₃ | H | 6-pyridyl-CH₂-piperazine-CH₂CH₂OH |
| 975 | HN | n-pentyl | C(O)CH₃ | H | 6-pyridyl-CH₂-piperazine-CH₂CH₂OH |

TABLE 4-continued

TABLE 4-continued

| Compound No. | L | R¹ | R² | R³ | ![structure](Y-Z / N=X with R⁴) |
|---|---|---|---|---|---|
| 980 | -HN- | ethyl | -C(CH₃)(OH)- (stereo) | H | pyridazine-piperazine-N-methyl |
| 981 | -HN- | isopropyl | -C(CH₃)(OH)- (stereo) | F | pyridine-piperazinone |
| 982 | -HN- | ethyl | -C(CH₃)(OH)- (stereo) | H | pyridine-CH₂-(S)-methylpiperazine-CH₂CH₂OH |
| 983 | -HN- | ethyl | -C(CH₃)(OH)- (stereo) | H | pyridine-CH₂-(R)-methylpiperazine-CH₂CH₂OH |

TABLE 4-continued

| Compound No. | L | R¹ | R² | R³ | ![Y-Z/N=X-R⁴] |
|---|---|---|---|---|---|
| 984 | HN | ethyl | CH(CH₃)OH | Cl | 6-[4-(2-hydroxyethyl)piperazin-1-ylmethyl]pyridin-3-yl |
| 985 | HN | isopropyl | CH(CH₃)OH | H | 6-[(2S)-2-methylpiperazin-1-yl]pyridin-3-yl |
| 986 | HN | isopropyl | CH(CH₃)OH | H | 6-[(2S)-2-methylpiperazin-1-yl]pyridin-3-yl |
| 987 | HN | isopropyl | CH(CH₃)OH | H | 6-[4-(hydroxyacetyl)piperazin-1-ylmethyl]pyridin-3-yl |

TABLE 4-continued

| Compound No. | L | R¹ | R² | R³ | ![Y-Z-X-N ring with R⁴] |
|---|---|---|---|---|---|
| 988 | -HN- | isopropyl | -CH(CH₃)OMe | H | pyridine-CH₂-piperazine-C(O)CH₂OH |
| 989 | -HN- | isopropyl | -CH(CH₃)OH | H | * faster isomer; pyridazine-piperazine with (S)-CF₃ |
| 990 | -HN- | isopropyl | -CH(CH₃)OH | H | * later isomer; pyridazine-piperazine with (S)-CF₃ |

TABLE 4-continued

| Compound No. | L | R¹ | R² | R³ | (structure with Y-Z, N=X, R⁴) |
|---|---|---|---|---|---|
| 991 | HN linker | isopropyl | C(CH₃)(OH)- (wedge) | H | pyridazine-piperazine-CH₂C(O)N(CH₃)₂ |
| 992 | HN linker | isopropyl | *faster isomer tetrahydrofuran-2-yl | H | pyridine-piperazine (NH) |
| 993 | HN linker | isopropyl | *later isomer tetrahydrofuran-2-yl | H | pyridine-piperazine (NH) |
| 994 | HN linker | tetrahydrofuran-3-yl | C(CH₃)(OH)- | H | pyridine-piperazine (NH) |

TABLE 4-continued

| Compound No. | L | R¹ | R² | R³ | (structure with Y-Z/N=X/R⁴) |
|---|---|---|---|---|---|
| 995 | HN | tetrahydrofuran-3-yl | C(CH₃)(OH)CH₃ | H | 5-(piperazin-1-yl)pyridin-2-yl |
| 996 | HN | sec-butyl | C(CH₃)(OH)CH₃ | H | 5,6,7,8-tetrahydro-1,6-naphthyridin-2-yl |
| 997 | HN | cyclopropyl | C(CH₃)(OH)CH₃ | H | 6-((4-(2-hydroxyethyl)piperazin-1-yl)methyl)pyridin-3-yl |
| 998 | HN | cyclobutyl | C(CH₃)(OH)CH₃ | H | 6-((4-(2-hydroxyethyl)piperazin-1-yl)methyl)pyridin-3-yl |

TABLE 4-continued

| Compound No. | L | R¹ | R² | R³ | (structure column) |
|---|---|---|---|---|---|
| 999 | | | | H | |
| 1000 | | | | H | |
| 1001 | | | | H | |
| 1002 | | | | H | |

TABLE 4-continued

| Compound No. | L | R¹ | R² | R³ | ![Y-Z-R⁴ with N=X ring] |
|---|---|---|---|---|---|
| 1003 | -HN- | n-propyl | 3-methyloxetan-3-yl | H | 6-(piperazin-1-ylmethyl)pyridin-3-yl |
| 1004 | -HN- | n-propyl | tetrahydrofuran-3-yl | H | 6-(piperazin-1-yl)pyridin-3-yl |
| 1005 | -HN- | n-propyl | tetrahydrofuran-3-yl | H | 6-(piperazin-1-ylmethyl)pyridin-3-yl |
| 1006 | -HN- | isopropyl | 3-methyloxetan-3-yl | H | 6-(piperazin-1-yl)pyridin-3-yl |

TABLE 4-continued

| Compound No. | L | R¹ | R² | R³ | |
|---|---|---|---|---|---|
| 1007 | -HN- | isopropyl | tetrahydrofuran-3-yl | H | pyridine-piperazine |
| 1008 | -HN- | neopentyl-like | (S)-1-methoxyethyl | H | pyridine-2-azaspiro[3.3]heptane-NHMe |
| 1009 | -HN- | (R)-tetrahydropyran-3-yl | (S)-1-methoxyethyl | H | pyridine-2-azaspiro[3.3]heptane-NHMe |
| 1010 | -HN- | isopropyl | tetrahydrofuran-3-yl | H | pyridine-CH₂-piperazine-CH₂CH₂OH |

TABLE 4-continued

| Compound No. | L | R¹ | R² | R³ | |
|---|---|---|---|---|---|
| 1011 | HN | tetrahydropyran-3-yl | tetrahydrofuran-3-yl | H | 6-[4-(2-hydroxyethyl)piperazin-1-ylmethyl]pyridin-3-yl |
| 1012 | HN | isopropyl | tetrahydrofuran-3-yl | H | 6-[4-(cyanomethyl)piperazin-1-ylmethyl]pyridin-3-yl |
| 1013 | HN | tetrahydropyran-3-yl | tetrahydrofuran-3-yl | H | 6-[4-(cyanomethyl)piperazin-1-ylmethyl]pyridin-3-yl |
| 1014 | HN | isopropyl | tetrahydrofuran-3-yl | H | 6-[4-(cyanomethyl)piperazin-1-ylmethyl]pyridin-3-yl |

TABLE 4-continued

| Compound No. | L | R¹ | R² | R³ | ![structure](Y-Z, N=X, R⁴) |
|---|---|---|---|---|---|
| 1015 | —HN— | isopropyl | —C(CH₃)(OH)— | H | pyridine-piperazine-CH₂CN |
| 1016 | —HN— | isopropyl | —C(CH₃)(OH)— | H | pyridine-piperidine-CH₂OH |
| 1017 | —HN— | isopropyl | —C(CH₃)(OH)— | H | pyridine-piperazine-CH₂C(O)NHCH₃ |
| 1018 | —HN— | isopropyl | —C(CH₃)(OH)— | H | pyridine-piperazine-CH₂C(O)N(CH₃)₂ |

TABLE 4-continued

| Compound No. | L | R¹ | R² | R³ | ![structure] |
|---|---|---|---|---|---|
| 1019 | -HN- | isopropyl | -C(CH₃)(OH)- | H | pyridine-CH₂-N(piperidine-4-OH) |
| 1020 | -HN- | tert-butyl | -C(CH₃)(OH)- | H | pyridine-CH₂-N(piperidine-4-OH) |
| 1021 | -HN- | tert-butyl | -C(CH₃)(OH)- | H | pyridine-CH₂-N(piperidine-4-CH₂OH) |
| 1022 | -HN- | n-butyl | -C(CH₃)(OH)- | H | pyridine-CH₂-N(piperidine-4-OH) |

TABLE 4-continued

| Compound No. | L | R¹ | R² | R³ | ![Y-Z-X-N ring with R⁴] |
|---|---|---|---|---|---|
| 1023 | HN | isobutyl | CH(CH₃)OH | H | pyridine-CH₂-piperidine-OH |
| 1024 | HN | isobutyl | CH(CH₃)OH | H | pyridine-CH₂-piperidine-CH₂OH |
| 1025 | HN | n-butyl | *faster isomer tetrahydrofuran-2-yl | H | pyridine-piperazine |
| 1026 | HN | n-butyl | *later isomer tetrahydrofuran-2-yl | H | pyridine-piperazine |

TABLE 4-continued

| Compound No. | L | R¹ | R² | R³ | ![Y-Z-R⁴ ring with N=X] |
|---|---|---|---|---|---|
| 1027 | HN (branched) | isopropyl | C(=O)CH₃ | H | 5,6,7,8-tetrahydro-1,6-naphthyridin-2-yl |
| 1028 | HN (branched) | sec-butyl | C(=O)CH₃ | H | 6-(piperazin-1-yl)pyridin-3-yl |
| 1029 | HN (branched) | isopropyl | C(=O)CH₃ | H | 6-(3-oxo-1,4-diazepan-1-yl)pyridin-3-yl |
| 1030 | HN (branched) | isopropyl | C(=O)CH₂CH₃ | H | 6-(3-oxopiperazin-1-yl)pyridin-3-yl |

TABLE 4-continued

| Compound No. | L | R¹ | R² | R³ | $\begin{smallmatrix}Y-Z\\|\phantom{x}\phantom{x}\phantom{x}|\\N=X\end{smallmatrix}-R^4$ |
|---|---|---|---|---|---|
| 1031 | HN | iPr | C(=O)CH₃ | Cl | 6-(2-oxopiperazin-1-yl)pyridin-3-yl |
| 1032 | HN | iPr | CH(OH)CH₃ | H | 6-(5-methyl-2-oxopiperazin-1-yl)pyridin-3-yl |
| 1033 | HN | iPr | CH(OH)CH₃ | H | 6-(6-methyl-2-oxopiperazin-1-yl)pyridin-3-yl |
| 1034 | HN | iPr | *faster isomer CH(OH)CH₂— | H | 6-(piperazin-1-yl)pyridin-3-yl |

TABLE 4-continued

| Compound No. | L | R¹ | R² | R³ | ![](Y-Z/N=X-R⁴) |
|---|---|---|---|---|---|
| 1035 | -HN- | -CH(CH₃)₂ | *later isomer -C(CH₃)(OH)CH₂CH₃ | H | 5-(piperazin-1-yl)pyridin-2-yl |
| 1036 | -HN- | -CH(CH₃)₂ | *faster isomer -C(CH₃)(OH)CH₂CH₃ | H | 5-(3-oxopiperazin-1-yl)pyridin-2-yl |
| 1037 | -HN- | -CH(CH₃)₂ | *later isomer -C(CH₃)(OH)CH₂CH₃ | H | 5-(3-oxopiperazin-1-yl)pyridin-2-yl |
| 1038 | -HN- | -CH(CH₃)₂ | -CH(CH₃)(OH) | H | 5-(piperidin-1-ylmethyl)pyridin-2-yl |

TABLE 4-continued

| Compound No. | L | R¹ | R² | R³ | ![Y-Z/N=X-R⁴ ring] |
|---|---|---|---|---|---|
| 1039 | HN (branched) | isopropyl | C(CH₃)(OH) (wedge) | H | pyridine-CH₂-N(Et)₂ |
| 1040 | HN (branched) | sec-butyl | C(CH₃)(OH) (wedge) | H | pyridine-CH₂-N(piperidine-4-CH₂OH) |
| 1041 | HN (branched) | isopropyl | C(CH₃)(OH) (wedge) | H | pyridine-CH₂-N(3-hydroxypyrrolidine) |
| 1042 | HN (branched) | isopropyl | 3,3-difluorocyclobutyl-C(CH₃) | H | pyridine-N(2-oxopiperazine) |

TABLE 4-continued

| Compound No. | L | R¹ | R² | R³ | ![Y-Z/N=X-R⁴ structure] |
|---|---|---|---|---|---|
| 1043 | HN | cyclopropylmethyl | C(CH₃)₂OH | H | 5-(2-oxopiperazin-1-yl)pyridin-2-yl |
| 1044 | HN | cyclopropyl (quaternary) | C(CH₃)₂OH | H | 5-(2-oxopiperazin-1-yl)pyridin-2-yl |
| 1045 | HN | cyclobutyl | C(CH₃)₂OH | H | 5-(2-oxopiperazin-1-yl)pyridin-2-yl |
| 1046 | HN | C(CH₃)₂CH₂CH₃ | C(CH₃)₂OH | H | 6-{[4-(2-hydroxyethyl)piperazin-1-yl]methyl}-2-methylpyridin-3-yl |

TABLE 4-continued

| Compound No. | L | R¹ | R² | R³ | ![Y-Z/N=X-R⁴ structure] |
|---|---|---|---|---|---|
| 1047 | -HN- | propyl | -C(CH₃)(OH)- | H | 6-methyl-5-((4-(2-hydroxyethyl)piperazin-1-yl)methyl)pyridin-2-yl |
| 1048 | -HN- | cyclobutyl | -C(CH₃)(OH)- | H | 6-methyl-5-(2-oxopiperazin-1-yl)pyridin-2-yl |
| 1049 | -HN- | isopropyl | -C(CH₃)(OH)- | H | 5-(piperazin-1-ylmethyl)pyrazin-2-yl |
| 1050 | -HN- | isopropyl | -C(CH₃)(OH)- | H | 5-((4-(2-hydroxyethyl)piperazin-1-yl)methyl)pyrazin-2-yl |

TABLE 4-continued

| Compound No. | L | R¹ | R² | R³ | ![structure](Y-Z/N=X with R⁴) |
|---|---|---|---|---|---|
| 1051 | HN | cyclopropylmethyl | C(CH₃)₂OH | H | 6-(piperazin-1-yl)pyridin-3-yl |
| 1052 | HN | cyclopropylmethyl | C(=O)CH₃ | H | 6-(piperazin-1-yl)pyridin-3-yl |
| 1053 | HN | sec-butyl | C(CH₃)₂OH | H | 4-methyl-6-[(4-(2-hydroxyethyl)piperazin-1-yl)methyl]pyridin-3-yl |
| 1054 | HN | n-butyl | C(CH₃)₂OH | H | 4-methyl-6-[(4-(2-hydroxyethyl)piperazin-1-yl)methyl]pyridin-3-yl |

TABLE 4-continued

| Compound No. | L | R¹ | R² | R³ | ⸝⸝⸝–Y=Z\ /N=X–R⁴ (ring) |
|---|---|---|---|---|---|
| 1055 | HN (branched) | isopropyl | C(CH₃)(OH)CH₃ | H | 2-methyl-4-methyl-pyridin-5-yl-CH₂-piperazin-N-CH₂CH₂OH |
| 1056 | HN (branched) | (3)-tetrahydropyran-3-yl | CH(CH₃)OCH₃ | H | pyridazin-3-yl-piperazin-4-yl-C(O)OCH₃ |
| 1057 | HN (branched) | isopropyl | C(CH₃)(OH)CH₃ | H | pyridin-2-yl-5-CH₂-(3-hydroxypiperidin-1-yl) |
| 1058 | HN (branched) | isopropyl | C(CH₃)(OH)CH₃ | H | pyridin-2-yl-5-O-[(3R)-1-(2-hydroxyethyl)pyrrolidin-3-yl] |

TABLE 4-continued

| Compound No. | L | R¹ | R² | R³ | ![](Y-Z/N=X-R⁴) |
|---|---|---|---|---|---|
| 1059 | -HN- | propyl | -C(CH₃)(OH)- (stereo) | H | pyridin-2-yl with 5-O-[1-(2-hydroxyethyl)pyrrolidin-3-yl]oxy |
| 1060 | -HN- | ethyl | -C(CH₃)(OH)- (stereo) | H | pyridin-2-yl with 5-[(4-hydroxypiperidin-1-yl)methyl] |
| 1061 | -HN- | butyl | -C(CH₃)(OH)- (stereo) | H | pyridin-2-yl with 5-[(4-hydroxypiperidin-1-yl)methyl] |
| 1062 | -HN- | cyclopropylmethyl | -C(CH₃)(OH)- (stereo) | H | pyridin-2-yl with 5-[(4-hydroxypiperidin-1-yl)methyl] |

TABLE 4-continued

| Compound No. | L | R¹ | R² | R³ | ![Y-Z/N=X structure with R⁴] |
|---|---|---|---|---|---|
| 1063 | -HN- | cyclobutyl | -C(CH₃)(OH)- | H | 6-(piperidin-1-ylmethyl)pyridin-3-yl with 4-hydroxypiperidine |
| 1064 | -HN- | trans-4-hydroxycyclohexyl | -C(CH₃)(OH)- | H | 6-(piperidin-1-ylmethyl)pyridin-3-yl with 4-hydroxypiperidine |
| 1065 | -HN- | (tetrahydropyran-4-yl)methyl | -C(CH₃)(OH)- | H | 6-(piperidin-1-ylmethyl)pyridin-3-yl with 4-hydroxypiperidine |
| 1066 | -HN- | isopropyl | *faster isomer, -CH(OCH₃)CH₂CH₃ | H | 6-(piperazin-1-ylmethyl)pyridin-3-yl |

TABLE 4-continued

| Compound No. | L | R¹ | R² | R³ | ![Y-Z-R⁴ ring with N=X] |
|---|---|---|---|---|---|
| 1067 | -HN- | isopropyl | *later isomer, -CH(OMe)Et | H | 6-(piperazin-1-ylmethyl)pyridin-3-yl |
| 1068 | -HN- | isopropyl | *faster isomer, -CH(OMe)Et | H | 6-(piperazin-1-yl)pyridazin-3-yl |
| 1069 | -HN- | isopropyl | *later isomer, -CH(OMe)Et | H | 6-(piperazin-1-yl)pyridazin-3-yl |
| 1070 | -HN- | cyclopentyl | -CH(OH)Et | H | 6-{[4-(2-hydroxyethyl)piperazin-1-yl]methyl}pyridin-3-yl |

TABLE 4-continued

| Compound No. | L | R¹ | R² | R³ | ![structure](Y-Z/N=X with R⁴) |
|---|---|---|---|---|---|
| 1071 | -HN- | tert-butyl | -CH(CH₃)OH | H | pyridin-2-yl with 5-(CH₂-piperazin-N-CH₂CH₂OH) |
| 1072 | -HN- | sec-butyl | -CH(CH₃)OH | H | pyridin-2-yl with 5-(CH₂-piperazin-N-CH₂CH₂CH₂OH) |
| 1073 | -HN- | sec-butyl | -CH(CH₃)OH | H | pyridin-2-yl with 5-(CH₂-piperazin-N-CH₂C(CH₃)₂OH) |
| 1074 | -HN- | 4-fluorobutyl | -CH(CH₃)OH | H | pyridin-2-yl with 5-(CH₂-piperazin-N-CH₂CH₂OH) |

TABLE 4-continued

| Compound No. | L | R¹ | R² | R³ | ![Y-Z-R⁴ ring] |
|---|---|---|---|---|---|
| 1075 | -HN- | n-butyl | -C(CH₃)(OH)- | H | pyridine-CH₂-piperazine-CH₂CH(OH)CH₃ |
| 1076 | -HN- | n-butyl | -C(CH₃)(OH)- | H | pyridine-CH₂-(2-methylpiperazine)-CH₂CH₂OH |
| 1077 | -HN- | n-butyl | -C(CH₃)(OH)- | H | pyridine-CH₂-(2-methylpiperazine)-CH₂CH₂OH |
| 1078 | -HN- | cyclopentyl | -C(CH₃)(OH)- | H | pyridine-(2-oxopiperazine) |

TABLE 4-continued

| Compound No. | L | R¹ | R² | R³ | ⸺⟨Y=Z⟩⸺R⁴ (N=X) |
|---|---|---|---|---|---|
| 1079 | -HN- | -(CH₂)₃-F | -C(CH₃)(OH)- | H | 5-(3-oxopiperazin-1-yl)pyridin-2-yl |
| 1080 | -HN- | -CH₂CH₃ (ethyl) | -C(CH₃)(OH)- | H | 5-((3-hydroxypiperidin-1-yl)methyl)pyridin-2-yl |
| 1081 | -HN- | -(CH₂)₂CH₃ (propyl) | -C(CH₃)(OH)- | H | 5-((3-hydroxypiperidin-1-yl)methyl)pyridin-2-yl |
| 1082 | -HN- | -(CH₂)₂CH₃ (propyl) | -C(CH₃)(OH)- | H | 5-((3-hydroxypiperidin-1-yl)methyl)pyridin-2-yl |

TABLE 4-continued

| Compound No. | L | R¹ | R² | R³ | ![Y-Z/N=X-R⁴ structure] |
|---|---|---|---|---|---|
| 1083 | HN | cyclopropylmethyl | CH(OH)CH₃ | H | 6-(5-hydroxypiperidin-1-ylmethyl)pyridin-3-yl |
| 1084 | HN | cyclobutyl | CH(OH)CH₃ | H | 6-(5-hydroxypiperidin-1-ylmethyl)pyridin-3-yl |
| 1085 | HN | isobutyl | CH(OH)CH₃ | H | 6-(5-hydroxypiperidin-1-ylmethyl)pyridin-3-yl |
| 1086 | HN | 4-hydroxycyclohexyl | CH(OH)CH₃ | H | 6-(5-hydroxypiperidin-1-ylmethyl)pyridin-3-yl |

TABLE 4-continued

| Compound No. | L | R¹ | R² | R³ | ![Y-Z ring structure] |
|---|---|---|---|---|---|
| 1087 | HN linker | tetrahydropyran-4-ylmethyl | CH(CH₃)OH | H | pyridine-CH₂-(3-hydroxypiperidin-1-yl) |
| 1088 | HN linker | sec-butyl | CH(CH₃)OH | H | *faster isomer; pyridine-CH₂-piperazine-N-CH(CH₃)CH₂OH |
| 1089 | HN linker | sec-butyl | CH(CH₃)OH | H | *later isomer; pyridine-CH₂-piperazine-N-CH(CH₃)CH₂OH |
| 1090 | HN linker | isobutyl | CH(CH₃)OH | H | pyridine-piperazine-N-C(O)CH₂OH |

TABLE 4-continued

| Compound No. | L | R¹ | R² | R³ | ![Y-Z/N=X-R⁴] |
|---|---|---|---|---|---|
| 1091 | -HN- | ethyl | -C(CH₃)(OH)- | H | 6-(2-methyl-5-piperazin-1-yl-pyridin-3-yl) |
| 1092 | -HN- | n-butyl | -C(CH₃)(OH)- | H | 6-(2-methyl-5-piperazin-1-yl-pyridin-3-yl) |
| 1093 | -HN- | isobutyl | -C(CH₃)(OH)- | H | 6-(2-methyl-5-piperazin-1-yl-pyridin-3-yl) |
| 1094 | -HN- | cyclobutyl | -C(CH₃)(OH)- | H | 6-(2-methyl-5-piperazin-1-yl-pyridin-3-yl) |

TABLE 4-continued

| Compound No. | L | R¹ | R² | R³ | $\begin{smallmatrix}Y-Z\\\|\phantom{a}\phantom{a}\|\\N=X\end{smallmatrix}R^4$ |
|---|---|---|---|---|---|
| 1095 | -HN- | cyclopropylmethyl | -C(CH₃)₂CH(OH)CH₃ | H | 2-methyl-3-(piperazin-1-yl)pyridin-6-yl |
| 1096 | -HN- | ethyl | -CHF₂ | H | 6-[(4-carboxypiperidin-1-yl)methyl]pyridin-3-yl |
| 1097 | -HN- | n-propyl | -CHF₂ | H | 6-[(4-carboxypiperidin-1-yl)methyl]pyridin-3-yl |
| 1098 | -HN- | isobutyl | -CHF₂ | H | 6-[(4-carboxypiperidin-1-yl)methyl]pyridin-3-yl |

TABLE 4-continued

| Compound No. | L | R¹ | R² | R³ | ![](Y-Z/N=X-R⁴) |
|---|---|---|---|---|---|
| 1099 | HN | cyclobutyl | CHF₂ | H | 6-(1-(carboxypiperidin-4-yl)methyl)pyridin-3-yl |
| 1100 | HN | CH₂-cyclopropyl | CHF₂ | H | 6-(1-(carboxypiperidin-4-yl)methyl)pyridin-3-yl |
| 1101 | HN | C(CH₃)₂CH₂OH | CH(CH₃)OH | H | 6-(4-methylpiperazin-1-yl)pyridazin-3-yl |
| 1102 | HN | sec-butyl | CH(CH₃)OH | H | 6-(4-methylpiperazin-1-yl)pyridazin-3-yl |

TABLE 4-continued

| Compound No. | L | R¹ | R² | R³ | ![Y-Z-R⁴ ring with N=X] |
|---|---|---|---|---|---|
| 1103 | -HN- | ethyl | -C(CH₃)(OH)- | H | pyridine-CH₂-N(piperazine)-N-CH₃ |
| 1104 | -HN- | n-butyl | -C(CH₃)(OH)- | H | pyridine-CH₂-N(piperazine)-N-CH₃ |
| 1105 | -HN- | -CH(CH₃)CH₂OCH₃ | -C(CH₃)(OH)- | H | pyridine-CH₂-N(piperazine)-N-CH₃ |
| 1106 | -HN- | -C(CH₃)₂CH₂OH | -C(CH₃)(OH)- | H | pyridine-CH₂-N(piperazine)-N-CH₃ |

TABLE 4-continued

| Compound No. | L | R¹ | R² | R³ | ![Y-Z/N=X-R⁴ structure] |
|---|---|---|---|---|---|
| 1107 | HN | ethyl | methyloxetane | H | 6-(piperazin-1-ylmethyl)pyridin-3-yl |
| 1108 | HN | cyclobutyl | methyloxetane | H | 6-(piperazin-1-ylmethyl)pyridin-3-yl |
| 1109 | HN | cyclopropylmethyl | methyloxetane | H | 6-(piperazin-1-ylmethyl)pyridin-3-yl |
| 1110 | HN | (3,3-difluorocyclobutyl)methyl | methyloxetane | H | 6-(piperazin-1-ylmethyl)pyridin-3-yl |

TABLE 4-continued

| Compound No. | L | R¹ | R² | R³ | ![Y-Z/N=X-R⁴ ring] |
|---|---|---|---|---|---|
| 1111 | HN linker | propyl | CH(OMe)- | H | tetrahydro-1,6-naphthyridine with N-C(O)CH₂OH |
| 1112 | HN linker | ethyl (branched) | CH(OMe)- | H | tetrahydro-1,6-naphthyridine with N-C(O)CH₂OH |
| 1113 | HN linker | tetrahydropyran-3-yl | CH(OMe)- | H | tetrahydro-1,6-naphthyridine with N-C(O)CH₂OH |
| 1114 | HN linker | tetrahydropyran-3-yl | tetrahydrofuran-3-yl | H | tetrahydro-1,6-naphthyridine with N-C(O)CH₂OH |

TABLE 4-continued

| Compound No. | L | R¹ | R² | R³ | ![Y-Z / N=X with R⁴] |
|---|---|---|---|---|---|
| 1115 | -HN- | tetrahydropyran-3-yl | 3-methyloxetan-3-yl | H | 2-(hydroxyacetyl)-1,2,3,4-tetrahydro-2,6-naphthyridin-7-yl |
| 1116 | -HN- | sec-butyl | 1-hydroxyethyl (with methyl) | H | 2-(hydroxyacetyl)-1,2,3,4-tetrahydro-2,6-naphthyridin-7-yl |
| 1117 | -HN- | ethyl | 1-hydroxyethyl (with methyl) | H | 2-(hydroxyacetyl)-1,2,3,4-tetrahydro-2,6-naphthyridin-7-yl |
| 1118 | -HN- | tetrahydropyran-3-yl | 1-hydroxyethyl (with methyl) | H | 2-(hydroxyacetyl)-1,2,3,4-tetrahydro-2,6-naphthyridin-7-yl |

TABLE 4-continued

| Compound No. | L | R¹ | R² | R³ | ![Y-Z/N=X-R⁴ structure] |
|---|---|---|---|---|---|
| 1119 | HN | propyl | (S)-OMe | H | 2-(7,8-dihydro-1,6-naphthyridin-6(5H)-yl)ethanol |
| 1120 | HN | ethyl | (S)-OMe | H | 2-(7,8-dihydro-1,6-naphthyridin-6(5H)-yl)ethanol |
| 1121 | HN | tetrahydropyran-3-yl | (S)-OMe | H | 2-(7,8-dihydro-1,6-naphthyridin-6(5H)-yl)ethanol |
| 1122 | HN | tetrahydropyran-3-yl | tetrahydrofuran-3-yl | H | 2-(7,8-dihydro-1,6-naphthyridin-6(5H)-yl)ethanol |

TABLE 4-continued

| Compound No. | L | R¹ | R² | R³ | (structure with Y-Z, N=X, R⁴) |
|---|---|---|---|---|---|
| 1123 | HN | (propyl) | CH(OH)- | H | 2-(hydroxyethyl)-1,2,3,4-tetrahydro-2,6-naphthyridine |
| 1124 | HN | (ethyl) | CH(OH)- | H | 2-(hydroxyethyl)-1,2,3,4-tetrahydro-2,6-naphthyridine |
| 1125 | HN | tetrahydropyran-3-yl | CH(OH)- | H | 2-(hydroxyethyl)-1,2,3,4-tetrahydro-2,6-naphthyridine |
| 1126 | HN | tetrahydropyran-3-yl | CH(OH)- | H | 5-((4-hydroxypiperidin-1-yl)methyl)pyridin-2-yl |

TABLE 4-continued

TABLE 4-continued

| Compound No. | L | R¹ | R² | R³ | ![Y-Z-R⁴ ring with N=X] |
|---|---|---|---|---|---|
| 1131 | HN linker | ethyl | methoxy (stereo) | H | 2-(dimethylamino)ethyl-substituted tetrahydro-1,6-naphthyridine |
| 1132 | HN linker | tetrahydropyran-3-yl | methoxy (stereo) | H | 2-(dimethylamino)ethyl-substituted tetrahydro-1,6-naphthyridine |
| 1133 | HN linker | n-propyl | methoxy (stereo) | H | tetrahydro-1,6-naphthyridine with N-C(O)O-CH₂CH₂-N(CH₃)₂ carbamate |
| 1134 | HN linker | ethyl | methoxy (stereo) | H | tetrahydro-1,6-naphthyridine with N-C(O)O-CH₂CH₂-N(CH₃)₂ carbamate |

TABLE 4-continued

TABLE 4-continued

| Compound No. | L | R¹ | R² | R³ | ⦃—Y—Z⦄ ⦃  ⦄R⁴ ⦃N=X⦄ |
|---|---|---|---|---|---|
| 1139 | HN | ethyl | CH(CH₃)OH | H | 2-(2-(dimethylamino)ethyl)-1,2,3,4-tetrahydro-2,7-naphthyridin-6-yl |
| 1140 | HN | tetrahydropyran-3-yl | CH(CH₃)OH | H | 2-(2-(dimethylamino)ethyl)-1,2,3,4-tetrahydro-2,7-naphthyridin-6-yl |
| 1141 | HN | propyl | CH(CH₃)OH | H | 2-((2-(dimethylamino)ethoxy)carbonyl)-1,2,3,4-tetrahydro-2,7-naphthyridin-6-yl |
| 1142 | HN | ethyl | CH(CH₃)OH | H | 2-((2-(dimethylamino)ethoxy)carbonyl)-1,2,3,4-tetrahydro-2,7-naphthyridin-6-yl |

TABLE 4-continued

| Compound No. | L | R¹ | R² | R³ | ![structure](Y-Z/N=X with R⁴) |
|---|---|---|---|---|---|
| 1143 | HN | tetrahydropyran-3-yl | C(CH₃)(OH)- | H | 5,6,7,8-tetrahydro-1,6-naphthyridin-2-yl with N-C(O)O-CH₂CH₂-N(CH₃)₂ |
| 1144 | HN | trans-4-hydroxycyclohexyl | CH(CH₃)OMe | H | 5,6,7,8-tetrahydro-1,6-naphthyridin-2-yl with N-C(O)CH₂OH |
| 1145 | HN | trans-4-hydroxycyclohexyl | tetrahydrofuran-3-yl | H | 5,6,7,8-tetrahydro-1,6-naphthyridin-2-yl with N-C(O)CH₂OH |
| 1146 | HN | trans-4-hydroxycyclohexyl | 3-methyloxetan-3-yl | H | 5,6,7,8-tetrahydro-1,6-naphthyridin-2-yl with N-C(O)CH₂OH |

TABLE 4-continued

| Compound No. | L | R¹ | R² | R³ | ![Y-Z/N=X-R⁴ structure] |
|---|---|---|---|---|---|
| 1147 | HN | ethyl | CH(CH₃)OH | H | pyridine-CH₂-piperidine-CH₂OH |
| 1148 | HN | n-butyl | CH(CH₃)OH | H | pyridine-CH₂-piperidine-CH₂OH |
| 1149 | HN | CH₂-cyclopropyl | CH(CH₃)OH | H | pyridine-CH₂-piperidine-CH₂OH |
| 1150 | HN | cyclobutyl | CH(CH₃)OH | H | pyridine-CH₂-piperidine-CH₂OH |

TABLE 4-continued

| Compound No. | L | R¹ | R² | R³ | ![Y-Z/N=X-R⁴ structure] |
|---|---|---|---|---|---|
| 1151 | HN | cyclohexyl-OH | C(CH₃)(OH)H | H | pyridine-CH₂-piperidine-CH₂OH |
| 1152 | HN | CH₂-tetrahydropyran | C(CH₃)(OH)H | H | pyridine-CH₂-piperidine-CH₂OH |
| 1153 | HN | cyclohexyl-OH | C(CH₃)(OMe)H | H | tetrahydronaphthyridine-CH₂CH₂OH |
| 1154 | HN | cyclohexyl-OH | tetrahydrofuran-3-yl | H | tetrahydronaphthyridine-CH₂CH₂OH |

TABLE 4-continued

| Compound No. | L | R¹ | R² | R³ | (Y-Z, N=X, R⁴ group) |
|---|---|---|---|---|---|
| 1155 | HN | 4-hydroxycyclohexyl | 3-methyloxetan-3-yl | H | 2-(2-hydroxyethyl)-1,2,3,4-tetrahydro-2,6-naphthyridin-6-yl substituted pyridine |
| 1156 | HN | tetrahydro-2H-pyran-3-yl | (S)-1-hydroxyethyl | H | 5-((4-(hydroxymethyl)piperidin-1-yl)methyl)pyridin-2-yl |
| 1157 | HN | isopropyl | (S)-1-methoxyethyl | H | 5-((4-(tetrahydrofuran-2-carbonyl)piperazin-1-yl)methyl)pyridin-2-yl |
| 1158 | HN | tert-butyl | (S)-1-methoxyethyl | H | 5-((4-(tetrahydrofuran-3-carbonyl)piperazin-1-yl)methyl)pyridin-2-yl |

TABLE 4-continued

| Compound No. | L | R¹ | R² | R³ | ![Y-Z/N=X-R⁴] |
|---|---|---|---|---|---|
| 1159 | -HN- | propyl | -C(CH₃)(OH)H (stereo) | H | pyridazine-piperidine-N(CH₃)₂ |
| 1160 | -HN- | isopropyl | -C(CH₃)(OH)H (stereo) | H | pyridine-C(O)-N-methylpiperazine |
| 1161 | -HN- | isopropyl | -C(CH₃)(OH)H (stereo) | H | pyridine-C(O)-piperidine-N(CH₃)₂ |
| 1162 | -HN- | isopropyl | -C(CH₃)(OH)H (stereo) | H | pyridine-C(O)-(3S)-pyrrolidine-N(CH₃)₂ |

TABLE 4-continued

| Compound No. | L | R¹ | R² | R³ | ![Y-Z/N=X with R⁴] |
|---|---|---|---|---|---|
| 1163 | —HN— | isopropyl | —C(CH₃)(OH)— | H | pyridine-C(O)-N-(3R)-(dimethylamino)pyrrolidine |
| 1164 | —HN— | isopropyl | —C(CH₃)(OH)— | H | pyridine-C(O)NH-CH₂CH₂-N(CH₃)₂ |
| 1165 | —HN— | isopropyl | —C(CH₃)(OH)— | H | pyridine-C(O)-N-piperazine-N-CH₂CH₂OH |
| 1166 | —HN— | isopropyl | —C(CH₃)(OH)— | H | pyridine-C(O)-N-(2S)-methylpiperazine |
| 1167 | —HN— | isopropyl | —C(CH₃)(OH)— | H | pyridine-C(O)-N-(2R)-methylpiperazine |

TABLE 4-continued

| Compound No. | L | R¹ | R² | R³ | ![structure](Y-Z / N=X-R⁴) |
|---|---|---|---|---|---|
| 1168 | HN (branched) | ethyl | C(CH₃)(OH) | CH₃ | 6-pyridyl-3-CH₂-N(piperazine)-N-CH₂CH₂OH |
| 1169 | HN (branched) | ethyl | C(CH₃)(OH) | H | 6-pyridyl-3-CH₂-N(2,2-dimethylpiperazine)-N-CH₂CH₂OH |
| 1170 | HN (branched) | CH₂CF₃ | C(CH₃)(OH) | H | 6-pyridyl-3-CH₂-N(piperazine)-N-CH₂CH₂OH |
| 1171 | HN (branched) | 3-fluorocyclobutyl | C(CH₃)(OH) | H | 6-pyridyl-3-CH₂-N(piperazine)-N-CH₂CH₂OH |

TABLE 4-continued

| Compound No. | L | R¹ | R² | R³ | ⧫-Y=Z-R⁴ structure with N=X |
|---|---|---|---|---|---|
| 1172 | HN | propyl | C(CH₃)(OH)H | H | 6-pyridyl-CH₂-piperazine-CH₂-CH(OH)CH₃ |
| 1173 | HN | 1-methylcyclopropyl | C(CH₃)(OH)H | H | 6-pyridyl-piperazinone |
| 1174 | HN | CH₂CF₃ | C(CH₃)(OH)H | H | 6-pyridyl-piperazinone |
| 1175 | HN | 1-methylcyclopropyl | C(CH₃)(OH)H | H | pyridazinyl-piperazine |

TABLE 4-continued

| Compound No. | L | R¹ | R² | R³ | (Y-Z-X-N ring with R⁴) |
|---|---|---|---|---|---|
| 1176 | HN | isopropyl | (S)-CH(CH₃)OCH₃ | H | pyridazine-piperazine-C(O)-tetrahydrofuran-2-yl |
| 1177 | HN | isopropyl | (S)-CH(CH₃)OCH₃ | H | pyridazine-piperazine-C(O)-tetrahydrofuran-3-yl |
| 1178 | HN | tetrahydropyran-3-yl | tetrahydrofuran-3-yl | H | 2-(dimethylaminoethyl)-5,6,7,8-tetrahydro-1,6-naphthyridin-2-yl |
| 1179 | HN | tetrahydropyran-3-yl | 3-methyloxetan-3-yl | H | 2-(dimethylaminoethyl)-5,6,7,8-tetrahydro-1,6-naphthyridin-2-yl |

TABLE 4-continued

| Compound No. | L | R¹ | R² | R³ | ⟨Y−Z⟩−R⁴ (N=X) |
|---|---|---|---|---|---|
| 1180 | HN | cyclohexyl-OH (trans) | CH(CH₃)OMe | H | 2-(7-(2-(dimethylamino)ethyl)-5,6,7,8-tetrahydro-1,7-naphthyridin-3-yl) |
| 1181 | HN | cyclohexyl-OH (trans) | tetrahydrofuran-3-yl | H | 2-(7-(2-(dimethylamino)ethyl)-5,6,7,8-tetrahydro-1,7-naphthyridin-3-yl) |
| 1182 | HN | cyclohexyl-OH (trans) | 3-methyloxetan-3-yl | H | 2-(7-(2-(dimethylamino)ethyl)-5,6,7,8-tetrahydro-1,7-naphthyridin-3-yl) |
| 1183 | HN | isopropyl | CH(CH₃)OH | H | 6-(4-(tetrahydrofuran-2-carbonyl)piperazin-1-yl)pyridazin-3-yl |

TABLE 4-continued

| Compound No. | L | R¹ | R² | R³ | ![Y-Z/N=X with R⁴] |
|---|---|---|---|---|---|
| 1184 | HN | isopropyl | C(CH₃)(OH)— | H | pyridazine-piperazine-C(O)-tetrahydrofuran |
| 1185 | HN | n-pentyl (sec) | C(CH₃)(OH)— | H | pyridine-CH₂-(3S)-3-hydroxypiperidine |
| 1186 | HN | isobutyl | C(CH₃)(OH)— | H | pyridine-CH₂-(3S)-3-hydroxypiperidine |
| 1187 | HN | trans-4-hydroxycyclohexyl | C(CH₃)(OH)— | H | pyridine-CH₂-(3S)-3-hydroxypiperidine |

TABLE 4-continued

| Compound No. | L | R¹ | R² | R³ | ![Y-Z/N=X-R⁴ structure] |
|---|---|---|---|---|---|
| 1188 | HN | pentyl | CH(OH)CH₃ | H | 6-[(3S)-3-hydroxypiperidin-1-ylmethyl]pyridin-3-yl |
| 1189 | HN | isobutyl-methyl | CH(OH)CH₃ | H | 6-[(3S)-3-hydroxypiperidin-1-ylmethyl]pyridin-3-yl |
| 1190 | HN | trans-4-hydroxycyclohexyl | CH(OH)CH₃ | H | 6-[(3S)-3-hydroxypiperidin-1-ylmethyl]pyridin-3-yl |
| 1191 | HN | isopropyl-methyl | CH(OH)CH₃ | H | 6-[4-(2-dimethylaminoacetyl)piperazin-1-yl]pyridazin-3-yl |

TABLE 4-continued

| Compound No. | L | R¹ | R² | R³ | [Y-Z / N=X-R⁴ ring] |
|---|---|---|---|---|---|
| 1192 | NH (branched) | isopropyl | C(CH₃)(OH)- | H | pyridin-2-yl-CH₂-piperazine-C(O)-tetrahydrofuran-2-yl |
| 1193 | NH (branched) | isopropyl | C(CH₃)(OH)- | H | pyridin-2-yl-CH₂-piperazine-C(O)-tetrahydrofuran-3-yl |
| 1194 | NH (branched) | isopropyl | C(CH₃)(OH)- | H | pyridin-2-yl-CH₂-piperazine-C(O)-CH₂-N(CH₃)₂ |
| 1195 | NH (branched) | n-propyl | C(CH₃)(OH)- | H | pyridin-2-yl-CH₂-(3S)-3-hydroxypiperidin-1-yl |

TABLE 4-continued

| Compound No. | L | R¹ | R² | R³ | ![Y-Z/N=X-R⁴ structure] |
|---|---|---|---|---|---|
| 1196 | HN | isopropyl | CH(CH₃)OH | H | pyridine-CH₂-N-piperidine-OH |
| 1197 | HN | tert-butyl | CH(CH₃)OH | H | pyridine-CH₂-N-piperidine-OH |
| 1198 | HN | n-propyl | CH(CH₃)OH | H | pyridine-CH₂-N-piperidine-OH |
| 1199 | HN | isopropyl | CH(CH₃)OH | H | pyridine-CH₂-N-piperidine-OH |

TABLE 4-continued

| Compound No. | L | R¹ | R² | R³ | ![structure](Y-Z/X=N-R⁴) |
|---|---|---|---|---|---|
| 1200 | HN | t-Bu | CH(CH₃)OH | H | pyridine-CH₂-N(3-OH-piperidine) |
| 1201 | HN | 1-methylcyclopropyl | CH(CH₃)OH | H | pyridine-CH₂-N(piperazine)-CH₂CH₂OH |
| 1202 | HN | sec-butyl | CH(CH₃)OH | F | pyridine-CH₂-N(piperazine)-CH₂CH₂OH |
| 1203 | HN | sec-butyl | CH(CH₃)OH | H | pyridine-CH₂-N(2,2-dimethylpiperazine)-CH₂CH₂OH |

TABLE 4-continued

| Compound No. | L | R¹ | R² | R³ | ![structure](Y-Z/N=X-R⁴) |
|---|---|---|---|---|---|
| 1204 | HN | 3,3-difluorocyclobutyl | CH(OH)CH₃ | H | 6-[[4-(2-hydroxyethyl)piperazin-1-yl]methyl]pyridin-3-yl |
| 1205 | HN | bicyclo[1.1.1]pentyl | CH(OH)CH₃ | H | 6-[[4-(2-hydroxyethyl)piperazin-1-yl]methyl]pyridin-3-yl |
| 1206 | HN | n-propyl | CH(OH)CH₃ | H | *faster isomer; 6-[[4-(1-hydroxypropan-2-yl)piperazin-1-yl]methyl]pyridin-3-yl |
| 1207 | HN | n-propyl | CH(OH)CH₃ | H | *later isomer; 6-[[4-(1-hydroxypropan-2-yl)piperazin-1-yl]methyl]pyridin-3-yl |

TABLE 4-continued

| Compound No. | L | R¹ | R² | R³ | (structure with Y-Z, N=X, R⁴) |
|---|---|---|---|---|---|
| 1208 | -HN- | n-butyl | -C(CH₃)(OH)- | H | 6-{[(2S)-4-(2-hydroxyethyl)-3-methylpiperazin-1-yl]methyl}pyridin-3-yl |
| 1209 | -HN- | isobutyl | -C(CH₃)(OH)- | H | 6-{[(2S)-4-(2-hydroxyethyl)-3-methylpiperazin-1-yl]methyl}pyridin-3-yl |
| 1210 | -HN- | 3-fluorocyclobutyl | -C(CH₃)(OH)- | H | 6-(3-oxopiperazin-1-yl)pyridin-3-yl |
| 1211 | -HN- | 3,3-difluorocyclobutyl | -C(CH₃)(OH)- | H | 6-(3-oxopiperazin-1-yl)pyridin-3-yl |

TABLE 4-continued

| Compound No. | L | R¹ | R² | R³ | ![Y-Z-R⁴ ring with N=X] |
|---|---|---|---|---|---|
| 1212 | -HN- | 4-fluorobutyl | -C(CH₃)(OH)H | H | 5-(piperazin-1-yl)pyridin-2-yl |
| 1213 | -HN- | 3,3-difluoropropyl-methyl | -C(CH₃)(OH)H | H | 6-{[4-(2-hydroxyethyl)piperazin-1-yl]methyl}pyridin-3-yl (attached at 2-position) |
| 1214 | -HN- | 3,3,3-trifluoropropyl-methyl | -C(CH₃)(OH)H | H | 6-{[4-(2-hydroxyethyl)piperazin-1-yl]methyl}pyridin-3-yl |
| 1215 | -HN- | 2,2-difluoropropyl-methyl | -C(CH₃)(OH)H | H | 6-{[4-(2-hydroxyethyl)piperazin-1-yl]methyl}pyridin-3-yl |

TABLE 4-continued

| Compound No. | L | R¹ | R² | R³ | ![structure] |
|---|---|---|---|---|---|
| 1216 | HN | ethyl | CH(OH)CH₃ | H | pyridine-CH₂-N(diazepane)-N-CH₂CH₂OH |
| 1217 | HN | isopropyl | CH(OH)CH₃ | H | pyridine-piperazinone |
| 1218 | HN | 4-hydroxycyclohexyl | CH(OH)CH₃ | H | pyridazine-piperidine-COOH |
| 1219 | HN | isopropyl | CH(OH)CH₃ | H | pyridazine-pyrrolidine-N(CH₃)₂ |

TABLE 4-continued

| Compound No. | L | R¹ | R² | R³ | ![Y-Z/N=X with R⁴] |
|---|---|---|---|---|---|
| 1220 | HN | isopropyl | CH(OH)CH₃ | H | pyridazine-piperidine-N(CH₃)₂ |
| 1221 | HN | n-butyl | CH(OH)CH₃ | H | pyridine-C(O)-piperazine-N-CH₃ |
| 1222 | HN | ethyl | CH(OH)CH₃ | H | 6-aminopyridine-CH₂-diazabicyclo-N-CH₃ |
| 1223 | HN | n-butyl | CH(OH)CH₃ | H | 6-aminopyridine-CH₂-diazabicyclo-N-CH₃ |
| 1224 | HN | isopropyl | CH(OH)CH₃ | H | 6-aminopyridine-CH₂-diazabicyclo-N-CH₃ |

TABLE 4-continued

| Compound No. | L | R¹ | R² | R³ | (Y-Z-X-N ring with R⁴) |
|---|---|---|---|---|---|
| 1225 | HN | isopropyl | CH(CH₃)OH | H | 6-aminopyridazin-3-yl-CH₂-piperazin-1-yl |
| 1226 | HN | 4-fluorobutyl | CH(CH₃)OMe | H | 6-(piperazin-1-yl)pyridazin-3-yl |
| 1227 | HN | 4-fluorobutyl | CH(CH₃)OMe | H | 6-(piperazin-1-ylmethyl)pyridin-3-yl |
| 1228 | HN | isopropyl | CH(CH₃)OH | H | 6-[2-(dimethylamino)ethyl(methyl)amino]pyridin-3-yl |

TABLE 4-continued

| Compound No. | L | R¹ | R² | R³ | (structure with Y-Z, N=X, R⁴) |
|---|---|---|---|---|---|
| 1229 | -HN- | isopropyl | 3-tetrahydrofuranyl | H | 2-(hydroxyethyl)-5,6,7,8-tetrahydro-1,6-naphthyridin-2-yl |
| 1230 | -HN- | isopropyl | 3-tetrahydrofuranyl | H | 6-(2-(dimethylamino)ethyl)-5,6,7,8-tetrahydro-1,6-naphthyridin-2-yl |
| 1231 | -HN- | isopropyl | 3-tetrahydrofuranyl | H | 6-(hydroxyacetyl)-5,6,7,8-tetrahydro-1,6-naphthyridin-2-yl |
| 1232 | -HN- | isopropyl | 3-tetrahydrofuranyl | H | 6-(carboxymethyl)-5,6,7,8-tetrahydro-1,6-naphthyridin-2-yl |

TABLE 4-continued

TABLE 4-continued

| Compound No. | L | R¹ | R² | R³ | ⟨structure with Y-Z, N=X, R⁴⟩ |
|---|---|---|---|---|---|
| 1236 | HN | (propyl) | CH(CH₃)OH | H | 6-(4-methyl-2-oxopiperazin-1-yl)pyridin-3-yl |
| 1237 | HN | (butyl) | CH(CH₃)OH | H | 6-(4-methyl-2-oxopiperazin-1-yl)pyridin-3-yl |
| 1238 | HN | isopropyl | CH(CH₃)OH | H | 6-(4-methyl-2-oxopiperazin-1-yl)pyridin-3-yl |
| 1239 | HN | isobutyl | CH(CH₃)OH | H | 6-(4-methyl-2-oxopiperazin-1-yl)pyridin-3-yl |

*: The compounds separated as optically active isomers by HPLC purification with a chiral column (note: absolute configuration is not determined).

Abbreviations

DEA: diethylamine, TEA=triethylamine, DCM: dichloromethane, IPA: isopropylalcohol (1) Compound 581: DAICEL CHIRALPAK AD 5 µm, n-hexane/MeOH/IPA, RT=12.31 min.: optically active isomer with shorter retention time.
(1) Compound 582: DAICEL CHIRALPAK AD 5 µm, n-hexane/MeOH/IPA, RT=15.35 min.: optically active isomer with longer retention time.
(2) Compound 671: CHIRALPAK IA-3 µm, 100% EtOH, RT=4.388 min.: optically active isomer with shorter retention time.
(2) Compound 672: CHIRALPAK IA-3 µm, 100% EtOH, RT=6.490 min.: optically active isomer with longer retention time.
(3) Compound 689: DAICEL CHIRALPAK AD-H 5 µm, n-hexane/EtOH, RT=17.61 min.: optically active isomer with shorter retention time.
(3) Compound 690: DAICEL CHIRALPAK AD-H 5 µm, n-hexane/EtOH, RT=20.71 min.: optically active isomer with longer retention time.
(4) Compound 704: CHIRALPAK AD-3 µm, Hexane (0.2% TEA)/EtOH=50:50, RT=6.446 min.: optically active isomer with longer retention time.
(4) Compound 705: CHIRALPAK AD-3 µm, Hexane (0.2% TEA)/EtOH=50:50, RT=4.679 min.: optically active isomer with shorter retention time.
(5) Compound 713: CHIRALPAK IA-3 µm, 100% MeOH (0.1% DEA), RT=3.628 min.: optically active isomer with longer retention time.
(5) Compound 714: CHIRALPAK IA-3 µm, 100% MeOH (0.1% DEA), RT=2.533 min.: optically active isomer with shorter retention time.
(6) Compound 724: CHIRALPAK AD-3, Hexane (0.1% DEA)/EtOH=50:50, RT=4.32 min.: optically active isomer with shorter retention time.
(6) Compound 725: CHIRALPAK AD-3, Hexane (0.1% DEA)/EtOH=50:50, RT=5.06 min.: optically active isomer with longer retention time.
(7) Compound 729: CHIRALPAK IA-3, 0.46*5 cm; 3 µm, Hexane (0.1% IPA)/EtOH=50:50, RT=4.01 min.: optically active isomer with longer retention time.
(7) Compound 730: CHIRALPAK IA-3, 0.46*5 cm; 3 µm, Hexane (0.1% IPA)/EtOH=50:50, RT=1.68 min.: optically active isomer with shorter retention time.
(8) Compound 735: DAICEL CHIRALPAK AD-H 5 µm, Hexane/IPA=90/10, RT=9.18 min.: optically active isomer with shorter retention time.
(8) Compound 736: DAICEL CHIRALPAK AD-H 5 µm, Hexane/IPA=90/10, RT=10.65 min.: optically active isomer with longer retention time.
(9) Compound 773: DAICEL CHIRALPAK IA 5 µm, MeOH/IPA=6/4, RT=17.90 min.: optically active isomer with shorter retention time.
(9) Compound 774: DAICEL CHIRALPAK IA 5 µm, MeOH/IPA=6/4, RT=21.84 min.: optically active isomer with longer retention time.
(10) Compound 775: DAICEL CHIRALPAK IA 5 µm, Hexane/MeOH/IPA=6/1/1, RT=10.25 min.: optically active isomer with shorter retention time.
(10) Compound 776: DAICEL CHIRALPAK IA 5 µm, Hexane/MeOH/IPA=6/1/1, RT=14.71 min.: optically active isomer with longer retention time.
(11) Compound 809: DAICEL CHIRALPAK AD-H 5 µm, 4.6*250 mm, n-Hexane/EtOH/MeOH=70/15/15, RT=21.62 min.: optically active isomer with shorter retention time.
(11) Compound 810: DAICEL CHIRALPAK AD-H 5 µm, 4.6*250 mm, n-Hexane/EtOH/MeOH=70/15/15, RT=25.87 min.: optically active isomer with longer retention time.
(12) Compound 865: CHIRALPAK IA-3; 0.46*5 cm; 3 µm; Hexane (0.1% DEA)/EtOH=70:30, RT=4.81 min.: optically active isomer with shorter retention time.
(12) Compound 866: CHIRALPAK IA-3; 0.46*5 cm; 3 µm; Hexane (0.1% DEA)/EtOH=70:30, RT=5.48 min.: optically active isomer with longer retention time.
(13) Compound 869: CHIRALPAK IA-3; 0.46*5 cm; 3 µm; Hexane (0.1% DEA)/EtOH=60:40, RT=2.27 min.: optically active isomer with shorter retention time.
(13) Compound 870: CHIRALPAK IA-3; 0.46*5 cm; 3 µm; Hexane (0.1% DEA)/EtOH=60:40, RT=2.93 min.: optically active isomer with longer retention time.
(14) Compound 875: DAICEL CHIRALPAK AD-H 5 µm, Hexane/MeOH/EtOH=80/10/10, RT=22.30 min.: optically active isomer with shorter retention time.
(14) Compound 876: DAICEL CHIRALPAK AD-H 5 µm, Hexane/MeOH/EtOH=80/10/10, RT=29.24 min.: optically active isomer with longer retention time.
(15) Compound 938: DAICEL CHIRALPAK AD-H 5 µm, (100% EtOH+0.1% DEA), RT=33.58 min.: optically active isomer with shorter retention time.
(15) Compound 939: DAICEL CHIRALPAK AD-H 5 µm, (100% EtOH+0.1% DEA), RT=42.68 min.: optically active isomer with longer retention time.
(16) Compound 940: DAICEL CHIRALPAK AD-H 5 µm, (Hexane/MeOH/EtOH+0.1% DEA=6/2/2), RT=20.23 min.: optically active isomer with shorter retention time.
(16) Compound 941: DAICEL CHIRALPAK AD-H 5 µm, (Hexane/MeOH/EtOH+0.1% DEA=6/2/2), RT=22.07 min.: optically active isomer with longer retention time.
(17) Compound 942: DAICEL CHIRALPAK AD-H 5 µm, (Hexane/MeOH/EtOH+0.1% DEA=6/2/2), RT=13.99 min.: optically active isomer with shorter retention time.
(17) Compound 943: DAICEL CHIRALPAK AD-H 5 µm, (Hexane/MeOH/EtOH+0.1% DEA=6/2/2), RT=15.66 min.: optically active isomer with longer retention time.
(18) Compound 989: CHIRALPAK IA, n-Hexane/EtOH=70/30, RT=13.32 min.: optically active isomer with shorter retention time.
(18) Compound 990: CHIRALPAK IA, n-Hexane/EtOH=70/30, RT=16.69 min.: optically active isomer with longer retention time.
(19) Compound 992: CHIRALPAK IA-3: 0.46*5 cm; 3 µm, Hexane (0.1% DEA)/EtOH=50:50, 1.5 ml/min, RT=1.87 min.: optically active isomer with shorter retention time.
(19) Compound 993: CHIRALPAK IA-3: 0.46*5 cm; 3 µm, Hexane (0.1% DEA)/EtOH=50:50, 1.5 ml/min, RT=3.56 min.: optically active isomer with longer retention time.
(20) Compound 1025: CHIRALPAK IA, 0.46*25 cm; 5 n, MeOH (0.1% DEA)/DCM=75:25, 1.0 mL/min., RT=6.597 min.: optically active isomer with shorter retention time.

(20) Compound 1026: CHIRALPAK IA, 0.46*25 cm; 5 μm, MeOH (0.1% DEA)/DCM=75:25, 1.0 mL/min., RT=8.199 min.: optically active isomer with longer retention time.

(21) Compound 1034: CHIRALPAK AS-3, 0.46*10 cm; 3 nm, Hexane (0.1% DEA)/(MeOH/EtOH=1:1)=70:30, 1.0 mL/min., RT=6.23 min.: optically active isomer with shorter retention time.

(21) Compound 1035: CHIRALPAK AS-3, 0.46*10 cm; 3 μm, Hexane (0.1% DEA)/(MeOH/EtOH=1:1)=70:30, 1.0 mL/min., RT=9.94 min.: optically active isomer with longer retention time.

(22) Compound 1036: CHIRALPAK IC-3, 0.46*10 cm; 3 μm, DCM (0.1% DEA)/MeOH=20:80, 1.0 mL/min., RT=5.10 min.: optically active isomer with shorter retention time.

(22) Compound 1037: CHIRALPAK IC-3, 0.46*10 cm; 3 μm, DCM (0.1% DEA)/MeOH=20:80, 1.0 mL/min., RT=5.95 min.: optically active isomer with longer retention time.

(23) Compound 1066: CHIRALPAK IC-3, 0.46*10 cm; 3 μm, MeOH (0.1% DEA)/DCM=95:5, 1.0 ml/min., RT=5.421 min.: optically active isomer with shorter retention time.

(23) Compound 1067: CHIRALPAK IC-3, 0.46*10 cm; 3 μm, MeOH (0.1% DEA)/DCM=95:5, 1.0 ml/min., RT=6.00 min.: optically active isomer with longer retention time.

(24) Compound 1068: CHIRALPAK IC, 0.46*25 cm; 5 μm, MeOH (0.1% DEA)/DCM=90:10, 1.0 ml/min., RT=17.429 min.: optically active isomer with shorter retention time.

(24) Compound 1069: CHIRALPAK IC, 0.46*25 cm; 5 μm, MeOH (0.1% DEA)/DCM=90:10, 1.0 ml/min., RT=20.57 min.: optically active isomer with longer retention time.

(25) Compound 1088: CHIRALPAK IA, n-Hexane/EtOH/MeOH=50/25/25, 1.0 mL/min., RT=15.21 min.: optically active isomer with shorter retention time.

(25) Compound 1089: CHIRALPAK IA, n-Hexane/EtOH/MeOH=50/25/25, 1.0 mL/min., RT=18.59 min.: optically active isomer with longer retention time.

*: Compound separated as diastereomers by reversed phase HPLC purification (note: absolute configuration is not determined).

(1) Compound 831: C-18: RT=1.67 min.: diastereomer with shorter retention time.

(1) Compound 832: C-18: RT=1.71 min.: diastereomer with longer retention time.

*: Compound represented its relative configurations of two substituents.

Compound#: 577, 607, 608, 609, 610, 618, 619, 621, 622, 645, 646, 647, 673, 708, 739, 742, 799, 801, and 864.

Lengthy table referenced here

US10124004-20181113-T00001

Please refer to the end of the specification for access instructions.

Example 20

Human CDK4/Cyclin D3 Inhibitory Activity

Each compound was analyzed for CDK4/cyclin D3 inhibitory activity with an assay kit (QS S Assist CDK4/Cyclin D3_FP Kit, available from Carna Biosciences, Inc.). This assay kit determines kinase activity on the basis of the IMAP technology by Molecular Devices. Specifically, the kinase activity is determined through quantification of a variation in fluorescent polarization caused by binding of a kinase-phosphorylated fluorescent substance to an IMAP-binding reagent.

Each solution was prepared with the 10× assay buffer attached to the kit or a separately prepared assay buffer having the same composition as the assay buffer attached to the kit. An assay buffer was prepared by 10-fold dilution of the 10× assay buffer with distilled water. The assay buffer contains 20 mM HEPES (pH 7.4), 0.01% Tween20, and 2 mM dithiothreitol. A test compound solution was prepared by dilution of the test compound with dimethyl sulfoxide (DMSO) to a concentration 100 times higher than the final concentration and then 25-fold dilution with the assay buffer to a concentration four times higher than the final concentration. An ATP/substrate/Metal solution was prepared by five-fold dilution of the 5×ATP/substrate/Metal solution attached to the kit with the assay buffer. An enzyme solution was prepared by dilution of the CDK4/cyclin D3 attached to the kit with the assay buffer to a concentration twice higher than the final concentration (final concentration of CDK4/cyclin D3:12.5 to 25 ng/well). A detection reagent was prepared by five-fold dilution of each of 5× IMAP-binding buffer A and 5×IMAP-binding buffer B with distilled water, mixing of IMAP-binding buffer A with IMAP-binding buffer B at a ratio of 85:15, and 400-fold dilution of the IMAP-binding reagent with the mixed buffer.

The test compound solution (5 μL/well) and the ATP/substrate/Metal solution (5 μL/well) were added to a 384-well plate, and the enzyme solution or the assay buffer (10 μL/well) was added to the plate (total amount of the reaction mixture: 20 μL/well) for initiation of enzymatic reaction. The reaction mixture had a composition of 20 mM HEPES (pH 7.4), 0.01% Tween 20, 2 mM dithiothreitol, 100 nM FITC-labeled peptide substrate (the sequence of the substrate peptide is not disclosed by Carna Biosciences, Inc.), 10 μM ATP, 1 mM magnesium chloride, 1% DMSO, and 12.5 to 25 ng/well CDK4/cyclin D3. The reaction was performed at room temperature for 45 minutes, and the detection reagent (60 μL/well) was then added to the plate, followed by further reaction for 30 minutes at room temperature under light shielding conditions. Subsequently, fluorescent polarization was determined with a microplate reader at an excitation wavelength of 485 nm and an emission wavelength of 535 nm.

The percent inhibition of enzyme activity was calculated for each test compound (note: enzyme activity=100% in the case of addition of the enzyme solution and addition of DMSO instead of the test compound solution, whereas enzyme activity=0% in the case of addition of the assay buffer instead of the enzyme solution, and addition of DMSO instead of the test compound solution). The percent inhibition of enzyme activity was fitted to a dose-response curve, to determine a 50% inhibitory concentration against CDK4/cyclin D3.

The inhibitory activity of each compound against CDK4/cyclin D3 was shown in tables described below.

In each table, "+++" corresponds to $IC_{50}<10$ nM, "++" $10$ nM$\leq IC_{50}<100$ nM, and "+" $100$ nM$\leq IC_{50}$.

Example 21

Human CDK2/Cyclin $A^2$ Inhibitory Activity

Each compound was analyzed for CDK2/cyclin A2 inhibitory activity with an assay kit (QS S Assist CDK2/

Cyclin A2_FP Kit, available from Carna Biosciences, Inc.). This assay kit determines kinase activity on the basis of the IMAP technology by Molecular Devices. Specifically, the kinase activity is determined through quantification of a variation in fluorescent polarization caused by binding of a kinase-phosphorylated fluorescent substance to an IMAP-binding reagent.

An assay buffer was prepared by 10-fold dilution of the 10× assay buffer attached to the kit with distilled water, and each solution was prepared with the assay buffer. The assay buffer contained 20 mM HEPES (pH 7.4), 0.01% Tween 20, and 2 mM dithiothreitol. A test compound solution was prepared by dilution of the test compound with dimethyl sulfoxide (DMSO) to a concentration 100 times higher than the final concentration and then 25-fold dilution with the assay buffer to a concentration four times higher than the final concentration. An ATP/substrate/Metal solution was prepared by five-fold dilution of the 5×ATP/substrate/Metal solution attached to the kit with the assay buffer. An enzyme solution was prepared by dilution of the CDK2/cyclin A2 attached to the kit with the assay buffer to a concentration twice higher than the final concentration (final concentration of CDK2/cyclin A2: 2.5 ng/well). A detection reagent was prepared by five-fold dilution of 5×IMAP-binding buffer A with distilled water and 400-fold dilution of the IMAP-binding reagent with the diluted buffer.

The test compound solution (5 μL/well) and the ATP/substrate/Metal solution (5 μL/well) were added to a 384-well plate, and the enzyme solution or the assay buffer (10 μL/well) was added to the plate (total amount of the reaction mixture: 20 μL/well) for initiation of enzymatic reaction. The reaction mixture had a composition of 20 mM HEPES (pH 7.4), 0.01% Tween 20, 2 mM dithiothreitol, 100 nM FITC-labeled peptide substrate (the sequence of the substrate peptide is not disclosed by Carna Biosciences, Inc.), 30 μM ATP, 5 mM magnesium chloride, 1% DMSO, and 2.5 ng/well CDK2/cyclin A2. The reaction was performed at room temperature for 60 minutes, and the detection reagent (60 μL/well) was then added to the plate, followed by further reaction for 30 minutes at room temperature under light shielding conditions. Subsequently, fluorescent polarization was determined with a microplate reader at an excitation wavelength of 485 nm and an emission wavelength of 535 nm.

The percent inhibition of enzyme activity was calculated for each test compound (note: enzyme activity=100% in the case of addition of the enzyme solution and addition of DMSO instead of the test compound solution, whereas enzyme activity=0% in the case of addition of the assay buffer instead of the enzyme solution and addition of DMSO instead of the test compound solution). The percent inhibition of enzyme activity was fitted to a dose-response curve, to determine a 50% inhibitory concentration against CDK2/cyclin A2.

The inhibitory activity of each compound against CDK2/cyclin A2 was shown in tables described below.

In each table, "+++" corresponds to $IC_{50} < 10$ nM, "++" $10$ nM $\leq IC_{50} < 100$ nM, and "+" $100$ nM $\leq IC_{50}$.

TABLE 6

| Compound No. | CDK4 Activity symbol | CDK2 Activity symbol | Compound No. | CDK4 Activity symbol | CDK2 Activity symbol |
|---|---|---|---|---|---|
| 1 | +++ | ++ | 2 | +++ | ++ |
| 3 | +++ | ++ | 4 | +++ | ++ |
| 5 | +++ | + | 6 | +++ | ++ |
| 7 | +++ | + | 8 | +++ | + |
| 9 | +++ | + | 10 | +++ | + |
| 11 | ++ | + | 12 | +++ | + |
| 13 | +++ | ++ | 14 | +++ | + |
| 15 | +++ | + | 16 | +++ | + |
| 17 | +++ | + | 18 | +++ | + |
| 19 | +++ | + | 20 | +++ | + |
| 21 | +++ | + | 22 | ++ | + |
| 23 | +++ | + | 24 | +++ | + |
| 25 | + | + | 26 | +++ | + |
| 27 | ++ | + | 28 | +++ | + |
| 29 | +++ | + | 30 | +++ | ++ |
| 31 | +++ | + | 32 | +++ | + |
| 33 | + | + | 34 | ++ | + |
| 35 | +++ | + | 36 | + | + |
| 37 | +++ | + | 38 | +++ | + |
| 39 | +++ | + | 40 | +++ | + |
| 41 | +++ | + | 42 | +++ | ++ |
| 43 | +++ | ++ | 44 | +++ | + |
| 45 | +++ | + | 46 | +++ | ++ |
| 47 | +++ | ++ | 48 | +++ | + |
| 49 | +++ | ++ | 50 | +++ | ++ |
| 51 | ++ | + | 52 | +++ | ++ |
| 53 | +++ | ++ | 54 | +++ | + |
| 55 | +++ | ++ | 56 | +++ | + |
| 57 | +++ | + | 58 | ++ | + |
| 59 | +++ | + | 60 | +++ | + |
| 61 | +++ | + | 62 | +++ | + |
| 63 | +++ | + | 64 | +++ | + |
| 65 | ++ | + | 66 | +++ | + |
| 67 | +++ | ++ | 68 | +++ | + |
| 69 | +++ | + | 70 | +++ | + |
| 71 | +++ | + | 72 | +++ | + |
| 73 | +++ | ++ | 74 | +++ | + |
| 75 | +++ | + | 76 | +++ | + |
| 77 | +++ | + | 78 | +++ | + |
| 79 | +++ | + | 80 | +++ | ++ |
| 81 | +++ | ++ | 82 | ++ | + |
| 83 | +++ | ++ | 84 | +++ | ++ |
| 85 | ++ | ++ | 86 | ++ | + |
| 87 | +++ | +++ | 88 | + | + |
| 89 | +++ | ++ | 90 | ++ | ++ |
| 91 | +++ | + | 92 | +++ | + |
| 93 | +++ | + | 94 | +++ | + |
| 95 | + | ++ | 96 | ++ | ++ |
| 97 | ++ | + | 98 | + | + |
| 99 | + | + | 100 | ++ | + |
| 101 | +++ | + | 102 | ++ | + |
| 103 | +++ | + | 104 | ++ | + |
| 105 | +++ | + | 106 | +++ | + |
| 107 | ++ | + | 108 | +++ | ++ |
| 109 | ++ | + | 110 | + | + |
| 111 | ++ | + | 112 | ++ | ++ |
| 113 | +++ | + | 114 | ++ | + |
| 115 | +++ | + | 116 | ++ | + |
| 117 | +++ | + | 118 | +++ | ++ |
| 119 | ++ | + | 120 | ++ | + |
| 121 | +++ | ++ | 122 | ++ | + |
| 123 | ++ | + | 124 | ++ | + |
| 125 | +++ | ++ | 126 | + | + |
| 127 | +++ | ++ | 128 | +++ | ++ |
| 129 | +++ | ++ | 130 | +++ | ++ |
| 131 | +++ | ++ | 132 | +++ | ++ |
| 133 | ++ | + | 134 | +++ | ++ |
| 135 | +++ | + | 136 | ++ | + |
| 137 | +++ | ++ | 138 | +++ | ++ |
| 139 | +++ | ++ | 140 | +++ | + |
| 141 | +++ | + | 142 | +++ | ++ |
| 143 | ++ | + | 144 | +++ | + |
| 145 | +++ | ++ | 146 | +++ | + |
| 147 | +++ | ++ | 148 | ++ | + |
| 149 | ++ | + | 150 | +++ | ++ |
| 151 | +++ | ++ | 152 | +++ | ++ |
| 153 | +++ | ++ | 154 | +++ | + |

TABLE 6-continued

| Compound No. | CDK4 Activity symbol | CDK2 Activity symbol | Compound No. | CDK4 Activity symbol | CDK2 Activity symbol |
| --- | --- | --- | --- | --- | --- |
| 155 | +++ | ++ | 156 | +++ | + |
| 157 | ++ | + | 158 | ++ | + |
| 159 | +++ | + | 160 | +++ | |
| 161 | +++ | ++ | 162 | ++ | + |
| 163 | +++ | + | 164 | +++ | ++ |
| 165 | +++ | + | 166 | +++ | ++ |
| 167 | +++ | + | 168 | +++ | ++ |
| 169 | +++ | ++ | 170 | +++ | + |
| 171 | +++ | ++ | 172 | ++ | + |
| 173 | +++ | ++ | 174 | +++ | ++ |
| 175 | +++ | ++ | 176 | ++ | + |
| 177 | +++ | ++ | 178 | +++ | + |
| 179 | ++ | + | 180 | ++ | + |
| 181 | +++ | ++ | 182 | ++ | + |
| 183 | +++ | ++ | 184 | +++ | ++ |
| 185 | +++ | ++ | 186 | ++ | + |
| 187 | ++ | + | 188 | ++ | + |
| 189 | +++ | ++ | 190 | +++ | ++ |
| 191 | +++ | ++ | 192 | ++ | + |
| 193 | ++ | + | 194 | +++ | ++ |
| 195 | +++ | + | 196 | +++ | + |
| 197 | ++ | + | 198 | ++ | + |
| 199 | ++ | + | 200 | +++ | + |
| 201 | ++ | + | 202 | ++ | + |
| 203 | +++ | ++ | 204 | +++ | + |
| 205 | +++ | ++ | 206 | +++ | + |
| 207 | +++ | + | 208 | +++ | + |
| 209 | ++ | + | 210 | ++ | + |
| 211 | ++ | ++ | 212 | +++ | + |
| 213 | +++ | ++ | 214 | +++ | + |
| 215 | +++ | + | 216 | ++ | + |
| 217 | +++ | + | 218 | +++ | ++ |
| 219 | +++ | ++ | 220 | +++ | + |
| 221 | +++ | + | 222 | ++ | + |
| 223 | +++ | + | 224 | +++ | + |
| 225 | +++ | + | 226 | +++ | ++ |
| 227 | +++ | + | 228 | ++ | + |
| 229 | +++ | + | 230 | +++ | + |
| 231 | ++ | + | 232 | +++ | + |
| 233 | +++ | + | 234 | +++ | + |
| 235 | ++ | + | 236 | +++ | ++ |
| 237 | ++ | + | 238 | +++ | + |
| 239 | +++ | + | 240 | +++ | + |
| 241 | +++ | + | 242 | ++ | + |
| 243 | +++ | + | 244 | +++ | + |
| 245 | +++ | + | 246 | +++ | + |
| 247 | +++ | + | 248 | ++ | + |
| 249 | +++ | + | 250 | +++ | + |
| 251 | +++ | + | 252 | +++ | + |
| 253 | +++ | + | 254 | +++ | + |
| 255 | +++ | + | 256 | +++ | + |
| 257 | +++ | + | 258 | +++ | + |
| 259 | +++ | + | 260 | +++ | + |
| 261 | +++ | + | 262 | ++ | + |
| 263 | +++ | + | 264 | +++ | + |
| 265 | +++ | + | 266 | +++ | + |
| 267 | +++ | + | 268 | ++ | + |
| 269 | +++ | + | 270 | +++ | + |
| 271 | +++ | + | 272 | +++ | + |
| 273 | +++ | + | 274 | +++ | + |
| 275 | ++ | + | 276 | +++ | + |
| 277 | + | + | 278 | +++ | + |
| 279 | ++ | + | 280 | + | + |
| 281 | ++ | + | 282 | +++ | + |
| 283 | +++ | + | 284 | +++ | + |
| 285 | +++ | + | 286 | +++ | + |
| 287 | +++ | + | 288 | +++ | + |
| 289 | +++ | + | 290 | +++ | + |
| 291 | +++ | + | 292 | ++ | + |
| 293 | +++ | + | 294 | +++ | + |
| 295 | ++ | + | 296 | + | + |
| 297 | +++ | + | 298 | ++ | + |
| 299 | ++ | + | 300 | +++ | + |
| 301 | +++ | + | 302 | +++ | + |
| 303 | +++ | + | 304 | +++ | + |
| 305 | +++ | + | 306 | ++ | + |
| 307 | +++ | + | 308 | + | + |
| 309 | + | + | 310 | +++ | + |
| 311 | +++ | + | 312 | +++ | + |
| 313 | +++ | + | 314 | +++ | + |
| 315 | + | + | 316 | + | + |
| 317 | +++ | + | 318 | +++ | + |
| 319 | +++ | + | 320 | +++ | + |
| 321 | +++ | + | 322 | ++ | + |
| 323 | +++ | + | 324 | + | + |
| 325 | ++ | + | 326 | +++ | + |
| 327 | ++ | + | 328 | +++ | + |
| 329 | +++ | + | 330 | +++ | + |
| 331 | + | + | 332 | +++ | + |
| 333 | +++ | + | 334 | ++ | + |
| 335 | +++ | + | 336 | +++ | + |
| 337 | +++ | + | 338 | +++ | + |
| 339 | ++ | + | 340 | +++ | + |
| 341 | +++ | + | 342 | +++ | + |
| 343 | +++ | + | 344 | +++ | + |
| 345 | +++ | + | 346 | +++ | + |
| 347 | +++ | + | 348 | +++ | + |
| 349 | ++ | + | 350 | +++ | + |
| 351 | +++ | + | 352 | +++ | + |
| 353 | +++ | + | 354 | ++ | + |
| 355 | +++ | + | 356 | ++ | |
| 357 | +++ | | 358 | +++ | + |
| 359 | ++ | | 360 | +++ | + |
| 361 | +++ | | 362 | ++ | |
| 363 | +++ | + | 364 | +++ | ++ |
| 365 | +++ | + | 366 | +++ | + |
| 367 | +++ | + | 368 | +++ | + |
| 369 | +++ | + | 370 | +++ | + |
| 371 | +++ | + | 372 | +++ | + |
| 373 | +++ | + | 374 | ++ | |
| 375 | + | | 376 | +++ | + |
| 377 | ++ | | 378 | +++ | + |
| 379 | +++ | + | 380 | +++ | + |
| 381 | +++ | + | 382 | +++ | + |
| 383 | ++ | + | 384 | ++ | + |
| 385 | +++ | + | 386 | +++ | + |
| 387 | +++ | ++ | 388 | +++ | + |
| 389 | +++ | ++ | 390 | +++ | |
| 391 | ++ | | 392 | +++ | |
| 393 | ++ | | 394 | ++ | |
| 395 | +++ | + | 396 | + | |
| 397 | +++ | | 398 | +++ | |
| 399 | ++ | | 400 | +++ | + |
| 401 | ++ | | 402 | +++ | |
| 403 | ++ | | 404 | +++ | |
| 405 | ++ | | 406 | ++ | |
| 407 | ++ | | 408 | ++ | |
| 409 | +++ | | 410 | +++ | |
| 411 | +++ | | 412 | +++ | |
| 413 | +++ | | 414 | ++ | |
| 415 | +++ | | 416 | ++ | |
| 417 | +++ | | 418 | +++ | |
| 419 | ++ | | 420 | +++ | |
| 421 | ++ | | 422 | ++ | |
| 423 | +++ | | 424 | +++ | |
| 425 | +++ | | 426 | +++ | |
| 427 | +++ | | 428 | +++ | |
| 429 | +++ | | 430 | +++ | |
| 431 | +++ | | 432 | +++ | + |
| 433 | ++ | | 434 | +++ | |
| 435 | ++ | | 436 | ++ | |
| 437 | + | | 438 | +++ | |
| 439 | ++ | | 440 | ++ | |
| 441 | + | | 442 | + | |
| 443 | ++ | | 444 | + | |
| 445 | +++ | | 446 | ++ | |
| 447 | ++ | | 448 | + | |
| 449 | + | | 450 | +++ | |
| 451 | +++ | | 452 | +++ | |
| 453 | +++ | | 454 | +++ | |
| 455 | +++ | | 456 | +++ | + |
| 457 | +++ | | 458 | +++ | |

TABLE 6-continued

| Compound No. | CDK4 Activity symbol | CDK2 Activity symbol | Compound No. | CDK4 Activity symbol | CDK2 Activity symbol |
|---|---|---|---|---|---|
| 459 | +++ | | 460 | +++ | |
| 461 | ++ | | 462 | ++ | |
| 463 | +++ | + | 464 | +++ | |
| 465 | +++ | | 466 | +++ | + |
| 467 | +++ | + | 468 | +++ | |
| 469 | ++ | | 470 | + | |
| 471 | ++ | | 472 | ++ | |
| 473 | ++ | | 474 | +++ | + |
| 475 | ++ | | 476 | +++ | |
| 477 | +++ | | 478 | +++ | |
| 479 | +++ | | 480 | ++ | |
| 481 | ++ | | 482 | +++ | |
| 483 | +++ | | 484 | +++ | |
| 485 | +++ | | 486 | +++ | |
| 487 | +++ | | 488 | +++ | |
| 489 | +++ | | 490 | +++ | |
| 491 | +++ | + | 492 | +++ | ++ |
| 493 | +++ | | 494 | +++ | |
| 495 | +++ | | 496 | +++ | |
| 497 | +++ | + | 498 | +++ | |
| 499 | +++ | ++ | 500 | +++ | |
| 501 | +++ | | 502 | +++ | |
| 503 | +++ | + | 504 | +++ | |
| 505 | ++ | | 506 | ++ | |
| 507 | +++ | + | 508 | +++ | + |
| 509 | +++ | + | 510 | +++ | + |
| 511 | +++ | ++ | 512 | +++ | + |
| 513 | ++ | | 514 | ++ | |
| 515 | ++ | | 516 | ++ | |
| 517 | +++ | | 518 | +++ | |
| 519 | +++ | + | 520 | +++ | |
| 521 | +++ | ++ | 522 | +++ | ++ |
| 523 | +++ | | 524 | +++ | + |
| 525 | +++ | | 526 | +++ | + |
| 527 | ++ | | 528 | +++ | |
| 529 | +++ | + | 530 | +++ | |
| 531 | +++ | | 532 | +++ | + |
| 533 | +++ | | 534 | +++ | |
| 535 | +++ | | 536 | +++ | |
| 537 | +++ | + | 538 | +++ | |
| 539 | ++ | | 540 | +++ | |
| 541 | +++ | | 542 | ++ | |
| 543 | +++ | | 544 | +++ | |
| 545 | +++ | | 546 | +++ | |
| 547 | +++ | | 548 | +++ | + |
| 549 | +++ | + | 550 | +++ | + |
| 551 | ++ | | 552 | +++ | |
| 553 | +++ | + | 554 | +++ | + |
| 555 | +++ | + | 556 | +++ | ++ |
| 557 | +++ | + | 558 | +++ | ++ |
| 559 | +++ | + | 560 | +++ | + |
| 561 | +++ | + | 562 | +++ | + |
| 563 | +++ | | 564 | +++ | |
| 565 | +++ | | 566 | +++ | + |
| 567 | +++ | + | 568 | +++ | |
| 569 | +++ | + | 570 | +++ | |
| 571 | +++ | | 572 | +++ | + |
| 573 | +++ | + | 574 | +++ | + |
| 575 | +++ | + | 576 | +++ | + |
| 577 | +++ | | 578 | +++ | |
| 579 | +++ | + | 580 | ++ | |
| 581 | +++ | + | 582 | +++ | |
| 583 | +++ | + | 584 | +++ | + |
| 585 | +++ | + | 586 | +++ | + |
| 587 | +++ | | 588 | +++ | + |
| 589 | +++ | + | 590 | +++ | + |
| 591 | +++ | + | 592 | +++ | + |
| 593 | +++ | + | 594 | +++ | |
| 595 | +++ | + | 596 | +++ | + |
| 597 | +++ | + | 598 | +++ | |
| 599 | ++ | | 600 | +++ | |
| 601 | +++ | + | 602 | +++ | + |
| 603 | +++ | | 604 | +++ | + |
| 605 | +++ | ++ | 606 | +++ | + |
| 607 | +++ | | 608 | +++ | + |
| 609 | +++ | + | 610 | +++ | + |
| 611 | +++ | + | 612 | +++ | ++ |
| 613 | ++ | | 614 | +++ | + |
| 615 | +++ | + | 616 | +++ | |
| 617 | +++ | | 618 | +++ | + |
| 619 | +++ | + | 620 | +++ | |
| 621 | +++ | + | 622 | +++ | + |
| 623 | +++ | ++ | 624 | +++ | + |
| 625 | +++ | + | 626 | +++ | + |
| 627 | +++ | + | 628 | +++ | + |
| 629 | +++ | + | 630 | +++ | + |
| 631 | +++ | ++ | 632 | +++ | + |
| 633 | +++ | + | 634 | +++ | + |
| 635 | +++ | + | 636 | +++ | + |
| 637 | +++ | + | 638 | +++ | + |
| 639 | +++ | + | 640 | +++ | + |
| 641 | +++ | + | 642 | +++ | + |
| 643 | +++ | + | 644 | +++ | + |
| 645 | +++ | + | 646 | +++ | + |
| 647 | +++ | + | 648 | +++ | + |
| 649 | +++ | + | 650 | +++ | + |
| 651 | +++ | + | 652 | +++ | + |
| 653 | +++ | + | 654 | +++ | + |
| 655 | ++ | + | 656 | +++ | + |
| 657 | +++ | + | 658 | +++ | + |
| 659 | +++ | + | 660 | +++ | + |
| 661 | +++ | + | 662 | +++ | + |
| 663 | +++ | + | 664 | +++ | + |
| 665 | +++ | + | 666 | +++ | + |
| 667 | +++ | + | 668 | +++ | + |
| 669 | ++ | + | 670 | + | + |
| 672 | +++ | + | 673 | +++ | + |
| 674 | +++ | + | 675 | +++ | + |
| 676 | +++ | + | 677 | +++ | + |
| 678 | ++ | + | 679 | ++ | + |
| 680 | ++ | + | 681 | ++ | + |
| 682 | +++ | + | 683 | +++ | + |
| 684 | ++ | | 685 | ++ | |
| 686 | +++ | + | 687 | +++ | |
| 688 | +++ | | 689 | +++ | |
| 690 | +++ | | 691 | +++ | + |
| 692 | +++ | + | 693 | +++ | + |
| 694 | ++ | + | 695 | +++ | + |
| 696 | +++ | + | 697 | ++ | |
| 698 | +++ | | 699 | ++ | |
| 700 | +++ | + | 701 | +++ | + |
| 702 | ++ | + | 703 | ++ | + |
| 704 | +++ | | 705 | +++ | |
| 706 | +++ | + | 707 | +++ | |
| 708 | +++ | | 709 | +++ | + |
| 710 | +++ | | 711 | +++ | + |
| 712 | +++ | | 713 | +++ | + |
| 714 | + | + | 715 | ++ | + |
| 716 | ++ | + | 717 | ++ | + |
| 718 | ++ | + | 719 | +++ | + |
| 720 | +++ | + | 721 | +++ | |
| 722 | +++ | + | 723 | +++ | + |
| 724 | +++ | + | 725 | +++ | + |
| 726 | +++ | + | 727 | +++ | + |
| 728 | +++ | + | 729 | +++ | + |
| 730 | ++ | + | 731 | +++ | + |
| 732 | +++ | + | 733 | ++ | + |
| 734 | +++ | + | 735 | +++ | + |
| 736 | +++ | + | 737 | +++ | + |
| 738 | +++ | + | 739 | +++ | + |
| 740 | +++ | + | 741 | +++ | + |
| 742 | +++ | + | 743 | +++ | + |
| 744 | +++ | + | 745 | +++ | + |
| 746 | +++ | + | 747 | ++ | + |
| 748 | ++ | + | 749 | +++ | + |
| 750 | +++ | + | 751 | +++ | + |
| 752 | ++ | + | 753 | +++ | + |
| 754 | ++ | + | 755 | +++ | + |
| 756 | ++ | + | 757 | +++ | + |
| 758 | ++ | + | 759 | ++ | + |
| 760 | ++ | + | 761 | +++ | + |
| 762 | +++ | + | 763 | +++ | + |

TABLE 6-continued

| Compound No. | CDK4 Activity symbol | CDK2 Activity symbol | Compound No. | CDK4 Activity symbol | CDK2 Activity symbol |
|---|---|---|---|---|---|
| 764 | +++ | + | 765 | +++ | + |
| 766 | ++ | + | 767 | +++ | + |
| 768 | +++ | + | 769 | +++ | + |
| 770 | ++ | + | 771 | +++ | + |
| 772 | +++ | + | 773 | +++ | + |
| 774 | ++ | + | 775 | +++ | + |
| 776 | +++ | + | 777 | +++ | + |
| 778 | +++ | + | 779 | +++ | + |
| 780 | ++ | + | 781 | +++ | + |
| 782 | +++ | + | 783 | +++ | + |
| 784 | +++ | + | 785 | +++ | + |
| 786 | +++ | + | 787 | +++ | + |
| 788 | +++ | + | 789 | +++ | + |
| 790 | +++ | + | 791 | +++ | ++ |
| 792 | ++ | + | 793 | ++ | + |
| 794 | +++ | + | 795 | +++ | ++ |
| 796 | +++ | + | 797 | ++ | + |
| 798 | +++ | + | 799 | +++ | + |
| 800 | +++ | + | 801 | +++ | + |
| 802 | +++ | + | 803 | +++ | + |
| 804 | +++ | + | 805 | +++ | + |
| 806 | +++ | + | 807 | ++ | + |
| 808 | +++ | + | 809 | +++ | ++ |
| 810 | +++ | + | 811 | +++ | ++ |
| 812 | ++ | + | 813 | +++ | + |
| 814 | +++ | + | 815 | +++ | + |
| 816 | +++ | + | 817 | +++ | + |
| 818 | +++ | + | 819 | +++ | + |
| 820 | +++ | ++ | 821 | +++ | ++ |
| 822 | +++ | ++ | 823 | ++ | + |
| 824 | +++ | + | 825 | +++ | + |
| 826 | +++ | + | 827 | +++ | + |
| 828 | ++ | + | 829 | +++ | + |
| 830 | +++ | + | 831 | ++ | + |
| 832 | ++ | + | 833 | +++ | + |
| 834 | +++ | + | 835 | ++ | + |
| 836 | ++ | + | 837 | +++ | ++ |
| 838 | +++ | + | 839 | +++ | + |
| 840 | + | + | 841 | +++ | + |
| 842 | ++ | + | 843 | +++ | + |
| 844 | +++ | + | 845 | +++ | + |
| 846 | +++ | + | 847 | +++ | + |
| 848 | +++ | ++ | 849 | +++ | ++ |
| 850 | ++ | ++ | 851 | ++ | + |
| 852 | +++ | + | 853 | +++ | + |
| 854 | +++ | + | 855 | +++ | + |
| 856 | +++ | + | 857 | +++ | + |
| 858 | +++ | + | 859 | +++ | + |
| 860 | +++ | + | 861 | +++ | + |
| 862 | +++ | + | 863 | +++ | + |
| 864 | +++ | + | 865 | +++ | + |
| 866 | +++ | + | 867 | +++ | + |
| 868 | +++ | + | 869 | +++ | ++ |
| 870 | +++ | + | 871 | ++ | + |
| 872 | ++ | + | 873 | +++ | + |
| 874 | +++ | + | 875 | +++ | + |
| 876 | +++ | + | 877 | +++ | + |
| 878 | +++ | + | 879 | +++ | + |
| 880 | +++ | + | 881 | +++ | + |
| 882 | +++ | + | 883 | +++ | + |
| 884 | +++ | + | 885 | +++ | + |
| 886 | +++ | + | 887 | +++ | + |
| 888 | +++ | + | 889 | ++ | + |
| 890 | ++ | + | 891 | ++ | + |
| 892 | ++ | + | 893 | ++ | + |
| 894 | ++ | + | 895 | +++ | + |
| 896 | +++ | + | 897 | ++ | + |
| 898 | +++ | + | 899 | +++ | + |
| 900 | +++ | + | 901 | +++ | + |
| 902 | +++ | + | 903 | +++ | ++ |
| 904 | +++ | + | 905 | +++ | + |
| 906 | ++ | + | 907 | +++ | + |
| 908 | +++ | + | 909 | +++ | + |
| 910 | ++ | + | 911 | +++ | + |
| 912 | +++ | + | 913 | +++ | + |
| 914 | +++ | + | 915 | +++ | + |
| 916 | +++ | + | 917 | +++ | + |
| 918 | +++ | + | 919 | +++ | + |
| 920 | +++ | + | 921 | +++ | + |
| 922 | +++ | + | 923 | +++ | + |
| 924 | +++ | + | 925 | +++ | + |
| 926 | +++ | + | 927 | +++ | + |
| 928 | +++ | + | 929 | +++ | + |
| 930 | +++ | + | 931 | +++ | + |
| 932 | +++ | + | 933 | +++ | + |
| 934 | +++ | + | 935 | ++ | + |
| 936 | +++ | + | 937 | +++ | + |
| 938 | +++ | + | 939 | +++ | + |
| 940 | +++ | + | 941 | +++ | + |
| 942 | +++ | + | 943 | ++ | + |
| 944 | +++ | + | 945 | +++ | + |
| 946 | +++ | + | 947 | +++ | + |
| 948 | +++ | + | 949 | +++ | + |
| 950 | +++ | + | 951 | +++ | + |
| 952 | +++ | + | 953 | +++ | + |
| 954 | +++ | + | 955 | +++ | + |
| 956 | +++ | + | 957 | +++ | + |
| 958 | +++ | + | 959 | ++ | + |
| 960 | +++ | + | 961 | +++ | + |
| 962 | +++ | + | 963 | +++ | + |
| 964 | +++ | + | 965 | ++ | + |
| 966 | +++ | + | 967 | +++ | + |
| 968 | +++ | + | 969 | ++ | + |
| 970 | +++ | + | 971 | +++ | + |
| 972 | +++ | + | 973 | ++ | + |
| 974 | ++ | + | 975 | ++ | + |
| 976 | +++ | + | 977 | +++ | + |
| 978 | +++ | + | 979 | +++ | + |
| 980 | +++ | + | 981 | +++ | ++ |
| 982 | +++ | + | 983 | +++ | + |
| 984 | +++ | + | 985 | +++ | + |
| 986 | +++ | + | 987 | +++ | + |
| 988 | +++ | + | 989 | +++ | + |
| 990 | +++ | + | 991 | +++ | + |
| 992 | ++ | + | 993 | +++ | + |
| 994 | +++ | + | 995 | +++ | + |
| 996 | +++ | + | 997 | +++ | + |
| 998 | +++ | + | 999 | +++ | + |
| 1000 | ++ | + | 1001 | +++ | + |
| 1002 | +++ | + | 1003 | +++ | + |
| 1004 | +++ | + | 1005 | +++ | + |
| 1006 | +++ | + | 1007 | +++ | + |
| 1008 | +++ | + | 1009 | +++ | + |
| 1010 | +++ | + | 1011 | +++ | + |
| 1012 | +++ | + | 1013 | +++ | + |
| 1014 | +++ | + | 1015 | +++ | + |
| 1016 | +++ | + | 1017 | +++ | + |
| 1018 | +++ | + | 1019 | +++ | + |
| 1020 | +++ | + | 1021 | +++ | + |
| 1022 | +++ | + | 1023 | +++ | + |
| 1024 | +++ | + | 1025 | + | + |
| 1026 | ++ | + | 1027 | +++ | + |
| 1028 | ++ | + | 1029 | +++ | + |
| 1030 | ++ | + | 1031 | +++ | + |
| 1032 | +++ | + | 1033 | +++ | + |
| 1034 | +++ | + | 1035 | +++ | + |
| 1036 | +++ | + | 1037 | ++ | + |
| 1038 | +++ | + | 1039 | +++ | + |
| 1040 | +++ | + | 1041 | +++ | + |
| 1042 | ++ | + | 1043 | +++ | + |
| 1044 | ++ | + | 1045 | +++ | + |
| 1046 | +++ | + | 1047 | +++ | + |
| 1048 | +++ | + | 1049 | +++ | + |
| 1050 | +++ | + | 1051 | +++ | + |
| 1052 | ++ | + | 1053 | ++ | + |
| 1054 | ++ | + | 1055 | ++ | + |
| 1056 | ++ | + | 1057 | +++ | + |
| 1058 | +++ | + | 1059 | +++ | + |
| 1060 | +++ | + | 1061 | +++ | + |
| 1062 | +++ | + | 1063 | +++ | + |
| 1064 | +++ | + | 1065 | +++ | + |
| 1066 | ++ | + | 1067 | +++ | + |

TABLE 6-continued

| Compound No. | CDK4 Activity symbol | CDK2 Activity symbol | Compound No. | CDK4 Activity symbol | CDK2 Activity symbol |
|---|---|---|---|---|---|
| 1068 | + | + | 1069 | ++ | + |
| 1070 | +++ | + | 1071 | +++ | + |
| 1072 | +++ | + | 1073 | +++ | + |
| 1074 | +++ | + | 1075 | +++ | + |
| 1076 | +++ | + | 1077 | +++ | + |
| 1078 | +++ | + | 1079 | +++ | + |
| 1080 | +++ | + | 1081 | +++ | + |
| 1082 | +++ | + | 1083 | +++ | + |
| 1084 | +++ | + | 1085 | +++ | + |
| 1086 | +++ | + | 1087 | +++ | + |
| 1088 | +++ | + | 1089 | +++ | + |
| 1090 | +++ | + | 1091 | +++ | + |
| 1092 | +++ | + | 1093 | +++ | + |
| 1094 | +++ | + | 1095 | +++ | + |
| 1096 | ++ | + | 1097 | ++ | + |
| 1098 | ++ | + | 1099 | +++ | + |
| 1100 | ++ | + | 1101 | +++ | + |
| 1102 | +++ | + | 1103 | +++ | + |
| 1104 | +++ | + | 1105 | +++ | + |
| 1106 | +++ | + | 1107 | +++ | + |
| 1108 | +++ | + | 1109 | +++ | + |
| 1110 | +++ | + | 1111 | ++ | + |
| 1112 | ++ | + | 1113 | ++ | + |
| 1114 | +++ | + | 1115 | +++ | + |
| 1116 | +++ | + | 1117 | ++ | + |
| 1118 | +++ | + | 1119 | +++ | + |
| 1120 | ++ | + | 1121 | +++ | + |
| 1122 | +++ | + | 1123 | ++ | + |
| 1124 | ++ | + | 1125 | +++ | + |
| 1126 | +++ | + | 1127 | +++ | + |
| 1128 | +++ | + | 1129 | +++ | + |
| 1130 | ++ | + | 1131 | ++ | + |
| 1132 | +++ | + | 1133 | +++ | + |
| 1134 | +++ | + | 1135 | +++ | + |
| 1136 | +++ | + | 1137 | +++ | + |
| 1138 | +++ | + | 1139 | +++ | + |
| 1140 | +++ | + | 1141 | +++ | + |
| 1142 | +++ | + | 1143 | +++ | + |
| 1144 | +++ | + | 1145 | +++ | + |
| 1146 | +++ | + | 1147 | +++ | + |
| 1148 | +++ | + | 1149 | +++ | + |
| 1150 | +++ | + | 1151 | +++ | + |
| 1152 | +++ | + | 1153 | +++ | + |
| 1154 | +++ | + | 1155 | +++ | + |
| 1156 | +++ | + | 1157 | ++ | + |
| 1158 | +++ | + | 1159 | +++ | + |
| 1160 | +++ | ++ | 1161 | +++ | ++ |
| 1162 | +++ | ++ | 1163 | +++ | ++ |
| 1164 | +++ | + | 1165 | +++ | ++ |
| 1166 | +++ | + | 1167 | +++ | ++ |
| 1168 | +++ | + | 1169 | +++ | + |
| 1170 | +++ | + | 1171 | +++ | + |
| 1172 | +++ | + | 1173 | +++ | + |
| 1174 | +++ | + | 1175 | +++ | + |
| 1176 | +++ | + | 1177 | +++ | + |
| 1178 | +++ | + | 1179 | +++ | + |
| 1180 | +++ | + | 1181 | +++ | + |
| 1182 | +++ | + | 1183 | +++ | + |
| 1184 | +++ | + | 1185 | +++ | + |
| 1186 | +++ | + | 1187 | +++ | + |
| 1188 | +++ | + | 1189 | +++ | + |
| 1190 | +++ | + | 1191 | +++ | + |
| 1192 | +++ | + | 1193 | +++ | + |
| 1194 | +++ | + | 1195 | +++ | + |
| 1196 | +++ | + | 1197 | +++ | + |
| 1198 | +++ | + | 1199 | +++ | + |
| 1200 | +++ | + | 1201 | +++ | + |
| 1202 | +++ | + | 1203 | ++ | + |
| 1204 | +++ | + | 1205 | +++ | + |
| 1206 | +++ | + | 1207 | +++ | + |
| 1208 | +++ | + | 1209 | +++ | + |
| 1210 | +++ | + | 1211 | ++ | + |
| 1212 | +++ | + | 1213 | +++ | + |
| 1214 | +++ | + | 1215 | +++ | + |
| 1216 | +++ | + | 1217 | ++ | + |
| 1218 | +++ | + | 1219 | +++ | + |
| 1220 | +++ | + | 1221 | +++ | + |
| 1222 | +++ | + | 1223 | +++ | + |
| 1224 | +++ | + | 1225 | +++ | + |
| 1226 | +++ | + | 1227 | +++ | + |
| 1228 | +++ | + | 1229 | +++ | + |
| 1230 | +++ | + | 1231 | +++ | + |
| 1232 | +++ | + | | | |

Example 22

Human CDK6/Cyclin D3 Inhibitory Activity

CDK6/cyclin D3 inhibitory activity was determined by the off-chip mobility shift assay (MSA). The MSA separates proteins from one another on the basis of a difference in electrophoretic mobility depending on the molecular weight or electric charge of the proteins. The kinase activity is determined by quantifying the degree of phosphorylation through electrophoretic analysis of a positive to negative change in electric charge of the substrate phosphorylated by the kinase.

Each solution was prepared with an assay buffer containing 20 mM HEPES (pH 7.5), 0.01% Triton X-100, and 2 mM dithiothreitol. A test compound solution was prepared by dilution of the test compound with dimethyl sulfoxide (DMSO) to a concentration 100 times higher than the final concentration and then 25-fold dilution with the assay buffer to a concentration four times higher than the final concentration. An ATP/substrate/metal solution was prepared to have a concentration four times higher than the final concentration. An enzyme solution was prepared to have a concentration twice higher than the final concentration. The final enzyme concentration was adjusted to an appropriate level on the basis of the enzyme activity signal and the inhibitory activity of a positive control compound.

The test compound solution (5 μL/well) and the ATP/substrate/metal solution (5 μL/well) were added to a 384-well plate, and the enzyme solution or the assay buffer (10 μL/well) was added to the plate (total amount of the reaction mixture: 20 μL/well) for initiation of enzymatic reaction. The reaction mixture had a composition of 20 mM HEPES (pH 7.5), 0.01% Triton X-100, 2 mM dithiothreitol, 1000 nM peptide substrate (DYRKtide-F), 300 μM ATP, 5 mM magnesium chloride, 1% DMSO, and a predetermined concentration of CDK6/cyclin D3. The reaction was performed at room temperature for five hours, and a termination buffer (QuickScout Screening Assist MSA, manufactured by Carna Biosciences, Inc.) (60 μL/well) was then added to the plate for termination of the reaction. Subsequently, the substrate peptide and the phosphorylated peptide in the reaction mixture were separated from each other and quantified with LabChip 3000 (manufactured by Caliper Lifesciences). The kinase reaction was evaluated by the product ratio (P/(P+S)) calculated from the peak height (S) of the substrate peptide and the peak height (P) of the phosphorylated peptide.

The percent inhibition of enzyme activity was calculated for each test compound (note: enzyme activity=100% in the case of addition of the enzyme solution and addition of DMSO instead of the test compound solution, whereas enzyme activity=0% in the case of addition of the assay buffer instead of the enzyme solution and addition of DMSO instead of the test compound solution). The percent inhibition of enzyme activity was fitted to a dose-response curve, to determine a 50% inhibitory concentration against CDK6/cyclin D3.

The inhibitory activity of each compound against CDK6/cyclin D3 was shown in tables described below. In each table, "+++" corresponds to $IC_{50} < 10$ nM, "++" $10$ nM $\leq IC_{50} < 100$ nM, and "+" $100$ nM $\leq IC_{50}$.

TABLE 7

| Compound No. | CDK6 Activity Symbol | Compound No. | CDK6 Activity Symbol |
|---|---|---|---|
| 3 | +++ | 16 | +++ |
| 217 | ++ | 220 | ++ |
| 221 | ++ | 230 | +++ |
| 300 | ++ | 304 | ++ |
| 363 | ++ | 672 | ++ |
| 749 | ++ | 778 | ++ |
| 779 | +++ | 818 | ++ |
| 819 | ++ | 843 | ++ |
| 844 | +++ | 879 | +++ |
| 883 | +++ | 904 | +++ |
| 929 | +++ | 938 | ++ |
| 941 | +++ | 954 | +++ |
| 1036 | ++ | | |

Example 23

A monoclonal antibody cocktail against type II collagen (Arthritogenic MoAb Cocktail (Chondrex #53100), 4.8 mg/mL) was intraperitoneally administered (250 µL/head) to a group of mice with collagen antibody-induced arthritis (CAIA) (vehicle/+, group of drug administration) (day 1). LPS (LPS Solution (*E. coli* 0111:B4) (Chondrex #9028), 0.5 mg/mL) was intraperitoneally administered (100 µL/head) on day 4, to induce the disease. The drug was evaluated on the basis of pathological scoring until day 9. The drug was orally administered consecutively from day 4 to day 8 once a day.

In mice of a non-disease-induced group (vehicle/-group), PBS (pH 7.2, Gibco #20012-027) was intraperitoneally administered (250 µL/head) on day 1, and LPS was intraperitoneally administered on day 4.

The drug was evaluated on the basis of the pathological scoring (score 0 to score 4 for each of the extremities, evaluated by the total score). Scoring criteria are as follows:
score 0: no change;
score 1: swelling of only one limb;
score 2: swelling of wrist and ankle or swelling of two or more limbs;
score 3: swelling of wrist and ankle and swelling of one or more limbs; and
score 4: swelling of wrist and ankle and swelling of all the limbs.

FIG. 1 shows the results (scores) on day 9 (final day).

LENGTHY TABLES

The patent contains a lengthy table section. A copy of the table is available in electronic form from the USPTO web site (http://seqdata.uspto.gov/?pageRequest=docDetail&DocID=US10124004B2). An electronic copy of the table will also be available from the USPTO upon request and payment of the fee set forth in 37 CFR 1.19(b)(3).

The invention claimed is:
1. A compound represented by Formula (I) or a pharmaceutically acceptable salt thereof:

[Formula 1]

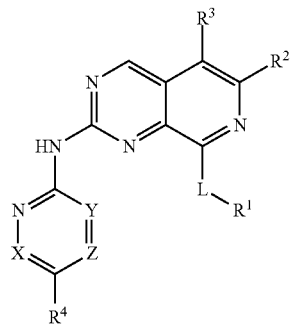

(I)

[where
L represents —NR$^5$—, —O—, or —S—;
R$^5$ represents a hydrogen atom or a C$_{1-6}$ alkyl group substituted with zero to two —OH groups, zero to two C$_{1-8}$ alkoxy groups, and zero to six fluorine atoms;
R$^1$ represents a C$_{1-8}$ alkyl, C$_{3-12}$ cycloalkyl, (C$_{3-12}$ cycloalkyl)-C$_{1-6}$ alkyl, 4- to 12-membered heterocyclyl, (4- to 12-membered heterocyclyl)-C$_{1-6}$ alkyl, C$_{6-10}$ aryl, (C$_{6-10}$ aryl)-C$_{1-6}$ alkyl, 5- to 10-membered heteroaryl, (5- to 10-membered heteroaryl)-C$_{1-6}$ alkyl, C$_{1-8}$ alkylsulfonyl, or C$_{1-8}$ acyl group;
each of the heteroatom-containing groups represented by R$^1$ contains one to four heteroatoms selected from oxygen, sulfur, and nitrogen atoms;
R$^1$ is optionally substituted with one to six substituents selected from the group consisting of a halogen atom, =O, —OH, —CN, —COOH, —COOR$^6$, —R$^7$, a C$_{3-6}$ cycloalkyl group substituted with zero to two —OH groups, zero to two C$_{1-8}$ alkoxy groups, and zero to six fluorine atoms, a 3- to 10-membered heterocyclyl group substituted with zero to two —OH groups, zero to two C$_{1-8}$ alkoxy groups, and zero to six fluorine atoms, a C$_{1-8}$ acyl group substituted with zero to two —OH groups, zero to two C$_{1-8}$ alkoxy groups, and zero to six fluorine atoms, and a C$_{1-8}$ alkoxy group substituted with zero to two —OH groups, zero to two C$_{1-8}$ alkoxy groups, and zero to six fluorine atoms;
R$^6$ and R$^7$ each independently represent a C$_{1-6}$ alkyl group substituted with zero to two —OH groups, zero to two C$_{1-8}$ alkoxy groups, and zero to six fluorine atoms;
R$^2$ represents a C$_{1-8}$ alkyl, C$_{3-8}$ cycloalkyl, 4- to 6-membered heterocyclyl, or C$_{1-8}$ acyl group, —COOR$^8$, or —CONR$^9$R$^{10}$;
each of the C$_{1-8}$ alkyl and C$_{3-8}$ cycloalkyl groups represented by R$^2$ is substituted with zero or one —OH group, zero to two C$_{1-8}$ alkoxy groups substituted with zero or one —OH group, zero or one $C_{1-4}$ alkoxy group, and zero to three fluorine atoms, and zero to five fluorine atoms;

$R^2$ is neither an unsubstituted $C_{1-8}$ alkyl, nor unsubstituted $C_{3-8}$ cycloalkyl, nor trifluoromethyl group;

$R^8$, $R^9$, and $R^{10}$ each independently represent a hydrogen atom or a $C_{1-8}$ alkyl group;

the 4- to 6-membered heterocyclyl group represented by $R^2$ is optionally substituted with one to four substituents selected from the group consisting of a fluorine atom, —OH, and $C_{1-4}$ alkyl and $C_{1-4}$ alkoxy groups;

each of the $C_{1-8}$ acyl group, —COOR$^8$, and —CONR$^9$R$^{10}$ represented by $R^2$ is optionally substituted with one to four substituents selected from the group consisting of a fluorine atom, —OH, and a $C_{1-4}$ alkoxy group;

$R^9$ and $R^{10}$ of —CONR$^9$R$^{10}$ represented by $R^2$ are optionally bonded via a single bond or —O— to form a ring including the nitrogen atom bonded to $R^9$ and $R^{10}$;

the heterocyclyl group represented by $R^2$ having a 4- or 5-membered ring contains one oxygen heteroatom, and the heterocyclyl group having a 6-membered ring contains one or two oxygen heteroatoms;

$R^3$ represents a hydrogen atom, a $C_{1-8}$ alkyl group, or a halogen atom;

X represents $CR^{11}$ or a nitrogen atom;

Y represents $CR^{12}$ or a nitrogen atom;

Z represents $CR^{13}$ or a nitrogen atom;

$R^{11}$ to $R^{13}$ each independently represent a hydrogen, fluorine, or chlorine atom or a $C_{1-6}$ alkyl or $C_{1-6}$ alkoxy group;

$R^4$ represents -$A^1$-$A^2$-$A^3$;

$A^1$ represents a single bond or a $C_{1-8}$ alkylene, $C_{2-8}$ alkenylene, or $C_{2-8}$ alkynylene group;

one or two sp$^3$ carbon atoms at any positions of $A^1$ are optionally replaced with one or two structures selected from the group consisting of —O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$—, and a structure of —O—O—, —O—NR$^{14}$—, —NR$^{14}$—O—, —O—CH$_2$—O—, —O—CH$_2$—NR$^{14}$—, or —NR$^{14}$—CH$_2$—O— is not formed in the case of replacement of two sp$^3$ carbon atoms;

$A^2$ represents a single bond or a $C_{1-7}$ alkylene, $C_{3-12}$ cycloalkylene, $C_{3-12}$ cycloalkylidene, 4- to 12-membered heterocyclylene, 4- to 12-membered heterocyclylidene, $C_{6-10}$ arylene, or 5- to 10-membered heteroarylene group;

$A^3$ represents a halogen atom, —CN, —NO$_2$, —R$^{25}$, —OR$^{26}$, —NR$^{27}$R$^{28}$, —C(=O)R$^{29}$, —C(=O)OR$^{30}$, —O—C(=O)R$^{31}$, —O—C(=O)—NR$^{32}$R$^{33}$, —C(=O)—NR$^{34}$R$^{35}$, —NR$^{36}$—C(=O)R$^{37}$, —NR$^{38}$—C(=O)—OR$^{39}$, —S(=O)$_2$—R$^{40}$, —S(=O)$_2$—NR$^{41}$R$^{42}$, or —NR$^{43}$—S(=O)$_2$R$^{44}$;

$A^3$ represents —R$^{25}$, if the $A^1$ end on the $A^2$ side has a structure selected from the group consisting of —O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$— and $A^2$ is a single bond;

$R^{14}$, $R^{32}$, $R^{34}$, $R^{36}$, $R^{38}$, $R^{41}$, and $R^{43}$ each independently represent a hydrogen atom or a $C_{1-8}$ alkyl, $C_{1-8}$ acyl, $C_{1-8}$ alkylsulfonyl, 4- to 12-membered heterocyclyl, $C_{3-12}$ cycloalkyl, $C_{6-10}$ aryl, 5- to 10-membered heteroaryl, (4- to 12-membered heterocyclyl)-$C_{1-3}$ alkyl, ($C_{3-12}$ cycloalkyl)-$C_{1-3}$ alkyl, ($C_{6-10}$ aryl)-$C_{1-3}$ alkyl, or (5- to 10-membered heteroaryl)-$C_{1-3}$ alkyl group;

$R^{15}$ to $R^{31}$, $R^{33}$, $R^{35}$, $R^{37}$, $R^{39}$, $R^{40}$, $R^{42}$, and $R^{44}$ each independently represent a hydrogen atom or a $C_{1-8}$ alkyl, 4- to 12-membered heterocyclyl, $C_{3-12}$ cycloalkyl, $C_{6-10}$ aryl, 5- to 10-membered heteroaryl, (4- to 12-membered heterocyclyl)-$C_{1-3}$ alkyl, ($C_{3-12}$ cycloalkyl)-$C_{1-3}$ alkyl, ($C_{6-10}$ aryl)-$C_{1-3}$ alkyl, or (5- to 10-membered heteroaryl)-$C_{1-3}$ alkyl group;

$A^1$, $A^2$, $A^3$, and $R^{14}$ to $R^{44}$ in $A^1$, $A^2$, and $A^3$ are each optionally substituted with one to four substituents selected from the group consisting of —OH, =O, —COOH, —SO$_3$H, —PO$_3$H, —CN, —NO$_2$, a halogen atom, a $C_{1-8}$ alkyl group substituted with zero to two —OH groups, zero to two —OR$^{45}$ groups, and zero to six fluorine atoms, a $C_{3-12}$ cycloalkyl group substituted with zero to two —OH groups, zero to two —OR$^{46}$ groups, and zero to six fluorine atoms, a $C_{1-8}$ alkoxy group substituted with zero to two —OH groups, zero to two —OR$^{47}$ groups, and zero to six fluorine atoms, and a 4- to 12-membered heterocyclyl group substituted with zero to two —OH groups, zero to two —OR$^{49}$ groups, and zero to six fluorine atoms;

$R^{14}$ to $R^{44}$ are optionally bonded in $A^1$, $A^2$, or $A^3$ or between $A^1$ and $A^2$, between $A^1$ and $A^3$, or between $A^2$ and $A^3$ via a single bond, —O—, —NR$^{50}$—, or —S(=O)$_p$— to form a ring;

$R^{11}$ or $R^{13}$ is optionally bonded to $A^1$, $A^2$, or $A^3$ via a single bond, —O—, —NR$^{51}$—, or —S(=O)$_p$— to form a ring;

$R^{45}$ to $R^{51}$ each represent a hydrogen atom or a $C_{1-4}$ alkyl group substituted with zero or one —OH group and zero to six fluorine atoms;

p represents an integer of 0 to 2; and each of the heteroatom-containing groups represented by $A^1$, $A^2$, and $A^3$ contains one to four heteroatoms selected from oxygen, sulfur, and nitrogen atoms].

2. The compound or pharmaceutically acceptable salt thereof according to claim 1, wherein L represents —NH—.

3. The compound or pharmaceutically acceptable salt thereof according to claim 1, wherein $R^1$ represents a $C_{1-8}$ alkyl, $C_{3-12}$ cycloalkyl, ($C_{3-12}$ cycloalkyl)-$C_{1-6}$ alkyl, 4- to 12-membered heterocyclyl, or (4- to 12-membered heterocyclyl)-$C_{1-6}$ alkyl group.

4. The compound or pharmaceutically acceptable salt thereof according to claim 1, wherein $R^2$ is a $C_{1-8}$ alkyl group substituted with one to four fluorine atoms.

5. The compound or pharmaceutically acceptable salt thereof according to claim 1, wherein $R^2$ is a $C_{1-8}$ alkyl group substituted with zero or one —OH group and zero to two $C_{1-8}$ alkoxy groups substituted with zero or one —OH group, zero or one $C_{1-4}$ alkoxy group, and zero to three fluorine atoms.

6. The compound or pharmaceutically acceptable salt thereof according to claim 1, wherein $R^2$ is a 4- to 6-membered heterocyclyl group optionally substituted with one to four substituents selected from the group consisting of a fluorine atom, —OH, and $C_{1-4}$ alkyl and $C_{1-4}$ alkoxy groups.

7. The compound or pharmaceutically acceptable salt thereof according to claim 1, wherein $R^2$ is —COOR$^8$, —CONR$^9$R$^{10}$, or a $C_{1-8}$ acyl group, optionally each group being substituted with one to four substituents selected from the group consisting of a fluorine atom, —OH, and a $C_{1-8}$ alkoxy group.

8. The compound or pharmaceutically acceptable salt thereof according to claim 1, wherein X represents $CR^{11}$, Y represents $CR^{12}$, and Z represents $CR^{13}$.

9. The compound or pharmaceutically acceptable salt thereof according to claim 1, wherein X represents a nitrogen atom, Y represents $CR^{12}$, and Z represents $CR^{13}$.

10. The compound or pharmaceutically acceptable salt thereof according to claim 1, wherein X represents $CR^{11}$, Y represents a nitrogen atom, and Z represents $CR^{13}$.

11. The compound or pharmaceutically acceptable salt thereof according to claim 1, wherein X represents $CR^{11}$, Y represents $CR^{12}$, and Z represents a nitrogen atom.

12. The compound or pharmaceutically acceptable salt thereof according to claim 1, wherein $A^1$ is a single bond.

13. The compound or pharmaceutically acceptable salt thereof according to claim 1, wherein $A^1$ represents a $C_{1-8}$ alkylene group, and no $sp^3$ carbon atom in $A^1$ is replaced with another structure.

14. The compound or pharmaceutically acceptable salt thereof according to claim 1, wherein $A^1$ represents a $C_{1-8}$ alkylene group, and one $sp^3$ carbon atom at any position of $A^1$ is replaced with —O—.

15. The compound or pharmaceutically acceptable salt thereof according to claim 1, wherein $A^1$ represents a $C_{1-8}$ alkylene group, and one $sp^3$ carbon atom at any position of $A^1$ is replaced with —$NR^{14}$—.

16. The compound or pharmaceutically acceptable salt thereof according to claim 1, wherein $A^1$ represents a $C_{1-8}$ alkylene group, one $sp^3$ carbon atom at any position of $A^1$ is replaced with —$NR^{14}$—, and one $sp^3$ carbon atom at any other position of $A^1$ is optionally replaced with —O—.

17. The compound or pharmaceutically acceptable salt thereof according to claim 1, wherein $A^2$ represents a 4- to 12-membered heterocyclylene group; and $A^2$ is optionally substituted with one to four substituents selected from the group consisting of —OH, —COOH, —$SO_3H$, —$PO_3H$, —CN, —$NO_2$, a halogen atom, a $C_{1-8}$ alkyl group substituted with zero to two —OH groups, zero to two —$OR^{45}$ groups, and zero to six fluorine atoms, a $C_{3-12}$ cycloalkyl group substituted with zero to two —OH groups, zero to two —$OR^{46}$ groups, and zero to six fluorine atoms, a $C_{1-8}$ alkoxy group substituted with zero to two —OH groups, zero to two —$OR^{47}$ groups, and zero to six fluorine atoms, and a 4- to 12-membered heterocyclyl group substituted with zero to two —OH groups, zero to two —$OR^{49}$ groups, and zero to six fluorine atoms.

18. The compound or pharmaceutically acceptable salt thereof according to claim 1, wherein $A^2$ represents a 4- to 12-membered heterocyclylene group substituted with =O; and $A^2$ is optionally substituted with one to four substituents selected from the group consisting of —OH, =O, —COOH, —$SO_3H$, —$PO_3H$, —CN, —$NO_2$, a halogen atom, a $C_{1-8}$ alkyl group substituted with zero to two —OH groups, zero to two —$OR^{45}$ groups, and zero to six fluorine atoms, a $C_{3-12}$ cycloalkyl group substituted with zero to two —OH groups, zero to two —$OR^{46}$ groups, and zero to six fluorine atoms, a $C_{1-8}$ alkoxy group substituted with zero to two —OH groups, zero to two —$OR^{47}$ groups, and zero to six fluorine atoms, and a 4- to 12-membered heterocyclyl group substituted with zero to two —OH groups, zero to two —$OR^{49}$ groups, and zero to six fluorine atoms.

19. The compound or pharmaceutically acceptable salt thereof according to claim 1, wherein X represents $CR^{11}$, Y represents $CR^{12}$, Z represents $CR^{13}$, and $R^{11}$ or $R^{13}$ is bonded to $A^1$, $A^2$, or $A^3$ via a single bond, —O—, —$NR^{51}$—, or —S(=O)$_p$— to form a ring.

20. The compound or pharmaceutically acceptable salt thereof according to claim 1, wherein $A^3$ is a hydrogen atom.

21. The compound or pharmaceutically acceptable salt thereof according to claim 1, wherein $A^3$ is a halogen atom, —CN, —$R^{25}$, —$OR^{26}$, —$NR^{27}R^{28}$, —C(=O)$R^{29}$, or —C(=O)—$OR^{30}$, and $R^{25}$ to $R^{30}$ each independently represent a hydrogen atom, an optionally substituted $C_{1-8}$ alkyl group, an optionally substituted 4- to 12-membered heterocyclyl group, an optionally substituted $C_{3-12}$ cycloalkyl group, an optionally substituted (4- to 12-membered heterocyclyl)-$C_{1-3}$ alkyl group, or an optionally substituted ($C_{3-12}$ cycloalkyl)-$C_{1-3}$ alkyl group.

22. The compound or pharmaceutically acceptable salt thereof according to claim 1, wherein $R^3$ is a hydrogen atom.

23. The compound or pharmaceutically acceptable salt thereof according to claim 1, wherein $R^3$ represents a $C_{1-4}$ alkyl group, a fluorine atom, or a chlorine atom.

24. The compound, or pharmaceutically acceptable salt thereof, selected from;

6-(difluoromethyl)-N8-isopropyl-N2-(5-piperazin-1-yl-2-pyridyl)pyrido[3,4-d]pyrimidine-2,8-diamine (1R)-1-[8-(isopropylamino)-2-[(5-piperazin-1-yl-2-pyridyl)amino]pyrido[3,4-d]pyrimidin-6-yl]ethanol 1-[2-[(5-piperazin-1-yl-2-pyridyl)amino]-8-(tetrahydrofuran-3-ylamino)pyrido[3,4-d]pyrimidin-6-yl]ethanol 1-[2-[(5-piperazin-1-yl-2-pyridyl)amino]-8-(tetrahydropyran-3-ylamino)pyrido[3,4-d]pyrimidin-6-yl]ethanol N8-isopropyl-6-[(1R)-1-methoxyethyl]-N2-(6-piperazin-1-ylpyridazin-3-yl)pyrido[3,4-d]pyrimidine-2,8-diamine N8-isopropyl-6-[(1R)-1-methoxyethyl]-N2-[5-(piperazin-1-ylmethyl)-2-pyridyl]pyrido[3,4-d]pyrimidine-2,8-diamine 1-[6-[[6-[(1R)-1-hydroxyethyl]-8-(isopropylamino)pyrido[3,4-d]pyrimidin-2-yl]amino]-3-pyridyl]piperazin-2-one 1-[6-[[5-chloro-6-[(1R)-1-hydroxyethyl]-8-(isopropylamino)pyrido[3,4-d]pyrimidin-2-yl]amino]-3-pyridyl]piperazin-2-one (1R)-1-[2-[(6-piperazin-1-ylpyridazin-3-yl)amino]-8-(tetrahydropyran-4-ylamino)pyrido[3,4-d]pyrimidin-6-yl]ethanol (1R)-1-[2-[(6-piperazin-1-ylpyridazin-3-yl)amino]-8-[[(3S)-tetrahydropyran-3-yl]amino]pyrido[3,4-d]pyrimidin-6-yl]ethanol (1R)-1-[2-[(6-piperazin-1-ylpyridazin-3-yl)amino]-8-[[(3R)-tetrahydropyran-3-yl]amino]pyrido[3,4-d]pyrimidin-6-yl]ethanol (1R)-1-[2-[[5-(piperazin-1-ylmethyl)-2-pyridyl]amino]-8-(tetrahydropyran-4-ylamino)pyrido[3,4-d]pyrimidin-6-yl]ethanol (1R)-1-[2-[[5-(piperazin-1-ylmethyl)-2-pyridyl]amino]-8-[[(3S)-tetrahydropyran-3-yl]amino]pyrido[3,4-d]pyrimidin-6-yl]ethanol (1R)-1-[2-[[5-(piperazin-1-ylmethyl)-2-pyridyl]amino]-8-[[(3R)-tetrahydropyran-3-yl]amino]pyrido[3,4-d]pyrimidin-6-yl]ethanol 1-[6-[[6-[(1R)-1-hydroxyethyl]-8-(isopropylamino)pyrido[3,4-d]pyrimidin-2-yl]amino]pyridazin-3-yl]piperidin-4-ol (1R)-1-[8-(isopropylamino)-2-[(6-piperazin-1-ylpyridazin-3-yl)amino]pyrido[3,4-d]pyrimidin-6-yl]ethanol 1-[[6-[[6-[(1R)-1-hydroxyethyl]-8-(isopropylamino)
pyrido[3,4-d]pyrimidin-2-yl]amino]-3-pyridyl]methyl]
piperazin-2-one
6-[(1R)-1-methoxyethyl]-N2-[5-(piperazin-1-ylmethyl)-
2-pyridyl]-N8-[(3S)-tetrahydropyran-3-yl]pyrido[3,4-
d]pyrimidine-2,8-diamine
6-[(1R)-1-methoxyethyl]-N2-(6-piperazin-1-ylpyridazin-
3-yl)-N8-[(3S)-tetrahydropyran-3-yl]pyrido[3,4-d]py-
rimidine-2,8-diamine
6-[(1R)-1-methoxyethyl]-N2-[5-(piperazin-1-ylmethyl)-
2-pyridyl]-N8-(tetrahydropyran-4-ylmethyl)pyrido[3,
4-d]pyrimidine-2,8-diamine
N8-isopropyl-6-[(1R)-1-methoxyethyl]-N2-(5-piperazin-
1-ylpyrazin-2-yl)pyrido[3,4-d]pyrimidine-2,8-diamine
N8-isopropyl-6-[(1R)-1-methoxyethyl]-N2-[6-[(2S)-2-
methylpiperazin-1-yl]pyridazin-3-yl]pyrido[3,4-d]py-
rimidine-2,8-diamine
N8-isopropyl-6-[(1R)-1-methoxyethyl]-N2-[6-[(2R)-2-
methylpiperazin-1-yl]pyridazin-3-yl]pyrido[3,4-d]py-
rimidine-2,8-diamine
(1R)-1-[2-[[6-(4,7-diazaspiro[2.5]octan-7-yl)pyridazin-3-
yl]amino]-8-(isopropylamino)pyrido[3,4-d]pyrimidin-
6-yl]ethanol
(1R)-1-[2-[[5-(4,7-diazaspiro[2.5]octan-7-ylmethyl)-2-
pyridyl]amino]-8-(isopropylamino)pyrido[3,4-d]py-
rimidin-6-yl]ethanol
2-[1-[[6-[[6-[(1R)-1-hydroxyethyl]-8-(isopropylamino)
pyrido[3,4-d]pyrimidin-2-yl]amino]-3-pyridyl]
methyl]-4-piperidyl]propan-2-ol
(1R)-1-[2-[[5-[[4-(2-hydroxyethyl)piperazin-1-yl]
methyl]-2-pyridyl]amino]-8-(isopropylamino)pyrido
[3,4-d]pyrimidin-6-yl]ethanol
(1R)-1-[2-[[5-[2-(dimethylamino)ethoxy]-2-pyridyl]
amino]-8-[[(3S)-tetrahydropyran-3-yl]amino]pyrido[3,
4-d]pyrimidin-6-yl]ethanol
(1R)-1-[2-[[6-(4-methylpiperazin-1-yl)pyridazin-3-yl]
amino]-8-[[(3S)-tetrahydropyran-3-yl]amino]pyrido[3,
4-d]pyrimidin-6-yl]ethanol
2-hydroxy-1-[4-[6-[[6-[(1R)-1-hydroxyethyl]-8-(isopro-
pylamino)pyrido[3,4-d]pyrimidin-2-yl]amino]
pyridazin-3-yl]piperazin-1-yl]ethanone
1-[6-[[8-(isopropylamino)-6-[(2S)-tetrahydrofuran-2-yl]
pyrido[3,4-d]pyrimidin-2-yl]amino]-3-pyridyl]piper-
azin-2-one
(1R)-1-[8-(isopropylamino)-2-(5,6,7,8-tetrahydro-1,6-
naphthyridin-2-ylamino)pyrido[3,4-d]pyrimidin-6-yl]
ethanol
2-[4-[[6-[[6-[(1R)-1-hydroxyethyl]-8-(isopropylamino)
pyrido[3,4-d]pyrimidin-2-yl]amino]-3-pyridyl]methyl]
piperazin-1-yl]-2-methyl-propan-1-ol
4-[6-[[6-[(1R)-1-hydroxyethyl]-8-(isopropylamino)
pyrido[3,4-d]pyrimidin-2-yl]amino]-3-pyridyl]-1-
[(2S)-2-hydroxypropyl]-1,4-diazepan-5-one
4-[6-[[6-[(1R)-1-hydroxyethyl]-8-(isopropylamino)
pyrido[3,4-d]pyrimidin-2-yl]amino]-3-pyridyl]-1-
[(2R)-2-hydroxypropyl]-1,4-diazepan-5-one
N8-isopropyl-N2-[5-(piperazin-1-ylmethyl)-2-pyridyl]-
6-[(2S)-tetrahydrofuran-2-yl]pyrido[3,4-d]pyrimidine-
2,8-diamine
1-[6-[[6-[(1R)-1-hydroxyethyl]-8-(isopropylamino)
pyrido[3,4-d]pyrimidin-2-yl]amino]-2-methyl-3-
pyridyl]piperazin-2-one
1-[6-[[8-(isopropylamino)-6-[(3S)-tetrahydrofuran-3-yl]
pyrido[3,4-d]pyrimidin-2-yl]amino]-3-pyridyl]piper-
azin-2-one (1R)-1-[2-(5,6,7,8-tetrahydro-1,6-naphthyridin-2-
ylamino)-8-[[(3S)-tetrahydropyran-3-yl]amino]pyrido
[3,4-d]pyrimidin-6-yl]ethanol
1-[6-[[8-(isopropylamino)-6-(3-methyloxetan-3-yl)
pyrido[3,4-d]pyrimidin-2-yl]amino]-3-pyridyl]piper-
azin-2-one
(1R)-1-[2-[[5-[4-(dimethylamino)cyclohexoxy]-2-
pyridyl]amino]-8-[[(3S)-tetrahydropyran-3-yl]amino]
pyrido[3,4-d]pyrimidin-6-yl]ethanol
6-[(1R)-1-methoxyethyl]-N2-[5-(piperazin-1-ylmethyl)-
2-pyridyl]-N8-propyl-pyrido[3,4-d]pyrimidine-2,8-di-
amine
6-[(1R)-1-methoxyethyl]-N2-(6-piperazin-1-ylpyridazin-
3-yl)-N8-propyl-pyrido[3,4-d]pyrimidine-2,8-diamine
1-[[6-[[6-(difluoromethyl)-8-[(4-methylcyclohexyl)
amino]pyrido[3,4-d]pyrimidin-2-yl]amino]-3-pyridyl]
methyl]piperidine-4-carboxylic acid
(1R)-1-[8-(ethylamino)-2-[[5-[[4-(2-hydroxyethyl)piper-
azin-1-yl]methyl]-2-pyridyl]amino]pyrido[3,4-d]py-
rimidin-6-yl]ethanol
(1R)-1-[2-[[5-[[4-(2-hydroxyethyl)piperazin-1-yl]
methyl]-2-pyridyl]amino]-8-(propylamino)pyrido[3,4-
d]pyrimidin-6-yl]ethanol
N8-isopropyl-6-(3-methyloxetan-3-yl)-N2-(6-piperazin-
1-ylpyridazin-3-yl)pyrido[3,4-d]pyrimidine-2,8-di-
amine
N8-isopropyl-6-(3-methyloxetan-3-yl)-N2-[5-(piperazin-
1-ylmethyl)-2-pyridyl]pyrido[3,4-d]pyrimidine-2,8-di-
amine
6-(3-methyloxetan-3-yl)-N2-[5-(piperazin-1-ylmethyl)-
2-pyridyl]-N8-[(3S)-tetrahydropyran-3-yl]pyrido[3,4-
d]pyrimidine-2,8-diamine
4-[6-[[6-[(1R)-1-hydroxyethyl]-8-[isopropyl(methyl)
amino]pyrido[3,4-d]pyrimidin-2-yl]amino]-3-pyridyl]-
1,4-diazepan-5-one
(1R)-1-[8-(isopropylamino)-2-[(6-methyl-5-piperazin-1-
yl-2-pyridyl)amino]pyrido[3,4-d]pyrimidin-6-yl]etha-
nol
(1R)-1-[2-[[6-(2-hydroxyethyl)-7,8-dihydro-5H-1,6-
naphthyridin-2-yl]amino]-8-(isopropylamino)pyrido
[3,4-d]pyrimidin-6-yl]ethanol
(1R)-1-[8-(isopropylamino)-2-[[6-[2-(methylamino)
ethyl]-7,8-dihydro-5H-1,6-naphthyridin-2-yl]amino]
pyrido[3,4-d]pyrimidin-6-yl]ethanol
N2-(6-piperazin-1-ylpyridazin-3-yl)-6-[(3S)-tetrahydro-
furan-3-yl]-N8-[(3S)-tetrahydropyran-3-yl]pyrido[3,4-
d]pyrimidine-2,8-diamine
N2-[5-(piperazin-1-ylmethyl)-2-pyridyl]-6-[(3R)-tetrahy-
drofuran-3-yl]-N8-[(3S)-tetrahydropyran-3-yl]pyrido
[3,4-d]pyrimidine-2,8-diamine
(1R)-1-[2-[[6-[2-(dimethylamino)ethyl]-7,8-dihydro-5H-
1,6-naphthyridin-2-yl]amino]-8-(isopropylamino)
pyrido[3,4-d]pyrimidin-6-yl]ethanol
(2S)-1-[4-[[6-[[8-(ethylamino)-6-[(1R)-1-hydroxyethyl]
pyrido[3,4-d]pyrimidin-2-yl]amino]-3-pyridyl]methyl]
piperazin-1-yl]propan-2-ol
(2R)-1-[4-[[6-[[8-(ethylamino)-6-[(1R)-1-hydroxyethyl]
pyrido[3,4-d]pyrimidin-2-yl]amino]-3-pyridyl]methyl]
piperazin-1-yl]propan-2-ol
(1R)-1-[8-(isopropylamino)-2-[[5-[(2R)-2-methylpiper-
azin-1-yl]-2-pyridyl]amino]pyrido[3,4-d]pyrimidin-6-
yl]ethanol
(1R)-1-[8-(isopropylamino)-2-[[5-[(2S)-2-methylpiper-
azin-1-yl]-2-pyridyl]amino]pyrido[3,4-d]pyrimidin-6-
yl]ethanol N8-isopropyl-N2-(5-piperazin-1-yl-2-pyridyl)-6-[(2S)-tetrahydrofuran-2-yl]pyrido[3,4-d]pyrimidine-2,8-diamine (1R)-1-[8-(cyclobutylamino)-2-[[5-[[4-(2-hydroxyethyl)piperazin-1-yl]methyl]-2-pyridyl]amino]pyrido[3,4-d]pyrimidin-6-yl]ethanol (1R)-1-[8-(cyclopropylmethylamino)-2-[[5-[[4-(2-hydroxyethyl)piperazin-1-yl]methyl]-2-pyridyl]amino]pyrido[3,4-d]pyrimidin-6-yl]ethanol 6-(3-methyloxetan-3-yl)-N2-(5-piperazin-1-yl-2-pyridyl)-N8-propyl-pyrido[3,4-d]pyrimidine-2,8-diamine 6-(3-methyloxetan-3-yl)-N2-[5-(piperazin-1-ylmethyl)-2-pyridyl]-N8-propyl-pyrido[3,4-d]pyrimidine-2,8-diamine N2-(5-piperazin-1-yl-2-pyridyl)-N8-propyl-6-tetrahydrofuran-3-yl-pyrido[3,4-d]pyrimidine-2,8-diamine N2-[5-(piperazin-1-ylmethyl)-2-pyridyl]-N8-propyl-6-tetrahydrofuran-3-yl-pyrido[3,4-d]pyrimidine-2,8-diamine N8-isopropyl-6-(3-methyloxetan-3-yl)-N2-(5-piperazin-1-yl-2-pyridyl)pyrido[3,4-d]pyrimidine-2,8-diamine N8-isopropyl-N2-(5-piperazin-1-yl-2-pyridyl)-6-tetrahydrofuran-3-yl-pyrido[3,4-d]pyrimidine-2,8-diamine 2-[4-[[6-[[8-(isopropylamino)-6-tetrahydrofuran-3-yl-pyrido[3,4-d]pyrimidin-2-yl]amino]-3-pyridyl]methyl]piperazin-1-yl]ethanol 2-[4-[[6-[[6-tetrahydrofuran-3-yl-8-[[(3S)-tetrahydropyran-3-yl]amino]pyrido[3,4-d]pyrimidin-2-yl]amino]-3-pyridyl]methyl]piperazin-1-yl]ethanol (1R)-1-[2-[[5-[[4-(hydroxymethyl)-1-piperidyl]methyl]-2-pyridyl]amino]-8-(isopropylamino)pyrido[3,4-d]pyrimidin-6-yl]ethanol 1-[[6-[[6-[(1R)-1-hydroxyethyl]-8-(isopropylamino)pyrido[3,4-d]pyrimidin-2-yl]amino]-3-pyridyl]methyl]piperidin-4-ol 1-[[6-[[8-(tert-butylamino)-6-[(1R)-1-hydroxyethyl]pyrido[3,4-d]pyrimidin-2-yl]amino]-3-pyridyl]methyl]piperidin-4-ol (1R)-1-[8-(tert-butylamino)-2-[[5-[[4-(hydroxymethyl)-1-piperidyl]methyl]-2-pyridyl]amino]pyrido[3,4-d]pyrimidin-6-yl]ethanol 1-[[6-[[6-[(1R)-1-hydroxyethyl]-8-(isobutylamino)pyrido[3,4-d]pyrimidin-2-yl]amino]-3-pyridyl]methyl]piperidin-4-ol (1R)-1-[2-[[5-[[4-(hydroxymethyl)-1-piperidyl]methyl]-2-pyridyl]amino]-8-(isobutylamino)pyrido[3,4-d]pyrimidin-6-yl]ethanol 1-[6-[[6-[(1R)-1-hydroxypropyl]-8-(isopropylamino)pyrido[3,4-d]pyrimidin-2-yl]amino]-3-pyridyl]piperazin-2-one (1R)-1-[2-[[5-[[4-(2-hydroxyethyl)piperazin-1-yl]methyl]-6-methyl-2-pyridyl]amino]-8-(propylamino)pyrido[3,4-d]pyrimidin-6-yl]ethanol.

25. A pharmaceutical composition comprising the compound or pharmaceutically acceptable salt thereof according to claim 1 and a pharmaceutically acceptable carrier.

26. A pharmaceutical composition exhibiting a CDK4/6 inhibitory activity, comprising the compound or pharmaceutically acceptable salt thereof according to claim 1 as an active ingredient.

27. A drug for prevention or treatment of rheumatoid arthritis, arteriosclerosis, pulmonary fibrosis, cerebral infarction, or cancer, the drug comprising the compound or pharmaceutically acceptable salt thereof according to claim 1 as an active ingredient.

* * * * *